US011084878B2

(12) United States Patent
Cook et al.

(10) Patent No.: US 11,084,878 B2
(45) Date of Patent: Aug. 10, 2021

(54) IL-11Rα ANTIBODIES

(71) Applicants: Singapore Health Services Pte. Ltd., Singapore (SG); National University of Singapore, Singapore (SG); Enleofen Bio Ptd. Ltd., Singapore (SG)

(72) Inventors: Stuart Alexander Cook, Singapore (SG); Sebastian Schaefer, Singapore (SG)

(73) Assignees: National University of Singapore, Singapore (SG); Singapore Health Services PTE LTD., Singapore (SG); Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/440,876

(22) Filed: Jun. 13, 2019

(65) Prior Publication Data
US 2019/0389957 A1 Dec. 26, 2019
US 2020/0377605 A9 Dec. 3, 2020

(30) Foreign Application Priority Data

Jun. 13, 2018 (GB) .................................... 1809700

(51) Int. Cl.
C07K 16/28 (2006.01)

(52) U.S. Cl.
CPC ...... *C07K 16/2866* (2013.01); *C07K 2317/21* (2013.01); *C07K 2317/24* (2013.01); *C07K 2317/565* (2013.01); *C07K 2317/92* (2013.01)

(58) Field of Classification Search
None
See application file for complete search history.

(56) References Cited

U.S. PATENT DOCUMENTS

2014/0219919 A1   8/2014   Edwards et al.

FOREIGN PATENT DOCUMENTS

WO   WO 2017/103108 A1   6/2017
WO   WO 2018/109170 A2   6/2018

OTHER PUBLICATIONS

International Search Report and Written Opinion for Application No. PCT/EP2019/065600, dated Oct. 14, 2019.
International Preliminary Report on Patentability for Application No. PCT/EP2019/065600, dated Dec. 24, 2020.
Affo et al., The Role of Cancer-Associated Fibroblasts and Fibrosis in Liver Cancer. Annu Rev Pathol. Jan. 24, 2017;12:153-186. Author manuscript, 39 pgs.
Angal et al., A Single Amino acid Substitution Abolishes the Heterogeneity of Chimeric Mouse/Human (IgG4) Antibody. Molecular Immunology. 1993;30(1):105-108.
Arunkumar et al., Science Behind Cisplatin-induced Nephrotoxicity in Humans: A Clinical Study. Asian Pacific journal of Tropical Biomedicine. 2012;2(8):640-644. Epub Aug. 28, 2012.
Baena et al., Fructose, but not glucose, impairs insulin signaling in the three major insulin-sensitive tissues. Scientific Reports. May 2016;6(26149):1-15. Epub May 19, 2016.
Bamba et al., Regulation of IL-11 expression in intestinal myofibroblasts: role of c-Jun AP-1-and MAPK-dependent pathways. American Journal of Physiology Gastrointestinal and Liver Physiology. May 21, 2003;285:529-538.
Blanc et al., Monoclonal antibodies against the human interleukin-11 receptor alpha-chain (IL-11Ralpha) and their use in studies of human mononuclear cells. J Immunol Methods. Jul. 31, 2000;241(1-2):43-59.
Boersma et al., Bispecific Designed Ankyrin Repeat Proteins (DARPins) Targeting Epidermal Growth Factor Receptor Inhibit A431 Cell Proliferation and Receptor Recycling. Journal of Biological Chemistry. Dec. 2, 2011;286(48):41273-41285.
Bonner-Weir et al., Islets in Type 2 Diabetes: in Honor of Dr. Robert C. Turner. Perspectives in Diabetes. Nov. 2008;57(11):2899-2904.
Brinkmann et al., The Making of Bispecific Antibodies. mAbs. 2017;9(2):182-212.
Buck et al., Detection of S-phase cell cycle progression using 5-ethynyl-2'-deoxyuridine incorporation with click chemistry, an alternative to using 5-bromo-2?-deoxyuridine antibodies. BioTechniques. Jun. 2008;44(7):927-929.
Chandrudu et al., Chemical Methods for Peptide and Protein Production. Molecules. Apr. 12, 2013;18:4373-4388.
Chen et al., Fusion Protein Linkers: Property, Design and Functionality. Adv Drug Deliv Rev. Oct. 15, 2013;65(10):1357-1369. Author Manuscript, 32 pages.
Chen et al., IL-11 receptor alpha in the pathogenesis of IL-13-induced inflammation and remodeling. J Immunol. Feb. 15, 2005;174(4):2305-13.
Chothia et al., Canonical Structures for the Hypervariable Regions of Immunoglobulins. Journal of Molecular Biology. 1987;196:901-917.
Ciliberto et al. Cytokine Inhibitors: Chapter 8. Marcel Dekker, Inc. 2001.
Concepcion et al., Label-free detection of biomolecular interactions using BioLayer interferometry for kinetic characterization. Comb Chem High Throughput Screen. Sep. 2009;12(8):791-800. doi: 10.2174/138620709789104915.
Curtis et al., Recombinant Soluble interleukin-11 (IL-11) Receptor Alpha-Chain Can Act as an IL-11 Antagonist. Blood. Dec. 1, 1997;90(11):4403-12.
Daba et al., Drug-induced pulmonary fibrosis. Saudi Med J. 2004;25(6):700-706.
Davies et al., Human IgG4: a structural perspective. Immunological Reviews. 2015;268:139-159.

(Continued)

*Primary Examiner* — Gary B Nickol
*Assistant Examiner* — Jegatheesan Seharaseyon
(74) *Attorney, Agent, or Firm* — Wolf, Greenfield & Sacks, P.C.

(57) ABSTRACT

Provided are antigen-binding molecules capable of binding to IL-11Rα, and methods of medical treatment and prophylaxis using the same.

6 Claims, 60 Drawing Sheets

Specification includes a Sequence Listing.

(56) References Cited

OTHER PUBLICATIONS

Dotti et al., Design and Development of Therapies using Chimeric Antigen Receptor-Expressing T cells. Immunol Rev. Jan. 2014;257(1)107-26, Author Manuscript. 35 pages.

Du et al., Interleukin-11: review of molecular, cell biology, and clinical use. Blood. Jun. 1, 1997;89(11):3897-908.

Emanuel et al., A fibronectin scaffold approach to bispecific inhibitors of epidermal growth factor receptor and insulin-like growth factor-I receptor. mAbs. 2011;3(1):38-48.

Ernst et al., STAT3 and STAT1 mediate IL-11-dependent and inflammation-associated gastric tumorigenesis in gp130 receptor mutant mice. The Journal of Clinical Investigation. May 2008;118(5):1727-1738.

Fearon et al., Definition and classification of cancer cachexia: an international consensus. Lancet Oncol. May 2011;12:489-495.

Fearon et al., Myopenia—a new universal term for muscle wasting. Journal of Cachexia, Sarcopenia and Muscle. 2011;2:1-3.

Frank et al., High-performance signal peptide prediction based on sequence alignment techniques. Bioinformatics. 2008;24(19):2172-2176.

French, How to make bispecific antibodies. Methods Mol Med. 2000;40:333-339.

Fulcher et al., Carboxyfluorescein succinimidyl ester-based proliferative assays for assessment of T cell function in the diagnostic laboratory. Immunology and Cell Biology. 1999;77:559-564.

Garbers et al., Interleukin-6 and interleukin-11: same same but different. Biol Chem. Sep. 2013;394(9):1145-61. doi: 10.1515/hsz-2013-0166.

Gräslund et al., Structural Genomics Consortium, Protein production and purification. Nat Methods. Feb. 2008;5(2):135-146, Author Manuscript. 25 pages.

Ha et al., Immunoglobulin Fc Heterodimer Platform Technology: from Design to Applications in Therapeutic Antibodies and Proteins. Frontiers in Immunology. Oct. 6, 2016;7(394):1-16.

Haverick et al., Separation of mAbs molecular variants by analytical hydrophobic interaction chromatography HPLC. mAbs. 2014;6(4):852-858. Epub Apr. 1, 2014.

Haynes et al., Redirecting mouse CTL against colon carcinoma: superior signaling efficacy of single-chain variable domain chimeras containing TCR-zeta vs Fc epsilon RI-gamma. J Immunol. Jan. 1, 2001;166(1):182-7. doi: 10.4049/jimmunol.166.1.182.

Hearty et al., Measuring antibody-antigen binding kinetics using surface plasmon resonance. Methods Mol Biol. 2012;907:411-42. doi: 10.1007/978-1-61779-974-7_24.

Hilton et al., Cloning of a Murine IL-11 Receptor Alpha-Chain; Requirement for gp130 for High Affinity Binding and Signal Transduction. EMBO J. Oct. 17, 1994;13(20):4765-75.

Hornbeck, Enzyme-Linked Immunosorbent Assays. Curr Protoc Immunol. 2015;110:2.1.1-2.1.23.

Hornig et al., Chapter 40: Production of bispecific antibodies: diabodies and tandem scFv. Methods Mol Biol. 2012;907:713-727. doi:10.1007/978-1-61779-974-7_40.

Hunter et al., IL-6 as a keystone cytokine in health and disease. Nature Immunology. May 2015;16(5)448-457. Epub Apr. 21, 2015.

Hurrell, Monoclonal Hybridoma Antibodies: Techniques and Applications. CRC Press. 1982.

Jansen et al., The Ascending Pathophysiology of Cholestatic Liver Disease. Hepatology. Feb. 2017;65(2):722-738.

Jerabek-Willemsen et al., Molecular interaction studies using microscale thermophoresis. Assay and Drug Development Technologies. Aug. 2011;9(4):342-353.

Johnstone et al., Emerging roles for IL-11 signaling in cancer development and progression: Focus on breast cancer. Cytokine Growth Factor Rev. Oct. 2015;26(5):489-98. doi: 10.1016/j.cytogfr.2015.07.015. Epub Jul. 14, 2015.

Karpovich et al., Expression and Function of interleukin-11 and Its Receptor Alpha in the Human Endometrium. Mol Hum Reprod. Feb. 2003;9(2):75-80. doi: 10.1093/molehr/gag012.

Katoh et al., MAFFT Multiple Sequence Alignment Software Version 7: Improvements in Performance and Usability. Molecular Biology and Evolution. Apr. 2013;30(4):772-780. Epub Jan. 16, 2013.

Khaw et al., Modulation of wound healing after glaucoma surgery. Curr Opin Ophthalmol. Apr. 2001;12(2):143-8.

Khoury et al., Drug Induced Liver Injury: Review With a Focus on Genetic Factors, Tissue Diagnosis, and Treatment Options. J Clin Transl Hepatol. Jun. 28, 2015;3(2):99-108. doi: 10.14218/JCTH.2015.00007.

Kunert et al., Advances in recombinant antibody manufacturing. Applied Microbiology and Biotechnology. 2016;100:3451-3461. Epub Mar. 3, 2016.

Lacob et al., Investigating monoclonal antibody aggregation using a combination of H/DX-MS and other biophysical measurements. J Pharm Sci., Dec. 2013;102(12):4315-4329, Author Manuscript, 25 pages.

Lad et al., High-Throughput Kinetic Screening of Hybridomas to Identify High-Affinity Antibodies Using Bio-Layer Interferometry. Journal of Biomolecular Screening. 2015;20(4):498-507.

Lassman et al., Kalign—an accurate and fast multiple sequence alignment algorithm. BMC Bioinformatics. Dec. 2005;6(298) https://doi.org/10.1186/1471-2105, 9 pages.

Lokau et al., Proteolytic Cleavage Governs Interleukin-11 Trans-signaling. Cell Rep. 2016; 14(7): 1761-1773.

Machado et al., Mouse Models of Diet-Induced Nonalcoholic Steatohepatitis Reproduce the Heterogeneity of the Human Disease. PLoS ONE. May 27, 2015;10(5)e0127991(1-16).

Martineau P., Affinity Measurements by Competition ELISA. Antibody Engineering. 2010;1:657-665.

Mead et al., Evaluation of Anti-TGF—2 Antibody as a New Postoperative Anti-scarring Agent in Glaucoma Surgery. IOVS. Aug. 2003;44(8):3394-3401.

Menzen et al., High-Throughput Melting-Temperature Analysis of a Monoclonal Antibody by Differential Scanning Fluorimetry in the Presence of Surfactants. Journal of Pharmaceutical Sciences. Feb. 2013;102(2):415-428.

Morrison et al., Chimeric human antibody molecules: mouse antigen-binding domains with human constant region domains. Proc Natl Acad Sci U S A. 1984;81(21):6851-6855.

Nandurkar et al., The Human IL-11 Receptor Requires gp130 for Signalling: Demonstration by Molecular Cloning of the Receptor. Oncogene. Feb. 1, 1996;12(3):585-93.

Neuberger et al. Antibody Engineering. 8th International Biotechnology Symposium Part 2. 1988:792-799.

Notredame et al., T-Coffee: A Novel Method for Fast and Accurate Multiple Sequence Alignment. Journal of Molecular Biology. 2000;302:205-217.

Obana et al., Therapeutic activation of signal transducer and activator of transcription 3 by interleukin-11 ameliorates cardiac fibrosis after myocardial infarction. Circulation. Feb. 9, 2010;121(5):684-91. doi: 10.1161/CIRCULATIONAHA.109.893677. Epub Jan. 25, 2010.

Oh et al., Cisplatin-induced Kidney Dysfunction and Perspectives on Improving Treatment Strategies. Electrolyte Blood Press. Dec. 2014;12(2):55-65. Epub Dec. 31, 2014.

Park et al., Monoclonal antibody therapy. Advances in Protein Chemistry. 2001;56:369-421. https://doi.org/10.1016/S0065-3233(01)56010-6.

Parslow et al., Antibody-Drug Conjugates for Cancer Therapy. Biomedicines. Jul. 11, 2016;4(14): 17 pgs.

Petersen et al., SignalP 4.0: discriminating signal peptides from transmembrane regions. Nat Methods. Sep. 29, 2011;8(10):785-6. doi: 10.1038/nmeth.1701.

Pflanz et al., A Fusion Protein of interleukin-11 and Soluble interleukin-11 Receptor Acts as a Superagonist on Cells Expressing gp130. FEBS Lett. Apr. 30, 1999;450(1-2):117-22. doi: 10.1016/s0014-5793(99)00477-9.

Pollock et al., Diagnostic considerations for cholestatic liver disease. Journal of Gastroenterology and Hepatology. 2017;32:1303-1309.

(56) References Cited

OTHER PUBLICATIONS

Putoczki et al., More Than a Sidekick: The IL-6 Family Cytokine IL-11 Links Inflammation to Cancer. J Leukoc Biol. Dec. 2010;88(6):1109-17. doi: 10.1189/jlb.0410226.

Retter et al., VBASE2, an integrative V gene database. Nucleic Acids Research. 2005;33:D671-D674.

Reverdatto et al., Peptide Aptamers: Development and Applications. Curr Top Med Chem. 2015;15(12):1082-1101. Author Manuscript, 38 pages.

Rich et al., Extracting kinetic rate constants from surface plasmon resonance array systems. Analytical Biochemistry. 2008;373(1):112-120. Epub Aug. 19, 2007.

Rowe et al., Hepatocyte-derived Snail propagates liver fibrosis progression. Mol Cell Biol. Jun. 2011;31(12):2392-403. doi: 10.1128/MCB.01218-10.

Salic et al., A chemical method for fast and sensitive detection of DNA synthesis in vivo. PNAS. Feb. 19, 2008;105(7):2415-2420.

Schaefer et al., IL-11 is a crucial determinant of cardiovascular fibrosis. Nature. 2017; 552(7683): 110-115.

Schroeder et al., Structure and Function of Immunoglobulins. J Allergy Clin Immunol. Feb. 2010;125(202):S41-s52. Author Manuscript, 24 pages.

Seet et al., Validation of the Glaucoma Filtration Surgical Mouse Model for Antifibrotic Drug Evaluation. Mol Med. 2011;17(5-6):557-567. Epub Jan. 11, 2011.

Sheng et al., Most Tissue-Resident Macrophages Except Microglia Are Derived from Fetal Hematopoietic Stem Cells. Immunity. Aug. 18, 2015;43:382-393.

Sittampalam et al., Assay Guidance Manual, Eli Lilly & Company and the National Center for Advancing Translational Sciences. 2004 (last updated Jul. 1, 2016), 10 pages.

Szendroi et al., Polarization colours of collagen fibres: a sign of collagen production activity in fibrotic processes. Acta Morphol Hung. 1984;32(1):47-55.

Söding J., Protein homology detection by HMM-HMM comparison. Bioinformatics. 2005;21(7):951-960. Epub Nov. 5, 2004.

Tang et al., Transforming Growth Factor-b Stimulates Interleukin-11 Transcription via Complex Activating Protein-1-dependent Pathways. J. Biol. Chem. 1998; 273(10): 5506-5513.

Tao et al., Cancer-associated fibroblasts treated with cisplatin facilitates chemoresistance of lung adenocarcinoma through IL-11/IL-11R/STAT3 signaling pathway. Sci Rep. Dec. 6, 2016;6:38408. doi: 10.1038/srep38408. 24 pages.

Tarnavski et al., Mouse cardiac surgery: comprehensive techniques for the generation of mouse models of human diseases and their application for genomic studies. Physiol Genomics. 2004;16:349-360. Epub Dec. 16, 2003.

Tisdale M.J., Cachexia in Cancer Patients. Nature. Nov. 2002;2:862-871.

Toda et al., Polarized in vivo expression of IL-11 and IL-17 between acute and chronic skin lesions. J Allergy Clin Immunol. Apr. 2003;111(4):875-81.

Trepicchio et al., Protective effect of rhIL-11 in a murine model of acetaminophen-induced hepatotoxicity. Toxicol Pathol. Mar.-Apr. 2001;29(2):242-9.

Unverdorben et al., Pharmacokinetic properties of IgG and various Fc fusion proteins in mice. MAbs. 2016;8(1):120-128.

Wong et al., Endogenous IL-11 is pro-inflammatory in acute methylated bovine serum albumin/interleukin-1-induced (mBSA/IL-1)arthritis. Cytokine. Jan. 21, 2005;29(2):72-6.

Wong et al., Matrix Metalloproteinase Inhibition Modulates Postoperative Scarring after Experimental Glaucoma Filtration Surgery. Investigative Ophthalmology & Visual Science. Mar. 2003;44(3):1097-1103.

Wong et al., Prolonged Antiscarring Effects of Ilomastat and MMC after Experimental Glaucoma Filtration Surgery. Investigative Ophthalmology & Visual Science. Jun. 2005;46(6):2018-2022.

Wynn et al., Mechanisms of fibrosis: therapeutic translation for fibrotic disease. Nat Med. 2012;18(7):1028-1040.

Wynn, Cellular and molecular mechanisms of fibrosis. J Pathol. Jan. 2008;214(2):199-210. Author Manuscript.

Xu et al., The role of IL-11 in immunity and cancer. Cancer Letters. 2016;373:156-163.

Yashiro et al., Transforming growth factor-beta stimulates interleukin-11 production by human periodontal ligament and gingival fibroblasts. J Clin Periodontol. Mar. 2006;33(3):165-71.

Zemella et al., Cell-Free Protein Synthesis: Pros and Cons of Prokaryotic and Eukaryotic Systems. ChemBioChem. 2015;16:2420-2431.

Zhang et al., IL-11 in multiple sclerosis. Oncotarget. Oct. 7, 2015;6(32):32297-32298.

Zhou et al., Aptamers as targeted therapeutics: current potential and challenges. Nat Rev Drug Discov. Mar. 2017;16(3):181-202. Author Manuscript, 52 pages.

Zhu et al., IL-11 Attenuates Liver Ischemia/Reperfusion Injury (IRI) through STAT3 Signaling Pathway in Mice. PLoS One. May 6, 2015;10(5):e0126296. doi: 10.1371/journal.pone.0126296.

Zola, Monoclonal Antibodies: A Manual of Techniques. CRC Press. 1988.

| ID | Clone |
|---|---|
| RA1 | BSO-1E3 |
| RA2 | BSO-2C1 |
| RA3 | BSO-2E5 |
| RA4 | BSO-4G3 |
| RA5 | BSO-5E5 |
| RA6 | BSO-7G9 |
| RA7 | BSO-9A7 |
| RA8 | BSO-10D11 |
| RA9 | BSO-13B10 |
| RA10 | BSW-1D3 |
| RA11 | BSW-1F6 |
| RA12 | BSW-4G5 |
| RA13 | BSW-6H3 |
| RA14 | BSW-7E9 |
| RA15 | BSW-7G8 |
| RA16 | BSW-7H8 |
| RA17 | BSW-8B7 |

| Antibody Candidate | Human IL11 activated fibroblasts (norm.) | Mouse IL11 activated fibroblasts (norm.) | Trans IL11 MMP2 (norm.) |
|---|---|---|---|
| Unstimulated | 1 | 1 | 1 |
| Stimulated | 1.58 | 2.24 | 2.34 |
| Industry Standard | 0.89 | 1.44 | 1.92 |
| RA1 | 0.86 | 1.54 | 1.07 |
| RA2 | 1.12 | 1.98 | 2.41 |
| RA3 | 1.35 | 2.03 | 1.29 |
| RA4 | 1.30 | 1.93 | 1.69 |
| RA5 | 0.82 | 1.11 | 1.08 |
| RA6 | 1.05 | 2.12 | 1.97 |
| RA7 | 0.95 | 1.11 | 1.11 |
| RA8 | 1.09 | 1.89 | 1.61 |
| RA9 | 0.85 | 1.08 | 1.00 |
| RA10 | 1.54 | 1.77 | 1.67 |
| RA11 | 1.10 | 2.07 | 1.66 |
| RA12 | 1.00 | 2.15 | 1.15 |
| RA13 | 1.50 | 1.82 | 1.39 |
| RA14 | 1.19 | 1.54 | 2.03 |
| RA15 | 1.70 | 1.54 | 1.93 |
| RA16 | 1.37 | 2.28 | 2.09 |
| RA17 | 1.32 | 1.73 | 1.90 |

| No | Clone | GMFI | % positive | isotype |
|---|---|---|---|---|
| 1 | BSO-1E3 | 4697 | 15% | n.d./kappa |
| 2 | BSO-2C1 | 44127 | 140% | IgG1/kappa |
| 3 | BSO-2E5 | 9545 | 30% | IgG2b/kappa |
| 4 | BSO-4G3 | 9302 | 30% | IgG1/kappa |
| 5 | BSO-5E5 | 8780 | 28% | IgG1/IgG2b/kappa |
| 6 | BSO-7G9 | 18649 | 59% | IgG2a&2c /kappa |
| 7 | BSO-9A7 | 34771 | 111% | IgG1/kappa |
| 8 | BSO-10D11 | 13139 | 42% | IgG1/kappa |
| 9 | BSO-13B10 | 10931 | 35% | IgG1/kappa |
| | positive control | 31429 | 100% | |
| | negative control | 930 | 3% | |

incubated on cells transfected with pB1-IL11-hum.FL; flow cytometry (Attunes); Results of subcloning

| Ligand | $k_a$ (1/Ms) | $k_d$ (1/s) | $K_D$ (M) | $Chi^2$ (RU$^2$) |
|---|---|---|---|---|
| Mouse 9A7(1) | 9.66E+04 | 7.59E-04 | 7.85E-09 | 0.181 |
| Mouse 9A7 (2) | 1.60E+05 | 8.75E-04 | 5.46E-09 | 0.0356 |

IL-11Rα ANTIBODIES

This application claims priority under 35 U.S.C. § 119(a)-(d) to United Kingdom Patent Application Number GB1809700.6, filed Jun. 13, 2018, the contents of which are herein incorporated by reference in their entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Sep. 10, 2019, is named E060170006US00-SEQ-JOB, and is 88.8 kilobytes in size.

FIELD OF THE INVENTION

The present invention relates to the fields of molecular biology, more specifically antibody technology. The present invention also relates to methods of medical treatment and prophylaxis. In particular, antigen-binding molecules capable of binding to IL-11Rα are provided.

BACKGROUND TO THE INVENTION

IL-11-mediated signalling has been shown to stimulate haematopoiesis, stimulate osteoclast activity, stimulate neurogenesis, inhibit adipogenesis, reduce pro inflammatory cytokine expression, modulate extracellular matrix (ECM) metabolism, and mediate normal growth control of gastrointestinal epithelial cells.

The physiological role of Interleukin 11 (IL-11) remains unclear. IL-11/IL-11R signalling has been most strongly linked with activation of haematopoetic cells and with platelet production, but has also been suggested to be pro-inflammatory as well as anti-inflammatory, pro-angiogenic and important for neoplasia.

SUMMARY OF THE INVENTION

In a first aspect, the present invention provides an antigen-binding molecule, optionally isolated, which is capable of binding to IL-11Rα, wherein the antigen-binding molecule comprises:
(i) a heavy chain variable (VH) region incorporating the following CDRs:
HC-CDR1 having the amino acid sequence of SEQ ID NO:18
HC-CDR2 having the amino acid sequence of SEQ ID NO:52
HC-CDR3 having the amino acid sequence of SEQ ID NO:21; and
(ii) a light chain variable (VL) region incorporating the following CDRs:
LC-CDR1 having the amino acid sequence of SEQ ID NO:22
LC-CDR2 having the amino acid sequence of SEQ ID NO:23
LC-CDR3 having the amino acid sequence of SEQ ID NO:24.
In some embodiments the antigen-binding molecule comprises:
(i) a heavy chain variable (VI) region incorporating the following CDRs:
HC-CDR1 having the amino acid sequence of SEQ ID NO:18
HC-CDR2 having the amino acid sequence of SEQ ID NO:19
HC-CDR3 having the amino acid sequence of SEQ ID NO:21; and
(ii) a light chain variable (VL) region incorporating the following CDRs:
LC-CDR1 having the amino acid sequence of SEQ ID NO:22
LC-CDR2 having the amino acid sequence of SEQ ID NO:23
LC-CDR3 having the amino acid sequence of SEQ ID NO:24.
In some embodiments the antigen-binding molecule comprises:
(i) a heavy chain variable (VH) region incorporating the following CDRs:
HC-CDR1 having the amino acid sequence of SEQ ID NO:18
HC-CDR2 having the amino acid sequence of SEQ ID NO:20
HC-CDR3 having the amino acid sequence of SEQ ID NO:21; and
(ii) a light chain variable (VL) region incorporating the following CDRs:
LC-CDR1 having the amino acid sequence of SEQ ID NO:22
LC-CDR2 having the amino acid sequence of SEQ ID NO:23
LC-CDR3 having the amino acid sequence of SEQ ID NO:24.
In some embodiments the antigen-binding molecule comprises:
a VH region comprising an amino acid sequence having at least 70% sequence identity to the amino acid sequence of SEQ ID NO:7, 8, 9, 10, 11 or 12; and
a VL region comprising an amino acid sequence having at least 70% sequence identity to the amino acid sequence of SEQ ID NO:13, 14, 15, 16 or 17.
In some embodiments the antigen-binding molecule comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:70. In some embodiments the antigen-binding molecule comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:73. In some embodiments the antigen-binding molecule comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:74. In some embodiments the antigen-binding molecule comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:70 or 73, and a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:74.

In some embodiments the antigen-binding molecule is capable of inhibiting IL-11 mediated signalling.

The present invention also provides an antigen-binding molecule, optionally isolated, comprising (i) an antigen-binding molecule described herein, and (ii) an antigen-binding molecule capable of binding to an antigen other than IL-11Rα.

In some embodiments the antigen-binding molecule is capable of inhibiting interaction between IL-11Rα or a complex comprising IL-11Rα and an interaction partner for IL-11Rα or the complex comprising IL-11Rα.

The present invention also provides a chimeric antigen receptor (CAR) comprising an antigen-binding molecule described herein.

The present invention also provides a nucleic acid, or a plurality of nucleic acids, optionally isolated, encoding an antigen-binding molecule or a CAR described herein.

The present invention also provides an expression vector, or a plurality of expression vectors, comprising a nucleic acid or a plurality of nucleic acids described herein.

The present invention also provides a cell comprising an antigen-binding molecule, a CAR, a nucleic acid or a plurality of nucleic acids, or an expression vector or a plurality of expression vectors described herein.

The present invention also provides a method comprising culturing a cell comprising a nucleic acid or a plurality of nucleic acids or an expression vector or a plurality of expression vectors described herein under conditions suitable for expression of the antigen-binding molecule or CAR from the nucleic acid(s) or expression vector(s).

The present invention also provides a composition comprising an antigen-binding molecule, a CAR, a nucleic acid or a plurality of nucleic acids, an expression vector or a plurality of expression vectors, or a cell described herein.

The present invention also provides an antigen-binding molecule, a CAR, a nucleic acid or a plurality of nucleic acids, an expression vector or a plurality of expression vectors, a cell, or a composition as described herein for use in a method of medical treatment or prophylaxis.

The present invention also provides an antigen-binding molecule, a CAR, a nucleic acid or a plurality of nucleic acids, an expression vector or a plurality of expression vectors, a cell, or a composition as described herein, for use in a method of treatment or prevention of fibrosis, a disease characterised by fibrosis, a cancer, inflammation, or a disease characterised by inflammation.

The present invention also provides the use of an antigen-binding molecule, a CAR, a nucleic acid or a plurality of nucleic acids, an expression vector or a plurality of expression vectors, a cell, or a composition as described herein, in the manufacture of a medicament for use in a method of treatment or prevention of fibrosis, a disease characterised by fibrosis, a cancer, inflammation, or a disease characterised by inflammation.

The present invention also provides a method of treating or preventing fibrosis, a disease characterised by fibrosis, a cancer, inflammation, or a disease characterised by inflammation, comprising administering to a subject a therapeutically or prophylactically effective amount of an antigen-binding molecule, a CAR, a nucleic acid or a plurality of nucleic acids, an expression vector or a plurality of expression vectors, a cell, or a composition as described herein.

The present invention also provides a method of inhibiting IL-11 mediated signalling, comprising contacting IL-11Rα-expressing cells with an antigen-binding molecule as described herein.

The present invention also provides an in vitro complex, optionally isolated, comprising an antigen-binding molecule as described herein bound to IL-11Rα or a complex comprising IL-11Rα.

The present invention also provides a method comprising contacting a sample containing, or suspected to contain, IL-11Rα or a complex comprising IL-11Rα with an antigen-binding molecule described herein, and detecting the formation of a complex of the antigen-binding molecule with IL-11Rα or a complex comprising IL-11Rα.

The present invention also provides a method of selecting or stratifying a subject for treatment with an IL-11Rα-targeted agent, the method comprising contacting, in vitro, a sample from the subject with an antigen-binding molecule described herein and detecting the formation of a complex of the antigen-binding molecule with IL-11Rα or a complex comprising IL-11Rα.

The present invention also provides the use of an antigen-binding molecule described herein as an in vitro or In vivo diagnostic or prognostic agent.

DESCRIPTION

The present invention relates to novel IL-11Rα-binding molecules having improved properties as compared to known anti-IL-11Rα antibodies. The IL-11Rα-binding molecules of the present invention are provided with combinations of desirable biophysical and functional properties as compared to IL-11Rα-binding antigen-binding molecules disclosed in the prior art.

Interleukin 11 and receptors for IL-11 Interleukin 11 (IL-11), also known as adipogenesis inhibitory factor, is a pleotropic cytokine and a member of the IL-6 family of cytokines that includes IL-6, IL-11, IL-27, IL-31, oncostatin, leukemia inhibitory factor (LIF), cardiotrophin-1 (CT-1), cardiotrophin-like cytokine (CLC), ciliary neurotrophic factor (CNTF) and neuropoetin (NP-1).

Interleukin 11 (IL-11) is expressed in a variety of mesenchymal cell types. IL-11 genomic sequences have been mapped onto chromosome 19 and the centromeric region of chromosome 71, and is transcribed with a canonical signal peptide that ensures efficient secretion from cells. The activator protein complex of IL-11, cJun/AP-1, located within its promoter sequence is critical for basal transcriptional regulation of IL-11 (Du and Williams., Blood 1997, Vol 89: 3897-3908). The immature form of human IL-11 is a 199 amino acid polypeptide whereas the mature form of IL-11 encodes a protein of 178 amino acid residues (Garbers and Scheller., Biol. Chem. 2013; 394(9):1145-1161). The human IL-11 amino acid sequence is available under UniProt accession no. P20809 (P20809.1 GI:124294; SEQ ID NO:1). Recombinant human IL-11 (oprelvekin) is also commercially available. IL-11 from other species, including mouse, rat, pig, cow, several species of bony fish and primates, have also been cloned and sequenced.

In this specification "IL-11" refers to an IL-11 from any species and includes isoforms, fragments, variants or homologues of an IL-11 from any species. As used herein, a "fragment", "variant" or "homologue" of a protein may optionally be characterised as having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of the reference protein. In some embodiments fragments, variants, isoforms and homologues of a reference protein may be characterised by ability to perform a function performed by the reference protein.

A "fragment" generally refers to a fraction of the reference protein. A "variant" generally refers to a protein having an amino acid sequence comprising one or more amino acid substitutions, insertions, deletions or other modifications relative to the amino acid sequence of the reference protein, but retaining a considerable degree of sequence identity (e.g. at least 60%) to the amino acid sequence of the reference protein. An "isoform" generally refers to a variant of the reference protein expressed by the same species as the species of the reference protein. A "homologue" generally refers to a variant of the reference protein produced by a different species as compared to the species of the reference protein. Homologues include orthologues. A "fragment" may be of any length (by number of amino acids), although may optionally be at least 20% of the length of the reference protein (that is, the protein from which the fragment is derived) and may have a maximum length of one of 50%, 75%, 80%, 85%, 90%, 91%, 92%, 93%, 94%, 95%, 96%, 97%, 98%, or 99% of the length of the reference protein. A fragment of IL-11 may have a minimum length of 10 amino acids, and a maximum length of one of 15, 20, 25, 30, 40, 50, 100, 110, 120, 130, 140, 150, 160, 170, 180, 190 or 195 amino acids.

In some embodiments, the IL-11 is IL-11 from a mammal (e.g. a primate (rhesus, cynomolgous, non-human primate or human) and/or a rodent (e.g. rat or murine) IL-11). Isoforms, fragments, variants or homologues of IL-11 may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of an immature or mature IL-11 isoform from a given species, e.g. human. In some embodiments, the IL-11 of the present disclosure comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:1.

Isoforms, fragments, variants or homologues of an IL-11 may optionally be characterised by ability to bind an IL-11 receptor (e.g. IL-11Rα, gp130 and/or a complex comprising IL-11Rα and gp130, preferably from the same species) and stimulate signal transduction in cells expressing IL-11Rα and gp130 (e.g. as described in Curtis et al. Blood, 1997, 90(11); or Karpovich et al. Mol. Hum. Reprod. 2003 9(2): 75-80).

IL-11 signals through a homodimer of the ubiquitously expressed glycoprotein 130 (gp130; also known as glycoprotein 130, IL-6ST, IL-6-beta or CD130). Gp130 is a transmembrane protein that forms one subunit of the type I cytokine receptor with the IL-6 receptor family. Specificity is gained through an individual interleukin 11 receptor subunit alpha (IL-11Rα), which does not directly participate in signal transduction, although the initial cytokine binding event to the α-receptor leads to the final complex formation with gp130.

Human gp130 (including the 22 amino acid signal peptide) is a 918 amino acid protein, and the mature form is 866 amino acids, comprising a 597 amino acid extracellular domain, a 22 amino acid transmembrane domain, and a 277 amino acid intracellular domain. The extracellular domain of the protein comprises the cytokine-binding module (CBM) of gp130. The CBM of gp130 comprises the Ig-like domain D1, and the fibronectin-type III domains D2 and D3 of gp130. The amino acid sequence of human gp130 is available under UniProt accession no. P40189-1 (SEQ ID NO:2).

Human IL-11Rα is a 422 amino acid polypeptide (UniProt Q14626) and shares—85% nucleotide and amino acid sequence identity with the murine IL-11Rα (Du and Williams., Blood Vol, 89, No, 11, Jun. 1, 1997). Two isoforms of IL-11Rα have been reported—HCR1 (SEQ ID NO:3) and HCR2 (SEQ ID NO:4)—which differ in the cytoplasmic domain; the C-terminal 32 amino acids of isoform HCR1 are absent from HCR2 (Du and Williams, supra). The IL-11 receptor α-chain (IL-11Rα) shares many structural and functional similarities with the IL-6 receptor α-chain (IL-6Rα). The extracellular domain shows 24% amino acid identity including the characteristic conserved Trp-Ser-X-Trp-Ser (WSXWS) motif. The short cytoplasmic domain lacks the Box 1 and 2 regions that are required for activation of the JAK/STAT signalling pathway.

The receptor binding sites on murine IL-11 have been mapped and three sites—sites I, II and III—identified. Binding to gp130 is reduced by substitutions in the site II region and by substitutions in the site III region. Site III mutants show no detectable agonist activity and have IL-11Rα antagonist activity (Cytokine Inhibitors Chapter 8; edited by Gennaro Ciliberto and Rocco Savino, Marcel Dekker, Inc. 2001).

In this specification an IL-11 receptor/receptor for IL-11 (IL-11R) refers to a polypeptide or polypeptide complex capable of binding IL-11 and/or a complex comprising IL-11. In some embodiments an IL-11 receptor is capable of binding IL-11 and/or a complex comprising IL-11 and inducing signal transduction in cells expressing the IL-11 receptor. A "complex comprising IL-11" may be a non-covalent complex of IL-11 and a polypeptide capable of non-covalent association with IL-11.

An IL-11 receptor may be from any species and includes isoforms, fragments, variants or homologues of an IL-11 receptor from any species. In preferred embodiments the species is human (*Homo sapiens*).

In some embodiments the IL-11 receptor (IL-11R) may be IL-11Rα. In some embodiments a receptor for IL-11 may be a polypeptide complex comprising IL-11Rα. In some embodiments the IL-11 receptor may be a polypeptide complex comprising IL-11Rα and gp130. In some embodiments the IL-11 receptor may be gp130 or a complex comprising gp130 to which IL-11 binds.

In this specification "IL-11Rα" refers to an IL-11Rα from any species and includes isoforms, fragments, variants or homologues of an IL-11Rα from any species. A fragment of IL-11Rα may have a minimum length of 10 amino acids, and a maximum length of one of 15, 20, 25, 30, 40, 50, 100, 110, 120, 130, 140, 150, 160, 170, 180, 190, 200, 250, 300, 400, or 415 amino acids.

In some embodiments, the IL-11Rα is IL-11Rα from a mammal (e.g. a primate (rhesus, cynomogous, non-human primate or human) and/or a rodent (e.g. rat or murine) IL-11). Isoforms, fragments, variants or homologues of IL-11Rα may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of an immature or mature IL-11Rα isoform from a given species, e.g. human. In some embodiments, the IL-11Rα of the present disclosure comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:3 or 4.

Isoforms, fragments, variants or homologues of an IL-11Rα may optionally be characterised by ability to bind IL-11 and/or a complex comprising IL-11 (preferably from the same species) and stimulate signal transduction in cells expressing the IL-11Rα and gp130 (e.g. as described in Curtis et al. Blood, 1997, 90(11) or Karpovich et al. Mol. Hum. Reprod. 2003 9(2): 75-80).

IL-11/IL-11R Signalling

IL-11 binds to IL-11Rα with low affinity (Kd~10 nmol/L), and interaction between these binding partners alone is insufficient to transduce a biological signal. The generation of a high affinity receptor (Kd~400 to 800 pmol/L) capable of signal transduction requires co-expression of the IL-11Rα and gp130 (Curtis et al (Blood 1997 Dec. 1; 90 (11):4403-12; Hilton et al., EMBO J 13:4765, 1994; Nandurkar et al., Oncogene 12:585, 1996). Binding of IL-11 to cell-surface IL-11Rα induces heterodimerization, tyrosine phosphorylation, activation of gp130 and downstream signalling, predominantly through the mitogen-activated protein kinase (MAPK)-cascade and the Janus kinase/signal transducer and activator of transcription (Jak/STAT) pathway (Garbers and Scheller, supra).

In principle, a soluble IL-11Rα can also form biologically active soluble complexes with IL-11 (Pflanz et al., 1999 FEBS Lett, 450, 117-122) raising the possibility that, similar to IL-6. IL-11 may in some instances bind soluble IL-11Rα prior to binding cell-surface gp130 (Garbers and Scheller, supra). Curtis et al (Blood 1997 Dec. 1; 90 (11):4403-12) describe expression of a soluble murine IL-11Rα chain (sIL-11R) and examined signalling in cells expressing gp130. In the presence of gp130 but not transmembrane IL-11R the sIL-11R mediated IL-11 dependent differentiation of M1 leukemic cells and proliferation in Ba/F3 cells and early intracellular events including phosphorylation of gp130, STAT3 and SHP2 similar to signalling through transmembrane IL-11R. Activation of signalling through cell-membrane bound gp130 by IL-11 bound to soluble IL-11Rα has recently been demonstrated (Lokau et al., 2016 Cell Reports 14, 1761-1773). This so-called IL-11 trans signalling may be a very important component of IL-11-mediated signalling, and may even be the most common form of IL-11-mediated signalling, because whilst the expression of IL-11Rα is restricted to a relatively small subset of cell types, gp130 is expressed on a wide range of cell types.

As used herein, "IL-11 signalling", "IL-11-mediated signalling" and "IL-11/IL-11R signalling" refers to signalling mediated by binding of IL-11, a fragment thereof having the function of the mature IL-11 molecule, or a complex comprising IL-11 or a fragment thereof having the function of the mature IL-11 molecule to a receptor for IL-11.

As used herein, 'IL-11 trans signalling' is used to refer to signaling which is triggered by binding of IL-11 bound to IL-11Rα, to gp130. The IL-11 may be bound to IL-11Rα as a non-covalent complex. The gp130 is membrane-bound and expressed by the cell in which signalling occurs following binding of the IL-11:IL-11Rα complex to gp130. In some embodiments the IL-11Rα may be a soluble IL-11Rα. In some embodiments, the soluble IL-11Rα is a soluble (secreted) isoform of IL-11Rα (e.g. lacking a transmembrane domain). In some embodiments, the soluble IL-11Rα is the liberated product of proteolytic cleavage of the extracellular domain of cell membrane bound IL-11Rα. In some embodiments, the IL-11Rα may be cell membrane-bound, and signalling through gp130 may be triggered by binding of IL-11 bound to cell-membrane-bound IL-11Rα, termed "IL-11 cis signalling".

IL-11-mediated signalling has been shown to stimulate haematopoiesis and thrombopoiesis, stimulate osteoclast activity, stimulate neurogenesis, inhibit adipogenesis, reduce pro inflammatory cytokine expression, modulate extracellular matrix (ECM) metabolism, and mediate normal growth control of gastrointestinal epithelial cells (Du and Williams, supra).

The physiological role of Interleukin 11 (IL-11) remains unclear. IL-11 has been most strongly linked with activation of haematopoetic cells and with platelet production, but has also been suggested to be pro-inflammatory as well as anti-inflammatory, pro-angiogenic and important for neoplasia. It is known that TGFβ1 or tissue injury can induce IL-11 expression (Zhu, M. et al. PLOS ONE 10, (2015); Yashiro, R. et al. J. Clin. Periodontol. 33, 165-71 (2006); Obana, M. et al. Circulation 121, 684-91 (2010); Tang, W et al. J. Biol. Chem. 273, 5506-13 (1998)).

IL-11 is an important post-transcriptional modulator of TGFβ-mediated signalling. TGFβ1 has been shown to stimulate the AP-1 promoter region of IL-11, and TGFβ-induced secretion of IL-11 has been shown to induce activation of ERK p42/44 and p38 MAP kinases in intestinal myofibroblasts (Bamba et al. Am J Physiol Gastrointest Liver Physiol. (2003) (285(3):G529-38). MAP kinase inhibitors are able to significantly reduce TGFβ-induced IL-11 secretion, and p38 MAP kinase-mediated stabilization of mRNA has been shown to be critical for TGFβ-induced secretion of IL-11.

IL-11 mediated signalling has recently been demonstrated to play a key role in fibrotic processes in a wide variety of tissues; see for example WO 2017/103108 A1 and Schafer et al. (2017) Nature 552: 110-115, both of which are hereby incorporated by reference in their entirety.

WO 2017/103108 A1 (hereby incorporated by reference in its entirety) reports a pro-fibrotic role for IL-11 mediate signalling, and establishes the therapeutic utility of antagonists of IL-11 mediated signalling in the treatment/prevention of fibrosis. Example 2 and FIGS. 7A and 7B of WO 2017/103108 A1 demonstrate that incubation of primary human atrial fibroblasts with recombinant human IL-11 increases deposition of collagen by fibroblasts, a well-established fibrotic process. Treatment with neutralising anti-IL-11 antibody (but not isotype control antibody) was shown to abrogate collagen production induced by stimulation of the fibroblasts with TGFβ1 (a known pro-fibrotic stimulus). Example 3 and FIG. 10 of WO 2017/103108 A1 further demonstrate the ability of neutralising anti-IL-11 antibody to abrogate increased collagen production by human atrial fibroblasts in response to various other pro-fibrotic stimuli (ANG2, PDGF, ET-1). Example 5.2 and FIGS. 20A-20E of WO 2017/103108 A1 provide further data supporting a pro-fibrotic role for IL-11 in heart tissue. Human atrial fibroblasts were shown to display significantly increased production of extracellular matrix components (collagen, perostin) and increased expression of pro-fibrotic markers (αSMA, IL-6, MMP2, TIMP1) in response to treatment with human IL-11 protein, in the same way as production of these factors is increased in response to treatment with the pro-fibrotic stimulus TGFβ1. Example 5.3.1 and FIGS. 38A to 38D of WO 2017/103108 A1 likewise show increased production of extracellular matrix components and increased expression of fibrotic markers by human primary liver fibroblasts in response to treatment with human IL-11, and also the ability of neutralising anti-IL-11 antibody to abrogate the profibrotic effects of stimulation with TGFβ1. FIGS. 22A to 22F and 23A and 23B of WO 2017/103108 A1 show that TGFβ1-mediated fibrosis can be inhibited by treatment with neutralising anti-IL-11 antibody, and FIG. 24 moreover shows that IL-11-binding decoy receptor molecules, neutralising anti- IL-11Rα antibodies and oligonucleotides encoding siRNA for antisense knockdown of IL-11 and IL-11RA gene expression are similarly able to inhibit TGFβ1-mediated transition of fibroblasts to myofibroblasts (fibrosis effector cells). Further data showing inhibition of the TGFβ1-mediated fibrotic response using decoy IL-11 receptors is provided at FIGS. 32A and 32B of WO 2017/103108 A1. Example 5.3.3 and FIGS. 21B and 21C of WO 2017/103108 A1 provide in vivo data demonstrating IL-11 to be profibrotic in a variety of tissues. Injection of mice with recombinant mouse IL-11 caused an increase in the relative weight of heart, kidney, lung and liver (FIG. 21B), and that this was associated with increased collagen content in these tissues (FIG. 21C). Further in vivo data supporting a profibrotic role for IL-11 is provided at Examples 7.2 and 7.3, and FIGS. 27A to 27D and FIG. 28 of WO 2017/103108 A1. These experiments show that IL-11 RA knockout mice are protected from fibrosis of the heart and kidney tissues induced by profibrotic stimuli, indicating signalling through the IL-11 receptor as an important mediator of fibrotic processes. Further still, FIGS. 31A and 31B, summarised at the legend to FIG. 31 of WO 2017/103108 A1 report that more fibrosis was detected in eye sections obtained from wildtype mice than IL-11RA knockout mice at 7 days following trabeculedomy. Thus WO 2017/103108 A1 provides abundant data from both in vitro and in vivo studies proving that IL-11/IL-11R signalling is a key mediator of fibrosis in a wide range of tissues, and demonstrates that inhibition of IL-11 mediated signalling reduces fibrosis, as determined by analysis of a variety of markers of the fibrotic response.

Antigen-Binding Molecules Capable of Binding to IL-11Rα

The present invention provides antigen-binding molecules capable of binding to IL-11Rα.

An "antigen-binding molecule" refers to a molecule which is capable of binding to a target antigen, and encompasses monoclonal antibodies, polyclonal antibodies, monospecific and multispecific antibodies (e.g., bispecific antibodies), and antibody fragments (e.g. Fv, scFv, Fab, scFab, F(ab')$_2$, Fab$_2$, diabodies, triabodies, scFv-Fc, minibodies, single domain antibodies (e.g. VhH), etc.), as long as they display binding to the relevant target molecule(s). By "antibody" we include fragments and derivatives thereof, including synthetic antibodies and fragments. As used herein, an antibody is a polypeptide capable of binding specifically to the relevant target molecule (i.e. the antigen for which the antibody is specific). Antibodies and antigen-binding molecules according to the present invention may be provided in isolated form.

In view of contemporary techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "Monocional Antibodies: A manual of techniques", H Zola (CRC Press, 1988) and in "Monocional Hybridoma Antibodies: Techniques and Applications", J G R Hurrell (CRC Press, 1982). Chimeric antibodies are discussed by Neuberger et al (1988, 8$^{th}$ International Biotechnology Symposium Part 2, 792-799).

Monoclonal antibodies (mAbs) are useful in the methods of the invention and are a homogenous population of antibodies specifically targeting a single epitope on an antigen.

Antigen binding fragments of antibodies, such as Fab and Fab$_2$ fragments may also be used/provided as can genetically engineered antibodies and antibody fragments. The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parent antibody (Morrison et al (1984) Proc. Natl. Acad. Sd. USA 81, 6851-6855).

In some embodiments, the antigen-binding molecule of the invention is a fully human antibody/antibody fragment. A fully human antibody/antibody fragment is encoded by human nucleic acid sequence(s). Fully human antibodies/antibody fragments are devoid of non-human amino acid sequences.

The two most commonly employed techniques to the production of fully human antibodies are (i) phage display, in which human antibody genes are expressed in phage display libraries, and (ii) production of antibodies in transgenic mice engineered to have human antibody genes (described in Park and Smolen Advances in Protein Chemistry (2001) 56: 369-421). Briefly, in the human antibody gene-phage display technique, genes encoding the VH and VL chains are generated by PCR amplification and cloning from "naive" human lymphocytes, and assembled into a library from which they can be expressed either as disulfide-linked Fab fragments or as single-chain Fv (scFv) fragments. The Fab- or scFv-encoding genes are fused to a surface coat protein of filamentous bacteriophage and Fab or scFv capable of binding to the target of interest can then be identified by screening the library with antigen. Molecular evolution or affinity maturation procedures can be employed to enhance the affinity of the Fab/scFv fragment. In the transgenic mouse technique, mice in which the endogenous murine Ig gene loci have been replaced by homologous recombination with their human homologues are immunized with antigen, and monoclonal antibody is prepared by conventional hybridoma technology, to yield fully human monoclonal antibody.

In some embodiments, the antigen-binding molecule of the invention is a murine antibody/antibody fragment. In some embodiments the antibody/antibody fragment may be prepared by phage display using a human naïve antibody gene library.

In some embodiments, the antigen-binding molecule of the invention is a mouse/human chimeric antibody/antibody fragment (e.g., an antigen-binding molecule comprising murine variable domains and human constant regions). In some embodiments, the antigen-binding molecule is a humanised antibody/antibody fragment (e.g., an antigen-binding molecule comprising murine CDRs and human framework and constant regions).

A mouse/human chimeric antigen-binding molecule can be prepared from a mouse monoclonal antibody by the process of chimerisation, e.g. as described in Human Monoclonal Antibodies: Methods and Protocols, Michael Steinitz (Editor), Methods in Molecular Biology 1060, Springer Protocols, Humana Press (2014), in Chapter 8 thereof, in particular section 3 of Chapter 8.

A humanised antigen-binding molecule can be prepared from a mouse antibody by the process of humanization, e.g. as described in Human Monoclonal Antibodies: Methods and Protocols, Michael Steintz (Editor), Methods in Molecular Biology 1060, Springer Protocols, Humana Press (2014), in Chapter 7 thereof, in particular section 3.1 of Chapter 7 entitled 'Antibody Humanization'.

The antigen-binding molecule of the present invention comprises a moiety capable of binding to a target antigen(s). In some embodiments, the moiety capable of binding to a target antigen comprises an antibody heavy chain variable region (VH) and an antibody light chain variable region (VL) of an antibody capable of specific binding to the target antigen. In some embodiments, the moiety capable of binding to a target antigen comprises or consists of an aptamer capable of binding to the target antigen, e.g. a nucleic acid aptamer (reviewed, for example, in Zhou and Rossi Nat Rev Drug Discov. 2017 16(3):181-202). In some embodiments, the moiety capable of binding to a target antigen comprises or consists of a antigen-binding peptide/polypeptide, e.g. a peptide aptamer, thioredoxin, monobody, anticalin, Kunitz domain, avimer, knottin, fynomer, atrimer, DARPin, affibody, nanobody (i.e. a single-domain antibody (sdAb)) affilin, armadillo repeat protein (ArmRp), OBody or fibronectin—reviewed e.g. in Reverdatto et al., Curr Top Med Chem. 2015; 15(12): 1082-1101, which is hereby incorporated by reference in its entirety (see also e.g. Boersma et al., J Biol Chem (2011) 286:41273-85 and Emanuel et al., Mabs (2011) 3:38-48).

The antigen-binding molecules of the present invention generally comprise an antigen-binding domain comprising a VH and a VL of an antibody capable of specific binding to the target antigen. The antigen-binding domain formed by a VH and a VL may also be referred to herein as an Fv region.

An antigen-binding molecule may be, or may comprise, an antigen-binding polypeptide, or an antigen-binding polypeptide complex. An antigen-binding molecule may comprise more than one polypeptide which together form an antigen-binding domain. The polypeptides may associate covalently or non-covalently. In some embodiments the polypeptides form part of a larger polypeptide comprising the polypeptides (e.g. In the case of scFv comprising VH and VL, or in the case of scFab comprising VH-CH1 and VL-CL).

An antigen-binding molecule may refer to a non-covalent or covalent complex of more than one polypeptide (e.g. 2, 3, 4, 6, or 8 polypeptides), e.g. an IgG-like antigen-binding molecule comprising two heavy chain polypeptides and two light chain polypeptides.

The antigen-binding molecules of the present invention may be designed and prepared using the sequences of monoclonal antibodies (mAbs) capable of binding to IL-11Rα. Antigen-binding regions of antibodies, such as single chain variable fragment (scFv), Fab and F(ab)$_2$ fragments may also be used/provided. An "antigen-binding region" is any fragment of an antibody which is capable of binding to the target for which the given antibody is specific.

Antibodies generally comprise six complementarity-determining regions CDRs; three in the heavy chain variable (VH) region: HC-CDR1, HC-CDR2 and HC-CDR3, and three in the light chain variable (VL) region: LC-CDR1, LC-CDR2, and LC-CDR3. The six CDRs together define the paratope of the antibody, which is the part of the antibody which binds to the target antigen.

The VH region and VL region comprise framework regions (FRs) either side of each CDR, which provide a scaffold for the CDRs. From N-terminus to C-terminus, VH regions comprise the following structure: N term-[HC-FR1]-[HC-CDR1]-[HC-FR2]-[HC-CDR2]-[HC-FR3]-[HC-CDR3]-[HC-FR4]-C term; and VL regions comprise the following structure: N term-[LC-FR1]-[LC-CDR1]-[LC-FR2]-[LC-CDR2]-[LC-FR3]-LC-CDR3-[LC-FR4]-C term.

There are several different conventions for defining antibody CDRs and FRs, such as those described in Kabat et al., Sequences of Proteins of Immunological Interest, 5th Ed. Public Health Service, National Institutes of Health, Bethesda, Md. (1991), Chothia et al., J. Mol. Biol. 196:901-917 (1987), and VBASE2, as described In Retter et al., Nucl. Acids Res. (2005) 33 (suppl 1): D671-D674. The CDRs and FRs of the VH regions and VL regions of the antibody clones described herein were defined according to the Kabat system.

In some embodiments, the antigen-binding molecule comprises the CDRs of an antigen-binding molecule which is capable of binding to IL-11Rα. In some embodiments, the antigen-binding molecule comprises the FRs of an antigen-binding molecule which is capable of binding to IL-11Rα. In some embodiments, the antigen-binding molecule comprises the CDRs and the FRs of an antigen-binding molecule which is capable of binding to IL-11Rα. That is, in some embodiments the antigen-binding molecule comprises the VH region and the VL region of an antigen-binding molecule which is capable of binding to IL-11Rα.

In some embodiments the antigen-binding molecule comprises a VH region and a VL region which is, or which is derived from, the VH/VL region of an IL-11Rα-binding antibody clone described herein (e.g. anti-IL-11Rα antibody clone BSO-9A7 (comprising 9A7 VH, 9A7 VH 1, 9A7 VH 2, 9A7 VH 3, 9A7 VH 4 or 9A7 VH 5 and 9A7 VL, 9A7 VL 1, 9A7 VL 2, 9A7 VL 3 or 9A7 VL 4)).

In some embodiments the antigen-binding molecule comprises a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:13, 14, 15, 16 or 17, wherein the position corresponding to position 91 is not arginine, and/or wherein the position corresponding to position 105 is not methionine.

In some embodiments the antigen-binding molecule comprises a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:13, 14, 15, 16 or 17, wherein the position corresponding to position 91 is serine, and/or wherein the position corresponding to position 105 is leucine or isoleucine.

In some embodiments the antigen-binding molecule comprises a VL region having less than 100% sequence identity to the amino acid sequence of SEQ ID NO:59. In some embodiments the antigen-binding molecule does not comprise a VL region comprising or consisting of the amino acid sequence of SEQ ID NO:59. In some embodiments the antigen-binding molecule does not comprise a peptide/polypeptide comprising or consisting of the amino acid sequence of SEQ ID NO:59.

In some embodiments the antigen-binding molecule comprises LC-CDR3 having less than 100% sequence identity to the amino acid sequence of SEQ ID NO:60. In some embodiments the antigen-binding molecule does not comprise LC-CDR3 comprising or consisting of the amino acid sequence of SEQ ID NO:60. In some embodiments the antigen-binding molecule does not comprise a peptide/polypeptide comprising or consisting of the amino acid sequence of SEQ ID NO:60.

In some embodiments the antigen-binding molecule comprises a VH region according to one of (1) to (3) below:
(1) (9A7 VH, 9A7 VH 1, 9A7 VH 2, 9A7 VH 3, 9A7 VH 4, 9A7 VH 5) a VH region incorporating the following CDRs:

HC-CDR1 having the amino acid sequence of SEQ ID NO:18
HC-CDR2 having the amino acid sequence of SEQ ID NO:52
HC-CDR3 having the amino acid sequence of SEQ ID NO:21,
or a variant thereof in which one or two or three amino acids in one or more of HC-CDR1, HC-CDR2, or HC-CDR3 are substituted with another amino acid.
(2) (9A7 VH, 9A7 VH 1, 9A7 VH 2, 9A7 VH 3, 9A7 VH 4) a VH region incorporating the following CDRs:
HC-CDR1 having the amino acid sequence of SEQ ID NO:18
HC-CDR2 having the amino acid sequence of SEQ ID NO:19
HC-CDR3 having the amino acid sequence of SEQ ID NO:21,
or a variant thereof in which one or two or three amino acids in one or more of HC-CDR1, HC-CDR2, or HC-CDR3 are substituted with another amino acid.
(3) (9A7 VH 5) a VH region incorporating the following CDRs:
HC-CDR1 having the amino acid sequence of SEQ ID NO:18
HC-CDR2 having the amino acid sequence of SEQ ID NO:20
HC-CDR3 having the amino acid sequence of SEQ ID NO:21,
or a variant thereof in which one or two or three amino acids in one or more of HC-CDR1, HC-CDR2, or HC-CDR3 are substituted with another amino acid.

In some embodiments the antigen-binding molecule comprises a VH region according to one of (4) to (9) below:
(4) (9A7 VH) a VH region incorporating the following FRs:
HC-FR1 having the amino acid sequence of SEQ ID NO:25
HC-FR2 having the amino acid sequence of SEQ ID NO:29
HC-FR3 having the amino acid sequence of SEQ ID NO:33
HC-FR4 having the amino acid sequence of SEQ ID NO:37,
or a variant thereof in which one or two or three amino acids in one or more of HC-FR1, HC-FR2, HC-FR3, or HC-FR4 are substituted with another amino acid.
(5) (9A7 VH 1) a VH region incorporating the following FRs:
HC-FR1 having the amino acid sequence of SEQ ID NO:26
HC-FR2 having the amino acid sequence of SEQ ID NO:30
HC-FR3 having the amino acid sequence of SEQ ID NO:34
HC-FR4 having the amino acid sequence of SEQ ID NO:38,
or a variant thereof in which one or two or three amino acids in one or more of HC-FR1, HC-FR2, HC-FR3, or HC-FR4 are substituted with another amino acid.
(6) (9A7 VH 2) a VH region incorporating the following FRs:
HC-FR1 having the amino acid sequence of SEQ ID NO:27
HC-FR2 having the amino acid sequence of SEQ ID NO:30
HC-FR3 having the amino acid sequence of SEQ ID NO:35
HC-FR4 having the amino acid sequence of SEQ ID NO:38,
or a variant thereof in which one or two or three amino acids in one or more of HC-FR1, HC-FR2, HC-FR3, or HC-FR4 are substituted with another amino acid.
(7) (9A7 VH 3) a VH region incorporating the following FRs:
HC-FR1 having the amino acid sequence of SEQ ID NO:28
HC-FR2 having the amino acid sequence of SEQ ID NO:31
HC-FR3 having the amino acid sequence of SEQ ID NO:35
HC-FR4 having the amino acid sequence of SEQ ID NO:38,
or a variant thereof in which one or two or three amino acids In one or more of HC-FR1, HC-FR2, HC-FR3, or HC-FR4 are substituted with another amino acid.
(8) (9A7 VH 4) a VH region incorporating the following FRs:
HC-FR1 having the amino acid sequence of SEQ ID NO:28
HC-FR2 having the amino acid sequence of SEQ ID NO:31
HC-FR3 having the amino acid sequence of SEQ ID NO:36
HC-FR4 having the amino acid sequence of SEQ ID NO:38,
or a variant thereof in which one or two or three amino acids in one or more of HC-FR1, HC-FR2, HC-FR3, or HC-FR4 are substituted with another amino acid.
(9) (9A7 VH 5) a VH region incorporating the following FRs:
HC-FR1 having the amino acid sequence of SEQ ID NO:28
HC-FR2 having the amino acid sequence of SEQ ID NO:32
HC-FR3 having the amino acid sequence of SEQ ID NO:36
HC-FR4 having the amino acid sequence of SEQ ID NO:38,
or a variant thereof in which one or two or three amino acids in one or more of HC-FR1, HC-FR2, HC-FR3, or HC-FR4 are substituted with another amino acid.

In some embodiments the antigen-binding molecule comprises a VH region comprising the CDRs according to one of (1) to (3) above, and the FRs according to one of (4) to (9) above.

In some embodiments the antigen-binding molecule comprises a VH region according to one of (10) to (15) below:
(10) (9A7 VH) a VH region comprising the CDRs according to (2) and the FRs according to (4).
(11) (9A7 VH 1) a VH region comprising the CDRs according to (2) and the FRs according to (5).
(12) (9A7 VH 2) a VH region comprising the CDRs according to (2) and the FRs according to (6).
(13) (9A7 VH 3) a VH region comprising the CDRs according to (2) and the FRs according to (7).
(14) (9A7 VH 4) a VH region comprising the CDRs according to (2) and the FRs according to (8).
(15) (9A7 VH 5) a VH region comprising the CDRs according to (3) and the FRs according to (9).

In some embodiments the antigen-binding molecule comprises a VH region according to one of (16) to (21) below:
(16) (9A7 VH) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:7.

(17) (9A7 VH 1) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:8.

(18) (9A7 VH 2) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:9.

(19) (9A7 VH 3) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:10.

(20) (9A7 VH 4) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:11.

(21) (9A7 VH 5) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:12.

In some embodiments the antigen-binding molecule comprises a VL region according to (22) below:

(22) (9A7 VL, 9A7 VL 1, 9A7 VL 2, 9A7 VL 3, 9A7 VL 4) a VL region incorporating the following CDRs:
  LC-CDR1 having the amino acid sequence of SEQ ID NO:22
  LC-CDR2 having the amino acid sequence of SEQ ID NO:23
  LC-CDR3 having the amino acid sequence of SEQ ID NO:24,
  or a variant thereof in which one or two or three amino acids in one or more of LC-CDR1, LC-CDR2, or LC-CDR3 are substituted with another amino acid.

In some embodiments the antigen-binding molecule comprises a VL region according to one of (23) to (27) below:

(23) (9A7 VL) a VL region incorporating the following FRs:
  LC-FR1 having the amino acid sequence of SEQ ID NO:39
  LC-FR2 having the amino acid sequence of SEQ ID NO:41
  LC-FR3 having the amino acid sequence of SEQ ID NO:45
  LC-FR4 having the amino acid sequence of SEQ ID NO:50,
  or a variant thereof in which one or two or three amino acids in one or more of LC-FR1, LC-FR2, LC-FR3, or LC-FR4 are substituted with another amino acid.

(24) (9A7 VL 1) a VL region incorporating the following FRs:
  LC-FR1 having the amino acid sequence of SEQ ID NO:40
  LC-FR2 having the amino acid sequence of SEQ ID NO:42
  LC-FR3 having the amino acid sequence of SEQ ID NO:46
  LC-FR4 having the amino acid sequence of SEQ ID NO:51,
  or a variant thereof in which one or two or three amino acids In one or more of LC-FR1, LC-FR2, LC-FR3, or LC-FR4 are substituted with another amino acid.

(25) (9A7 VL 2) a VL region incorporating the following FRs:
  LC-FR1 having the amino acid sequence of SEQ ID NO:40
  LC-FR2 having the amino acid sequence of SEQ ID NO:43
  LC-FR3 having the amino acid sequence of SEQ ID NO:47
  LC-FR4 having the amino acid sequence of SEQ ID NO:51,
  or a variant thereof in which one or two or three amino acids in one or more of LC-FR1, LC-FR2, LC-FR3, or LC-FR4 are substituted with another amino acid.

(26) (9A7 VL 3) a VL region incorporating the following FRs:
  LC-FR1 having the amino acid sequence of SEQ ID NO:40
  LC-FR2 having the amino acid sequence of SEQ ID NO:44
  LC-FR3 having the amino acid sequence of SEQ ID NO:48
  LC-FR4 having the amino acid sequence of SEQ ID NO:51,
  or a variant thereof in which one or two or three amino acids in one or more of LC-FR1, LC-FR2, LC-FR3, or LC-FR4 are substituted with another amino acid.

(27) (9A7 VL 4) a VL region incorporating the following FRs:
  LC-FR1 having the amino acid sequence of SEQ ID NO:40
  LC-FR2 having the amino acid sequence of SEQ ID NO:44
  LC-FR3 having the amino acid sequence of SEQ ID NO:49
  LC-FR4 having the amino acid sequence of SEQ ID NO:51,
  or a variant thereof in which one or two or three amino acids in one or more of LC-FR1, LC-FR2, LC-FR3, or LC-FR4 are substituted with another amino acid.

In some embodiments the antigen-binding molecule comprises a VL region comprising the CDRs according to (22) above, and the FRs according to one of (23) to (27) above.

In some embodiments the antigen-binding molecule comprises a VL region according to one of (28) to (32) below:
(28) (9A7 VL) a VL region comprising the CDRs according to (22) and the FRs according to (23).
(29) (9A7 VL 1) a VL region comprising the CDRs according to (22) and the FRs according to (24).
(30) (9A7 VL 2) a VL region comprising the CDRs according to (22) and the FRs according to (25).
(31) (9A7 VL 3) a VL region comprising the CDRs according to (22) and the FRs according to (26).
(32) (9A7 VL 4) a VL region comprising the CDRs according to (22) and the FRs according to (27).

In some embodiments the antigen-binding molecule comprises a VL region according to one of (33) to (37) below:
(33) (9A7 VL) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:13.

(34) (9A7 VL 1) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:14.

(35) (9A7 VL 2) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:15.

(36) (9A7 VL 3) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:16.

(37) (9A7 VL 4) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:17.

In some embodiments the antigen-binding molecule comprises a VH region according to any one of (1) to (21) above, and a VL region according to any one of (22) to (37) above.

In some embodiments the antigen-binding molecule comprises a VH region according to (10) or (16) and a VL region according to (28) or (33).

In some embodiments the antigen-binding molecule comprises a VH region according to (14) or (20) and a VL region according to (32) or (37). In some embodiments the antigen-binding molecule comprises a VH region according to (14) and a VI region according to (32). In some embodiments the antigen-binding molecule comprises a VH region according to (20) and a VL region according to (37).

In some embodiments the antigen-binding molecule comprises a VH region according to (13) or (19) and a VL region according to (30) or (35). In some embodiments the antigen-binding molecule comprises a VH region according to (13) or (19) and a VL region according to (31) or (36). In some embodiments the antigen-binding molecule comprises a VH region according to (13) or (19) and a VL region according to (32) or (37). In some embodiments the antigen-binding molecule comprises a VH region according to (14) or (20) and a VL region according to (30) or (35). In some embodiments the antigen-binding molecule comprises a VH region according to (14) or (20) and a VL region according to (31) or (36).

In embodiments in accordance with the present invention in which one or more amino acids are substituted with another amino acid, the substitutions may conservative substitutions, for example according to the following Table. In some embodiments, amino acids in the same block in the middle column are substituted. In some embodiments, amino acids in the same line in the rightmost column are substituted:

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

In some embodiments, substitution(s) may be functionally conservative. That is, in some embodiments the substitution may not affect (or may not substantially affect) one or more functional properties (e.g. target binding) of the antigen-binding molecule comprising the substitution as compared to the equivalent unsubstituted molecule.

In some embodiments substitution(s) relative to a reference VH or VL sequence may be focussed in a particular region or regions of the VH or VL sequence. For example, variation from a reference VH or VL sequence may be focussed in one or more of the framework regions (FR1. FR2. FR3 and/or FR4).

The VH and VL region of an antigen-binding region of an antibody together constitute the Fv region. In some embodiments, the antigen-binding molecule according to the present invention comprises, or consists of, an Fv region which binds to IL-11Rα. In some embodiments the VH and VL regions of the Fv are provided as single polypeptide joined by a linker region, i.e. a single chain Fv (scFv).

In some embodiments the antigen-binding molecule of the present invention comprises one or more regions of an immunoglobulin heavy chain constant sequence. In some embodiments the immunoglobulin heavy chain constant sequence is, or is derived from, the heavy chain constant sequence of an IgG (e.g. IgG1, IgG2, IgG3, IgG4), IgA (e.g. IgA1, IgA2), IgD, IgE or IgM.

In some embodiments the immunoglobulin heavy chain constant sequence is human immunoglobulin G1 constant (IGHG1; UniProt: P01857-1, v1; SEQ ID NO:53). Positions 1 to 98 of SEQ ID NO:53 form the CH1 region (SEQ ID NO:54). Positions 99 to 110 of SEQ ID NO:53 form a hinge region between CH1 and CH2 regions (SEQ ID NO:55). Positions 111 to 223 of SEQ ID NO:53 form the CH2 region (SEQ ID NO:56). Positions 224 to 330 of SEQ ID NO:53 form the CH3 region (SEQ ID NO:57).

In some embodiments a CH1 region comprises or consists of the sequence of SEQ ID NO:54, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:54. In some embodiments a CH1-CH2 hinge region comprises or consists of the sequence of SEQ ID NO:55, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:55. In some embodiments a CH2 region comprises or consists of the sequence of SEQ ID NO:56, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:56. In some embodiments a CH3 region comprises or consists of the sequence of SEQ ID NO:57 or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:57.

In some embodiments the immunoglobulin heavy chain constant sequence is human immunoglobulin G 4 constant (IGHG4; UniProt: P01861, v1; SEQ ID NO:61). Positions 1-98 of SEQ ID NO:61 form the CH1 region (SEQ ID NO:62). Positions 99-110 of SEQ ID NO:61 form a hinge region between CH1 and CH2 regions (SEQ ID NO:63). Positions 111-220 of SEQ ID NO:61 form the CH2 region (SEQ ID NO:64). Positions 221-327 of SEQ ID NO:61 form the CH3 region (SEQ ID NO:65).

In some embodiments a CH1 region comprises or consists of the sequence of SEQ ID NO:62, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:62. In some embodiments a CH1-CH2 hinge region comprises or consists of the sequence of SEQ ID NO:63, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:63. In some embodiments a CH2 region comprises or consists of the sequence of SEQ ID NO:64, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID N064. In some embodiments a CH3 region comprises or consists of the sequence of SEQ ID NO:65 or a sequence having at least 60%, preferably one of 70%, 75%, 80%, 85%, 90%, 91%, 92%, 93%, 94%, 95%, 986%, 97%, 98%, 99% or 100% amino acid sequence identity to the amino acid sequence of SEQ ID NO:65.

In some embodiments the immunoglobulin heavy chain constant sequence is human immunoglobulin G 4 constant (IGHG4; UniProt: P01861, v1) comprising amino acid substitutions which impart improved properties on the antigen-binding molecules of the invention. In some embodiments the immunoglobulin heavy chain constant sequence is human IgG4 comprising substitutions S241P and/or L248E. The S241P mutation is hinge stabilising while the L248E mutation further reduces the already low ADCC effector function of IgG4 (Davies and Sutton, Immunol Rev. 2015 November; 268(1):139-159; Angal et al Mol Immunol. 1993 January; 30(1):105-8). The lower ADCC activity is advantageous for potential subcutaneous administration of the antibody.

In some embodiments the immunoglobulin heavy chain constant sequence is human immunoglobulin G 4 constant (IGHG4; UniProt: P01861, v1) comprising substitution S241P (numbered according to the Kabat system), as described in SEQ ID NO:66. Positions 1-98 of SEQ ID NO:066 form the CH1 region (SEQ ID NO:62). Positions 99-110 of SEQ ID NO:66 form a hinge region between CH1 and CH2 regions (SEQ ID NO:67) comprising the S241P substitution. Positions 111-220 of SEQ ID NO:66 form the CH2 region (SEQ ID NO:64). Positions 221-327 of SEQ ID NO:66 form the CH3 region (SEQ ID NO:65).

In some embodiments a CH1 region comprises or consists of the sequence of SEQ ID NO:62, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:62. In some embodiments a CH1-CH2 hinge region comprises or consists of the sequence of SEQ ID NO:67, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:67. In some embodiments a CH2 region comprises or consists of the sequence of SEQ ID NO:64, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:064. In some embodiments a CH3 region comprises or consists of the sequence of SEQ ID NO:65 or a sequence having at least 60%, preferably one of 70%, 75%, 80%, 85%, 90%, 91%, 92%, 93%, 94%, 95%, 98%, 97%, 98%, 99% or 100% amino acid sequence identity to the amino acid sequence of SEQ ID NO:65.

In some embodiments the immunoglobulin heavy chain constant sequence is human immunoglobulin G 4 constant (IGHG4; UniProt: P01861, v1) comprising substitutions S241P and L248E (numbered according to the Kabat system), as described in SEQ ID NO:68. Positions 1-98 of SEQ ID NO:68 form the CH1 region (SEQ ID NO:62). Positions 99-110 of SEQ ID NO:68 form a hinge region between CH1 and CH2 regions (SEQ ID NO:67) comprising the S241P substitution. Positions 111-220 of SEQ ID NO:68 form the CH2 region (SEQ ID NO:69), comprising the L248E substitution. Positions 221-327 of SEQ ID NO:68 form the CH3 region (SEQ ID NO:65).

In some embodiments a CH1 region comprises or consists of the sequence of SEQ ID NO:62, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:62. In some embodiments a CH1-CH2 hinge region comprises or consists of the sequence of SEQ ID NO:67, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:67.

In some embodiments a CH2 region comprises or consists of the sequence of SEQ ID NO:69, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:69. In some embodiments a CH3 region comprises or consists of the sequence of SEQ ID NO:65 or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:65.

In some embodiments the antigen-binding molecule of the present invention comprises one or more regions of an immunoglobulin light chain constant sequence. In some embodiments the immunoglobulin light chain constant sequence is human immunoglobulin kappa constant (IGKC; Cκ; UniProt: P01834-1, v2; SEQ ID NO:58). In some embodiments the immunoglobulin light chain constant sequence is a human immunoglobin lambda constant (IGLC; Cλ), e.g. IGLC1, IGLC2, IGLC3, IGLC6 or IGLC7 (SEQ ID NO:75, 76, 77, 78, or 79. In some embodiments a CL region comprises or consists of the sequence of SEQ ID NO:58, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:58. In some embodiments a CL region comprises or consists of the sequence of SEQ ID NO:75, 76, 77, 78, or 79, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:75, 76, 77, 78, or 79.

The VL and light chain constant (CL) region, and the VH region and heavy chain constant 1 (CH1) region of an antigen-binding region of an antibody together constitute the Fab region. In some embodiments the antigen-binding molecule comprises a Fab region comprising a VH, a CH1, a VL and a CL (e.g. Cκ or Cλ). In some embodiments the Fab region comprises a polypeptide comprising a VH and a CH1 (e.g. a VH-CH1 fusion polypeptide), and a polypeptide comprising a VL and a CL (e.g. a VL-CL fusion polypeptide). In some embodiments the Fab region comprises a polypeptide comprising a VH and a CL (e.g. a VH-CL fusion polypeptide) and a polypeptide comprising a VL and a CH (e.g. a VL-CH1 fusion polypeptide); that is, in some embodiments the Fab region is a CrossFab region. In some embodiments the VH, CH1, VL and CL regions of the Fab or CrossFab are provided as single polypeptide joined by linker regions, i.e. as a single chain Fab (scFab) or a single chain CrossFab (scCrossFab).

In some embodiments, the antigen-binding molecule of the present invention comprises, or consists of, a Fab region which binds to IL-11Rα.

In some embodiments, the antigen-binding molecule described herein comprises, or consists of, a whole antibody which binds to IL-11Rα. As used herein, "whole antibody" refers to an antibody having a structure which is substantially similar to the structure of an immunoglobulin (Ig). Different kinds of immunoglobulins and their structures are described e.g. in Schroeder and Cavacini J Allergy Clin Immunol. (2010) 125(202): S41-S52, which is hereby incorporated by reference in its entirety.

Immunoglobulins of type G (i.e. IgG) are ~150 kDa glycoproteins comprising two heavy chains and two light chains. From N- to C-terminus, the heavy chains comprise a VH followed by a heavy chain constant region comprising three constant domains (CH1, CH2, and CH3), and similarly the light chain comprise a VL followed by a CL. Depending on the heavy chain, immunoglobulins may be classed as IgG (e.g. IgG1, IgG2, IgG3, IgG4), IgA (e.g. IgA1, IgA2), IgD, IgE, or IgM. The light chain may be kappa (κ) or lambda (λ).

In some embodiments, the antigen-binding molecule described herein comprises, or consists of, an IgG (e.g. IgG1, IgG2, IgG3, IgG4), IgA (e.g. IgA1, IgA2), IgD, IgE, or IgM which binds to IL-11Rα.

In some embodiments, the antigen-binding molecule of the present invention is at least monovalent binding for IL-11Rα. Binding valency refers to the number of binding sites in an antigen-binding molecule for a given antigenic determinant. Accordingly, in some embodiments the antigen-binding molecule comprises at least one binding site for IL-11Rα.

In some embodiments the antigen-binding molecule comprises more than one binding site for IL-11Rα, e.g. 2, 3 or 4 binding sites. The binding sites may be the same or different. In some embodiments the antigen-binding molecule is e.g. bivalent, trivalent or tetravalent for IL-11Rα.

Aspects of the present invention relate to multispecific antigen-binding molecules. By "multispecific" it is meant that the antigen-binding molecule displays specific binding to more than one target. In some embodiments the antigen-binding molecule is a bispecific antigen-binding molecule. In some embodiments the antigen-binding molecule comprises at least two different antigen-binding domains (i.e. at least two antigen-binding domains, e.g. comprising non-identical VHs and VLs).

In some embodiments the antigen-binding molecule binds to IL-11Rα and another target (e.g. an antigen other than IL-11Rα), and so is at least bispecific. The term "bispecific" means that the antigen-binding molecule is able to bind specifically to at least two distinct antigenic determinants.

It will be appreciated that an antigen-binding molecule according to the present invention (e.g. a multispecific antigen-binding molecule) may comprise antigen-binding molecules capable of binding to the targets for which the antigen-binding molecule is specific. For example, an antigen-binding molecule which is capable of binding to IL-11Rα and an antigen other than IL-11Rα may comprise: (i) an antigen-binding molecule which is capable of binding to IL-11Rα, and (k) an antigen-binding molecule which is capable of binding to an antigen other than IL-11Rα.

It will also be appreciated that an antigen-binding molecule according to the present invention (e.g. a multispecific antigen-binding molecule) may comprise antigen-binding polypeptides or antigen-binding polypeptide complexes capable of binding to the targets for which the antigen-binding molecule is specific. For example, an antigen-binding molecule according to the invention may comprise e.g. (I) an antigen-binding polypeptide complex capable of binding to IL-11Rα, comprising a light chain polypeptide (comprising the structure VL-CL) and a heavy chain polypeptide (comprising the structure VH-CH1-CH2-CH3), and (ii) an antigen-binding polypeptide complex capable of binding to an antigen other than IL-11Rα, comprising a light chain polypeptide (comprising the structure VL-CL) and a heavy chain polypeptide (comprising the structure VH-CH1-CH2-CH3)

In some embodiments, a component antigen-binding molecule of a larger antigen-binding molecule (e.g. a multispecific antigen-biding molecule) may be referred to e.g. as an "antigen-binding domain" or "antigen-binding region" of the larger antigen-binding molecule.

In some embodiments the antigen-binding molecule comprises an antigen-binding molecule capable of binding to IL-11Rα, and an antigen-binding molecule capable of binding to an antigen other than IL-11Rα. In some embodiments, the antigen other than IL-11Rα is an immune cell surface molecule. In some embodiments, the antigen other than IL-11Rα is a cancer cell antigen. In some embodiments the antigen other than IL-11Rα is a receptor molecule, e.g. a cell surface receptor. In some embodiments the antigen other than IL-11Rα is a cell signalling molecule, e.g. a cytokine, chemokine, interferon, interleukin or lymphokine. In some embodiments the antigen other than IL-11Rα is a growth factor or a hormone.

A cancer cell antigen is an antigen which is expressed or over-expressed by a cancer cell. A cancer cell antigen may be any peptide/polypeptide, glycoprotein, lipoprotein, glycan, glycolipid, lipid, or fragment thereof. A cancer cell antigen's expression may be associated with a cancer. A cancer cell antigen may be abnormally expressed by a cancer cell (e.g. the cancer cell antigen may be expressed with abnormal localisation), or may be expressed with an abnormal structure by a cancer cell. A cancer cell antigen may be capable of eliciting an immune response. In some embodiments, the antigen is expressed at the cell surface of the cancer cell (i.e. the cancer cell antigen is a cancer cell surface antigen). In some embodiments, the part of the antigen which is bound by the antigen-binding molecule described herein is displayed on the external surface of the cancer cell (i.e. is extracellular). The cancer cell antigen may be a cancer-associated antigen. In some embodiments the cancer cell antigen is an antigen whose expression is associated with the development, progression or severity of symptoms of a cancer. The cancer-associated antigen may be associated with the cause or pathology of the cancer, or may be expressed abnormally as a consequence of the cancer. In some embodiments, the cancer cell antigen is an antigen whose expression is upregulated (e.g. at the RNA and/or protein level) by cells of a cancer, e.g. as compared to the level of expression of by comparable non-cancerous cells (e.g. non-cancerous cells derived from the same tissue/cell type). In some embodiments, the cancer-associated antigen may be preferentially expressed by cancerous cells, and not expressed by comparable non-cancerous cells (e.g. non-cancerous cells derived from the same tissue/cell type). In some embodiments, the cancer-associated antigen may be the product of a mutated oncogene or mutated tumor suppressor gene. In some embodiments, the cancer-associated antigen may be the product of an overexpressed cellular protein, a cancer antigen produced by an oncogenic virus, an oncofetal antigen, or a cell surface glycolipid or glycoprotein.

An immune cell surface molecule may be any peptide/polypeptide, glycoprotein, lipoprotein, glycan, glycolipid, lipid, or fragment thereof expressed at or on the cell surface of an immune cell. In some embodiments, the part of the immune cell surface molecule which is bound by the antigen-binding molecule of the present invention is on the external surface of the immune cell (i.e. is extracellular). The immune cell surface molecule may be expressed at the cell surface of any immune cell. In some embodiments, the immune cell may be a cell of hematopoietic origin, e.g. a neutrophil, eosinophil, basophil, dendritic cell, lymphocyte, or monocyte. The lymphocyte may be e.g. a T cell, B cell, natural killer (NK) cell, NKT cell or innate lymphoid cell (ILC), or a precursor thereof (e.g. a thymocyte or pre-B cell). In some embodiments the immune cell surface molecule may be a costimulatory molecule (e.g. CD28, OX40, 4-1BB, ICOS or CD27) or a ligand thereof. In some embodiments the immune cell surface molecule may be a checkpoint inhibitor (e.g. PD-1, CTLA-4, LAG-3, TIM-3, TIGIT or BTLA) or a ligand thereof.

Multispecific antigen-binding molecules according to the invention may be provided in any suitable format, such as those formats described in described in Brinkmann and Kontermann MAbs (2017) 9(2): 182-212, which is hereby incorporated by reference in its entirety. Suitable formats include those shown in FIG. 2 of Brinkmann and Kontermann MAbs (2017) 9(2): 182-212: antibody conjugates, e.g. $IgG_2$, $F(ab')_2$ or CovX-Body; IgG or IgG-like molecules, e.g. IgG, chimeric IgG, κλ-body common HC; CH1/CL fusion proteins, e.g. scFv2-CH1/CL, VHH2-CH1/CL; 'variable domain only' bispecific antigen-binding molecules, e.g. tandem scFv (taFV), triplebodies, diabodies (Db), dsDb, Db(kih), DART, scDB, dsFv-dsFv, tandAbs, triple heads, tandem dAbN/VHH, tertravalent dAb.VHH; Non-Ig fusion proteins, e.g. $scFv_2$-albumin, scDb-albumin, taFv-albumin, taFv-toxin, miniantibody, $DNL-Fab_2$, $DNL-Fab_2$-scFv, $DNL-Fab_2$-IgG-cytokine2, ImmTAC (TCR-scFv); modified Fc and CH3 fusion proteins, e.g. scFv-Fc(kih), scFv-Fc(CH3 charge pairs), scFv-Fc (EW-RVT), scFv-fc (HA-TF), scFv-Fc (SEEDbody), taFv-Fc(kih), scFv-Fc(kih)-Fv, Fab-Fc (kih)-scFv, Fab-scFv-Fc(kih), Fab-scFv-Fc(BEAT), Fab-scFv-Fc (SEEDbody), DART-Fc, scFv-CH3(kih), TriFabs; Fc fusions, e.g. Di-diabody, scDb-Fc, taFv-Fc, scFv-Fc-scFv, HCAb-VHH, Fab-scFv-Fc, $scFv_4$-Ig, $scFv_2$-Fcab; CH3 fusions, e.g. Dia-diabody, scDb-CH3; IgE/IgM CH2 fusions, e.g. scFv-EHD2-scFv, scFvMHD2-scFv Fab fusion proteins, e.g. Fab-scFv (bibody), $Fab-scFv_2$ (tribody), Fab-Fv, Fab-dsFv, Fab-VHH, orthogonal Fab-Fab; non-Ig fusion proteins, e.g. $DNL-Fab_3$, $DNL-Fab_2$-scFv, $DNL-Fab_2$-IgG-cytokine$_2$; asymmetric IgG or IgG-like molecules, e.g. IgG (kih), IgG(kih) common LC, ZW1 IgG common LC, Biclonics common LC, CrossMab, CrossMab(kih), scFab-IgG (kih), Fab-scFab-IgG(kih), orthogonal Fab IgG(kih), DuetMab, CH3 charge pairs+CH1/CL charge pairs, hinge/CH3 charge pairs, SEED-body, Duobody, four-in-one-CrossMab(kih), LUZ-Y common LC; LUZ-Y scFab-gG, FcFc*; appended and Fc-modified IgGs, e.g. IgG(kih)-Fv, IgG HA-TF-Fv, IgG(kih)scFab, scFab-Fc(kih)-scFv2, scFab-Fc(kih)-scFv, half DVD-Ig, DVI-Ig (four-in-one), CrossMab-Fab; modified Fc and CH3 fusion proteins, e.g. Fab-Fc(kih)-scFv, Fab-scFv-Fc(kih), Fab-scFv-Fc(BEAT), Fab-scFv-Fc-SEEDbody, TriFab; appended IgGs-HC fusions, e.g. IgG-HC, scFv, IgG-dAb, gG-taFV, IgG-Cross-Fab, IgG-orthogonal Fab, IgG-(CαCβ) Fab, scFv-HC-IgG, tandem Fab-IgG (orthogonal Fab) Fab-IgG(CαCβ Fab), Fab-IgG(CR3). Fab-hinge-IgG(CR3); appended IgGs-LC fusions, e.g. IgG-scFv(LC), scFv(LC)-IgG, dAb-IgG; appended IgGs—HC and LC fusions, e.g. DVD-Ig, TVD-Ig, CODV-Ig, scFv4-IgG, Zybody; Fc fusions, e.g. Fab-scFv-Fc, $scFv_4$-g; F(ab')2 fusions, e.g. $F(ab')_2$-$scFv_2$; CH1/CL fusion proteins e.g. $scFv_2$-CH1-hinge/CL; modified IgGs, e.g. DAF (two-in one-IgG), DutaMab, $Mab^2$; and non-Ig fusions, e.g. $DNL-Fab_4$-IgG.

The skilled person is able to design and prepare bispecific antigen-binding molecules. Methods for producing bispecific antigen-binding molecules include chemically crosslinking of antigen-binding molecules or antibody fragments, e.g. with reducible disulphide or non-reducible thioether bonds, for example as described in Segal and Bast, 2001. Production of Bispecific Antigen-binding molecules. Current Protocols in Immunology. 14:IV:2.13:2.13.1-2.13.16, which is hereby incorporated by reference in its entirety. For example, N-succinimidyl-3-(-2-pyridyldithio)-propionate (SPDP) can be used to chemically crosslink e.g. Fab fragments via hinge region SH— groups, to create disulfide-linked bispecific $F(ab)_2$ heterodimers.

Other methods for producing bispecific antigen-binding molecules include fusing antibody-producing hybridomas e.g. with polyethylene glycol, to produce a quadroma cell capable of secreting bispecific antibody, for example as described in D. M. and Bast, B. J. 2001. Production of Bispecific Antigen-binding molecules. Current Protocols in Immunology. 14:IV:2.13:2.13.1-2.13.16.

Bispecific antigen-binding molecules according to the present invention can also be produced recombinantly, by expression from e.g. a nucleic acid construct encoding polypeptides for the antigen-binding molecules, for example as described in Antibody Engineering: Methods and Protocols, Second Edition (Humana Press, 2012), at Chapter 40: Production of Bispecific Antigen-binding molecules: Diabodies and Tandem scFv (Homig and Färber-Schwarz), or French, How to make bispecific antigen-binding molecules, Methods Mol. Med. 2000; 40:333-339, the entire contents of both of which are hereby incorporated by reference. For example, a DNA construct encoding the light and heavy chain variable domains for the two antigen-binding fragments (i.e. the light and heavy chain variable domains for the antigen-binding fragment capable of binding IL-11Rα, and the light and heavy chain variable domains for the antigen-binding fragment capable of binding to another target protein), and including sequences encoding a suitable linker or dimerization domain between the antigen-binding fragments can be prepared by molecular cloning techniques. Recombinant bispecific antibody can thereafter be produced by expression (e.g. in vitro) of the construct in a suitable host cell (e.g. a mammalian host cell), and expressed recombinant bispecific antibody can then optionally be purified.

In some embodiments the antigen-binding molecules of the present invention comprise an Fc region. An Fc region is composed of CH2 and CH3 regions from one polypeptide, and CH2 and CH3 regions from another polypeptide. The CH2 and CH3 regions from the two polypeptides together form the Fc region.

In some embodiments, the antigen-binding molecule of the present invention comprises an Fc region comprising modification in one or more of the CH2 and CH3 regions promoting association of the Fc region. Recombinant co-expression of constituent polypeptides of an antigen-binding molecule and subsequent association leads to several possible combinations. To improve the yield of the desired combinations of polypeptides in antigen-binding molecules in recombinant production, it is advantageous to introduce in the Fc regions modification(s) promoting association of the desired combination of heavy chain polypeptides. Modifications may promote e.g. hydrophobic and/or electrostatic interaction between CH2 and/or CH3 regions of different polypeptide chains. Suitable modifications are described e.g. In Ha at al., Front. Immnol (2016) 7:394, which is hereby incorporated by reference in its entirety. In some embodiments the antigen antigen-binding molecule of the present invention comprises an Fc region comprising paired substitutions in the CH3 regions of the Fc region according to one of the following formats, as shown in Table 1 of Ha et al., Front. Immnol (2016) 7:394: KiH, KiH$_{s\text{-}s}$, HA-TF, ZW1, 7.8.60, DD-KK, EW-RVT, EW-RVT$_{s\text{-}s}$, SEED or A107.

Polypeptides

The present invention also provides polypeptide constituents of antigen-binding molecules. The polypeptides may be provided in isolated or substantially purified form.

The antigen-binding molecule of the present invention may be, or may comprise, a complex of polypeptides.

In the present specification where a polypeptide comprises more than one domain or region, it will be appreciated that the plural domains/regions are preferably present in the same polypeptide chain. That is, the polypeptide comprises more than one domain or region is a fusion polypeptide comprising the domains/regions.

In some embodiments a polypeptide according to the present invention comprises, or consists of, a VH as described herein. In some embodiments a polypeptide according to the present invention comprises, or consists of, a VL as described herein.

In some embodiments, the polypeptide additionally comprises one or more antibody heavy chain constant regions (CH). In some embodiments, the polypeptide additionally comprises one or more antibody light chain constant regions (CL). In some embodiments, the polypeptide comprises a CH1, CH2 region and/or a CH3 region of an immunoglobulin (Ig).

In some embodiments the polypeptide comprises one or more regions of an immunoglobulin heavy chain constant sequence. In some embodiments the polypeptide comprises a CH1 region as described herein. In some embodiments the polypeptide comprises a CH1-CH2 hinge region as described herein. In some embodiments the polypeptide comprises a CH2 region as described herein. In some embodiments the polypeptide comprises a CH3 region as described herein.

In some embodiments the polypeptide comprises a CH3 region comprising any one of the amino acid substitutions/ combinations of amino acid substitutions shown in Table 1 of Ha et al., Front. Immnol (2016) 7:394, incorporated by reference hereinabove.

In some embodiments the CH2 and/or CH3 regions of the polypeptide comprise one or more amino acid substitutions for promoting association of the polypeptide with another polypeptide comprising a CH2 and/or CH3 region.

In some embodiments the polypeptide comprises one or more regions of an immunoglobulin light chain constant sequence. In some embodiments the polypeptide comprises a CL region as described herein.

In some embodiments, the polypeptide according to the present invention comprises a structure from N- to C-terminus according to one of the following:
(i) VH
(ii) VL
(iii) VH-CH1
(iv) VL-CL
(v) VL-CH1
(vi) VH-CL
(vii) VH-CH1-CH2-CH3
(viii) VL-CL-CH2-CH3
(ix) VL-CH1-CH2-CH3
(x) VH-CL-CH2-CH3

Also provided by the present invention are antigen-binding molecules composed of the polypeptides of the present invention. In some embodiments, the antigen-binding molecule of the present invention comprises one of the following combinations of polypeptides:
(A) VH+VL
(B) VH-CH1+VL-CL
(C) VL-CH1+VH-CL
(D) VH-CH1-CH2-CH3+VL-CL
(E) VH-CL-CH2-CH3+VL-CH1
(F) VL-CH1-CH2-CH3+VH-CL
(G) VL-CL-CH2-CH3+VH-CH1
(H) VH-CH1-CH2-CH3+VL-CL-CH2-CH3
(I) VH-CL-CH2-CH3+VL-CH1-CH2-CH3

In some embodiments the antigen-binding molecule comprises more than one of a polypeptide of the combinations shown in (A) to (I) above. By way of example, with reference to (D) above, in some embodiments the antigen-binding molecule comprises two polypeptides comprising the structure VH-CH1-CH2-CH3, and two polypeptides comprising the structure VL-CL.

In some embodiments, the antigen-binding molecule of the present invention comprises one of the following combinations of polypeptides:
(J) VH (anti-IL-11Rα)+VL (anti-IL-11Rα)
(K) VH (anti-IL-11Rα)-CH1+VL (anti-IL-11Rα)-CL
(L) VL (anti-IL-11Rα)-CH1+VH (anti-IL-11Rα)-CL
(M) VH (anti-IL-11Rα)-CH1-CH2-CH3+VL (anti-IL-11Rα)-CL
(N) VH (anti-IL-11Rα)-CL-CH2-CH3+VL (anti-IL-11Rα)-CH1
(O) VL (anti-IL-11Rα)-CH1-CH2-CH3+VH (anti-IL-11Rα)-CL
(P) VL (anti-IL-11Rα)-CL-CH2-CH3+VH (anti-IL-11Rα)-CH1
(Q) VH (anti-IL-11Rα)-CH1-CH2-CH3+VL (anti-IL-11Rα)-CL-CH2-CH3
(R) VH (anti-IL-11Rα)-CL-CH2-CH3+VL (anti-IL-11Rα)-CH1-CH2-CH3

Wherein: "VH (anti-IL-11Rα)" refers to the VH of an antigen-binding molecule capable of binding to IL-11Rα as described herein, e.g. as defined in any one of (1) to (21), and "VL (anti-IL-11Rα)" refers to the VL of an antigen-binding molecule capable of binding to IL-11Rα as described herein, e.g. as defined in any one of (22) to (37).

In some embodiments the polypeptide comprises or consists of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of one of SEQ ID NOs:7 to 17.

In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:70. In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:71. In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:72. In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:73. In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:74. Linkers and additional sequences In some embodiments the antigen-binding molecules and polypeptides of the present invention comprise one or more linker sequences between amino acid sequences. A linker sequence may be provided at one or both ends of one or more of a VH, VL, CH1-CH2 hinge region, CH2 region and a CH3 region of the antigen-binding molecule/polypeptide.

Linker sequences are known to the skilled person, and are described, for example in Chen et al., Adv Drug Deliv Rev (2013) 65(10): 1357-1369, which is hereby incorporated by reference in its entirety. In some embodiments, a linker sequence may be a flexible linker sequence. Flexible linker sequences allow for relative movement of the amino acid sequences which are linked by the linker sequence. Flexible linkers are known to the skilled person, and several are identified in Chen et al., Adv Drug Deliv Rev (2013) 65(10): 1357-1369. Flexible linker sequences often comprise high proportions of glycine and/or serine residues.

In some embodiments, the linker sequence comprises at least one glycine residue and/or at least one serine residue. In some embodiments the linker sequence consists of glycine and serine residues. In some embodiments, the linker sequence has a length of 1-2, 1-3, 1-4, 1-5 or 1-10 amino acids.

The antigen-binding molecules and polypeptides of the present invention may additionally comprise further amino acids or sequences of amino acids. For example, the antigen-binding molecules and polypeptides may comprise amino acid sequence(s) to facilitate expression, folding, trafficking, processing, purification or detection of the antigen-binding molecule/polypeptide. For example, the antigen-binding molecule/polypeptide may comprise a sequence encoding a His, (e.g. 6×His), Myc, GST, MBP, FLAG, HA, E, or Biotin tag, optionally at the N- or C-terminus of the antigen-binding molecule/polypeptide. In some embodiments the antigen-binding molecule/polypeptide comprises a detectable moiety, e.g. a fluorescent, luminescent, immuno-detectable, radio, chemical, nucleic acid or enzymatic label.

The antigen-binding molecules and polypeptides of the present invention may additionally comprise a signal peptide (also known as a leader sequence or signal sequence). Signal peptides normally consist of a sequence of 5-30 hydrophobic amino acids, which form a single alpha helix. Secreted proteins and proteins expressed at the cell surface often comprise signal peptides.

The signal peptide may be present at the N-terminus of the antigen-binding molecule/polypeptide, and may be present in the newly synthesised antigen-binding molecule/polypeptide. The signal peptide provides for efficient trafficking and secretion of the antigen-binding molecule/polypeptide. Signal peptides are often removed by cleavage, and thus are not comprised in the mature antigen-binding molecule/polypeptide secreted from the cell expressing the antigen-binding molecule/polypeptide.

Signal peptides are known for many proteins, and are recorded in databases such as GenBank, UniProt, Swiss-Prot, TrEMBL, Protein Information Resource, Protein Data Bank, Ensembl, and InterPro, and/or can be identified/predicted e.g. using amino acid sequence analysis tools such as SignalP (Petersen et al., 2011 Nature Methods 8: 785-786) or Signal-BLAST (Frank and Sippl, 2008 Bioinformatics 24: 2172-2176).

Labels and Conjugates

In some embodiments the antigen-binding molecules of the present invention additionally comprise a detectable moiety or a chemical moiety.

In some embodiments the antigen-binding molecule comprises a detectable moiety, e.g. a fluorescent label, phosphorescent label, luminescent label, immuno-detectable label (e.g. an epitope tag), radiolabel, chemical, nucleic acid or enzymatic label. The antigen-binding molecule may be covalently or non-covalently labelled with the detectable moiety.

Fluorescent labels include e.g. fluorescein, rhodamine, allophycocyanin, eosine and NDB, green fluorescent protein (GFP) chelates of rare earths such as europium (Eu), terbium (Tb) and samarium (Sm), tetramethyl rhodamine. Texas Red, 4-methyl umbelliferone, 7-amino-4-methyl coumarin, Cy3, and Cy5. Radiolabels include radioisotopes such as Iodine$^{123}$, Iodine$^{125}$, Iodine$^{126}$, Iodine$^{131}$, Iodine$^{131}$, Bromine$^{77}$, Technetium$^{99m}$, Indium$^{111}$, Indium$^{113m}$, Gallium$^{67}$, Gallium$^{68}$, Ruthenium$^{95}$, Ruthenium$^{97}$, Ruthenium$^{103}$, Ruthenium$^{105}$, Mercury$^{207}$, Mercury$^{203}$, Rhenium$^{99m}$, Rhenium$^{101}$, Rhenium$^{105}$, Scandium$^{47}$, Tellurium$^{121m}$, Tellurium$^{122m}$, Tellurium$^{125m}$, Thulium$^{185}$, Thulium$^{167}$, Thulium$^{168}$, Copper$^{87}$, Fluorine$^{18}$, Yttrium$^{90}$, Palladium$^{100}$, Bismuth$^{217}$ and Antimony$^{211}$. Luminescent labels include as radioluminescent, chemiluminescent (e.g. acridinium ester, luminol, isoluminol) and bioluminescent labels. Immuno-detectable labels include haptens, peptides/polypeptides, antibodies, receptors and ligands such as biotin, avidin, streptavidin or digoxigenin. Nucleic acid labels include aptamers. Enzymatic labels include e.g. peroxidase, alkaline phosphatase, glucose oxidase, beta-galactosidase and luciferase.

In some embodiments the antigen-binding molecules of the present invention are conjugated to a chemical moiety. The chemical moiety may be a moiety for providing a therapeutic effect. Antibody-drug conjugates are reviewed e.g. in Parsiow et al., Biomedicines. 2016 September; 4(3): 14. In some embodiments, the chemical moiety may be a drug moiety (e.g. a cytotoxic agent). In some embodiments, the drug moiety may be a chemotherapeutic agent. In some embodiments, the drug moiety is selected from calicheamicin, DM1, DM4, monomethylauristatin E (MMAE), monomethylauristatin F (MMAF), SN-38, doxorubicin, duocarmycin, D6.5 and PBD.

Functional Properties of the Antigen-Binding Molecules

The antigen-binding molecules described herein may be characterised by reference to certain functional properties. In some embodiments, the antigen-binding molecule described herein may possess one or more of the following properties:
 a) Specific binding to IL-11Rα (e.g. human IL-11 and/or mouse IL-11Rα);
 b) Binding to IL-11Rα (e.g. human IL-11Rα) with an affinity of binding of EC50=less than 1000 ng/ml, e.g. as determined by ELISA;
 c) Inhibition of interaction between IL-11Rα and IL-11;
 d) Inhibition of interaction between IL-11Rα and gp130;
 e) Inhibition of interaction between IL-11Rα:gp130 receptor complex and IL-11;
 f) Inhibition of interaction between IL-11:IL-11Rα complex and gp130;
 g) Inhibition of IL-11/IL-11R signalling;
 h) Inhibition of signalling mediated by IL-11;
 i) Inhibition of signalling mediated by binding of IL-11 to IL-11Rα:gp130 receptor complex;
 j) Inhibition of signalling mediated by binding of IL-11:IL-11Rα complex to gp130 (i.e. IL-11 trans signalling);
 k) Inhibition of fibroblast proliferation;
 l) Inhibition of myofibroblast generation from fibroblasts;
 m) Reversal/regression of myofibroblast generation from fibroblasts;
 n) Inhibition of myofibroblast generation from stellate cells, e.g. hepatic or pancreatic stellate cells;
 o) Reversal/regression of myofibroblast generation from stellate cells, e.g. hepatic or pancreatic stellate cells;
 p) Inhibition of migratory and/or invasive behaviour (i.e. inhibition of migration and/or invasion) of fibroblasts, stellate cells or myofibroblasts;
 q) Inhibition of the presence of immune cells in an organ;
 r) Inhibition of a pathological process mediated by IL-11/IL-11R signaling;
 s) Inhibition of fibrosis;
 t) Reversal/regression of fibrosis;
 u) Inhibition of gene or protein expression in fibroblasts or stellate cells of one or more of collagen, fibronectin, periostin, IL-6, IL-11, αSMA (ACTA2), TIMP1, MMP2, TNFα, CCL2 e.g. following stimulation with a profibrotic factor;
 v) Inhibition of extracellular matrix production by fibroblasts or stellate cells;
 w) Inhibition of proliferation and/or survival of cells of a cancer;
 x) Inhibition of development and/or progression of cancer in vivo;
 y) Inhibition of tumour growth;
 z) Killing of cells expressing/comprising IL-11Rα or a complex comprising IL-11Rα.

Herein, 'inhibition' refers to a reduction, decrease or lessening relative to a control condition. For example, inhibition of a process by an antigen-binding molecule refers to a reduction, decrease or lessening of the extent/degree of that process in the absence of the antigen-binding molecule, and/or in the presence of an appropriate control antigen-binding molecule.

Inhibition may herein also be referred to as neutralisation or antagonism. That is, an IL-11Rα binding antigen-binding molecule which is capable of inhibiting a function or process (e.g. interaction, signalling or other activity mediated by IL-11Rα or an IL-11Rα-containing complex) may be said to be a 'neutralising' or 'antagonist' antigen-binding molecule with respect to the relevant function or process. For example, antigen-binding molecule which is capable of inhibiting IL-11 mediated signalling may be referred to as an antigen-binding molecule which is capable of neutralising IL-11 mediated signalling, or may be referred to as an antagonist of IL-11 mediated signalling.

The skilled person is able to identify an appropriate control condition for a given assay. For example, a control antigen-binding molecule may be an antigen-binding molecule directed against a target protein which is known not to have a role involved in the property being investigated in the assay. A control antigen-binding molecule may be of the same isotype as the anti-IL-11Rα antigen-binding molecule being analysed, and may e.g. have the same constant regions.

The antigen-binding molecules described herein preferably display specific binding to IL-11Rα. As used herein, "specific binding" refers to binding which is selective for the antigen, and which can be discriminated from non-specific binding to non-target antigen. An antigen-binding molecule that specifically binds to a target molecule preferably binds the target with greater affinity, and/or with greater duration than it binds to other, non-target molecules. In some embodiments the present antibodies/fragments may bind with greater affinity to IL-11Rα than to one or more members of the IL-6 receptor family. In some embodiments the present antigen-binding molecules may bind with greater affinity to IL-11Rα than to one or more of IL-6Rα, leukemia inhibitory factor receptor (LIFR), oncostatin M receptor (OSMR) and ciliary neurotrophic factor receptor alpha (CNTFRα).

In embodiments, inhibition of IL-11-mediated signalling is achieved by disrupting IL-11-mediated cis signalling but not disrupting IL-11-mediated trans signalling, e.g. Inhibition of IL-11-mediated signalling is achieved by inhibiting gp130-mediated cis complexes involving membrane bound IL-11Rα. In embodiments, inhibition of IL-11-mediated signalling is achieved by disrupting IL-11-mediated trans signalling but not disrupting IL-11-mediated cis signalling, i.e. inhibition of IL-11-mediated signaling is achieved by inhibiting gp130-mediated trans signalling complexes such as IL-11 bound to soluble IL-11Rα or IL-6 bound to soluble IL-6R. In embodiments, inhibition of IL-11-mediated signalling is achieved by disrupting IL-11-mediated cis signalling and IL-11-mediated trans signalling.

The ability of a given polypeptide to bind specifically to a given molecule can be determined by analysis according to methods known in the art, such as by ELISA, Surface Plasmon Resonance (SPR; see e.g. Hearty et al., Methods Mol Biol (2012) 907:411-442), Bio-Layer Interferometry (see e.g. Lad et al., (2015) J Biomol Screen 20(4): 498-507), flow cytometry, or by a radiolabeled antigen-binding assay (RIA) enzyme-linked immunosorbent assay. Through such analysis binding to a given molecule can be measured and quantified. In some embodiments, the binding may be the response detected in a given assay.

In some embodiments, the extent of binding of the antigen-binding molecule to a non-target molecule is less than about 10% of the binding of the antibody to the target molecule as measured, e.g. by ELISA. SPR, Bio-Layer Interferometry or by RIA. Alternatively, binding specificity may be reflected in terms of binding affinity where the antigen-binding molecule binds to IL-11Rα with a dissociation constant ($K_D$) that is at least 0.1 order of magnitude (i.e. $0.1 \times 10^n$, where n is an integer representing the order of magnitude) greater than the $K_D$ of the antigen-binding molecule towards a non-target molecule. This may optionally be one of at least 0.2, 0.3, 0.4, 0.5, 0.6, 0.7, 0.8, 0.9, 1.0, 1.5, or 2.0.

In some embodiments, the antigen-binding molecule displays binding to human IL-11Rα. In some embodiments, the antigen-binding molecule displays binding to mouse IL-11Rα. In some embodiments, the antigen-binding molecule displays binding to human IL-11Rα and mouse IL-11Rα. That is, in some embodiments the antigen-binding molecule is cross-reactive for human IL-11Rα and mouse IL-11Rα. In some embodiments the antigen-binding molecule of the present invention displays cross-reactivity with IL-11Rα of a non-human primate.

In some embodiments, the antigen-binding molecule according to the present invention binds to IL-11Rα with a $K_D$ of 5 µM or less, preferably one of ≤1 µM, ≤500 nM, ≤100 nM, ≤75 nM, ≤50 nM, ≤40 nM, ≤30 nM, ≤20 nM, ≤15 nM, ≤12.5 nM, ≤10 nM, ≤9 nM, ≤8 nM, ≤7 nM, ≤6 nM, ≤5 nM, ≤4 nM, ≤3 nM, ≤2 nM, ≤1 nM, ≤500 pM.

In some embodiments, the antigen-binding molecule according to the present invention binds to IL-11Rα (e.g. human IL-11Rα) with a $K_D$ of ≤20 nM, ≤15 nM, ≤12.5 nM, ≤10 nM, ≤9 nM, ≤8 nM, ≤7 nM or 06 nM, e.g. as determined by SPR analysis. In some embodiments, the antigen-binding molecule binds to IL-11Rα with a $K_D$ of 1 nM and 520 nM, e.g. ≥1 nM and ≤15 nM, or ≥1 nM and ≤10 nM. In some embodiments, the antigen-binding molecule binds to IL-11Rα with a $K_D$ of ≥5 nM and ≤20 nM, e.g. ≥5 nM and ≤15 nM, or ≤5 nM and ≤10 nM.

In some embodiments, the antigen-binding molecule according to the present invention binds to IL-11Rα with an affinity of binding (e.g. as determined by ELISA) of EC50=1000 ng/ml or less, preferably one of ≤900 ng/ml, ≤800 ng/ml, ≤700 ng/ml, ≤600 ng/ml, ≤500 ng/ml, ≤400 ng/ml, ≤300 ng/ml, ≤200 ng/ml, ≤100 ng/ml, ≤90 ng/ml, ≤80 ng/ml, ≤70 ng/ml, ≤60 ng/ml, ≤50 ng/ml, ≤40 ng/ml, ≤30 ng/ml, ≤20 ng/ml, ≤15 ng/ml, ≤10 ng/ml, ≤7.5 ng/ml, ≤5 ng/ml, ≤2.5 ng/ml, or ≤1 ng/ml.

Affinity of binding to IL-11Rα by an antigen-binding molecule may be analysed in vitro by ELISA assay. Suitable assays are well known in the art and can be performed by the skilled person, for example, as described in Antibody Engineering, vol. 1 ($2^{nd}$ Edn), Springer Protocols, Springer (2010), Part V, pp 657-665. For example, the affinity of binding to IL-11Rα by an antigen-binding molecule may be analysed according to the methodology described herein in the experimental examples.

The ability of an antigen-binding molecule to inhibit interaction between two proteins can be determined for example by analysis of interaction in the presence of, or following incubation of one or both of the interaction partners with, the antigen-binding molecule. An example of a suitable assay to determine whether a given antigen-binding molecule is capable of inhibiting interaction between two interaction partners is a competition ELISA assay.

An antigen-binding molecule which is capable of inhibiting an interaction (e.g. between IL-11Rα and IL-11, or between IL-11Rα and gp130, or between IL-11Rα:gp130 and IL-11, or between IL-11:IL-11Rα and gp130) is identified by the observation of a reduction/decrease in the level of interaction between the interaction partners in the presence of—or following incubation of one or both of the interaction partners with—the antigen-binding molecule, as compared to the level of interaction in the absence of the antigen-binding molecule (or in the presence of an appropriate control antigen-binding molecule). Suitable analysis can be performed in vitro, e.g. using recombinant interaction partners or using cells expressing the interaction partners. Cells expressing interaction partners may do so endogenously, or may do so from nucleic acid introduced into the cell. For the purposes of such assays, one or both of the interaction partners and/or the antigen-binding molecule may be labelled or used in conjunction with a detectable entity for the purposes of detecting and/or measuring the level of interaction.

Ability of an antigen-binding molecule to inhibit interaction between two binding partners can also be determined by analysis of the downstream functional consequences of such interaction, e.g. receptor signalling. For example, downstream functional consequences of interaction between IL-11Rα:gp130 and IL-11 or between IL-11:IL-11Rα and gp130 may include proliferation of fibroblasts, myofibroblast generation from fibroblasts, or gene or protein expression of one or more of collagen, fibronectin, periostin, IL-6, IL-11, αSMA, TIMP1, MMP2.

Fibroblasts according to the present disclosure may be derived from any tissue, including liver, lungs, kidney, heart, blood vessels, eye, skin, pancreas, spleen, bowel (e.g. large or small intestine), brain, and bone marrow. In particular embodiments, for the purposes of analysis of the antigen-binding molecule, the fibroblasts may be cardiac fibroblasts (e.g. atrial fibroblasts), skin fibroblasts, lung fibroblasts, kidney fibroblasts or liver fibroblasts. Fibroblasts may be characterised by gene or protein expression of one or more of COL1A, ACTA2, prolyl-4-hydroxylase, MAS516, and FSP1.

Gene expression can be measured by various means known to those skilled in the art, for example by measuring levels of mRNA by quantitative real-time PCR (qRT-PCR), or by reporter-based methods. Similarly, protein expression can be measured by various methods well known in the art, e.g. by antibody-based methods, for example by western blot, immunohistochemistry, immunocytochemistry, flow cytometry, ELISA, ELISPOT, or reporter-based methods.

In some embodiments, the antigen-binding molecule according to the present invention may inhibit protein expression of one or more markers of fibrosis, e.g. protein expression of one or more of collagen, fibronectin, periostin, IL-6, IL-11, αSMA, TIMP1, MMP2.

The ability of an antigen-binding molecule to inhibit interaction between IL-11Rα:gp130 and IL-11 can, for example, be analysed by stimulating fibroblasts with TGFβ1, incubating the cells in the presence of the antigen-binding molecule and analysing the proportion of cells having αSMA-positive phenotype after a defined period of time. In such example, inhibition of interaction between IL-11Rα:gp130 and IL-11 can be identified by observation of a lower proportion of cells having an αSMA-positive phenotype as compared to positive control condition in which cells are treated with TGFβ1 in the absence of the antigen-binding molecule (or in the presence of an appropriate control antigen-binding molecule), or in the presence of an appropriate control antigen-binding molecule.

Such assays are also suitable for analysing the ability of antigen-binding molecule to inhibit IL-11 mediated signalling.

In some embodiments, the antigen-binding molecule according to the present invention is capable of inhibiting interaction between IL-11Rα and IL-11 to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11Rα and IL-11 in the absence of the antigen-binding molecule (or in the presence of an appropriate control antigen-binding molecule). In some embodiments, the antigen-binding molecule according to the present invention is capable of inhibiting interaction between IL-11Rα and IL-11 to less than 1 times, e.g. one of 50.99 times, 50.95 times, 50.9 times, 50.85 times, 50.8 times, 50.75 times, 50.7 times, 50.65 times, 50.6 times, 50.55 times, 50.5 times, 50.45 times, 50.4 times, 50.35 times, 50.3 times, 50.25 times, 50.2 times, 50.15 times, 50.1 times the level of interaction between IL-11Rα and IL-11 in the absence of the antigen-binding molecule (or in the presence of an appropriate control antigen-binding molecule).

In some embodiments, the antigen-binding molecule according to the present invention is capable of inhibiting interaction between IL-11Rα and gp130 to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11Rα and gp130 in the absence of the antigen-binding molecule (or in the presence of an appropriate control antigen-binding molecule). In some embodiments, the antigen-binding molecule according to the present invention is capable of inhibiting interaction between IL-11Rα and gp130 to less than 1 times, e.g. one of $\leq 0.99$ times, $\leq 0.95$ times, $\leq 0.9$ times, $\leq 0.85$ times, $\leq 0.8$ times, $\leq 0.75$ times, $\leq 0.7$ times, $\leq 0.65$ times, $\leq 0.6$ times, $\leq 0.55$ times, $\leq 0.5$ times, $\leq 0.45$ times, $\leq 0.4$ times, $\leq 0.35$ times, $\leq 0.3$ times, $\leq 0.25$ times, $\leq 0.2$ times, $\leq 0.15$ times, $\leq 0.1$ times the level of interaction between IL-11Rα and gp130 in the absence of the antigen-binding molecule (or in the presence of an appropriate control antigen-binding molecule).

In some embodiments, the antigen-binding molecule according to the present invention is capable of inhibiting interaction between IL-11Rα:gp130 and IL-11 to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11Rα:gp130 and IL-11 in the absence of the antigen-binding molecule (or in the presence of an appropriate control antigen-binding molecule). In some embodiments, the antigen-binding molecule according to the present invention is capable of inhibiting interaction between IL-11Rα:gp130 and IL-11 to less than 1 times, e.g. one of $\leq 0.99$ times, $\leq 0.95$ times, $\leq 0.9$ times, $\leq 0.85$ times, $\leq 0.8$ times, $\leq 0.75$ times, $\leq 0.7$ times, $\leq 0.65$ times, $\leq 0.6$ times, $\leq 0.55$ times, $\leq 0.5$ times, $\leq 0.45$ times, $\leq 0.4$ times, $\leq 0.35$ times, $\leq 0.3$ times, $\leq 0.25$ times, $\leq 0.2$ times, $\leq 0.15$ times, $\leq 0.1$ times the level of interaction between IL-11Rα:gp130 and IL-11 in the absence of the antigen-binding molecule (or in the presence of an appropriate control antigen-binding molecule).

In some embodiments, the antigen-binding molecule according to the present invention is capable of inhibiting interaction between IL-11:IL-11Rα complex and gp130 to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11:IL-11Rα complex and gp130 in the absence of the antigen-binding molecule (or in the presence of an appropriate control antigen-binding molecule). In some embodiments, the antigen-binding molecule is capable of inhibiting interaction between IL-11:IL-11Rα complex and gp130 to less than 1 times, e.g. one of $\leq 0.99$ times, $\leq 0.95$ times, $\leq 0.9$ times, $\leq 0.85$ times, $\leq 0.8$ times, $\leq 0.75$ times, $\leq 0.7$ times, $\leq 0.65$ times, $\leq 0.6$ times, $\leq 0.55$ times, $\leq 0.5$ times, $\leq 0.45$ times, $\leq 0.4$ times, $\leq 0.35$ times, $\leq 0.3$ times, $\leq 0.25$ times, $\leq 0.2$ times, $\leq 0.15$ times, $\leq 0.1$ times the level of interaction between IL-11:IL-11Rα complex and gp130 in the absence of the antigen-binding molecule.

Inhibition of IL-11 mediated signalling can also be analysed using $^3$H-thymidine incorporation and/or Ba/F3 cell proliferation assays such as those described in e.g. Curtis et al. Blood, 1997, 90(11) and Karpovich et al. Mol. Hum. Reprod. 2003 9(2): 75-80. Ba/F3 cells co-express IL-11Rα and gp130.

As used herein, IL-11 mediated signalling and/or processes mediated by IL-11 mediated signalling includes signalling mediated by fragments of IL-11 or IL-11Rα and polypeptide complexes comprising IL-11, IL-11Rα or fragments thereof. IL-11 mediated signaling may be signalling mediated by human IL-11 or IL-11Rα and/or mouse IL-11 or IL-11Rα. IL-11 mediated signalling may occur following binding of IL-11 or an IL-11 containing complex to a receptor to which IL-11 or said complex binds.

In some embodiments, antibodies and fragments according to the present invention are capable of inhibiting the biological activity of IL-11, IL-11Rα or an IL-11- or IL-11Rα-containing complex. In some embodiments, the antibody/fragment binds IL-11Rα in a region which is important for binding to IL-11 or gp130, and thereby disrupts binding and/or IL-11 mediated signalling.

In some embodiments, the antigen-binding molecule according to the present invention is an antagonist of one or more signaling pathways which are activated by signal transduction through receptors comprising IL-11Rα and/or gp130, e.g. IL-11Rα:gp130. In some embodiments, the antigen-binding molecule is capable of inhibiting signalling through one or more immune receptor complexes comprising IL-11Rα and/or gp130, e.g. IL-11Rα:gp130.

In some embodiments, the antigen-binding molecule according to the present invention is capable of inhibiting IL-11-mediated signalling to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of signalling in the absence of the antigen-binding molecule (or in the presence of an appropriate control antigen-binding molecule). In some embodiments, the antigen-binding molecule is capable of reducing IL-11 mediated signalling to less than 1 times, e.g. one of $\leq 0.99$ times, $\leq 0.95$ times, $\leq 0.9$ times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of signalling in the absence of the antigen-binding molecule (or in the presence of an appropriate control antigen-binding molecule).

In some embodiments, the IL-11 mediated signalling is signaling mediated by binding of IL-11 to IL-11Rα:gp130 receptor. Such signalling can be analysed e.g. by treating cells expressing IL-11Rα and gp130 with IL-11, or by stimulating IL-11 production in cells which express IL-11Rα and gp130.

The $IC_{50}$ for antigen-binding molecule for inhibition of IL-11 mediated signalling may be determined, e.g. by culturing Ba/F3 cells expressing IL-11Rα and gp130 in the presence of human IL-11 and the IL-11 binding agent, and measuring $^3$H-thymidine incorporation into DNA.

In some embodiments, the antigen-binding molecule of the present invention may exhibit an $IC_{50}$ of 10 µg/ml or less, preferably one of ≤5 µg/ml, s 4 µg/ml, ≤3.5 µg/ml, ≤3 µg/ml, ≤2 µg/ml, ≤1 µg/ml, ≤0.9 µg/ml, ≤0.8 µg/ml, s 0.7 µg/ml, s 0.6 µg/ml, or ≤0.5 µg/ml in such an assay.

In some embodiments, the IL-11 mediated signalling may be signaling mediated by binding of IL-11:IL-11Rα complex to gp130. In some embodiments, the IL-11:IL-11Rα complex may be soluble. e.g. complex of extracellular domain of IL-11Rα and IL-11, or complex of soluble IL-11Rα isoform/fragment, and IL-11. In some embodiments, the soluble IL-11Rα is a soluble (secreted) isoform of IL-11Rα, or is the liberated product of proteolytic cleavage of the extracellular domain of cell membrane bound IL-11Rα. IL-11 mediated signalling which is mediated by binding of IL-11 bound to IL-11Rα, to gp130 is referred to herein as 'IL-11 trans signalling'.

In some embodiments, the IL-11:IL-11Rα complex may be cell-bound, e.g. complex of cell-membrane bound IL-11Rα and IL-11. Signalling mediated by binding of IL-11:IL-11Rα complex to gp130 can be analysed by treating cells expressing gp130 with IL-11:IL-11Rα complex, e.g. recombinant fusion protein comprising IL-11 joined by a peptide linker to the extracellular domain of IL-11Rα (e.g. hyper IL-11 as described herein).

In some embodiments, the antigen-binding molecule according to the present invention is capable of inhibiting signalling mediated by binding of IL-11:IL-11Rα complex to gp130, and is also capable of inhibiting signalling mediated by binding of IL-11 to IL-11Rα:gp130 receptor.

In some embodiments, the antigen-binding molecule is capable of inhibiting fibroblast proliferation. Proliferation of fibroblasts can be determined by analysing cell division over a period of time. Cell division for a given population of fibroblasts can be analysed, for example, by in vitro analysis of incorporation of $^3$H-thymidine or by CFSE dilution assay, e.g. as described in Fulcher and Wong, Immunol Cell Biol (1999) 77(6): 559-564, hereby incorporated by reference in entirety. Proliferating cells (e.g. proliferating fibroblasts) may also be identified by analysis of incorporation of 5-ethynyl-2'-deoxyuridine (EdU) by an appropriate assay, as described e.g. in Buck et al., Biotechniques. 2008 June; 44(7):927-9, and Sali and Mitchison, PNAS USA 2008 Feb. 19; 105(7): 2415-2420, both hereby incorporated by reference in their entirety.

Fibroblasts according to the present disclosure may be derived from any tissue, including liver, lungs, kidney, heart, blood vessels, eye, skin, pancreas, spleen, bowel (e.g. large or small intestine), brain, and bone marrow. In particular embodiments, for the purposes of analysis of the antigen-binding molecule, the fibroblasts may be cardiac fibroblasts (e.g. atrial fibroblasts), skin fibroblasts, lung fibroblasts, kidney fibroblasts or liver fibroblasts.

In some embodiments, the antigen-binding molecule according to the present invention is capable of inhibiting fibroblast proliferation to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of fibroblast proliferation in the absence of the antigen-binding molecule (or in the presence of an appropriate control antigen-binding molecule). In some embodiments, the antigen-binding molecule is capable of reducing fibroblast proliferation to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of fibroblast proliferation in the absence of the antigen-binding molecule (or in the presence of an appropriate control antigen-binding molecule).

In some embodiments, the antigen-binding molecule according to the present invention is capable of inhibiting a pathological process mediated by IL-11/IL-11R signalling, e.g. following stimulation with a profibrotic factor (e.g. TGFβ1). Pathological processes mediated by IL-11/IL-11R signaling include fibrosis, and can be evaluated either in vitro or in vivo.

In some embodiments, the antigen-binding molecule according to the present invention is capable of inhibiting fibrosis. In some embodiments, the antigen-binding molecule according to the present invention is capable of reversing or regressing fibrosis. In some embodiments the fibrosis is established or severe fibrosis. Inhibiting or the inhibition of fibrosis, as used herein, refers to the ability of an antigen-binding molecule to reduce, restrain or prevent the development of fibrosis. In some embodiments inhibition of fibrosis refers to e.g. a prophylactic effect whereby fibrosis is prevented from developing. In some embodiments inhibition of fibrosis refers to e.g. a treatment effect whereby existing early or late-stage fibrosis is prevented from developing or advancing to a more advanced stage. Reversing/reversal of or regressing/regression of fibrosis, as used herein, refers to the ability of an antigen-binding molecule to ameliorate the fibrotic state from a more developed state to a less developed state, or to lessen the severity of the fibrosis itself or its symptoms. Reversing/reversal of fibrosis may be associated with an improvement in the fibrotic state.

In the experimental examples herein, inhibition, reversal or regression of fibrosis is analysed for example by measuring the number or percentage of ACTA2$^{+ve}$ cells using Operetta high-content imaging system, measuring cell or organ collagen content by assessing hydroxyproline content, measuring ERK activation/phosphorylation by western blotting, and/or measuring the expression level of inflammation markers such as TNFα and CCL2 or fibrotic markers such as TGFβ1, αSMA (ACTA2), TIMP1, COL1A1, COL1A2 or COL3A1 by quantitative PCR. In tissues such as the liver, inhibition, reversal or regression of fibrosis is analysed for example by determining triglyceride content and serum ALT levels.

Fibrosis may be of a particular tissue or several tissues, e.g. liver, lung, kidney, heart, blood vessel, eye, skin, pancreas, spleen, bowel (e.g. large or small intestine), brain, or bone marrow. Fibrosis may be measured by means well known to the skilled person, for example by analysing gene or protein expression of one or more myofibroblast markers and/or gene or protein expression of one or more markers of fibrosis in a given tissue or tissues.

Myofibroblast markers may include one or more of increased αSMA, vimentin, paladin, cofilin or desmin. Markers of fibrosis include increased level of collagen, fibronectin, periostin, IL-6, IL-11, αSMA, TIMP1 and MMP2, extracellular matrix components, number/proportion of myofibroblasts, and organ weight.

Inhibition/reversal/regression of fibrosis can be measured in vitro or in vivo. For example, whether an antigen-binding molecule is capable of inhibiting/reversing/regressing fibrosis in a given tissue can be analysed in vitro by treating fibroblasts derived from that tissue with a profibrotic stimulus, and then analysing whether the antibody can reduce or reverse myofibroblast generation from the fibroblasts (or e.g. some other marker of fibrosis). Whether an antigen-binding molecule is capable of inhibiting/reversing/regressing fibrosis can be analysed in vivo, for example, by administering the antigen-binding molecule to a subject (e.g. a subject that has been exposed to a profibrotic stimulus), and analysing tissue(s) for one or more markers of fibrosis.

In some embodiments, the antigen-binding molecule according to the present invention is capable of inhibiting/reversing/regressing fibrosis to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of fibrosis in the absence of the antigen-binding molecule (or in the presence of an appropriate control antigen-binding molecule). In some embodiments, the antigen-binding molecule is capable of reducing/reversing/regressing fibrosis to less than 1 times, e.g. one of ≤0.99 times, ≤0.95 times, ≤0.9 times, ≤0.8 times, ≤0.85 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of fibrosis in the absence of the antigen-binding molecule (or in the presence of an appropriate control antigen-binding molecule).

In some embodiments, the antigen-binding molecule according to the present invention is capable of inhibiting myofibroblast generation from fibroblasts or stellate cells (e.g. hepatic or pancreatic stellate cells), e.g. following exposure of the fibroblasts or stellate cells to profibrotic factor. Myofibroblast generation from fibroblasts or stellate cells can be investigated by analysis for myofibroblast markers. A profibrotic factor according to the present disclosure may be e.g. TGFβ1, IL-11, IL-13, PDGF, ET-1, oncostatin M (OSM) or ANG2 (AngII). In some embodiments, the antigen-binding molecule according to the present invention is capable of inhibiting fibroblast or stellate cell activation by profibrotic factor.

In some embodiments the antigen-binding molecule according to the present invention is capable of promoting stellate cell senescence. Senescence may be measured by detecting expression of senescence markers such as P16, P21 and P53.

In some embodiments, the antigen-binding molecule is capable of inhibiting gene or protein expression in fibroblasts, stellate cells, or fibroblast/stellate cell-derived cells (e.g. myofibroblasts), of one or more of collagen, fibronectin, periostin, IL-6, IL-11, αSMA, TIMP1, MMP2, TNFα, CCL2 e.g. following stimulation with a profibrotic factor. In some embodiments, the antigen-binding molecule is capable of inhibiting gene or protein expression in fibroblasts, or fibroblast-derived cells (e.g. myofibroblasts), of one or more extracellular matrix components, e.g. following stimulation with a profibrotic factor.

In the experimental examples herein, myofibroblast generation from fibroblasts or stellate cells is analysed by measuring αSMA protein expression levels using Operetta High-Content Imaging System following stimulation of the fibroblasts with TGFβ1.

In some embodiments, the antigen-binding molecule according to the present invention is capable of inhibiting myofibroblast generation from fibroblasts or stellate cells to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of myofibroblast generation from fibroblasts or stellate cells in the absence of the antigen-binding molecule (or in the presence of an appropriate control antigen-binding molecule). In some embodiments, the antigen-binding molecule is capable of reducing myofibroblast generation from fibroblasts or stellate cells to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of myofibroblast generation from fibroblasts or stellate cells in the absence of the antigen-binding molecule (or in the presence of an appropriate control antigen-binding molecule).

In some embodiments, the antigen-binding molecule according to the present invention is capable of inhibiting gene or protein expression in fibroblasts, stellate cells or myofibroblasts of one or more of collagen, fibronectin, periostin, IL-6, IL-11, αSMA, TIMP1, MMP2, TNFα, CCL2 e.g. following stimulation with a profibrotic factor (e.g. TGFβ1). In some embodiments, the antigen-binding molecule according to the present invention is capable of inhibiting gene or protein expression to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of gene or protein expression in the absence of the antigen-binding molecule (or in the presence of an appropriate control antigen-binding molecule). In some embodiments, the antigen-binding molecule is capable of reducing gene or protein expression to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of gene or protein expression in the absence of the antigen-binding molecule (or in the presence of an appropriate control antigen-binding molecule).

In some embodiments, the antigen-binding molecule according to the present invention is capable of inhibiting extracellular matrix production by fibroblasts or stellate cells, e.g. following stimulation with a profibrotic factor (e.g. TGFβ1). Extracellular matrix production can be evaluated, for example, by measuring the level of an extracellular matrix component. Extracellular matrix components according to the present invention include e.g. proteoglycan, heparan sulphate, chondroitin sulphate, keratan sulphate, hyaluronic acid, collagen, periostin, fibronectin, vitronectin, elastin, fibronectin, laminin, nidogen, gelatin and aggrecan. In some embodiments, the antigen-binding molecule according to the present invention is capable of inhibiting collagen secretion from fibroblasts, stellate cells and/or myofibroblasts.

In some embodiments, the antigen-binding molecule according to the present invention is capable of inhibiting extracellular matrix production by fibroblasts or stellate cells to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of extracellular matrix production by fibroblasts or stellate cells in the absence of the antigen-binding molecule (or in the presence of an appropriate control antigen-binding molecule). In some embodiments, the antigen-binding molecule is capable of reducing extracellular matrix production by fibroblasts or stellate cells to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of extracellular matrix production in the absence of the antigen-binding molecule (or in the presence of an appropriate control antigen-binding molecule).

In some embodiments the antigen-binding molecule according to the present invention is capable of upregulating gene or protein expression in hepatic cells of one or more genes/proteins involved in lipogenesis and/or β-oxidation. Such genes/proteins may be e.g. ACOX1 (acyl-CoA oxidase 1), SCD1 (stearoyl-CoA desaturase 1), FASN (fatty acid synthase), or SREBF1 (sterol regulatory element-binding protein 1). In some embodiments, the antigen-binding molecule according to the present invention is capable of upregulating gene or protein expression by more than 1 times, e.g. one of ≥1.01 times, ≥1.05 times, ≥1.1 times, ≥1.15 times, ≥1.2 times, ≥1.25 times, ≥1.3 times, ≥1.35 times, ≥1.4 times, ≥1.45 times, ≥1.5 times, ≥1.55 times, ≥1.6 times, ≥1.65 times, ≥1.7 times, ≥1.75 times, ≥1.8 times, ≥1.85 times, ≥1.9 times, ≥1.95 times, ≥2 times, ≥2.5 times, ≥3 times, ≥3.5 times, ≥4 times, ≥4.5 times, ≥5 times, ≥6 times, ≥7 times, ≥8 times, ≥9 times or ≥10 times the level of gene or protein expression in the absence of the antigen-binding molecule (or in the presence of an appropriate control antigen-binding molecule).

In some embodiments the antigen-binding molecule according to the present invention is capable of inhibiting migratory and/or invasive behaviour, i.e. inhibiting migration and/or invasion, of fibroblasts, stellate cells or myofibroblasts. Migration and invasion of such cells can be critical in the pathology of fibrosis. Migration of cells can be evaluated using e.g. polycarbonate membranes and invasive stimulants such as TGFβ1 or CCL2. Invasion of cells can be measured using e.g. Boyden chamber invasion assays or ECM-coated matrigel. In some embodiments the antigen-binding molecule according to the present invention is capable of inhibiting migration and/or invasion of fibroblasts, stellate cells or myofibroblasts to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of migration and/or invasion in the absence of the antigen-binding molecule (or in the presence of an appropriate control antigen-binding molecule). In some embodiments, the antigen-binding molecule is capable of reducing migration and/or invasion to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of migration and/or invasion In the absence of the antigen-binding molecule (or in the presence of an appropriate control antigen-binding molecule).

In some embodiments the antigen-binding molecule according to the present invention is capable of inhibiting the presence of immune cells in an organ. In some embodiments the antigen-binding molecule according to the present invention is capable of reducing the number of immune cells in an organ. The organ may be an organ susceptible to, or suffering from, fibrosis, e.g. liver or kidney. The immune cells may be CD45$^+$ cells, e.g. CD3$^+$CD4$^+$ T cells, CD3$^+$CD8$^+$ T cells, B lymphocytes, granulocytes and monocytes. The immune cells may express murine monocyte marker LyC6. In some embodiments the antigen-binding molecule according to the present invention is capable of reducing the number of immune cells in an organ to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the number of immune cells in an organ In the absence of the antigen-binding molecule (or in the presence of an appropriate control antigen-binding molecule). In some embodiments, the antigen-binding molecule is capable of reducing the number of immune cells in an organ to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the number of immune cells in an organ in the absence of the antigen-binding molecule (or in the presence of an appropriate control antigen-binding molecule).

In some embodiments, the antigen-binding molecule according to the present invention is capable of inhibiting proliferation and/or survival of cells of a cancer. The skilled person is able to determine whether an antigen-binding molecule is capable of inhibiting proliferation and/or survival of cells of a cancer for example by analysing the effect of the antigen-binding molecule on cells of the cancer. For example, proliferation of cells can be measured as described herein, e.g. by $^3$H thymidine incorporation or CFSE dilution assays. Cell survival can be analysed by measuring cells for markers of cell viability/cell death following treatment with the antigen-binding molecule.

In some embodiments, the antigen-binding molecule according to the present invention is capable of inhibiting proliferation and/or survival of cells of a cancer to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of proliferation and/or survival of cells of a cancer in the absence of the antigen-binding molecule (or In the presence of an appropriate control antigen-binding molecule). In some embodiments, the antigen-binding molecule is capable of reducing proliferation and/or survival of cells of a cancer to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of proliferation and/or survival of cells of a cancer in the absence of the antigen-binding molecule (or in the presence of an appropriate control antigen-binding molecule).

In some embodiments, the antigen-binding molecule of the present invention inhibits the development and/or progression of cancer in vivo. In some embodiments the antigen-binding molecule causes killing of cancer cells, e.g. by effector immune cells. In some embodiments the antigen-binding molecule causes a reduction in the number of cancer cells in vivo, e.g. as compared to an appropriate control condition. In some embodiments the antigen-binding molecule inhibits tumor growth, e.g. as determined by measuring tumor size/volume over time.

The antigen-binding molecule of the present invention may be analysed for the ability to inhibit development and/or progression of cancer in an appropriate in vivo model. The cancer may be a cancer in which IL-11 mediated signalling and/or cells expressing/comprising IL-11Rα or a complex comprising IL-11Rα are pathologically implicated. Such cancers include those described in Xu et al., Cancer Lett. (2016) 373(2):156-63 and Johnstone et al., Cytokine & Growth Reviews (2015) 26(5): 489-498, both of which are hereby incorporated by reference in their entirety.

In some embodiments, administration of an antigen-binding molecule according to the present invention may cause one or more of: inhibition of the development/progression of the cancer, a delay to/prevention of onset of the cancer, a reduction in/delay to/prevention of tumor growth, a reduction in/delay to/prevention of metastasis, a reduction in the severity of the symptoms of the cancer, a reduction in the number of cancer cells, a reduction in tumour size/volume, and/or an increase in survival (e.g. progression free survival), e.g. as determined in an appropriate in vivo model of the cancer. In some embodiments an antigen-binding molecule according to the present invention provides an additive effect when administered in conjunction, e.g. separately, simultaneously or sequentially, with a chemotherapeutic agent, compared to the chemotherapeutic agent administered alone. The additive effect may be any effect described herein, such as reduction of IL-11 signalling, inhibition of the development/progression of a cancer and/or inhibition of tumour growth.

In some embodiments, the antigen-binding molecule according to the present invention is capable of inhibiting tumour growth to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of tumour growth in the absence of the antigen-binding molecule (or in the presence of an appropriate control antigen-binding molecule). In some embodiments, the antigen-binding molecule is capable of reducing tumour growth to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of tumour growth in the absence of the antigen-binding molecule (or in the presence of an appropriate control antigen-binding molecule).

In some embodiments, the antigen-binding molecule of the present invention is capable of causing killing of cells expressing/comprising IL-11Rα or a complex comprising IL-11Rα. Killing of cells expressing/comprising IL-11Rα or a complex comprising IL-11Rα may be increased through an effector function of the antigen-binding molecule. In embodiments wherein antigen-binding molecule comprises an Fc region the antigen-binding molecule may cause killing of cells expressing/comprising IL-11Rα or a complex comprising IL-11Rα through one or more of complement dependent cytotoxicity (CDC), antibody-dependent cell-mediated cytotoxicity (ADCC) and antibody-dependent cellular phagocytosis (ADCP).

An antigen-binding molecule which is capable of causing killing of cells expressing/comprising IL-11Rα or a complex comprising IL-11Rα can be identified by observation of a level of killing of cells expressing/comprising IL-11Rα or a complex comprising IL-11Rα in the presence of—or following incubation of the cells expressing/comprising IL-11Rα or a complex comprising IL-11Rα with—the antigen-binding molecule, as compared to the level of cell killing detected in the absence of the antigen-binding molecule (or in the presence of an appropriate control antigen-binding molecule), in an appropriate assay. Assays of CDC, ADCC and ADCP are well known to the skilled person. The level of killing of cells expressing/comprising IL-11Rα or a complex comprising IL-11Rα can also be determined by measuring the number/proportion of viable and/or non-viable cells expressing/comprising IL-11Rα or a complex comprising IL-11Rα following exposure to different treatment conditions.

In some embodiments, the antigen-binding molecule of the present invention is capable of causing killing of cells expressing/comprising IL-11Rα or a complex comprising IL-11Rα to more than 1 times, e.g. ≥1.01 times, ≥1.02 times, ≥1.03 times, ≥1.04 times, ≥1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times or ≥10 times the level of killing observed in the absence of the antigen-binding molecule (or in the presence of an appropriate control antigen-binding molecule).

In some embodiments, the antigen-binding molecule of the present invention is capable of reducing the number of cells expressing/comprising IL-11Rα or a complex comprising IL-11Rα to less than 1 times, e.g. ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or s≤0.01 times the number of cells expressing/comprising IL-11Rα or a complex comprising IL-11Rα detected following incubation in the absence of the antigen-binding molecule (or following incubation in the presence of an appropriate control antigen-binding molecule), in a comparable assay. Cell numbers and proportions can be determined e.g. by flow cytometry analysis using antibodies allowing detection of cell types.

In some embodiments, the antigen-binding molecule according to the present invention has one or more similar or improved properties as compared to a reference antibody/antigen-binding fragment thereof capable of binding to IL-11Rα.

In some embodiments, the antigen-binding molecule of the present invention displays one or more of the following properties as compared to a reference antibody/antigen-binding fragment thereof capable of binding to IL-11Rα:

(i) binds to IL-11Rα with similar or greater specificity (i.e. has similar or reduced cross-reactivity for proteins of the IL-6 cytokine receptor family other than IL-11Rα);

(ii) binds to IL-11Rα (e.g. human IL-11Rα and/or mouse IL-11Rα) with similar or greater affinity (e.g. has similar or lower EC50 as determined by ELISA; e.g. has similar or lower $K_D$ as determined by SPR analysis);

(iii) similar or greater inhibition of interaction between IL-11Rα and IL-11Rα;

(iv) similar or greater inhibition of interaction between IL-11Rα and gp130;

(v) similar or greater inhibition of interaction between IL-11Rα:gp130 receptor complex and IL-11;

(vi) similar or greater inhibition of interaction between IL-11:IL-11Rα complex and gp130;

(vii) similar or greater inhibition of IL-11/IL-11R signalling;

(viii) similar or greater inhibition of signalling mediated by IL-11 (e.g. has similar or lower IC50 as determined by ELISA in a suitable assay);

(ix) similar or greater inhibition of signalling mediated by binding of IL-11 to IL-11Rα:gp130 receptor complex;

(x) similar or greater inhibition of signalling mediated by binding of IL-11:IL-11Rα complex to gp130 (i.e. IL-11 trans signalling);

(xi) similar or greater inhibition of fibroblast proliferation;

(xii) similar or greater inhibition of myofibroblast generation from fibroblasts;

(xiii) similar or greater inhibition reversal/regression of myofibroblast generation from fibroblasts;

(xiv) similar or greater inhibition of myofibroblast generation from stellate cells, e.g. hepatic or pancreatic stellate cells;

(xv) similar or greater reversal/regression of myofibroblast generation from stellate cells, e.g. hepatic or pancreatic stellate cells;

(xvi) similar or greater inhibition of migratory and/or invasive behaviour (i.e. inhibition of migration and/or invasion) of fibroblasts, stellate cells or myofibroblasts;

(xvii) similar or greater inhibition of the presence of immune cells in an organ;

(xvii) similar or greater inhibition of a pathological process mediated by IL-11/IL-11R signalling;

(xix) similar or greater inhibition of fibrosis;

(xx) similar or greater reversal/regression of fibrosis;

(xxi) similar or greater inhibition of gene or protein expression in fibroblasts of one or more of collagen, fibronectin, periostin, IL-6, IL-11, αSMA (ACTA2), TIMP1, MMP2, TNFα, CCL2 e.g. following stimulation with a profibrotic factor;

(xxii) similar or greater inhibition of extracellular matrix production by fibroblasts or stellate cells;

(xxiii) similar or greater inhibition of proliferation and/or survival of cells of a cancer;

(xxvi) similar or greater inhibition of development and/or progression of cancer in vivo;

(xxv) similar or greater inhibition of tumour growth;

(xxvi) similar or greater killing of cells expressing/comprising IL-11Rα or a complex comprising IL-11Rα.

In some embodiments, "greater specificity" or "greater affinity" or "a greater inhibition" or "greater killing" refers, respectively, to a level of specificity, affinity, inhibition or killing which is greater than 1 times, e.g. ≥1.01 times, ≥1.02 times, ≥1.03 times, ≥1.04 times, ≥1.05 times, ≥1.06 times, ≥1.07 times, ≥1.08 times, ≥1.09 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥2.1 times, ≥2.2 times, ≥2.3 times, ≥2.4 times, ≥2.5 times, ≥2.6 times, ≥2.7 times, ≥2.8 times, ≥2.9 times, ≥3 times, ≥3.5 times, ≥4 times, ≥4.5 times, ≥5 times, ≥6 times, ≥7 times, ≥8 times, ≥9 times, ≥10 times, ≥15 times, ≥20 times, ≥25 times, ≥30 times, ≥35 times, ≥40 times, ≥45 times, ≥50 times, ≥60 times, ≥70 times, ≥80 times, ≥90 times, ≥100 times, ≥200 times, ≥300 times, ≥400 times, ≥500 times, ≥600 times, ≥700 times, ≥800 times, ≥900 times, ≥1000 times the level displayed by the reference antibody/antigen-binding fragment thereof capable of binding to IL-11Rα, as determined in an appropriate assay.

In some embodiments, "similar specificity" or "similar affinity" or "a similar inhibition" or "similar killing" refers, respectively, to a level of specificity, affinity, inhibition or killing which is ≥0.2 times and ≤5 times, e.g. ≥0.3 times and ≤4 times, ≥0.4 times and ≤3 times, ≥0.5 times and ≤2 times, ≥0.6 times and ≤1.75 times, ≥0.7 times and ≤1.5 times, ≥0.75 times and ≤1.25 times, ≥0.8 times and ≤1.2 times, ≥0.85 times and ≤1.15 times, ≥0.9 times and ≤1.1 times, ≥0.91 times and ≤1.09 times, ≥0.92 times and ≤1.08 times, ≥0.93 times and ≤1.07 times, ≥0.94 times and ≤1.06 times, ≥0.95 times and ≤1.05 times, ≥0.96 times and ≤1.04 times, ≥0.97 times and ≤1.03 times, ≥0.98 times and ≤1.02 times, or ≥0.99 times and ≤1.01 times the level displayed by the reference antibody/antigen-binding fragment thereof capable of binding to IL-11Rα, as determined in an appropriate assay.

In some embodiments the reference antibody/antibody fragment capable of binding to IL-11Rα may comprise the CDRs of anti-IL-11Rα antibody clone BSO-9A7. In some embodiments the reference antibody/antibody fragment capable of binding to IL-11Rα may comprise or consist of the VH and VL sequences of anti-IL-11Rα antibody clone BSO-9A7.

In some embodiments the reference antibody/antibody fragment capable of binding to IL-11Rα may comprise a VH comprising or consisting of the amino acid sequence of SEQ ID NO:7, and a VL comprising or consisting of the amino acid sequence of SEQ ID NO:59.

Chimeric Antigen Receptors (CARs)

The present invention also provides Chimeric Antigen Receptors (CARs) comprising the antigen-binding molecules or polypeptides of the present invention.

CARs are recombinant receptors that provide both antigen-binding and T cell activating functions. CAR structure and engineering is reviewed, for example, in Dotti et al., Immunol Rev (2014) 257(1), hereby incorporated by reference in its entirety. CARs comprise an antigen-binding region linked to a cell membrane anchor region and a signalling region. An optional hinge region may provide separation between the antigen-binding region and cell membrane anchor region, and may act as a flexible linker.

The CAR of the present invention comprises an antigen-binding region which comprises or consists of the antigen-binding molecule of the present invention, or which comprises or consists of a polypeptide according to the invention.

The cell membrane anchor region is provided between the antigen-binding region and the signalling region of the CAR and provides for anchoring the CAR to the cell membrane of a cell expressing a CAR, with the antigen-binding region in the extracellular space, and signalling region inside the cell. In some embodiments, the CAR comprises a cell membrane anchor region comprising or consisting of an amino acid sequence which comprises, consists of, or is derived from, the transmembrane region amino acid sequence for one of CD3-ζ, CD4, CD8 or CD28. As used herein, a region which is 'derived from' a reference amino acid sequence comprises an amino acid sequence having at least 60%, e.g. one of at least 65%, 70%, 75%, 80%, 85%, 90%, 91%, 92%, 93%, 94%, 95%, 96%, 97%, 98%, 99% or 100% sequence identity to the reference sequence.

The signalling region of a CAR allows for activation of the T cell. The CAR signalling regions may comprise the amino acid sequence of the intracellular domain of CD3-ζ, which provides immunoreceptor tyrosine-based activation motifs (ITAMs) for phosphorylaton and activation of the CAR-expressing T cell. Signalling regions comprising sequences of other ITAM-containing proteins such as FcγRI have also been employed in CARs (Haynes et al., 2001 J Immunol 166(1):182-187). Signalling regions of CARs may also comprise co-stimulatory sequences derived from the signalling region of co-stimulatory molecules, to facilitate activation of CAR-expressing T cells upon binding to the target protein. Suitable co-stimulatory molecules include CD28, OX40, 4-1 BB, ICOS and CD27. In some cases CARs are engineered to provide for co-stimulation of different intracellular signalling pathways. For example, signalling associated with CD28 costimulation preferentially activates the phosphatidylinositol 3-kinase (P13K) pathway, whereas the 4-1BB-mediated signalling is through TNF receptor associated factor (TRAF) adaptor proteins. Signalling regions of CARs therefore sometimes contain co-stimulatory sequences derived from signalling regions of more than one co-stimulatory molecule. In some embodiments, the CAR of the present invention comprises one or more co-stimulatory sequences comprising or consisting of an amino acid sequence which comprises, consists of, or is derived from, the amino acid sequence of the intracellular domain of one or more of CD28, OX40, 4-1BB, ICOS and CD27.

An optional hinge region may provide separation between the antigen-binding domain and the transmembrane domain, and may act as a flexible linker. Hinge regions may be derived from IgG1. In some embodiments, the CAR of the present invention comprises a hinge region comprising or consisting of an amino acid sequence which comprises, consists of, or is derived from, the amino acid sequence of the hinge region of IgG1.

Also provided is a cell comprising a CAR according to the invention. The CAR according to the present invention may be used to generate CAR-expressing immune cells, e.g. CAR-T or CAR-NK cells. Engineering of CARs into immune cells may be performed during culture, in vitro.

The antigen-binding region of the CAR of the present invention may be provided with any suitable format, e.g. scFv, scFab, etc.

Nucleic Acids and Vectors

The present invention provides a nucleic acid, or a plurality of nucleic acids, encoding an antigen-binding molecule, polypeptide or CAR according to the present invention.

In some embodiments, the nucleic acid is purified or isolated, e.g. from other nucleic acid, or naturally-occurring biological material. In some embodiments the nucleic acid(s) comprise or consist of DNA and/or RNA.

The present invention also provides a vector, or plurality of vectors, comprising the nucleic acid or plurality of nucleic acids according to the present invention.

The nucleotide sequence may be contained in a vector, e.g. an expression vector. A "vector" as used herein is a nucleic acid molecule used as a vehicle to transfer exogenous nucleic acid into a cell. The vector may be a vector for expression of the nucleic acid in the cell. Such vectors may include a promoter sequence operably linked to the nucleotide sequence encoding the sequence to be expressed. A vector may also include a termination codon and expression enhancers. Any suitable vectors, promoters, enhancers and termination codons known in the art may be used to express a peptide or polypeptide from a vector according to the invention.

The term "operably linked" may include the situation where a selected nucleic acid sequence and regulatory nucleic acid sequence (e.g. promoter and/or enhancer) are covalently linked in such a way as to place the expression of nucleic acid sequence under the influence or control of the regulatory sequence (thereby forming an expression cassette). Thus a regulatory sequence is operably linked to the selected nucleic acid sequence if the regulatory sequence is capable of effecting transcription of the nucleic acid sequence. The resulting transcript(s) may then be translated into a desired peptide(s)/polypeptide(s).

Suitable vectors include plasmids, binary vectors, DNA vectors, mRNA vectors, viral vectors (e.g. gammaretroviral vectors (e.g. murine Leukemia virus (MLV)-derived vectors), lentiviral vectors, adenovirus vectors, adeno-associated virus vectors, vaccinla virus vectors and herpesvirus vectors), transposon-based vectors, and artificial chromosomes (e.g. yeast artificial chromosomes).

In some embodiments, the vector may be a eukaryotic vector, e.g. a vector comprising the elements necessary for expression of protein from the vector in a eukaryotic cell. In some embodiments, the vector may be a mammalian vector, e.g. comprising a cytomegalovirus (CMV) or SV40 promoter to drive protein expression.

Constituent polypeptides of an antigen-binding molecule according to the present invention may be encoded by different nucleic acids of the plurality of nucleic acids, or by different vectors of the plurality of vectors.

Cells Comprising/Expressing the Antigen-Binding Molecules and Polypeptides

The present invention also provides a cell comprising or expressing an antigen-binding molecule, polypeptide or CAR according to the present invention. Also provided is a cell comprising or expressing a nucleic acid, a plurality of nucleic acids, a vector or a plurality of vectors according to the invention.

The cell may be a eukaryotic cell, e.g. a mammalian cell. The mammal may be a primate (rhesus, cynomolgous, non-human primate or human) or a non-human mammal (e.g. rabbit, guinea pig, rat, mouse or other rodent (including any animal in the order Rodentia), cat, dog, pig, sheep, goat, cattle (including cows, e.g. dairy cows, or any animal in the order Bos), horse (including any animal in the order Equidae), donkey, and non-human primate).

The present invention also provides a method for producing a cell comprising a nucleic acid(s) or vector(s) according to the present invention, comprising introducing a nucleic acid, a plurality of nucleic acids, a vector or a plurality of vectors according to the present invention into a cell. In some embodiments, introducing an isolated nucleic acid(s) or vector(s) according to the invention into a cell comprises transformation, transfection, electroporation or transduction (e.g. retroviral transduction).

The present invention also provides a method for producing a cell expressing/comprising an antigen-binding molecule, polypeptide or CAR according to the present invention, comprising introducing a nucleic acid, a plurality of nucleic acids, a vector or a plurality of vectors according to the present invention in a cell. In some embodiments, the methods additionally comprise culturing the cell under conditions suitable for expression of the nucleic acid(s) or vector(s) by the cell. In some embodiments, the methods are performed in vitro.

The present invention also provides cells obtained or obtainable by the methods according to the present invention.

Producing the Antigen-Binding Molecules and Polypeptides

Antigen-binding molecules and polypeptides according to the invention may be prepared according to methods for the production of polypeptides known to the skilled person.

Polypeptides may be prepared by chemical synthesis, e.g. liquid or solid phase synthesis. For example, peptides/polypeptides can by synthesised using the methods described in, for example, Chandrudu et al., Molecules (2013), 18: 4373-4388, which is hereby incorporated by reference in its entirety.

Alternatively, antigen-binding molecules and polypeptides may be produced by recombinant expression. Molecular biology techniques suitable for recombinant production of polypeptides are well known in the art, such as those set out in Green and Sambrook, Molecular Cloning: A Laboratory Manual (4th Edition), Cold Spring Harbor Press, 2012, and in Nat Methods. (2008); 5(2): 135-146 both of which are hereby incorporated by reference in their entirety. Methods for the recombinant production of antigen-binding molecules are also described in Frenzel et al., Front Immunol. (2013); 4: 217 and Kunert and Reinhart, Appl Microblol Biotechnol. (2016) 100: 3451-3461, both of which are hereby incorporated by reference in their entirety.

In some cases the antigen-binding molecule of the present invention are comprised of more than one polypeptide chain. In such cases, production of the antigen-binding molecules may comprise transcription and translation of more than one polypeptide, and subsequent association of the polypeptide chains to form the antigen-binding molecule.

For recombinant production according to the invention, any cell suitable for the expression of polypeptides may be used. The cell may be a prokaryote or eukaryote. In some embodiments the cell is a prokaryotic cell, such as a cell of archaea or bacteria. In some embodiments the bacteria may be Gram-negative bacteria such as bacteria of the family Enterobacteriaceae, for example *Escherichia coli*. In some embodiments, the cell is a eukaryotic cell such as a yeast cell, a plant cell, insect cell or a mammalian cell, e.g. CHO, HEK (e.g. HEK293), HeLa or COS cells. In some embodiments, the cell is a CHO cell that transiently or stably expresses the polypeptides.

In some cases the cell is not a prokaryotic cell because some prokaryotic cells do not allow for the same folding or post-translational modifications as eukaryotic cells. In addition, very high expression levels are possible in eukaryotes and proteins can be easier to purify from eukaryotes using appropriate tags. Specific plasmids may also be utilised which enhance secretion of the protein into the media.

In some embodiments polypeptides may be prepared by cell-free-protein synthesis (CFPS), e.g. according using a system described in Zemella et al. Chembiochem (2015) 16(17): 2420-2431, which is hereby incorporated by reference in its entirety.

Production may involve culture or fermentation of a eukaryotic cell modified to express the polypeptide(s) of interest. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted polypeptide(s). Culture, fermentation and separation techniques are well known to those of skill in the art, and are described, for example, in Green and Sambrook, Molecular Cloning: A Laboratory Manual (4th Edition; incorporated by reference herein above).

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culturing the cells that express the antigen-binding molecule/polypeptide(s), the polypeptide(s) of interest may be isolated. Any suitable method for separating proteins from cells known in the art may be used. In order to isolate the polypeptide it may be necessary to separate the cells from nutrient medium. If the polypeptide(s) are secreted from the cells, the cells may be separated by centrifugation from the culture media that contains the secreted polypeptide(s) of interest. If the polypeptide(s) of interest collect within the cell, protein isolation may comprise centrifugation to separate cells from cell culture medium, treatment of the cell pellet with a lysis buffer, and cell disruption e.g. by sonification, rapid freeze-thaw or osmotic lysis.

It may then be desirable to isolate the polypeptide(s) of interest from the supernatant or culture medium, which may contain other protein and non-protein components. A common approach to separating protein components from a supernatant or culture medium is by precipitation. Proteins of different solubilities are precipitated at different concentrations of precipitating agent such as ammonium sulfate. For example, at low concentrations of precipitating agent, water soluble proteins are extracted. Thus, by adding different increasing concentrations of precipitating agent, proteins of different solubilities may be distinguished. Dialysis may be subsequently used to remove ammonium sulfate from the separated proteins.

Other methods for distinguishing different proteins are known in the art, for example ion exchange chromatography and size chromatography. These may be used as an alternative to precipitation, or may be performed subsequently to precipitation.

Once the polypeptide(s) of interest have been isolated from culture it may be desired or necessary to concentrate the polypeptide(s). A number of methods for concentrating proteins are known in the art, such as ultrafiltration or lyophilisation.

Compositions

The present invention also provides compositions comprising the antigen-binding molecules, polypeptides, CARs, nucleic acids, expression vectors and cells described herein.

The antigen-binding molecules, polypeptides. CARs, nucleic acids, expression vectors and cells described herein may be formulated as pharmaceutical compositions or medicaments for clinical use and may comprise a pharmaceutically acceptable carrier, diluent, excipient or adjuvant. The composition may be formulated for topical, parenteral, systemic, intracavitary, intravenous, intra-arterial, intramuscular, intrathecal, intraocular, intraconjunctival, intratumoral, subcutaneous, intradermal, intrathecal, oral or transdermal routes of administration which may include injection or infusion.

Suitable formulations may comprise the antigen-binding molecule in a sterile or isotonic medium. Medicaments and pharmaceutical compositions may be formulated in fluid, including gel, form. Fluid formulations may be formulated for administration by injection or infusion (e.g. via catheter) to a selected region of the human or animal body.

In some embodiments the composition is formulated for injection or infusion, e.g. into a blood vessel or tumor.

In accordance with the invention described herein methods are also provided for the production of pharmaceutically useful compositions, such methods of production may comprise one or more steps selected from: producing an antigen-binding molecule, polypeptide, CAR, nucleic acid (or plurality thereof), expression vector (or plurality thereof) or cell described herein; isolating an antigen-binding molecule, polypeptide, CAR, nucleic acid (or plurality thereof), expression vector (or plurality thereof) or cell described herein; and/or mixing an antigen-binding molecule, polypeptide, CAR, nucleic acid (or plurality thereof), expression vector (or plurality thereof) or cell described herein with a pharmaceutically acceptable carrier, adjuvant, excipient or diluent.

For example, a further aspect the invention described herein relates to a method of formulating or producing a medicament or pharmaceutical composition for use in the treatment of a disease/condition (e.g. a cancer), the method comprising formulating a pharmaceutical composition or medicament by mixing an antigen-binding molecule, polypeptide, CAR, nucleic acid (or plurality thereof), expression vector (or plurality thereof) or cell described herein with a pharmaceutically acceptable carrier, adjuvant, excipient or diluent.

Therapeutic and Prophylactic Applications

The antigen-binding molecules, polypeptides, CARs, nucleic acids, expression vectors, cells and compositions described herein find use in therapeutic and prophylactic methods.

The present invention provides an antigen-binding molecule, polypeptide, CAR, nucleic acid (or plurality thereof), expression vector (or plurality thereof), cell or composition described herein for use in a method of medical treatment or prophylaxis. Also provided is the use of an antigen-binding molecule, polypeptide, CAR, nucleic acid (or plurality thereof), expression vector (or plurality thereof), cell or composition described herein in the manufacture of a medicament for treating or preventing a disease or condition. Also provided is a method of treating or preventing a disease or condition, comprising administering to a subject a therapeutically or prophylactically effective amount of an antigen-binding molecule, polypeptide, CAR, nucleic acid (or plurality thereof), expression vector (or plurality thereof), cell or composition described herein.

The methods may be effective to reduce the development or progression of a disease/condition, alleviation of the symptoms of a disease/condition or reduction in the pathology of a disease/condition. The methods may be effective to prevent progression of the disease/condition, e.g. to prevent worsening of, or to slow the rate of development of, the disease/condition. In some embodiments the methods may lead to an improvement in the disease/condition, e.g. a reduction in the symptoms of the disease/condition or reduction in some other correlate of the severity/activity of the disease/condition. In some embodiments the methods may prevent development of the disease/condition a later stage (e.g. a chronic stage or metastasis). In some embodiments the methods may be effective to reverse or regress the disease/condition, e.g. the pathology of a disease/condition may be reversed from a later developmental stage to an earlier developmental stage. In some embodiments the methods may be effective to reverse or regress the symptoms of the disease/condition or some other correlate of the severity/activity of the disease/condition. In some embodiments the methods may be effective to reverse/regress a disease/condition to a state similar to the state observed in a subject without the disease/condition.

It will be appreciated that the articles of the present invention may be used for the treatment/prevention of any disease/condition that would derive therapeutic or prophylactic benefit from a reduction in the level of (i.e. inhibition or antagonism of) IL-11 mediated signalling, or a reduction in the number and/or activity of cells expressing IL-11Rα or a complex comprising IL-11Rα.

For example, the disease/condition may be a disease/condition in which IL-11 mediated signalling is pathologically implicated, e.g. a disease/condition in which an increased level of IL-11 mediated signalling is positively associated with the onset, development or progression of the disease/condition, and/or severity of one or more symptoms of the disease/condition, or for which an increased level of IL-11 mediated signalling is a risk factor for the onset, development or progression of the disease/condition.

For example, the disease/condition may be a disease/condition in which cells expressing IL-11Rα are pathologically implicated, e.g. a disease/condition in which an increased number/proportion of cells expressing IL-11Rα is positively associated with the onset, development or progression of the disease/condition, and/or severity of one or more symptoms of the disease/condition, or for which an increased number/proportion of cells expressing IL-11Rα is a risk factor for the onset, development or progression of the disease/condition.

In some embodiments, the disease/condition to be treated/prevented in accordance with the present invention is a disease/condition characterised by an increase in the level of IL-11 mediated signalling or a correlate thereof (e.g. in an organ/tissue in which the symptoms of the disease/condition manifest) as compared to the level of IL-11 mediated signalling/correlate thereof in the absence of the disease/condition.

In some embodiments, the disease/condition to be treated/prevented in accordance with the present invention is a disease/condition characterised by an increase in the number/proportion/activity of cells expressing IL-11Rα, e.g. as compared to the number/proportion/activity of cells expressing IL-11Rα in the absence of the disease/condition.

In some embodiments, a subject may be selected for treatment/prophylaxis as described herein based on the detection of an increase in the level of IL-11 mediated signalling or a correlate thereof and/or an increase in the number/proportion/activity of cells expressing IL-11Rα, e.g. in the periphery, or in an organ/tissue which is affected by the disease/condition (e.g. an organ/tissue in which the symptoms of the disease/condition manifest). The disease/condition may affect any tissue or organ or organ system. In some embodiments the disease/condition may affect several tissues/organs/organ systems.

In some embodiments a subject may be selected for therapy/prophylaxis in accordance with the present invention based on determination that the subject has an increase in the level of IL-11 mediated signalling or a correlate thereof and/or an increase in the number/proportion/activity of cells expressing IL-11Rα, e.g. in the periphery, or in an organ/tissue relative to the level of L-11 mediated signalling/correlate thereof, or number/proportion/activity of cells expressing IL-11Rα in a healthy subject.

The antigen-binding molecules of the present invention are preferably able to bind to and inhibit the biological activity of IL-11Rα and IL-11Rα-containing molecules/complexes (e.g. IL-11:IL-11Rα complex). Accordingly, the antigen-binding molecules of the present invention find use in the treatment or prevention of diseases and disorders in which IL-11Rα is implicated in the pathology of the disease/disorder. That is, the antigen-binding molecules of the present invention find use in the treatment or prevention of diseases and disorders associated with IL-11 mediated signalling.

In some embodiments, the disease/disorder may be associated with increased IL-11, IL-11Rα and/or gp130 gene or protein expression, e.g. as compared to the control (i.e. non-diseased) state. In some embodiments, the disease/disorder may be associated with an increased level of IL-11-mediated signalling (e.g. IL-11/IL-11R signalling) as compared to the control state. In some embodiments, the disease/disorder may be associated with an increased level of signalling through ERK and/or STAT3 pathways as compared to the control state. In some embodiments, the increased expression/activity of IL-11, IL-11Rα and/or gp130, and/or the increased level of IL-11-mediated signalling, may be observed in effector cells of the disease/disorder. In some embodiments, the increased expression/activity of IL-11, IL-11Rα and/or gp130, and/or the increased level of IL-11-mediated signalling, may be observed in cells other than the effector cells.

Signalling through ERK can be measured e.g. using an assay for ERK phosphorylation such as an assay described in Assay Guidance Manual: Phospho-ERK Assays, Kim E. Garbison, Beverly A. Heinz, Mary E. Lajiness, Jeffrey R. Weidner, and G. Sitta Sittampalam, Eli Lilly & Company, Sittampalam G S, Coussens N P, Nelson H, et al., editors Bethesda (Md.): Eli Lilly & Company and the National Center for Advancing Translational Sciences; 2004. Signalling through STAT3 can be measured e.g. using an assay for phosphorylation of STAT3, such as the Phospho-STAT3 (Tyr705) Cellular Assay Kit (Cisbio Assays).

In some embodiments, the treatment is of a disease/disorder for which a reduction in IL-11 mediated signalling is therapeutic. In some embodiments, the treatment is of a disease/disorder associated with excess ERK and/or STAT3 signalling. In some embodiments, the treatment is of a disease/disorder associated with excess proliferation or hyperactivation of fibroblasts, or associated with an excess of myofibroblasts.

In some embodiments, the treatment may be aimed at preventing or treating a disease/disorder by decreasing the number or proportion of myofibroblasts or αSMA-positive fibroblasts.

In some embodiments, the disease/disorder may be fibrosis, a fibrotic condition, or a disease/disorder characterised by fibrosis. As used herein, "fibrosis" refers to the formation of excess fibrous connective tissue as a result of the excess deposition of extracellular matrix components, for example collagen. Fibrous connective tissue is characterised by having extracellular matrix (ECM) with a high collagen content. The collagen may be provided in strands or fibers, which may be arranged irregularly or aligned. The ECM of fibrous connective tissue may also include glycosaminoglycans.

As used herein, "excess fibrous connective tissue" refers to an amount of connective tissue at a given location (e.g. a given tissue or organ, or part of a given tissue or organ) which is greater than the amount of connective tissue present at that location In the absence of fibrosis, e.g. under normal, non-pathological conditions. As used herein, "excess deposition of extracellular matrix components" refers to a level of deposition of one or more extracellular matrix components which is greater than the level of deposition in the absence of fibrosis, e.g. under normal, non-pathological conditions.

The cellular and molecular mechanisms of fibrosis are described in Wynn, J. Pathol. (2008) 214(2): 199-210, and Wynn and Ramalingam, Nature Medicine (2012) 18:1028-1040, which are hereby incorporated by reference in their entirety. The main cellular effectors of fibrosis are myofibroblasts, which produce a collagen-rich extracellular matrix.

In response to tissue injury, damaged cells and leukocytes produce pro-fibrotic factors such as TGFβ, IL-13 and PDGF, which activate fibroblasts to αSMA-expressing myofibroblasts, and recruit myofibroblasts to the site of injury. Myofibroblasts produce a large amount of extracellular matrix, and are important mediators in aiding contracture and closure of the wound. However, under conditions of persistent infection or during chronic inflammation there can be overactivation and recruitment of myofibroblasts, and thus over-production of extracellular matrix components, resulting in the formation of excess fibrous connective tissue.

In some embodiments fibrosis may be triggered by pathological conditions, e.g. conditions, infections or disease states that lead to production of pro-fibrotic factors such as TGFβ1. In some embodiments, fibrosis may be caused by physical injury/stimuli, chemical injury/stimuli or environmental injury/stimuli. Physical injury/stimuli may occur during surgery, e.g. iatrogenic causes. Chemical injury/stimuli may include drug induced fibrosis, e.g. following chronic administration of drugs such as bleomycin, cyclophosphamide, amiodarone, procainamide, penicillamine, gold and nitrofurantoin (Daba et al., Saudi Med J 2004 June; 25(6): 700-6). Environmental injury/stimuli may include exposure to asbestos fibres or silica.

Fibrosis can occur in many tissues of the body. For example, fibrosis can occur in the lung, liver (e.g. cirrhosis), kidney, heart, blood vessels, eye, skin, pancreas, spleen, bowel (e.g. large or small intestine), brain, and bone marrow. Fibrosis may also occur in multiple organs at once.

In embodiments herein, fibrosis may involve an organ of the gastrointestinal system, e.g. of the liver, small intestine, large intestine, or pancreas. In some embodiments, fibrosis may involve an organ of the respiratory system. e.g. the lungs. In embodiments, fibrosis may involve an organ of the cardiovascular system, e.g. of the heart or blood vessels. In some embodiments, fibrosis may involve the skin. In some embodiments, fibrosis may involve an organ of the nervous system, e.g. the brain. In some embodiments, fibrosis may involve an organ of the urinary system, e.g. the kidneys. In some embodiments, fibrosis may involve an organ of the musculoskeletal system, e.g. muscle tissue.

In some preferred embodiments, the fibrosis is cardiac or myocardial fibrosis, hepatic fibrosis, or renal fibrosis. In some embodiments cardiac or myocardial fibrosis is associated with dysfunction of the musculature or electrical properties of the heart, or thickening of the walls or valves of the heart. In some embodiments fibrosis is of the atrium and/or ventricles of the heart. Treatment or prevention of atrial or ventricular fibrosis may help reduce risk or onset of atrial fibrillation, ventricular fibrillation, or myocardial infarction.

In some preferred embodiments hepatic fibrosis is associated with chronic liver disease or liver cirrhosis. In some preferred embodiments renal fibrosis is associated with chronic kidney disease.

Diseases/disorders characterised by fibrosis in accordance with the present invention include but are not limited to: respiratory conditions such as pulmonary fibrosis, cystic fibrosis, idiopathic pulmonary fibrosis (IPF), progressive massive fibrosis, scleroderma, obliterative bronchiolitis, Hermansky-Pudlak syndrome, asbestosis, silicosis, chronic pulmonary hypertension, AIDS associated pulmonary hypertension, sarcoidosis, tumor stroma in lung disease, and asthma; chronic liver disease, primary biliary cirrhosis (PBC), schistosomal liver disease, liver cirrhosis, steatohepatitis, non-alcoholic steatohepatitis (NASH), early-stage NASH, late-stage NASH, alcoholic steatohepatitis, steatosis; non-alcoholic fatty liver disease (NAFLD), pancreatic conditions such as chronic pancreatitis and pancreatic fibrosis; cardiovascular conditions such as hypertrophic cardiomyopathy, dilated cardiomyopathy (DCM), fibrosis of the atrium, atrial fibrillation, fibrosis of the ventricle, ventricular fibrillation, myocardial fibrosis, Brugada syndrome, myocarditis, endomyocardial fibrosis, myocardial infarction, fibrotic vascular disease, hypertensive heart disease, arrhythmogenic right ventricular cardiomyopathy (ARVC), tubulointerstitial and glomerular fibrosis, atherosclerosis, varicose veins, cerebral infarcts; neurological conditions such as gliosis and Alzheimer's disease: muscular dystrophy such as Duchenne muscular dystrophy (DMD) or Becker's muscular dystrophy (BMD); gastrointestinal conditions such as Crohn's disease, microscopic colitis and primary sclerosing cholangitis (PSC); skin conditions such as scleroderma, nephrogenic systemic fibrosis and cutis keloid; arthrofibrosis; Dupuytren's contracture; mediastinal fibrosis; retroperitoneal fibrosis; myelofibrosis; Peyronie's disease: adhesive capsulitis; kidney disease (e.g., renal fibrosis, nephritic syndrome, Alport's syndrome, HIV associated nephropathy, polycystic kidney disease, Fabry's disease, diabetic nephropathy, chronic glomerulonephritis, nephritis associated with systemic lupus, kidney interstitial fibrosis (IF)); kidney injury e.g. acute kidney injury/renal failure; nephrotoxicity; progressive systemic sclerosis (PSS); chronic graft versus host disease; diseases/disorders of the eye and associated processes, such as Grave's opthalmopathy, epiretinal fibrosis (e.g. diabetic retinopathy (DR)), glaucoma, subretinal fibrosis (e.g. associated with macular degeneration (e.g. wet or dry age-related macular degeneration (AMD))), macular edema, drusen formation, choroidal neovascularization (CNV), post-surgical fibrosis (e.g. of the posterior capsule following cataract surgery, or of the bleb following trabeculectomy for glaucoma), conjunctival fibrosis, subconjunctival fibrosis; arthritis; fibrotic pre-neoplastic and fibrotic neoplastic disease; and fibrosis induced by chemical or environmental insult (e.g., cancer chemotherapy, pesticides, radiation/cancer radiotherapy).

Early stage NASH refers herein to steatotic stages of fatty liver disease, e.g. non-alcoholic fatty liver disease (NAFLD), which may bridge into a NASH state in which the liver has become inflamed. Late-stage NASH refers herein to states of persistent liver inflammation which may include fibrosis.

It will be appreciated that many of the diseases/conditions listed above are interrelated. For example, fibrosis of the ventricle may occur post myocardial infarction, and is associated with DCM, HCM and myocarditis.

In particular embodiments, the disease/disorder may be one of pulmonary fibrosis, atrial fibrillation, ventricular fibrillation, hypertrophic cardiomyopathy (HCM), dilated cardiomyopathy (DCM), non-alcoholic steatohepatitis (NASH), cirrhosis, chronic kidney disease, scleroderma, systemic sclerosis, keloid, cystic fibrosis, Chron's disease, post-surgical fibrosis or retinal fibrosis, e.g. associated with wet age-related macular degeneration (AMD).

In some embodiments the methods may be effective to reverse or regress fibrosis. The fibrosis may be established or severe fibrosis and may be associated with any of the diseases/disorders described herein. In some embodiments the methods may be effective to reverse or regress any of the diseases/disorders provided herein.

Fibrosis can lead directly or indirectly to, and/or increase susceptibility to development of, diseases/disorders. For example, more than 80% of hepatocellular carcinomas (HCCs) develop In fibrotic or cirrhotic livers (Affo et al. 2016, Annu Rev Pathol.), suggesting an important role for liver fibrosis In the premalignant environment (PME) of the liver.

Accordingly, the antigen-binding molecules of the present invention find use in methods for the treatment and prevention of diseases/disorders associated with fibrosis, and/or for which fibrosis is a risk factor. In some embodiments, the disease/disorder associated with fibrosis, or for which fibrosis is a risk factor, is a cancer, e.g. cancer of the liver (e.g. hepatocellular carcinoma).

IL-11 mediated signalling is also implicated in the pathology of other diseases/disorders, and the antigen-binding molecules of the present invention accordingly find use in methods to treat, prevent, alleviate and/or reverse or regress the symptoms of these diseases/disorders also.

In some embodiments, fibrosis may be associated with angiogenesis e.g. in the eye. In some embodiments, methods of treating or preventing fibrosis, methods of determining the suitability of a subject for such treatment/prevention and methods of diagnosing/prognosing fibrosis as described herein are also applicable to treating/preventing/diagnosing/prognosing angiogenesis, and vice versa. Fibrosis of the eye may be associated with choroidal neovascularization (CNV).

In some embodiments the antigen-binding molecules of the present invention are provided for use in methods to treat and/or prevent metabolic diseases. That is, the present invention provides for the treatment/prevention of metabolic diseases through inhibition of IL-11 mediated signalling, in e.g. a cell, tissue/organ/organ system/subject. As used herein, a "metabolic disease" refers to any disease or condition which is caused by, or which is characterised by, abnormal metabolism. "Metabolism" in this context refers to the bodily conversion/processing of sources of energy, e.g. substances consumed to provide nutrition, into energy and/or for storage. "Normal metabolism" may be the metabolism of a healthy subject not having a disease, e.g. not having a metabolic disease, or not possessing a symptom/correlate of a metabolic disease.

A subject having a metabolic disease may display abnormal metabolism. A subject having a metabolic disease may have a symptom/correlate of abnormal metabolism. A subject having a metabolic disease may have been diagnosed as having metabolic disease. A subject may satisfy the diagnostic criteria for the diagnosis of a metabolic disease. In some embodiments, the present invention provides for the treatment/prevention of diseases/conditions in a subject for which a metabolic disease provides a poor prognosis.

In some embodiments, the metabolic disease affects one or more of: the liver, pancreas, cardiovascular system, digestive system, the excretory system, the respiratory system, the renal system, the reproductive system, the circulatory system, the muscular system, the endocrine system, the exocrine system, the lymphatic system, the immune system, the nervous system, and/or the skeletal system.

In some embodiments the metabolic disease is, or comprises (e.g. is characterised by), obesity, type 2 diabetes (T2D), type 1 diabetes (T1D), pre-diabetes, being overweight, metabolic syndrome, pregnancy-associated hyperglycemia (i.e. gestational diabetes), cholestatic liver disease, hyperglycaemia, hyperlipidaemia, hypertriglyceridemia, hypercholesterolemia, wasting, cachexia, chemotherapy-associated weight loss, pancreatic insufficiency, pancreatitis, acute pancreatitis, chronic pancreatitis, steatosis, non-alcoholic fatty liver disease (NAFLD), non-alcoholic fatty liver (NAFL), non-alcoholic steatohepatitis (NASH), lipodystrophy, lipohypertrophy, lipoatrophy, insulin deficiency, insulin resistance and hyperglucagonemia. In some embodiments the metabolic disease is, or comprises, obesity. In some embodiments the metabolic disease is, or comprises, cholestasis, i.e. a reduced flow of bile from the liver to the duodenum. The disease may be cholestatic liver disease (Jansen et al., Hepatology (2017) 65(2):722-738 and Pollock and Minuk, J Gastroenterol Hepatol (2017) 32(7):1303-1309, both of which are hereby incorporated by reference in their entirety), including e.g. primary biliary cholangitis (PBC) and primary sclerosing cholangitis (PSC).

Aspects of the present invention are concerned with the treatment and/or prevention of aberrant and/or insufficient function of cells/tissue(s)/organ(s)/organ systems having a role In metabolism. In particular, treatment and/or prevention of aberrant function and/or insufficient function of cells of the pancreas/pancreatic tissue/the pancreas is contemplated herein, as is the treatment and/or prevention of aberrant function and/or insufficient function of cells of the liver/hepatic tissue/the liver.

In some embodiments the metabolic disease is, or comprises, wasting. As used herein, the term "wasting" refers to involuntary weight loss, which may be progressive and/or degenerative. Wasting can be defined as loss of muscle with or without loss of fat mass, and typically involves significant, usually involuntary, loss of body mass (including skeletal muscle), and may or may not include loss of adipose tissue. In some instances, adipose tissue wasting can occur In isolation, as seen in lipodystrophy diseases. Wasting may be characterised by a negative protein and energy balance driven by a variable combination of reduced food intake and abnormal metabolism (Fearon et al. Lancet Oncol. (2011) 12(5):489-95). Wasting can lead to progressive functional impairment, impaired quality of life, increased risk for morbidity and mortality. In some cases, wasting leads to asthenia (abnormal physical weakness or lack of energy) and/or anemia (deficiency of red cells or haemoglobin in the blood). In some cases, wasting cannot be fully reversed by conventional nutritional support or by therapeutic interventions that have been trialled to date. Death usually occurs once weight loss has reached 30% of the patient's historic stable body weight (Tisdale, Nature Reviews Cancer, 2, 862-871 (2002)).

Diseases/conditions characterised by wasting include cachexia (non-age-related loss of muscle mass), sarcopenia (loss of muscle mass: e.g. age-related, disuse, space travel or denervation), anorexic disorders (protein-energy malnutrition), muscular dystrophies, lipodystrophies (e.g. abnormal or degenerative condition of adipose tissue), lipoatrophy (age-related loss of subcutaneous fat in the face and other tissues) and myopenia (muscle wasting in any chronic illness; proposed by Fearon et al. J Cachexia Sarcopenia Muscle. 2011; 2:1-3). Herein, diseases/conditions characterised by wasting are also referred to as "wasting disorders". In some embodiments a wasting disorder according to the present disclosure is cachexia, pre-cachexia, refractory cachexia, sarcopenia, anorexia, lipodystrophy, lipoatrophy and/or myopenia. In some embodiments according to the various aspects described herein, the wasting disorder is cachexia, pre-cachexia and/or refractory cachexia.

Wasting disorders arising due to chronic illness may include "mild muscle wasting disease" (with or without frailty), "moderate muscle wasting disease" (with or without frailty; sometimes known as "pre-cachexia"), or "severe muscle wasting disease" (sometimes called "cachexia", often with frailty present). Cachexia can be defined as involuntary weight loss of >5% from historical stable weight, a body mass index (BMI) of <20 kg/m2 (person younger than 65) or <22 kg/m2 (person aged 65 or older) with any degree of weight loss >2%, or a skeletal muscle index consistent with sarcopenia with any degree of weight loss >2%. The subject may also display <10% body fat and/or a low blood albumin level of <35 g/l. These criteria may also help to identify populations 'at-risk' of developing a wasting disorder (Fearon et al. Lancet Oncol. 2011; 12(5):489-95).

A three-step classification of cachexia has been proposed, with severity classified according to degree of depletion of energy stores and body protein (BMI) in combination with degree of ongoing weight loss.
1. Pre-cachexia—when a patient has weight loss <5%, but has not yet developed serious complications.
2. Cachexia—where the syndrome is progressing, with weight loss exceeding the above-mentioned parameters, but still potentially able to be treated.
3. Refractory cachexia—the point at which the disease is no longer responsive to treatment or when treatment benefits are outweighed by burden and risk (Fearon et al, supra). Often, the refractory stage is dictated by the overall stage of an underlying illness, described below, and the condition of the patient.

Metabolic diseases may be present in acute or chronic disease settings. Aspects of the present invention provide for the treatment/prevention of diseases/conditions associated with metabolic diseases. Disease/conditions associated with metabolic diseases include diseases/conditions that are positively associated with the onset of a metabolic disease. In some embodiments, the disease/condition associated with a metabolic disease is one which can cause/causes/has caused (i.e. can lead to, leads to or has led to) a metabolic disease.

Disease/conditions associated with metabolic diseases also include diseases/conditions which are caused and/or exacerbated (made worse, progressed and/or complicated) by a metabolic disease. In some embodiments a disease/condition associated with a metabolic disease, may be positively associated with the onset of a metabolic disease and may also be exacerbated by a metabolic disease. An "associated" disease/condition may be one comprising a metabolic disease-related pathology.

In embodiments of the invention, a metabolic disease, or a disease/condition associated with a metabolic disease may be present in or affect any organ/tissue, such as the heart, liver, kidney, brain, skin, muscular system, stomach, small intestine, large intestine, pancreas, mouth, salivary glands, pharynx, oesophagus, gallbladder, trachea, larynx, bladder, ovary, uterus, testes, glands of the endocrine system e.g. pituitary or thyroid, the lymphatic system e.g. spleen.

In embodiments of the invention, a disease/condition associated with a metabolic disease may be one or more of cancer, cardiac disease, kidney disease, lung disease, liver disease, chronic infection, neurological degenerative diseases, acute injury, traumatic injury/trauma, post-operative conditions, or ageing/senescence.

In accordance with various aspects of the present invention, a method of treating and/or preventing a metabolic disease according to the present invention may comprise one or more of the following:

Reducing blood lipid level;
Reducing blood glucose level;
Increasing glucose tolerance (e.g. of a glucose intolerant subject);
Increasing insulin tolerance (e.g. of an insulin resistant subject);
Increasing pancreatic function
Reducing body weight (e.g. of an overweight/obese subject);
Reducing body fat mass;
Increasing lean mass;
Reducing fasting blood glucose level;
Reducing serum triglyceride level;
Reducing serum cholesterol level;
Increasing glucose tolerance;
Increasing pancreatic function (e.g. exocrine and/or endocrine function);
Increasing the growth of pancreatic tissue;
Regenerating pancreatic tissue;
Increasing pancreas weight;
Reducing pancreatic islet cell hyperplasia;
Reducing glucagon expression;
Increasing Insulin expression;
Increasing body weight (e.g. of a subject having a wasting disease, e.g. cachexia);
Reducing expression of IL-11 protein in the liver
Reducing Erk activation in the liver;
Reducing steatosis. e.g. of the liver;
Reducing liver triglyceride level;
Reducing serum ALT level;
Reducing expression of a pro-inflammatory factor (e.g. TNFα. CCL2, CCL5, IL-6, CXCL5, and/or CXCL1);
Reducing expression of a pro-fibrotic factor (e.g. IL-11, TIMP1, ACTA2, TGFβ1, MMP2, TIMP2, MMP9, COL1A2, COL1A1 and/or COL3A1);
Reducing serum TGFβ1 level;
Reducing expression/production by HSCs of IL-11, ACTA2, MMP2, TGFβ1, PDGF, ANG II, bFGF, CCL2 and/or H2O2;
Inhibiting HSC-to-myofibroblast transition by HSCs;
Reducing the number/proportion of myofibroblasts in the liver;
Reducing liver hydroxyproline level;
Increasing liver function;
Increasing the function of an organ/tissue affected by a metabolic disease;
Reducing liver damage; and
Reducing the number/proportion of CD45+ cells in the liver.

IL-11 mediated signalling has been implicated in the development and progression of various cancers. Studies suggest that IL-11 mediated signalling is important for promoting chronic gastric inflammation and associated gastric, colonic, hepatocellular and breast cancer tumorigenesis through excessive activation of STAT3 (Ernst M, et al. J Clin Invest. (2008); 118:1727-1738), that IL-11 may promote tumorigenesis by triggering the JAK-STAT intracellular signalling pathway, and may also promote metastasis via signalling through the PI3K-AKT-mTORC1 pathway (Xu et al., Cancer Letters (2016) 373(2): 156-163). Through STAT3, IL-11 promotes survival, proliferation, invasion angiogenesis and metastasis, the IL-11/GP130/JAK/STAT3 signalling axis may be rate-limiting for the progression of gastrointestinal tumors, and elevated IL-11 expression is associated with poor prognosis of breast cancer patients (Johnstone et al., Cytokine & Growth Reviews (2015) 26(5): 489-498). IL-11 has also been shown to influence breast cancer stem cell dynamics and tumor heterogeneity (Johnstone et al., Cytokine & Growth Reviews (2015) 26(5): 489-498). Recently, IL-11 mediated signalling has been implicated in chemoresistance of lung adenocarcinoma; cancer associated fibroblasts were found to upregulate IL-11, and confer chemoresistance to lung cancer cells through activation of the IL-11/IL-11R/STAT3 anti-apoptotic signalling pathway (Tao et al. 2016, Sci Rep. 6; 6:38408). IL-11 mediated signalling may promote the fibroblast-to-myofibroblast transition and extracellular matrix production by fibroblasts in the pre-malignant environment (PME) and tumour micro-environment (TME).

In some embodiments, the antigen-binding molecules of the present invention are provided for use in methods to treat/prevent a cancer. In some embodiments, the cancer may be a cancer which leads directly or indirectly to inflammation and/or fibrosis.

A cancer may be any unwanted cell proliferation (or any disease manifesting itself by unwanted cell proliferation), neoplasm or tumor or increased risk of or predisposition to the unwanted cell proliferation, neoplasm or tumor. The cancer may be benign or malignant and may be primary or secondary (metastatic). A neoplasm or tumor may be any abnormal growth or proliferation of cells and may be located in any tissue.

In some embodiments, the antigen-binding molecules of the present invention are provided for use in methods to treat/prevent a cancer, e.g. an epithelial cell cancer, breast cancer, gastrointestinal cancer (e.g. esophageal cancer, stomach cancer, pancreatic cancer, liver cancer (e.g. HCC), gallbladder cancer, colorectal cancer, anal cancer, gastrointestinal carcinoid tumor), and lung cancer (e.g. non-small cell lung cancer (NSCLC) or small cell lung cancer (SCLC))). In some embodiments, the cancer is a cancer for which acute and/or chronic inflammation is a risk factor. In some embodiments, the cancer is a cancer for which a disease/disorder characterised by fibrosis (e.g. as described herein) is a risk factor.

In some embodiments, the cancer may be associated with increased IL-11, IL-11Rα and/or gp130 gene or protein expression. For example, cells of the cancer may have increased expression of IL-11. IL-11Rα and/or gp130 as compared to comparable, non-cancerous cells, or may be associated with increased expression of IL-11, IL-11Rα and/or gp130 by other cells (e.g. non-cancerous cells) as compared to the level of expression by comparable cells In the absence of a cancer (e.g. In a healthy control subject). In some embodiments, cells of the cancer may be determined to have an increased level of signaling through ERK and/or STAT3 pathways as compared to comparable non-cancerous cells.

In some embodiments, the cancer may be associated with a mutation in IL-11, IL-11Rα and/or gp130. In some embodiments, such mutation may be associated with increased level of gene or protein expression, or may be associated with an increased level of IL-11/IL-11R signalling relative to the level of expression/signalling observed in the absence of the mutation.

IL-11/IL-11R signalling has also been implicated in diseases/disorders characterised by inflammation. Intra-articular injection of IL-11 has been shown to cause joint inflammation (Wong et al., Cytokine (2005) 29:72-76), and IL-11 has been shown to be proinflammatory at sites of IL-13-mediated tissue inflammation (Chen et al., J Immunol (2005) 174:2305-2313). IL-11 expression has also been observed to be significantly increased in chronic skin lesions in atopic dermatitis, and is known to be involved in bronchial inflammation (Toda et al., J Allergy Clin Immunol (2003) 111: 875-881). IL-11-mediated signalling is implicated in inflammatory bowel disease (IBD) and asthma (Putoczki and Ernst, J Leuko Biol (2010) 88(6)1109-1117). IL-11 has also been identified as a risk factor for multiple sclerosis; IL-11 is elevated in the cerebrospinal fluid of patients with clinically isolated syndrome (CIS) as compared to control subjects, and serum levels of IL-11 are higher during relapses for patients with relapsing-remitting multiple sclerosis, and IL-11 may promote differentiation of CD4+ T cells to a TH17 phenotype-TH17 cells are important cells in the pathogenesis of multiple sclerosis (Zhang et al., Oncotarget (2015) 6(32): 32297-32298).

In some embodiments, the antigen-binding molecules of the present invention are provided for use in methods to treat/prevent a disease/disorder characterised by inflammation. In some embodiments, a disease or disorder characterised by inflammation may be a disease/disorder which leads directly or indirectly to a cancer and/or fibrosis. Diseases characterised by inflammation include e.g. allergic inflammation such as allergic asthma and bronchial inflammation, atopic dermatitis, allergic rhinitis and ocular allergic diseases, and autoimmune diseases such as multiple sclerosis, systemic lupus erythematosus, rheumatoid arthritis, chronic active hepatitis, type 1 diabetes mellitus, celiac disease, Grave's disease, uveitis, pemphigus, psoriasis, Crohn's disease, ulcerative colitis, inflammatory bowel disease, anaemia and autoimmune thyroiditis.

In some embodiments, the antigen-binding molecules of the present invention are provided for use in methods to treat/prevent hepatotoxicity and diseases/disorders characterised by hepatotoxicity. As used herein, hepatotoxicity refers to damage to and/or death of liver cells/tissue. Hepatotoxicity can refer to a state of toxic damage to the liver, specifically with death of the hepatocyte cells within the liver. Hepatotoxicity may be determined/diagnosed by detection of one or more correlates of hepatotoxicity as described hereinbelow. Hepatotoxicity may arise as a consequence of hepatotoxic insult. As used herein "hepatotoxic insult" refers to any treatment, event or conditions giving rise to hepatotoxicity. For example, hepatotoxic insult may be caused by a chemical/physical treatment/experience, or gaseous conditions. In some embodiments hepatotoxic insult is chemical, e.g. in the case of drug-induced liver injury, e.g. APAP-induced hepatotoxicity. In some embodiments hepatotoxic insult is physical, e.g. In the case of hepatotoxicity arising as a result of surgical damage to liver tissue, which may occur e.g. surgery to treat a disease and/or for liver transplantation (e.g. the hepatotoxicity may have Iatrogenic causes). In some embodiments hepatotoxic insult arises from hypoxia, e.g. as a consequence of ischaemia, or may result from reperfusion (e.g. the hepatotoxic insult may arise from IRI).

Hepatotoxicity may be chemical-driven liver damage, for example damage or injury caused by a medicine, chemical, ischaemia, reperfusion, sepsis or herbal or dietary supplements. In some embodiments hepatotoxicity refers to drug-induced liver injury (DILI). In some embodiments hepatotoxicity refers to liver injury caused by a hepatotoxin. A hepatotoxin may be alcohol. Hepatotoxicity may also be termed toxic hepatitis. Hepatotoxiclty may refer to acute and/or chronic hepatotoxicity.

Hepatotoxicity may be caused, directly or indirectly, by alcohol ingestion e.g. chronic alcohol consumption. Hepatotoxicity as referred to herein may be caused, directly or indirectly, by fasting, malnutrition, infection by an infectious agent (e.g. a hepatitis virus (e.g. hepatitis A, B, C, D or E), HIV), cancer or drug interactions.

Hepatotoxicity may be present in association with other disorders, diseases and conditions. Disorders, diseases or conditions associated with hepatotoxicity include acute liver injury (ALI), acute liver failure, acute liver disease, chronic liver disease, liver damage, hepatitis e.g. viral hepatitis, alcoholic hepatitis, liver ischemia-reperfusion injury (IRI) e.g. 'warm' ischemia-reperfusion (WIR), radiation-induced liver disease (RILD), drug-induced liver injury (DILI), autoimmune liver injury, cholestatic liver disease, HIV and cancer.

Drug-induced liver injury (DILI) includes intrinsic and idiosyncratic hepatotoxicity, and idiosyncratic DILI further includes allergic and nonallergic reaction. The intrinsic mechanism is related to dose dependent hepatotoxicity, whereas idiosyncratic hepatotoxicity is not dose dependent and may happen in an unpredictable fashion. Allergic diosyncratic hepatotoxicity is further characterized by the presence of symptoms and signs typical of an adaptive immune system reaction, including fever, skin reactions, eosinophilia, formation of autoantibodies, and a short latency time particularly after re-exposure (Khoury et al., J Clin Transl Hepatol. 2015 Jun. 28; 3(2): 99-108).

In some embodiments antigen-binding molecules of the present invention may be used for the diagnosis, treatment and prophylaxis of acetaminophen (APAP)-induced hepatotoxicity. Acetaminophen is also known as N-acetyl-p-aminophenol or paracetamol, or by the brand names Tylenol and Panadol. Acetaminophen intoxication results in hepatotoxicity associated with increased serum concentrations of hepatocellular leakage enzymes such as aspartate aminotransferase, lactate dehydrogenase, and alanine aminotransferase, centriiobular degeneration and necrosis, and activation of Kupffer cells (Trepicchio W. et al., Toxicol Pathol. 2001; 29(2):242-9).

In some embodiments the antigen-binding molecules of the present invention are provided for use in methods to treat/prevent kidney injury, e.g. acute kidney injury (AKI; acute renal failure), or a disease/disorder associated with kidney injury. Kidney injury may be characterised by damage to tubular epithelial cells (TECs) and/or the transition of TECs to an epithelial-to-mesenchymal cell-like phenotype (i.e. EMT). Transition of TECs to a mesenchymal cell-like phenotype may be characterised e.g. by reduced expression of E-cadherin, increased expression of SNAIL and/or increased expression of ACTA2. The kidney injury may have any cause, examples include kidney injury resulting from mechanical (i.e. physical) damage or injury, chemical damage or injury, ischemia or genetic predisposition. The cause or damage will normally result in impaired kidney function, which may lead to kidney failure. Mechanical damage or injury may include physical injury to the subject, to the kidney, to TECs or to podocytes. It may also include tubular obstruction/blockage. e.g. of the urinary tract. In some embodiments the kidney injury is drug-induced kidney injury or drug-induced acute kidney injury.

Ischemic damage may arise from a decrease in blood flow to the kidney which may be caused by a number of factors such as low blood pressure e.g. due to sepsis, blood loss or surgery, or the effect of a chemical agent, e.g. a medicine or drug, administered to the subject to treat another disease, disorder or condition. Kidney Injury caused by ischemia may be ischemia-induced kidney injury, or ischemia-induced acute kidney injury. Kidney injury caused by crush injury may be ischemia-induced kidney injury with vasoconstriction or can be caused by tubular cast mechanical factors or toxic effects of circulating factors e.g. myoglobin.

In some embodiments the kidney injury, which may be AKI, is characterised by damage to, which may in some cases include or lead to death of, tubular epithelial cells (TECs) of the kidney, i.e. renal tubular epithelial cells. The TECs may be proximal or distal, both of which may be damaged in AKI, as may also the podocytes in the kidney glomerulus. Damage to TECs may also be any type of damage, injury or insult. e.g. as described above this may be mechanical, chemical or ischemic damage. Damage to TECs is a common causative factor of kidney injury, particularly AKI. Proliferation of TECs provides a mechanism for recovery and restoration of kidney function, whereas failure of TECs to proliferate can lead to disease development and progression, e.g. to chronic kidney disease and renal failure. Proliferation of podocyte precursors to restore glomerulus function may also occur, but is not as well described as TEC proliferation. Mechanical damage may include e.g. unilateral ureteric obstruction (UUO).

In some embodiments the kidney injury is nephrotoxicity, referring to toxicity of the kidneys. Nephrotoxicity can arise as a result of toxic effects of certain substances on renal function, and may therefore be viewed as a consequence of chemical damage or injury. As with chemical damage or injury, nephrotoxicity may be a side effect of the administration of an agent to treat a disease or condition not occurring in the kidney, or occurring both in the kidney and in one or more other tissues. In some embodiments nephrotoxicty may be a side effect of administration of a chemotherapeutic agent administered to the subject In order to prevent or treat cancer. As such, nephrotoxicity may be a form of drug-induced kidney injury or drug-induced acute kidney injury. In some embodiments kidney injury may be induced by folic acid, i.e. is folate-induced kidney injury.

In some embodiments, the antigen-binding molecules are provided for use in the diagnosis, treatment and/or prophylaxis of cisplatin-induced kidney injury. This may include cisplatin-induced acute kidney injury or cisplatin-induced nephrotoxicity. Cisplatin (dichlorodiamino platinum; SP-4-2)-diaminedichloroplatinum(II)) is a chemotherapeutic agent that is widely used to treat a range of cancers including head and neck, breast, lung, testis, ovarian, brain, and bladder cancers and is widely acknowledged to lead to kidney injury and dysfunction involving tubular damage and necrosis (e.g. Oh et al., Electrolyte Blood Press 2014 December; 12(2): 55-65; P A Arunkumar et al., Asian Pac J Trop Biomed 2012 Aug. 2(8): 640-644). Other platinum-based chemotherapeutics agents also cause kidney damage.

It is recognised that a subject having kidney injury may also present with fibrosis of the kidney, either as a disease condition having a separable etiology or as a secondary effect of the kidney injury. In some embodiments the kidney injury being diagnosed, treated or prevented is not fibrosis of the kidney, e.g. renal fibrosis. In some embodiments the subject does not have fibrosis. In some embodiments TEC damage occurs in the absence of fibrosis. In some embodiments fibrosis arises separately (e.g. secondarily to) AKI, e.g. due to incomplete regeneration of TECs. In some embodiments, the damaged TECs in the subject are not pro-fibrotic TECs. In some embodiments, fibrosis does not arise.

In some embodiments, the antigen-binding molecules of the present invention are provided for use In methods to treat/prevent a disease/disorder associated with infection, in particular where infection leads directly or indirectly to fibrosis, cancer or inflammation. A disease associated with infection may be a disease which is caused or exacerbated by infection with the relevant infectious agent, or may be a disease for which infection with the relevant infectious agent is a risk factor.

An infection may be any infection or infectious disease, e.g. bacterial, viral, fungal, or parasitic infection. In particular embodiments, the disease/disorder may be associated with a viral infection. In some embodiments it may be particularly desirable to treat chronic/persistent infections, e.g. where such infections are associated with inflammation, cancer and/or fibrosis.

The infection may be chronic, persistent, latent or slow, and may be the result of bacterial, viral, fungal or parasitic infection. As such, treatment may be provided to patients having a bacterial, viral or fungal infection. Examples of bacterial infections include infection with *Helicobacter pylori* and *Mycobacterium tuberculosis* infection of the lung. Examples of viral infections include infection with EBV, HPV, HIV, hepatitis B or hepatitis C.

The treatment may involve ameliorating, treating, or preventing any disease/disorder/condition associated with IL-11 signalling, and/or described herein, by inhibiting the biological activity of IL-11Rα or a complex comprising IL-11Rα. The treatment may involve the reversal or regression of the disease/disorder by inhibiting the biological activity of IL-11Rα or a complex comprising IL-11Rα. Such methods may include the administration of the antibodies/fragments/compositions according to the present invention to bind to and inhibit the biological activity of IL-11Rα or a complex comprising IL-11Rα. Herein, inhibiting the biological activity of IL-11Rα or a complex comprising IL-11Rα may be referred to as 'neutralising'.

Methods of treatment may optionally include the co-administration of biological adjuvants (e.g., interleukins, cytokines, Bacillus Comette-Guerin, monophosphoryl lipid A, etc.) in combination with conventional therapies for treating cancer such as treatment with an agent for treating cancer (e.g. chemotherapy), radiation, or surgery. Methods of medical treatment may also involve in vivo, ex vivo, and adoptive immunotherapies, including those using autologous and/or heterologous cells or immortalized cell lines.

The treatment may be aimed at prevention of a disease/disorder associated with overactive/elevated IL-11 mediated signalling. As such, the antibodies, antigen binding fragments and polypeptides may be used to formulate pharmaceutical compositions or medicaments and subjects may be prophylactically treated against development of a disease state. This may take place before the onset of symptoms of the disease state, and/or may be given to subjects considered to be at greater risk of the disease or disorder.

Administration of the agents according to the present disclosure is preferably in a "therapeutically effective" or "prophylactically effective" amount, this being sufficient to show benefit to the subject. The actual amount administered, and rate and time-course of administration, will depend on the nature and severity of the disease/condition and the nature of the agent. Prescription of treatment, e.g. decisions on dosage etc., is within the responsibility of general practitioners and other medical doctors, and typically takes account of the disease/condition to be treated, the condition of the individual subject, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

The antigen-binding molecules, polypeptides, CARs, nucleic acids, expression vectors, cells and compositions described herein are preferably formulated as a medicament or pharmaceutical together with one or more other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilisers, solubilisers, surfactants (e.g., wetting agents), masking agents, colouring agents, flavouring agents, and sweetening agents. The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation. Suitable carriers, adjuvants, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 2nd edition, 1994.

The formulations may be prepared for administration as suitable for the disease/condition to be treated. For example, formulations may be formulated for topical, parenteral, systemic, intravenous, intra-arterial, intramuscular, intrathecal, intraocular, local ocular (e.g. subconjunctival, intravitreal, retrobulbar, intracameral), intra-conjunctival, subcutaneous, oral, or transdermal routes of administration which may include injection. The agents of the present disclosure may be formulated in fluid or solid form. Fluid formulations may be formulated for administration by injection or infusion to a selected region of the human or animal body. Injectable formulations may comprise the selected agent in a sterile or isotonic medium.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

In accordance with the present invention methods are also provided for the production of pharmaceutically useful compositions, such methods of production may comprise one or more steps selected from: isolating an antibody or antigen binding fragment as described herein; and/or mixing an isolated antibody or antigen binding fragment as described herein with a pharmaceutically acceptable carrier, adjuvant, excipient or diluent. For example, a further aspect of the present invention relates to a method of formulating or producing a medicament or pharmaceutical composition for use in a method of medical treatment, the method comprising formulating a pharmaceutical composition or medicament by mixing an antibody or antigen binding fragment as described herein with a pharmaceutically acceptable carrier, adjuvant, excipient or diluent.

Multiple doses of the antigen-binding molecule, polypeptide, CAR, nucleic acid (or plurality thereof), expression vector (or plurality thereof), cell or composition may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

The antigen-binding molecules, polypeptides, CARs, nucleic acids, expression vectors, cells and compositions described herein may be administered alone or in combination with other therapeutic or prophylactic intervention. Such other therapeutic or prophylactic intervention may occur before, during and/or after the therapies encompassed by the disclosure, and the deliveries of the other therapeutic or prophylactic interventions may occur via the same or different administration routes as the therapies of the disclosure.

In some embodiments, administration of the antigen-binding molecules, polypeptides. CARs, nucleic acids, expression vectors, cells and compositions described herein may be accompanied by an agent for treating or preventing infection (e.g. an antibiotic, anti-viral, anti-fungal or anti-parasitic agent). In some embodiments, treatment with an antibody, antigen binding fragment or composition of the present invention may be accompanied by an agent for treating or preventing inflammation (e.g. a non-steroidal anti-inflammatory drug (NSAID). In some embodiments, treatment with an antibody, antigen binding fragment or composition of the present invention may be accompanied by radiotherapy (i.e. treatment with ionising radiation, e.g. X-rays or γ-rays) and/or an agent for treating or preventing cancer (e.g. a chemotherapeutic agent). In some embodiments the chemotherapeutic agent is an alkylating agent, e.g. cisplatin. In some embodiments, the antibody, antigen binding fragment or composition of the present invention may be administered as part of a combination treatment with an immunotherapy.

Simultaneous administration refers to administration of the agents together, for example as a pharmaceutical composition containing the agents (i.e. a combined preparation), or immediately after each other and optionally via the same route of administration, e.g. to the same artery, vein or other blood vessel. In certain embodiments upon simultaneous administration the two or more of the agents may be administered via different routes of administration. In some embodiments simultaneous administration refers to administration at the same time, or within e.g. 1 hr, 2 hrs, 3 hrs, 4 hrs, 5 hrs, 6 hrs, 8 hrs, 12 hrs, 24 hrs, 36 hrs or 48 hrs.

Sequential administration refers to administration of one or more of the agents followed after a given time interval by separate administration of another of the agents. It is not required that the two agents are administered by the same route, although this is the case in some embodiments. The time interval may be any time interval, including hours, days, weeks, months, or years. In some embodiments sequential administration refers to administrations separated by a time interval of one of at least 10 min, 30 min, 1 hr, 6 hrs, 8 hrs, 12 hrs, 24 hrs, 36 hrs, 48 hrs, 3 days, 4 days, 5

Methods of Detection

The invention also provides the articles of the present invention for use in methods for detecting, localizing or imaging IL-11Rα or a complex comprising IL-11Rα, or cells expressing/comprising IL-11Rα or a complex comprising IL-11Rα. The antigen-binding molecules described herein may be used in methods that involve binding of the antigen-binding molecule to IL-11Rα or a complex comprising IL-11Rα. Such methods may involve detection of the bound complex of the antigen-binding molecule and IL-11Rα or a complex comprising IL-11Rα.

Detection of IL-11Rα or a complex comprising IL-11Rα may be useful in methods of diagnosing/prognosing a disease/condition in which IL-11 mediated signalling and/or cells expressing/comprising IL-11Rα or a complex comprising IL-11Rα are pathologically implicated, identifying subjects at risk of developing such diseases/conditions, and/or may be useful in methods of predicting a subject's response to a therapeutic intervention.

As such, a method is provided, comprising contacting a sample containing, or suspected to contain, IL-11Rα or a complex comprising IL-11Rα or cells expressing/comprising IL-11Rα or a complex comprising IL-11Rα with an antigen-binding molecule as described herein, and detecting the formation of a complex of the antigen-binding molecule and IL-11Rα/a complex comprising IL-11Rα. Also provided is a method comprising contacting a sample containing, or suspected to contain, a cell expressing/comprising IL-11Rα or a complex comprising IL-11Rα with an antigen-binding molecule as described herein and detecting the formation of a complex of the antigen-binding molecule and a cell expressing/comprising IL-11Rα or a complex comprising IL-11Rα.

Suitable method formats are well known in the art, including immunoassays such as sandwich assays, e.g. ELISA. The methods may involve labelling the antigen-binding molecule, or target(s), or both, with a detectable moiety, e.g. a fluorescent label, phosphorescent label, luminescent label, immuno-detectable label, radiolabel, chemical, nucleic acid or enzymatic label. IL-11Rα expression may be measured by immunohistochemistry (IHC), for example of a tissue sample obtained by biopsy. In some embodiments, the label may be selected from: a radionucleotide, positron-emitting radionuclide (e.g. for positron emission tomography (PET)), MRI contrast agent or fluorescent label.

Detection techniques are well known to those of skill in the art and can be selected to correspond with the labelling agent. Analysis in vitro or in vivo of processes mediated by IL-11/IL-11R signalling may involve analysis by positron emission tomography (PET), magnetic resonance imaging (MRI), or fluorescence imaging, e.g. by detection of appropriately labelled species.

Methods of this kind may provide the basis of a method of diagnosis of a disease or condition requiring detection and or quantitation of IL-11Rα or a complex comprising IL-11Rα. Such methods may be performed in vitro on a subject sample, or following processing of a subject sample. Once the sample is collected, the subject is not required to be present for the in vitro method of diagnosis to be performed and therefore the method may be one which is not practised on the human or animal body. In some embodiments the antigen-binding molecules, polypeptides, CARs, nucleic acids, expression vectors, cell or compositions according to the present disclosure are provided for use in any method of diagnosis, detection or quantification described herein.

Such methods may involve detecting or quantifying IL-11Rα or a complex comprising IL-11Rα, or cells expressing IL-11Rα or a complex comprising IL-11Rα, e.g. In a patient sample. Where the method comprises quantifying the relevant factor, the method may further comprise comparing the determined amount against a standard or reference value as part of the diagnostic or prognostic evaluation. Other diagnostic/prognostic tests may be used In conjunction with those described herein to enhance the accuracy of the diagnosis or prognosis or to confirm a result obtained by using the tests described herein.

Detection in a sample of IL-11Rα or a complex comprising IL-11Rα may be used for the purpose of diagnosis of an infectious disease, autoimmune disorder or a cancerous condition in the subject, diagnosis of a predisposition to an infectious disease, autoimmune disorder or a cancerous condition or for providing a prognosis (prognosticating) of an infectious disease, autoimmune disorder or a cancerous condition. The diagnosis or prognosis may relate to an existing (previously diagnosed) infectious, inflammatory or autoimmune disease/disorder or cancerous condition.

Where an increased level of IL-11Rα or a complex comprising IL-11Rα is detected, or where the presence of—or an increased number/proportion of—cells expressing/comprising IL-11Rα or a complex comprising IL-11Rα is detected in a sample obtained from a subject, the subject may be diagnosed as having a disease/condition a disease/condition according to the present disclosure, or being at risk of developing such a disease/condition. In such methods, an "increased" level of expression or number/proportion of cells refers to a level/number/proportion which is greater than the level/number/proportion determined for an appropriate control condition, such as the level/number/proportion detected in a comparable sample (e.g. a sample of the same kind, e.g. obtained from the same fluid, tissue, organ etc.). e.g. obtained from a healthy subject.

Where an increased level of IL-11Rα or a complex comprising IL-11Rα is detected, or where the presence of—or an increased number/proportion of—cells expressing/comprising IL-11 or a complex comprising IL-11Rα is detected in a sample obtained from a subject, the subject may be determined to have a poorer prognosis as compared to a subject determined to have a lower level of IL-11Rα or a complex comprising IL-11Rα, or a reduced number/proportion of cells expressing/comprising IL-11Rα or a complex comprising IL-11Rα in a comparable sample (e.g. a sample of the same kind, e.g. obtained from the same fluid, tissue, organ etc.).

Thus the present invention provides methods for selecting/stratifying a subject for treatment with the antigen-binding molecules, polypeptides. CARs, nucleic acids, expression vectors, cell or compositions according to the present invention. In some embodiments a subject is selected for treatment/prevention in accordance with the invention, or is identified as a subject which would benefit from such treatment/prevention, based on detection/quantification of IL-11Rα or a complex comprising IL-11Rα, or cells expressing IL-11Rα or a complex comprising IL-11Rα, e.g. In a sample obtained from the subject. The level of IL-11Rα or a complex comprising IL-11Rα present in a subject sample may be indicative that a subject may respond to treatment with an antigen-binding molecule or composition according to the present invention. The presence of a high level of IL-11Rα or a complex comprising IL-11Rα in a sample may be used to select a subject for treatment as described herein. The antigen-binding molecules of the present invention may therefore be used to select a subject for treatment with IL-11Rα-targeted therapy.

A sample may be taken from any tissue or bodily fluid. The sample may comprise or may be derived from: a quantity of blood; a quantity of serum derived from the individual's blood which may comprise the fluid portion of the blood obtained after removal of the fibrin clot and blood cells; a tissue sample or biopsy; pleural fluid; cerebrospinal fluid (CSF); or cells isolated from said individual. In some embodiments, the sample may be obtained or derived from a tissue or tissues which are affected by the disease/disorder (e.g. tissue or tissues in which symptoms of the disease manifest, or which are involved in the pathogenesis of the disease/disorder).

Methods of diagnosis or prognosis according to the present invention may be performed in vitro on a sample obtained from a subject, or following processing of a sample obtained from a subject. Once the sample is collected, the patient is not required to be present for the in vitro method of diagnosis or prognosis to be performed and therefore the method may be one which is not practised on the human or animal body. The term "in vitro" is intended to encompass experiments with cells in culture whereas the term "in vivo" is intended to encompass experiments with and/or treatment of intact multi-cellular organisms.

The diagnostic and prognostic methods of the present invention may be performed on samples obtained from a subject at multiple time points throughout the course of the disease and/or treatment, and may be used monitor development of the disease/condition over time, e.g. in response to treatment administered to the subject. The results of characterisation in accordance with the methods may be used to inform clinical decisions as to when and what kind of therapy to administer to a subject.

Subjects

The subject in accordance with aspects the invention described herein may be any animal or human. The subject is preferably mammalian, more preferably human. The subject may be a non-human mammal, but is more preferably human. The subject may be male or female. The subject may be a patient. A subject may have been diagnosed with a disease or condition requiring treatment (e.g. a cancer), may be suspected of having such a disease/condition, or may be at risk of developing/contracting such a disease/condition.

The subject/patient may have a disease/disorder that would derive therapeutic or prophylactic benefit from a reduction in the level of (i.e. inhibition or antagonism of) IL-11 mediated signalling, or a reduction in the number and/or activity of cells expressing IL-11Rα or a complex comprising IL-11Rα. The subject/patient may have a disease/disorder as described herein. The subject/patient may have been diagnosed with a disease/disorder as described herein requiring treatment, may be suspected of having such a disease/disorder, or may be at risk of developing such a disease/disorder.

In embodiments according to the present invention the subject is preferably a human subject. In some embodiments, the subject to be treated according to a therapeutic or prophylactic method of the invention herein is a subject having, or at risk of developing, a cancer. In embodiments according to the present invention, a subject may be selected for treatment according to the methods based on characterisation for certain markers of such disease/condition.

Kits

In some aspects of the invention described herein a kit of parts is provided. In some embodiments the kit may have at least one container having a predetermined quantity of an antigen-binding molecule, polypeptide, CAR, nucleic acid (or plurality thereof), expression vector (or plurality thereof), cell or composition described herein.

In some embodiments, the kit may comprise materials for producing an antigen-binding molecule, polypeptide, CAR, nucleic acid (or plurality thereof), expression vector (or plurality thereof), cell or composition described herein.

The kit may provide the antigen-binding molecule, polypeptide, CAR, nucleic acid (or plurality thereof), expression vector (or plurality thereof), cell or composition together with instructions for administration to a patient in order to treat a specified disease/condition.

In some embodiments the kit may further comprise at least one container having a predetermined quantity of another therapeutic agent (e.g. anti-infective agent or chemotherapy agent). In such embodiments, the kit may also comprise a second medicament or pharmaceutical composition such that the two medicaments or pharmaceutical compositions may be administered simultaneously or separately such that they provide a combined treatment for the specific disease or condition. The therapeutic agent may also be formulated so as to be suitable for injection or infusion to a tumor or to the blood.

Sequence Identity

As used herein, "sequence identity" refers to the percent of nucleotides/amino acid residues in a subject sequence that are identical to nucleotides/amino acid residues in a reference sequence, after aligning the sequences and, if necessary, introducing gaps, to achieve the maximum percent sequence identity between the sequences. Pairwise and multiple sequence alignment for the purposes of determining percent sequence identity between two or more amino acid or nucleic acid sequences can be achieved in various ways known to a person of skill in the art, for instance, using publicly available computer software such as ClustalOmega (Söding, J. 2005, Bioinformatics 21, 951-960), T-coffee (Notredame et al. 2000. J. Mol. Biol. (2000) 302, 205-217), Kalign (Lassmann and Sonnhammer 2005, BMC Bioinformatics, 6(298)) and MAFFT (Katoh and Standley 2013, Molecular Biology and Evolution, 30(4) 772-780 software. When using such software, the default parameters, e.g. for gap penalty and extension penalty, are preferably used.

Sequences

| SEQ ID NO: | DESCRIPTION | SEQUENCE |
|---|---|---|
| 1 | Human IL-11 (UniProt: P20809) | MNCVCRLVLWLSLWPDTAVAPGPPPGPPRVSPDPRAELDSTVLLTRSLLADTRQLAAQLRDKFP ADGDHNLDSLPTLAMSAGALGALQLPGVLTRLRADLLSYLRHVQWLRRAGGSSLKTLEPELGTLQ ARLDRLLRRLQLLMSRLALPQPPPDPPAPPLAPPSSAWGGIRAAHAILGGLHLTLDWAVRGLLLLK TRL |

| SEQ ID NO: | DESCRIPTION | SEQUENCE |
|---|---|---|
| 2 | Human gp130 (UniProt P40189-1) | MLTLQTWLVQALFIFLTTESTGELLDPCGYISPESPWQLHSNFTAVCVLKEKCMDYFHVNANYIV WKTNHFTIPKEQYTIINRTASSVTFTDIASLNIQLTCNILTFGQLEQNVYGITIISGLPPEKPKNLSCIV NEGKKMRCEWDGGRETHLETNFTLKSEWATHKFADCKAKRDTPTSCTVDYSTVYFVNIEVWVEA ENALGKVTSDHINFDPVYKVKPNPPHNLSVINSEELSSILKLTWTNPSIKSVIILKYNIQYRTKDAST WSQIPPEDTASTRSSFTVQDLKPFTEYVFRIRCMKEDGKGYWSDWSEEASGITYEDRPSKAPSF WYKIDPSHTQGYRTVQLVWKTLPPFEANGKILDYEVTLTRWKSHLQNYTVNATKLTVNLTNDRYL ATLTVRNLVGKSDAAVLTIPACDFQATHPVMDLKAFPKDNMLWVEWTTPRESVKKYILEWCVLSD KAPCITDWQQEDGTVHRTYLRGNLAESKCYLITVTPVYADGPGSPESIKAYLKQAPPSKGPTVRT KKVGKNEAVLEWDQLPVDVQNGFIRNYTIFYRTIIGNETAVNVDSSHTEYTLSSLTSDTLYMVRMA AYTDEGGKDGPEFTFTTPKFAQGEIEAIWPVCLAFLLTTLLGVLFCFNKRDLIKKHIWPNVPDPSK SHIAQWSPHTPPRHNFNSKDQMYSDGNFTDVSWEIEANDKKPFPEDLKSLDLFKKEKINTEGHS SGIGGSSCMSSSRPSISSSDENESSQNTSSTVQYSTWHSGYRHQVPSVQVFSRSESTQPLLDS EERPEDLQLVDHVDGGDGILPRQQYFKQNCSQHESSPDISHFERSKQVSSVNEEDFVRLKQQIS DHISQSCGSGQMKMFQEVSAADAFGPGTEGQVERFETVGMEAATDEGMPKSYLPQTVRQGGY MPQ |
| 3 | Human IL-11RA (isoform HCR1, UniProt Q14626-1) | MSSSCSGLSRVLVAVATALVSASSPCPQAWGPPGVQYGQPGRSVKLCCPGVTAGDPVSWFRD GEPKLLQGPDSGLGHELVLAQADSTDEGTYICQTLDGALGGTVTLQLGYPPARPWSCQAADYE NFSCTWSPSQISGLPTRYLTSYRKKTVLGADSQRRSPSTGPWPCPQDPLGAARCWHGAEFWS QYRINVTEVNPLGASTRLLDVSLQSILRPDPPQGLRVESVPGYPRRLRASWTYPASWPCQPHFLL KFRLQYRPAQHPAWSTVEPAGLEEVITDAVAGLPHAVRVSARDFLDAGTWSTWSPEAWGTPST GTIPKEIPAWGQLHTQPEVEPQVDSPAPPRPSLQPHPRLLDHRDSVEQVAVLASLGILSFLGLVAG ALALGLWLRLRRGGKDGSPKPGFLASVIPVDRRPGAPNL |
| 4 | Human IL-11RA (isoform HCR2, UniProt Q14626-2) | MSSSCSGLSRVLVAVATALVSASSPCPQAWGPPGVQYGQPGRSVKLCCPGVTAGDPVSWF RDGEPKLLQGPDSGLGHELVLAQADSTDEGTYICQTLDGALGGTVTLQLGYPPARPWSC QAADYENFSCTWSPSQISGLPTRYLTSYRKKTVLGADSQRRSPSTGPWPCPQDPLGAARC WHGAEFWSQYRINVTEVNPLGASTRLLDVSLQSILRPDPPQGLRVESVPGYPRRLRASW TYPASWPCQPHFLLKFRLQYRPAQHPAWSTVEPAGLEEVITDAVAGLPHAVRVSARDFLD AGTWSTWSPEAWGTPSTGTIPKEIPAWGQLHTQPEVEPQVDSPAPPRPSLQPHPRLLDHR DSVEQVAVLASLGILSFLGLVAGALALGLW |
| 5 | IL-11:IL-11Rα fusion protein | MGWSCIILFLVATATGVHSPQAWGPPGVQYGQPGRSVKLCCPGVTAGDPVSWFRDGEPKLLQG PDSGLGHELVLAQADSTDEGTYICQTLDGALGGTVTLQLGYPPARPWSCQAADYENFSCTWSP SQISGLPTRYLTSYRKKTVLGADSQRRSPSTGPWPCPQDPLGAARCWHGAEFWSQYRINVTEV NPLGASTRLLDVSLQSILRPDPPQGLRVESVPGYPRRLRASWTYPASWPCQPHFLLKFRLQYRPA QHPAWSTVEPAGLEEVITDAVAGLPHAVRVSARDFLDAGTWSTWSPEAWGTPSTGGPAGQSGG GGGSGGGSGGGSVPGPPPGPPRVSPDPRAELDSTVLLTRSLLADTRQLAAQLRDKFPADGDHN LDSLPTLAMSAGALGALQLPGVLTRLRADLLSYLRHVQWLRRAGGSSLKTLEPELGTLQARLDRL LRRLQLLMSRLALPQPPPDPPAPPLAPPSSAWGGIRAAHAILGGLHLTLDWAVRGLLLLKTRLHHH HHH |
| 6 | Nucleotide sequence encoding IL-11:IL-11Rα fusion proten | GAATTCCCGCCGCCACCATGGGCTGGTCCTGCATCATCCTGTTTCTGGTGGCCACAGCCACC GGCGTGCACTCTCCACAGGCTTGGGGACCTCCAGGCGTGCAGTATGGCCAGCCTGGCAGAT CCGTGAAGCTGTGCTGTCCTGGCGTGACAGCTGGCGACCCTGTGTCCTGGTTCAGAGATGG CGAGCCCAAGCTGCTGCAGGGCCCAGATTCTGGACTGGGCCACGAACTGGTGCTGGCCCAG GCCGATTCTACCGACGAGGGCACCTACATCTGCCAGACCCTGGATGGCGCCCTGGGCGGAA CAGTGACACTGCAGCTGGGCTACCCTCCCGCCAGACCTGTGGTGTCTTGTCAGGCCGCCGA CTACGAGAACTTCAGCTGCACATGGTCCCCAAGCCAGATCAGCGGCCTGCCCACCAGATACC TGACCAGCTACCGGAAGAAAACCGTGCTGGGCGCCGACAGCCAGAGAAGAAGCCCTTCTAC AGGCCCCTGGCCCTGCCCTCAGGATCCTCTGGGAGCTGCCAGATGTGTGGTGCCAGCGCC GAGTTCTGGTCCCAGTACCGGATCAACGTGACCGAAGTGAACCCCCTGGGCGCCTCCACAA GACTGCTGGATGTGTCCCTGCAGAGCATCCTGCGGCCCGATCCTCCACAGGGCCTGAGAGT GGAAAGCGTGCCCGGCTACCCCAGAAGGCTGAGAGCCAGCTGGACATACCCCGCCTCTTGG CCTTGCCAGCCCCACTTCCTGCTGAAGTTTCGGCTGCAGTACCGGCCCGCCCAGCACCCTG CTTGGAGCACAGTGGAACCTGCCGGCCTGGAAGAAGTGATCACAGACGCCGTGGCCGGACT GCCTCATGCTGTGCGGGTGTCCGCCAGAGACTTTCTGGATGCCGGCACCTGGTCTACCTGG TCCCCAGAAGCCTGGGCACACCTTCTACTGGCGGACCTGCTGGACAGTCTGGCGGAGGCG GAGGAAGTGGCGGAGGATCAGGGGGAGGATCTGTGCCTGGACCTCCTCCAGGACCCCCTA GAGTGTCCCCAGATCCTAGGGCCGAGCTGGACTCTACCGTGCTGCTGACCAGATCCCTGCT GGCCGACACAGGCAGCTGGCTGCCCAGCTGAGAGACAAGTTCCCCGCCGACGGCGACCA CAACCTGGATAGCCTGCCTACCCTGGCCATGTCTGCTGGCGCACTGGGGGCTCTGCAGCTG CCTGGGGTGCTGACTAGACTGAGAGCCGACCTGCTGAGCTACCTGCGGCATGTGCAGTGGC TGAAAGGGCTGGCGGCAGCAGCCTGAAAACCCTGGAACCTGAGCTGGGCACACTGCAGGC CAGACTGGACAGACTGCTGCGCAGACTGCAGCTGCTGATGAGCAGACTGGCTCTGCCCCAG CCTCCTCCTGACCCTCCTGCTCCTCCACTGGCTCCTCCAAGCTCTGCTTGGGGCGGAATTAG AGCCGCCCACGCCATTCTGGGAGGCCTGCACCTGACACTGGATTGGGCAGTGCGGGCCTG CTGCTGCTGAAAACCAGACIGCACCACCACCATCACCACTGATAAGCTT |
| 7 | 9A7 VH | QVQLQQPGAELVRPGSSVKLSCKASGYTFTNYWMHWLKQRPVQGLEWIGNIGPSDSKTHYNQK FKDKATLTVDKSSSTAYMQLNSLTSEDSAVYYCARGDYVLFTYWGQGTLVTVSA |
| 8 | 9A7 VH 1 | QVQLVQSGAELKKPGASVKLSCKASGYTFTNYWMHWLKQRPGQGLEWIGNIGPSDSKTHYNQK FKDRATLTVDKSTSTAYMQLNSLTSEDSAVYYCARGDYVLFTYWGQGTLVTVSS |

-continued

| SEQ ID NO: | DESCRIPTION | SEQUENCE |
|---|---|---|
| 9 | 9A7 VH 2 | QVQLVQSGAEVKKPGASVKLSCKASGYTFTNYWMHWLKQRPGQGLEWIGNIGPSDSKTHYNQK FKDRATLTVDKSTSTAYMELSSLRSEDTAVYYCARGDYVLFTYWGQGTLVTVSS |
| 10 | 9A7 VH 3 | QVQLVQSGAEVKKPGASVKVSCKASGYTFTNYWMHWLRQRPGQGLEWIGNIGPSDSKTHYNQK FKDRATLTVDKSTSTAYMELSSLRSEDTAVYYCARGDYVLFTYWGQGTLVTVSS |
| 11 | 9A7 VH 4 | QVQLVQSGAEVKKPGASVKVSCKASGYTFTNYWMHWLRQRPGQGLEWIGNIGPSDSKTHYNQK FKDRVTMTVDKSTSTAYMELSSLRSEDTAVYYCARGDYVLFTYWWGQGTLVTVSS |
| 12 | 9A7 VH5 | QVQLVQSGAEVKKPGASVKVSCKASGYTFTNYWMHWVRQAPGQGLEWIGNIGPSDSKTHYNQK FQDRVTMTVDKSTSTAYMELSSLRSEDTAVYYCARGDYVLFTYWWGQGTLVTVSS |
| 13 | 9A7 VL | DIVLTQSPATLSMTPGDSVSLSCRASQSISNNLHWYQQKSHESPRLLIKYASQSISGIPSRFSGSG SGTDFTLSFNSVETEDFGVYFCQQSYSWPLTFGAGTKLELK |
| 14 | 9A7 VL 1 | DIVLTQSPATLSLSPGERATLSCRASQSISNNLHWYQQKSHEAPRLLIKYASQSISGIPARFSGSGS GTDFTLSFSSLETEDFAVYFCQQSYSWPLTFGQGTKLEIK |
| 15 | 9A7 VL 2 | DIVLTQSPATLSLSPGERATLSCRASQSISNNLHWYQQKSGQAPRLLIKYASQSISGIPARFSGSG SGTDFTLTISSLETEDFAVYFCQQSYSWPLTFGQGTKLEIK |
| 16 | 9A7 VL 3 | DIVLTQSPATLSLSPGERATLSCRASQSISNNLHWYQQKPGQAPRLLIKYASQSISGIPARFSGSG SGTDFILTISSLEPEDFAVYFCQQSYSWPLTFGQGTKLEIK |
| 17 | 9A7 V4 | DIVLTQSPATLSLSPGERATLSCRASQSISNNLHWYQQKPGQAPRLLIKYASQSISGIPARFSGSG SGTDFTLTISSLEPEDFAVYYCQQSYSWPLTFGQGTKLEIK |
| 18 | 9A7 VH, 9A7 VH 1, 9A7 VH 2, 9A7 VH 3, 9A7 VH 4, 9A7 VH 5 HC-CDR1 | NYWMH |
| 19 | 9A7 VH, 9A7 VH 1, 9A7 VH 2, 9A7 VH 3, 9A7 VH 4 HC-CDR2 | NIGPSDSKTHYNQKFKD |
| 20 | 9A7 VH5 HC-CDR2 | NIGPSDSKTHYNQKFQD |
| 21 | 9A7 VH, 9A7 VH 1, 9A7 VH 2, 9A7 VH 3, 9A7 VH 4, 9A7 VH 5 HC-CDR3 | GDYVLFTY |
| 22 | 9A7 VL, 9A7 VL 1, 9A7 VL 2, 9A7 VL 3, 9A7 VL 4 LC-CDR1 | RASQSISNNLH |
| 23 | 9A7 VL, 9A7 VL 1, 9A7 VL 2, 9A7 VL 3, 9A7 VL 4 LC-CDR2 | YASQSIS |
| 24 | 9A7 VL, 9A7 VL 1, 9A7 VL 2, 9A7 VL 3, 9A7 VL 4 LC-CDR3 | QQSYSWPLT |

| SEQ ID NO: | DESCRIPTION | SEQUENCE |
|---|---|---|
| 25 | 9A7 VH HC-FR1 | QVQLQQPGAELVRPGSSVKLSCKASGYTFT |
| 26 | 9A7 VH 1 HC-FR1 | QVQLVQSGAELKKPGASVKLSCKASGYTFT |
| 27 | 9A7 VH 2 HC-FR1 | QVQLVQSGAEVKKPGASVKLSCKASGYTFT |
| 28 | 9A7 VH 3, 9A7 VH 4, 9A7 VH 5 HC-FR1 | QVQLVQSGAEVKKPGASVKVSCKASGYTFT |
| 29 | 9A7 VH HC-FR2 | WLKQRPVQGLEWIG |
| 30 | 9A7 VH 1, 9A7 VH 2 HC-FR2 | WLKQRPGQGLEWIG |
| 31 | 9A7 VH 3, 9A7 VH 4 HC-FR2 | WLRQRPGQGLEWIG |
| 32 | 9A7 VH 5 HC-FR2 | WVRQAPGQGLEWIG |
| 33 | 9A7 VH HC-FR3 | KATLTVDKSSSTAYMQLNSLTSEDSAVYYCAR |
| 34 | 9A7 VH 1 HC-FR3 | RATLTVDKSTSTAYMQLNSLTSEDSAVYYCAR |
| 35 | 9A7 VH 2, 9A7 VH 3 HC-FR3 | RATLTVDKSTSTAYMELSSLRSEDTAVYYCAR |
| 36 | 9A7 VH 4, 9A7 VH 5 HC-FR3 | RVTMTVDKSTSTAYMELSSLRSEDTAVYYCAR |
| 37 | 9A7 VH HC-FR4 | WGQGTLVTVSA |
| 38 | 9A7 VH 1, 9A7 VH 2, 9A7 VH 3, 9A7 VH 4, 9A7 VH 5 HC-FR4 | WGQGTLVTVSS |
| 39 | 9A7 VL LC-FR1 | DIVLTQSPATLSMTPGDSVSLSC |
| 40 | 9A7 VL 1, 9A7 VL 2, 9A7 VL 3, 9A7 VL 4 LC-FR1 | DIVLTQSPATLSLSPGERATLSC |
| 41 | 9A7 VL LC-FR2 | WYQQKSHESPRLLIK |
| 42 | 9A7 VL 1 LC-FR2 | WYQQKSHEAPRLLIK |
| 43 | 9A7 VL 2 LC-FR2 | WYQQKSGQAPRLLIK |
| 44 | 9A7 VL 3, 9A7 VL 4 LC-FR2 | WYQQKPGQAPRLLIK |

| SEQ ID NO: | DESCRIPTION | SEQUENCE |
|---|---|---|
| 45 | 9A7 VL LC-FR3 | GIPSRFSGSGSGTDFTLSFNSVETEDFGVYFC |
| 46 | 9A7 VL 1 LC-FR3 | GIPARFSGSGSGTDFTLSFSSLETEDFAVYFC |
| 47 | 9A7 VL 2 LC-FR3 | GIPARFSGSGSGTDFTLTISSLETEDFAVYFC |
| 48 | 9A7 VL 3 LC-FR3 | GIPARFSGSGSGTDFTLTISSLEPEDFAVYFC |
| 49 | 9A7 VL 4 LC-FR3 | GIPARFSGSGSGTDFTLTISSLEPEDFAVYYC |
| 50 | 9A7 VL LC-FR4 | FGAGTKLELK |
| 51 | 9A7 VL 1, 9A7 VL 2, 9A7 VL 3, 9A7 VL 4 LC-FR4 | FGQGTKLEIK |
| 52 | 9A7 VH HC-CDR2 consensus | NIGPSDSKTHYNQKFX1D<br>X1 = K or Q |
| 53 | Human IgG1 constant region (IGHG1; UniProt:P01857-1, v1) | ASTKGPSVFPLAPSSKSTSGGTAALGCLVKDYFPEPVTVSWNSGALTSGVHTFPAVLQSSGLYSL<br>SSVVTVPSSSLGTQTYICNVNHKPSNTKVDKKVEPKSCDKTHTCPPCPAPELLGGPSVFLFPPKP<br>KDTLMISRTPEVTCVVVDVSHEDPEVKFNWYVDGVEVHNAKTKPREEQYNSTYRVVSVLTVLHQ<br>DWLNGKEYKCKVSNKALPAPIEKTISKAKGQPREPQVYTLPPSRDELTKNQVSLTCLVKGFYPSDI<br>AVEWESNGQPENNYKTTPPVLDSDGSFFLYSKLTVDKSRWQQGNVFSCSVMHEALHNHYTQKS<br>LSLSPGK |
| 54 | CH1 IgG1 (positions 1-98 of P01857-1, v1) | ASTKGPSVFPLAPSSKSTSGGTAALGCLVKDYFPEPVTVSWNSGALTSGVHTFPAVLQSSGLYSL<br>SSVVTVPSSSLGTQTYICNVNHKPSNTKVDKKV |
| 55 | Hinge IgG1 (positions 99-110 of P01857-1, v1) | EPKSCDKTHTCP |
| 56 | CH2 IgG1 (positions 111-223 of P01857-1, v1) | PCPAPELLGGPSVFLFPPKPKDTLMISRTPEVTCVVVDVSHEDPEVKFNWYVDGVEVHNAKTKPR<br>EEQYNSTYRVVSVLTVLHQDWLNGKEYKCKVSNKALPAPIEKTISKAK |
| 57 | CH3 IgG1 (positions 224-330 of P01857-1, v1) | GQPREPQVYTLPPSRDELTKNQVSLTCLVKGFYPSDIAVEWESNGQPENNYKTTPPVLDSDGSF<br>FLYSKLTVDKSRWQQGNVFSCSVMHEALHNHYTQKSLSLSPGK |
| 58 | CK CL (IGCK; UniProt:P01834-1, v2) | RTVAAPSVFIFPPSDEQLKSGTASVVCLLNNFYPREAKVQWKVDNALQSGNSQESVTEQDSKDS<br>TYSLSSTLTLSKADYEKHKVYACEVTHQGLSSPVTKSFNRGEC |
| 59 | 9A7O VL | DIVLTQSPATLSMTPGDSVSLSCRASQSISNNLHWYQQKSHESPRLLIKYASQSISGIPSRFSGSG<br>SGTDFTLSFNSVETEDFGVYFCQQRYSWPLTFGAGTKLEMK |
| 60 | 9A7O VL LC-CDR3 | QQRYSWPLT |
| 61 | Human IgG4 constant region (IGHG4: UniProt: P01861, v1) | ASTKGPSVFPLAPCSRSTSESTAALGCLVKDYFPEPVTVSWNSGALTSGVHTFPAVLQSSGLYSL<br>SSVVTVPSSSLGTKTYTCNVDHKPSNTKVDKRVESKYGPPCPSCPAPEFLGGPSVFLFPPKPKDT<br>LMISRTPEVTCVVVDVSQEDPEVQFNWYVDGVEVHNAKTKPREEQFNSTYRVVSVLTVLHQDWL<br>NGKEYKCKVSNKGLPSSIEKTISKAKGQPREPQVYTLPPSQEEMTKNQVSLTCLVKGFYPSDIAVE<br>WESNGQPENNYKTTPPVLDSDGSFFLYSRLTVDKSRWQEGNVFSCSVMHEALHNHYTQKSLSL<br>SLGK |
| 62 | CH1 IgG4 (positions 1-98 of P01861, v1) | ASTKGPSVFPLAPCSRSTSESTAALGCLVKDYFPEPVTVSWNSGALTSGVHTFPAVLQSSGYSL<br>SSVVTVPSSSLGTKTYTCNVDHKPSNTKVDKRV |
| 67 | Hinge IgG4 (positions 99-110 of P01861, v1) | ESKYGPPCPSCP |

| SEQ ID NO: | DESCRIPTION | SEQUENCE |
|---|---|---|
| 64 | CH2 IgG4 (positions 111-220 of P01861 v1) | APEFLGGPSVFLFPPKPKDTLMISRTPEVTCVVVDVSQEDPEVQFNWYVDGVEVHNAKTKPREE QFNSTYRVVSVLTVLHQDWLNGKEYKCKVSNKGLPSSIEKTISKAK |
| 65 | CH3 IgG4 (positions 221-327 of P01861, v1) | GQPREPQVYTLPPSQEEMTKNQVSLTCLVKGFYPSDIAVEWESNGQPENNYKTTPPVLDS DGSFFLYSRLTVDKSRWQEGNVFSCSVMHEALHNHYTQKSLSLSLGK |
| 66 | Human IgG4 constant region IGHG4 UniProt: P01861, v1; S241P) | ASTKGPSVFPLAPCSRSTSESTAALGCLVKDYFPEPVTVSWNSGALTSGVHTFPAVLQSSGLYSL SSVVTVPSSSLGTKTYTCNVDHKPSNTKVDKRVESKYGPPCPPCPAPEFLGGPSVFLFPPKPKDT LMISRTPEVTCVVVDVSQEDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQVSLTCLVKGFYPSDIAVE WESNGQPENNYKTTPPVLDSDGSFFLYSRLTVDKSRWQEGNVFSCSVMHEALHNHYTQKSLSL SLGK |
| 67 | Hinge IgG4 (positions 99-110 of P01861, v1: S241P) | ESKYGPPCPPCP |
| 68 | Human IgG4 constant region IGHG4; UniProt: P01861, v1; S241P and L248E) | ASTKGPSVFPLAPCSRSTSESTAALGCLVKDYFPEPVTVSWNSGALTSGVHTFPAVLQSSGLYSL SSVVTVPSSSLGTKTYTCNVDHKPSNTKVDKRVESKYGPPCPPCPAPEFEGGPSVFLFPPKPKDT LMISRTPEVTCVVVDVSQEDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQVSLTCLVKGFYPSDIAVE WESNGQPENNYKTTPPVLDSDGSFFLYSRLTVDKSRWQEGNVFSCSVMHEALHNHYTQKSLSL SLGK |
| 69 | CH2 IgG4 (positions 111-220 of P01861, v1; L248E) | APEFEGGPSVFLFPPKPKDTLMISRTPEVTCVVVDVSQEDPEVQFNWYVDGVEVHNAKTKPREE QFNSTYRVVSVLTVLHQDWLNGKEYKCKVSNKGLPSSIEKTISKAK |
| 70 | 9A7 VH4-Human IgG1 constant region (IGHG1; UniProt:P01857-1, v1) | QVQLVQSGAEVKKPGASVKVSCKASGYTFTNYWMHWLRQRPGQGLEWIGNIGPSDSKTHYNQK FKDRVTMTVDKSTSTAYMELSSLRSEDTAVYYCARGDYVLFTYWGQGTLVTVSSASTKGPSVFP LAPSSKSTSGGTAALGCLVKDYFPEPVTVSWNSGALTSGVHTFPAVLQSSGLYSLSSVVTVPSSS LGTQTYICNVNHKPSNTKVDKKVEPKSCDKTHTCPPCPAPELLGGPSVFLFPPKPKDTLMISRTPE VTCVVVDVSHEDPEVKFNWYVDGVEVHNAKTKPREEQYNSTYRVVSVLTVLHQDWLNGKEYKC KVSNKALPAPIEKTISKAKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNHYTQKSLSLSPGK |
| 71 | 9A7 VH4-Human IgG4 constant region (IGHG4; UniProt: P01861, v1; S241P) | QVQLVQSGAEVKKPGASVKVSCKASGYTFTNYWMHWLRQRPGQGLEWIGNIGPSDSKTHYNQK FKDRVTMTVDKSTSTAYMELSSLRSEDTAVYYCARGDYVLFTYWGQGTLVTVSSASTKGPSVFP LAPCSRSTSESTAALGCLVKDYFPEPVTVSWNSGALTSGVHTFPAVLQSSGLYSLSSWTVPSSS LGTKTYTCNVDHKPSNTKVDKRVESKYGPPCPSCPAPEFLGGPSVFLFPPKPKDTLMISRTPEVT CVVVDVSQEDPEVQFNWYVDGVEVHNAKTKPREEQFNSTYRWSVLTVLHQDWLNGKEYKCKV SNKGLPSSIEKTISKAKGQPREPQVYTLPPSQEEMTKNQVSLTCLVKGFYPSDIAVEWESNGQPE NNYKTTPPVLDSDGSFFLYSRLTVDKSRWQEGNVFSCSVMHEALHNHYTQKSLSLSLGK |
| 72 | 9A7 VH4-Human IgG4 constant region (IGHG4; UniProt; P01861, v1; S241P) | QVQLVQSGAEVKKPGASVKVSCKASGYTFTNYWMHWLRQRPGQGLEWIGNIGPSDSKTHYNQK FKDRVTMTVDKSTSTAYMELSSLRSEDTAVYYCARGDYVLFTYWGQGTLVTVSSASTKGPSVFP LAPCSRSTSESTAALGCLVKDYFPEPVTVSWNSGALTSGVHTFPAVLQSSGLYSLSSWTVPSSS LGTKTYTCNVDHKPSNTKVDKRVESKYGPPCPPCPAPEFLGGPSVFLFPPKPKDTLMISRTPEVT CVVVDVSQEDPEVQFNWYVDGVEVHNAKTKPREEQFNSTYRWSVLTVLHQDWLNGKEYKCKV SNKGLPSSIEKTISKAKGQPREPQVYTLPPSQEEMTKNQVSLTCLVKGFYPSDIAVEWESNGQPE NNYKTTPPVLDSDGSFFLYSRLTVDKSRWQEGNVFSCSVMHEALHNHYTQKSLSLSLGK |
| 73 | 9A7 VH4-Human IgG4 constant region (IGHG4; UniProt: P01861, v1; S241P and L248E) | QVQLVQSGAEVKKPGASVKVSCKASGYTFTNYWMHWLRQRPGQGLEWIGNIGPSDSKTHYNQK FKDRVTMTVDKSTSTAYMELSSLRSEDTAVYYCARGDYVLFTYWGQGTLVTVSSASTKGPSVFP LAPCSRSTSESTAALGCLVKDYFPEPVTVSWNSGALTSGVHTFPAVLQSSGLYSLSSWTVPSSS LGTKTYTCNVDHKPSNTKVDKRVESKYGPPCPPCPAPEFEGGPSVFLFPPKPKDTLMISRTPEVT CVVVDVSQEDPEVQFNWYVDGVEVHNAKTKPREEQFNSTYRWSVLTVLHQDWLNGKEYKCKV SNKGLPSSIEKTISKAKGQPREPQVYTLPPSQEEMTKNQVSLTCLVKGFYPSDIAVEWESNGQPE NNYKTTPPVLDSDGSFFLYSRLTVDKSRWQEGNVFSCSVMHEALHNHYTQKSLSLSLGK |
| 74 | 9A7 VL4-VL-Cκ CL (IGCK; UniProt: P01834-1, v2) | DIVLTQSPATLSLSPGERATLSCRASQSISNNLHWYQQKPGQAPRLLIKYASQSISGIPARFSGSG SGTDFTLTISSLEPEDFAVYYCQQSYSWPLTFGQGTKLEIKRTVAAPSVFIFPPSDEQLKSGTASV VCLLNNFYPREAKVQWKVDNALQSGNSQESVTEQDSKDSTYSLSSTLTLSKADYEKHKVYACEV THQGLSSPVTKSFNRGEC |
| 75 | $C_L$ CL (IGLC1; UniProt: P0CG04, v1) | GQPKANPTVTLFPPSSEELQANKATLVCLISDFYPGAVTVAWKADGSPVKAGVETTKPSKQSNNK YAASSYLSLTPEQWKSHRSYSCQVTHEGSTVEKTVAPTECS |
| 76 | $C_L$ CL (IGCL2; UniProt: P0DOY2, v1) | GQPKAAPSVTLFPPSSEELQANKATLVCLISDFYPGAVTVAWKADSSPVKAGVETTTPSKQSNNK YAASSYLSLTPEQWKSHRSYSCQVTHEGSTVEKTVAPTECS |

| SEQ ID NO: | DESCRIPTION | SEQUENCE |
|---|---|---|
| 77 | $C_L$ CL (IGCL3; UniProt: P0DOY3, v1) | GQPKAAPSVTLFPPSSEELQANKATLVCLISDFYPGAVTVAWKADSSPVKAGVETTTPSKQSNNK YAASSYLSLTPEQWKSHKSYSCQVTHEGSTVEKTVAPTECS |
| 78 | $C_L$ CL (IGCL6; UniProt: P0CF74, v1) | GQPKAAPSVTLFPPSSEELQANKATLVCLISDFYPGAVKVAWKADGSPVNTGVETTTPSKQSNNK YAASSYLSLTPEQWKSHRSYSCQVTHEGSTVEKTVAPAECS |
| 79 | $C_L$ CL (IGCL7; UniProt:A0M8Q6, v3) | GQPKAAPSVTLFPPSSEELQANKATLVCLVSDFNPGAVTVAWKADGSPVKVGVETTKPSKQSNN KYAASSYLSLTPEQWKSHRSYSCRVTHEGSTVEKTVAPAECS |

Numbered Paragraphs (Paras) Relating to Aspects and Embodiments of the Invention:

1. An antigen-binding molecule, optionally isolated, which is capable of binding to IL-11Rα, wherein the antigen-binding molecule comprises:
   (i) a heavy chain variable (VH) region incorporating the following CDRs:
   HC-CDR1 having the amino acid sequence of SEQ ID NO:18
   HC-CDR2 having the amino acid sequence of SEQ ID NO:52
   HC-CDR3 having the amino acid sequence of SEQ ID NO:21; and
   (ii) a light chain variable (VL) region incorporating the following CDRs:
   LC-CDR1 having the amino acid sequence of SEQ ID NO:22
   LC-CDR2 having the amino acid sequence of SEQ ID NO:23
   LC-CDR3 having the amino acid sequence of SEQ ID NO:24.

2. The antigen-binding molecule according to para 1, wherein the antigen-binding molecule comprises:
   (i) a heavy chain variable (VH) region incorporating the following CDRs:
   HC-CDR1 having the amino acid sequence of SEQ ID NO:18
   HC-CDR2 having the amino acid sequence of SEQ ID NO:19
   HC-CDR3 having the amino acid sequence of SEQ ID NO:21; and
   (ii) a light chain variable (VL) region incorporating the following CDRs:
   LC-CDR1 having the amino acid sequence of SEQ ID NO:22
   LC-CDR2 having the amino acid sequence of SEQ ID NO:23
   LC-CDR3 having the amino acid sequence of SEQ ID NO:24.

3. The antigen-binding molecule according to para 1, wherein the antigen-binding molecule comprises:
   (i) a heavy chain variable (VH) region incorporating the following CDRs:
   HC-CDR1 having the amino acid sequence of SEQ ID NO:18
   HC-CDR2 having the amino acid sequence of SEQ ID NO:20
   HC-CDR3 having the amino acid sequence of SEQ ID NO:21; and
   (ii) a light chain variable (VL) region incorporating the following CDRs:
   LC-CDR1 having the amino acid sequence of SEQ ID NO:22
   LC-CDR2 having the amino acid sequence of SEQ ID NO:23
   LC-CDR3 having the amino acid sequence of SEQ ID NO:24.

4. The antigen-binding molecule according to any one of paras 1 to 3, wherein the antigen-binding molecule comprises:
   a VH region comprising an amino acid sequence having at least 70% sequence identity to the amino acid sequence of SEQ ID NO:7, 8, 9, 10, 11 or 12; and
   a VL region comprising an amino acid sequence having at least 70% sequence identity to the amino acid sequence of SEQ ID NO:13, 14, 15, 16 or 17.

5. The antigen-binding molecule according to any one of paras 1 to 4, wherein the antigen-binding molecule is capable of inhibiting IL-11 mediated signalling.

6. An antigen-binding molecule, optionally isolated, comprising (i) an antigen-binding molecule according to any one of paras 1 to 5, and (ii) an antigen-binding molecule capable of binding to an antigen other than IL-11Rα.

7. The antigen-binding molecule according to any one of paras 1 to 6, wherein the antigen-binding molecule is capable of inhibiting interaction between IL-11Rα or a complex comprising IL-11Rα and an interaction partner for IL-11Rα or the complex comprising IL-11Rα.

8. A chimeric antigen receptor (CAR) comprising an antigen-binding molecule according to any one of paras 1 to 7.

9. A nucleic acid, or a plurality of nucleic acids, optionally isolated, encoding an antigen-binding molecule according to any one of paras 1 to 7 or a CAR according to para 8.

10. An expression vector, or a plurality of expression vectors, comprising a nucleic acid or a plurality of nucleic acids according to para 9.

11. A cell comprising an antigen-binding molecule according to any one of paras 1 to 7, a CAR according to para 8, a nucleic acid or a plurality of nucleic acids according to para 9, or an expression vector or a plurality of expression vectors according to para 10.

12. A method comprising culturing a cell comprising a nucleic acid or a plurality of nucleic acids according to para 9, or an expression vector or a plurality of expression vectors according to para 10, under conditions suitable for expression of the antigen-binding molecule or CAR from the nucleic acid(s) or expression vector(s).

13. A composition comprising an antigen-binding molecule according to any one of paras 1 to 7, a CAR according to para 8, a nucleic acid or a plurality of nucleic acids according to para 9, an expression vector or a plurality of expression vectors according to para 10, or a cell according to para 11.

14. An antigen-binding molecule according to any one of paras 1 to 7, a CAR according to para 8, a nucleic acid or a plurality of nucleic acids according to para 9, an expression vector or a plurality of expression vectors according to para 10, a cell according to para 11, or a composition according to para 13 for use in a method of medical treatment or prophylaxis.

15. An antigen-binding molecule according to any one of paras 1 to 7, a CAR according to para 8, a nucleic acid or a plurality of nucleic acids according to para 9, an expression vector or a plurality of expression vectors according to para 10, a cell according to para 11, or a composition according to para 13, for use in a method of treatment or prevention of fibrosis, a disease characterised by fibrosis, a cancer, inflammation, or a disease characterised by inflammation.

16. Use of an antigen-binding molecule according to any one of paras 1 to 7, a CAR according to para 8, a nucleic acid or a plurality of nucleic acids according to para 9, an expression vector or a plurality of expression vectors according to para 10, a cell according to para 11, or a composition according to para 13, in the manufacture of a medicament for use in a method of treatment or prevention of fibrosis, a disease characterised by fibrosis, a cancer, inflammation, or a disease characterised by inflammation.

18. A method of treating or preventing fibrosis, a disease characterised by fibrosis, a cancer, inflammation, or a disease characterised by inflammation, comprising administering to a subject a therapeutically or prophylactically effective amount of an antigen-binding molecule according to any one of paras 1 to 7, a CAR according to para 8, a nucleic acid or a plurality of nucleic acids according to para 9, an expression vector or a plurality of expression vectors according to para 10, a cell according to para 11, or a composition according to para 13.

19. A method of inhibiting IL-11 mediated signalling, comprising contacting IL-11Rα-expressing cells with an antigen-binding molecule according to any one of paras 1 to 7.

20. An in vitro complex, optionally isolated, comprising an antigen-binding molecule according to any one of paras 1 to 7 bound to IL-11Rα or a complex comprising IL-11Rα.

21. A method comprising contacting a sample containing, or suspected to contain, IL-11Rα or a complex comprising IL-11Rα with an antigen-binding molecule according to any one of paras 1 to 7, and detecting the formation of a complex of the antigen-binding molecule with IL-11Rα or a complex comprising IL-11Rα.

22. A method of selecting or stratifying a subject for treatment with an IL-11Rα-targeted agent, the method comprising contacting, in vitro, a sample from the subject with an antigen-binding molecule according to any one of paras 1 to 7 and detecting the formation of a complex of the antigen-binding molecule with IL-11Rα or a complex comprising IL-11Rα.

23. Use of an antigen-binding molecule according to any one of paras 1 to 7 as an in vitro or in vivo diagnostic or prognostic agent.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise." and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value.

Similarly, when values are expressed as approximations, by the use of the antecedent "about," it will be understood that the particular value forms another embodiment.

Where a nucleic acid sequence is disclosed herein, the reverse complement thereof is also expressly contemplated.

Methods described herein may preferably performed in vitro. The term "In vitro" is intended to encompass procedures performed with cells in culture whereas the term "in vivo" is intended to encompass procedures with/on intact multi-cellular organisms.

BRIEF DESCRIPTION OF THE FIGURES

Embodiments and experiments illustrating the principles of the invention will now be discussed with reference to the accompanying figures.

NASH was stimulated by a high fat methionine/choline deficient (HFMCD) diet for 6 weeks, then treated with 4 weeks biweekly anti-IL-11Rα antibody treatment. IgG used as a control. (15A) Western blots of mouse hepatic ERK activation status. (15B) Relative liver hydroxyproline content. (15C) Serum ALT levels. (15D) NASH was stimulated by a single subcutaneous injection of streptozotocin and mice were fed on a normal chow diet for 4 weeks, then HFMCD diet for 7 weeks along with anti-IL-11Rα antibody or IgG control. Graph shows RNA expression of fibrosis and inflammation genes after 7 weeks.

Figure 16:
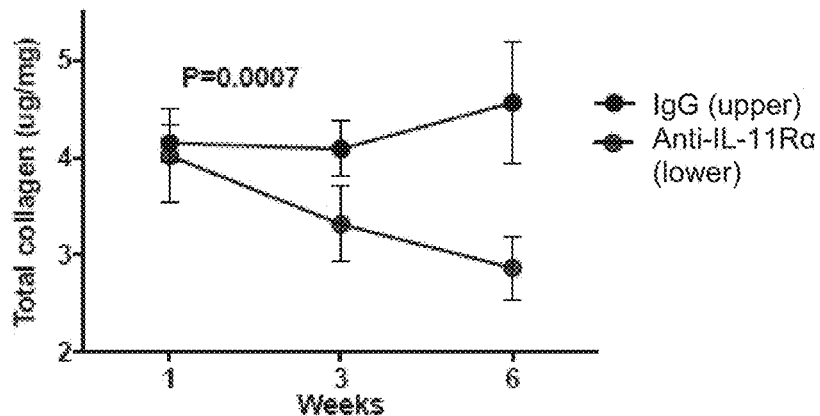
Figure 17A:
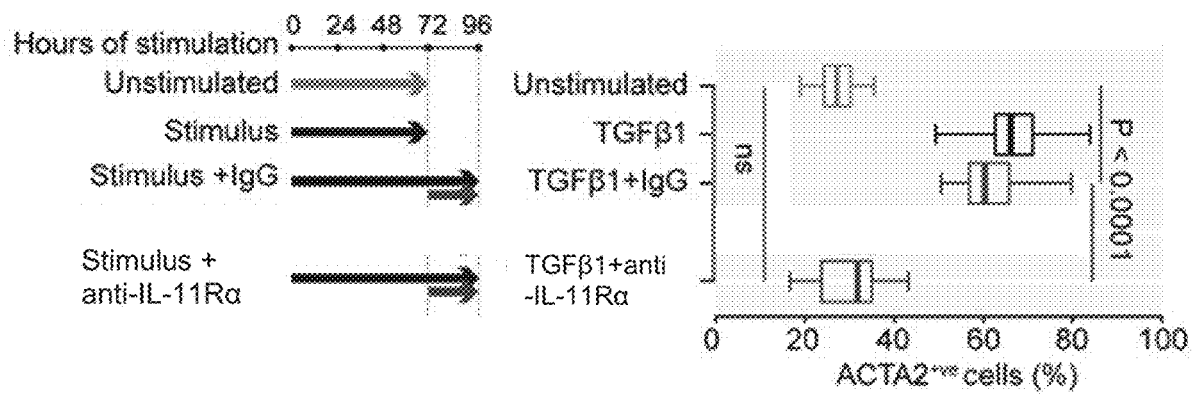
Figure 17B:
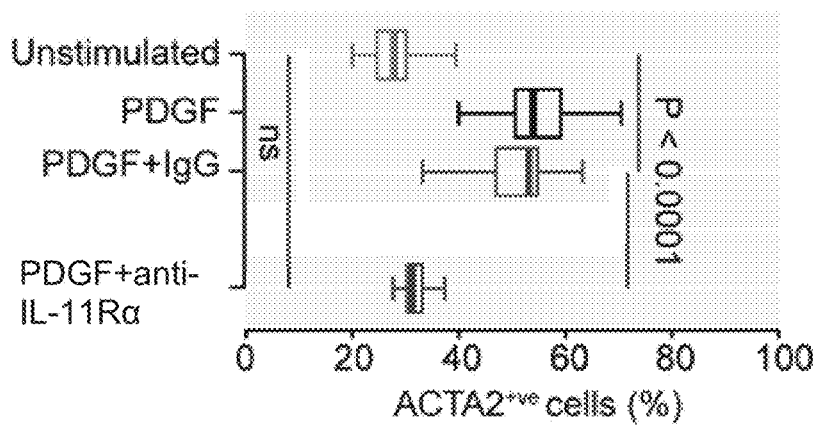
Figure 17C:
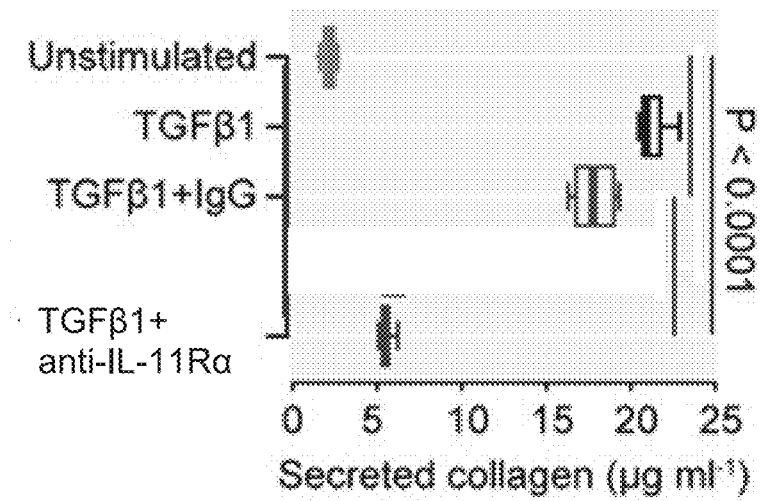
Figure 17D:
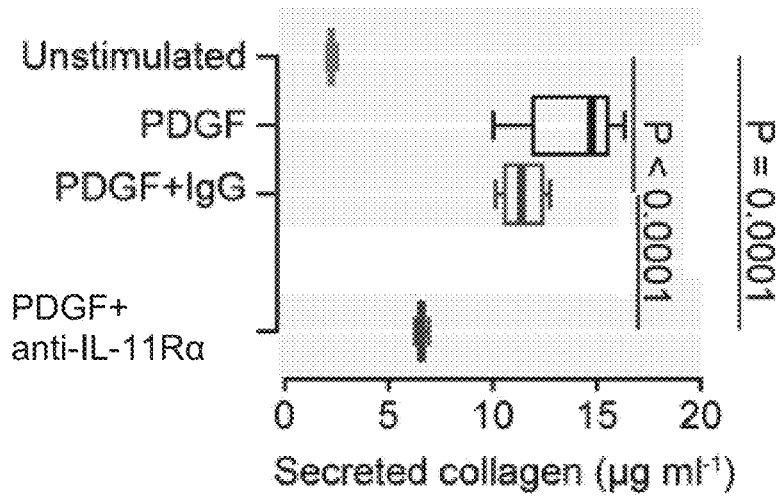
Figure 17E:
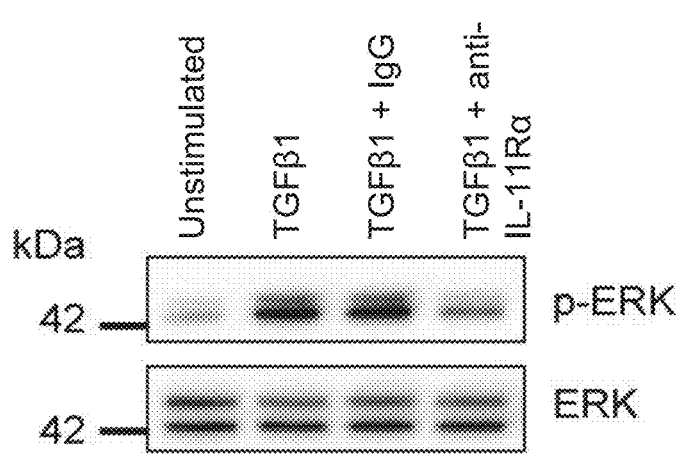
Figure 18A:
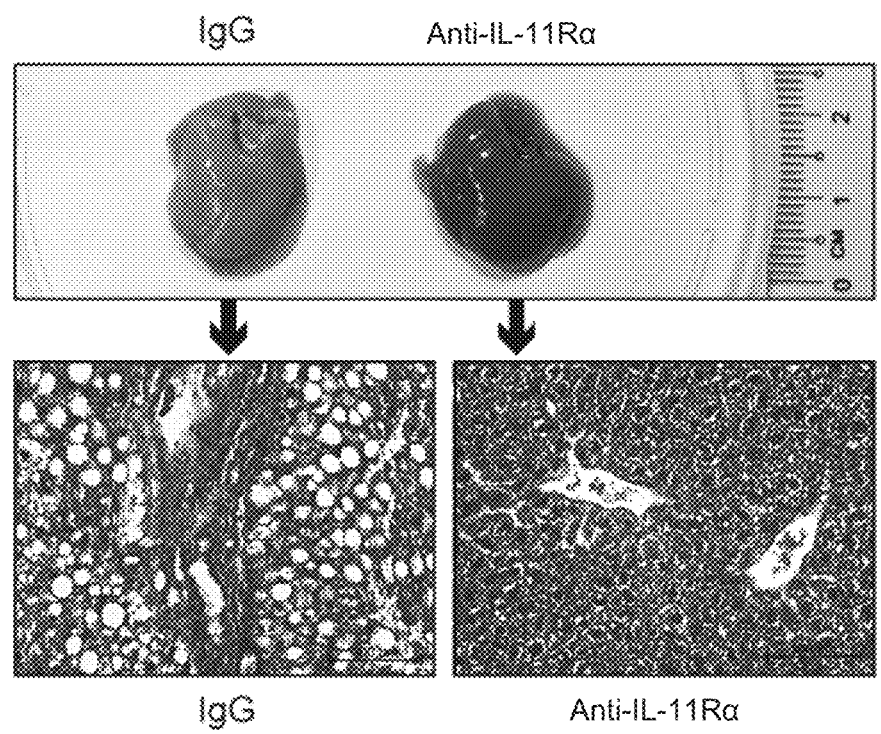
Figure 18B:
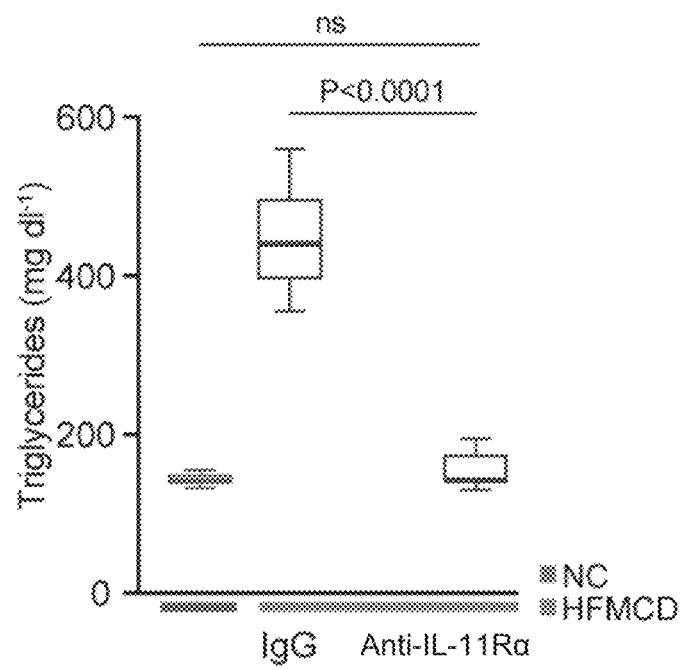
Figure 18C:
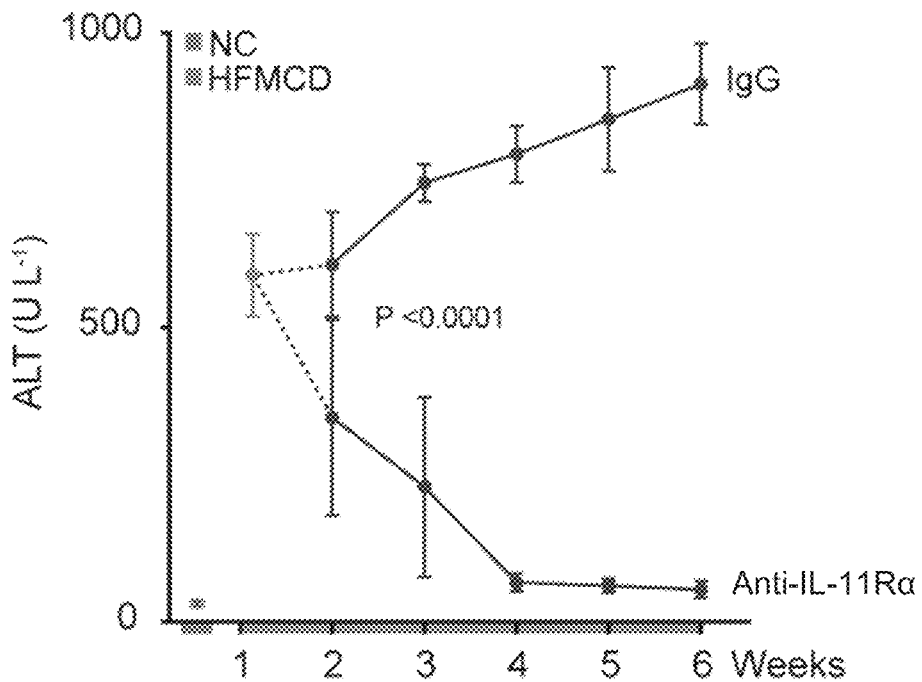
Figure 18D:
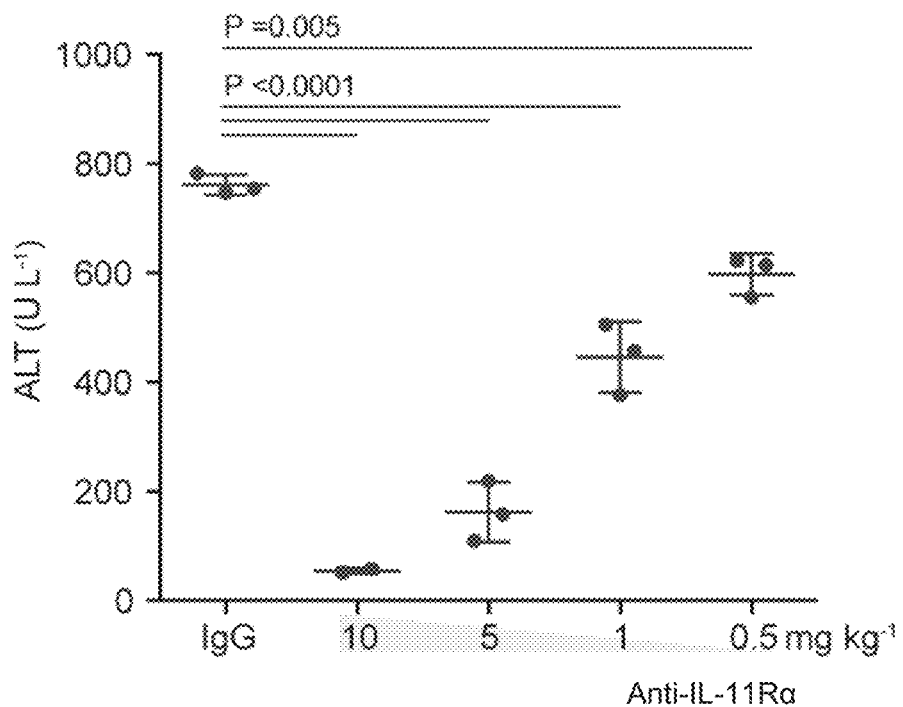
Figure 18E:
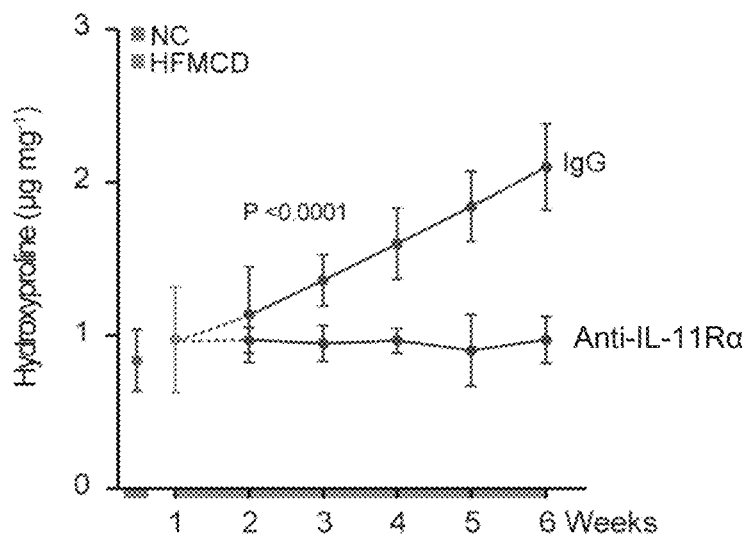
Figure 18F:
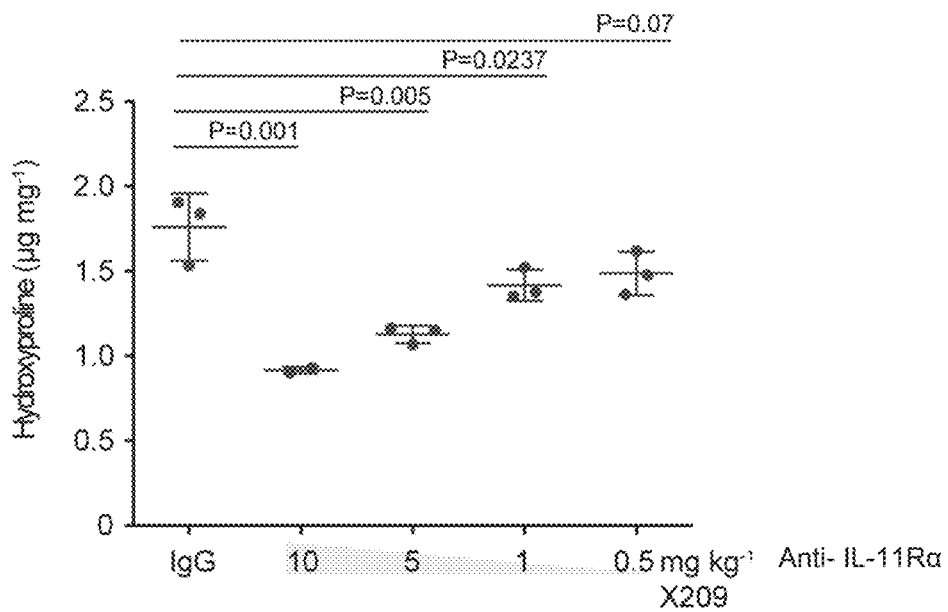
Figure 18G:
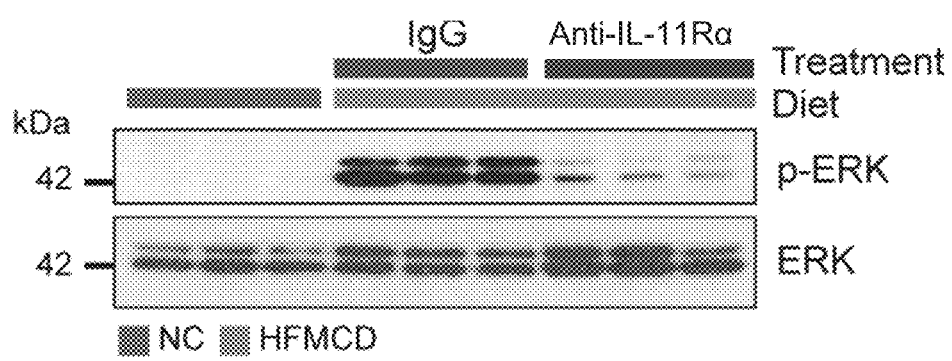
Figure 18H:
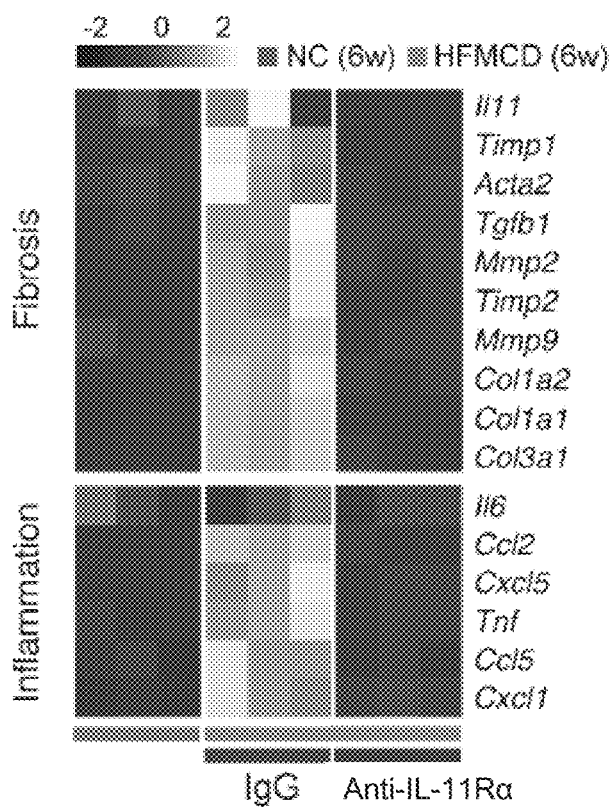
Figure 18I:
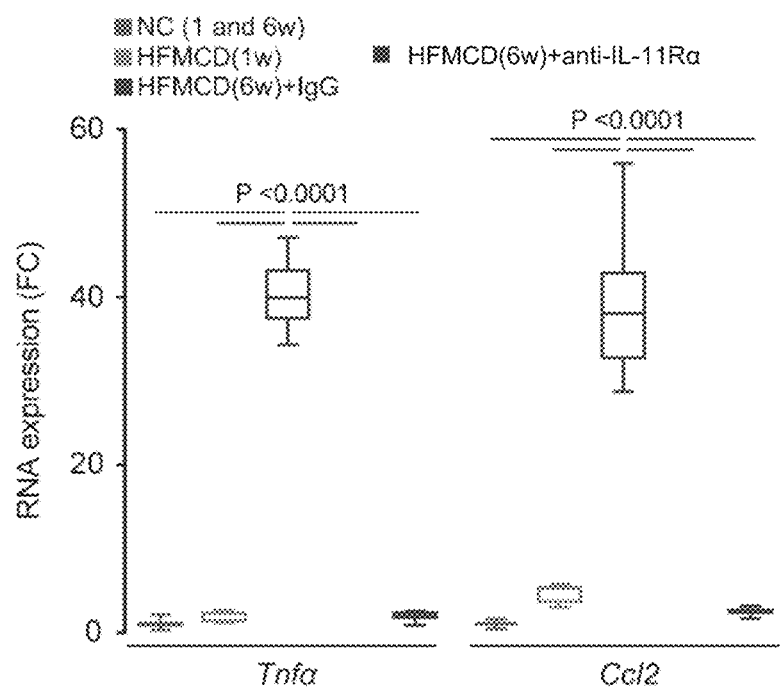
Figure 18J:
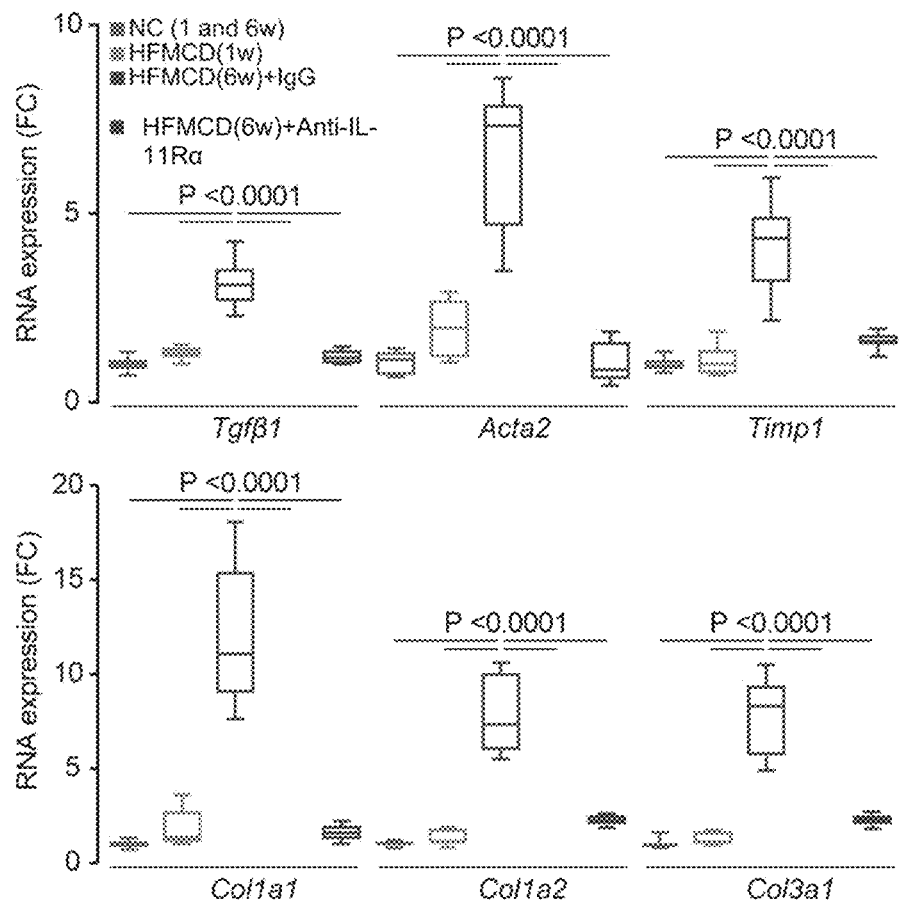
Figure 18K:
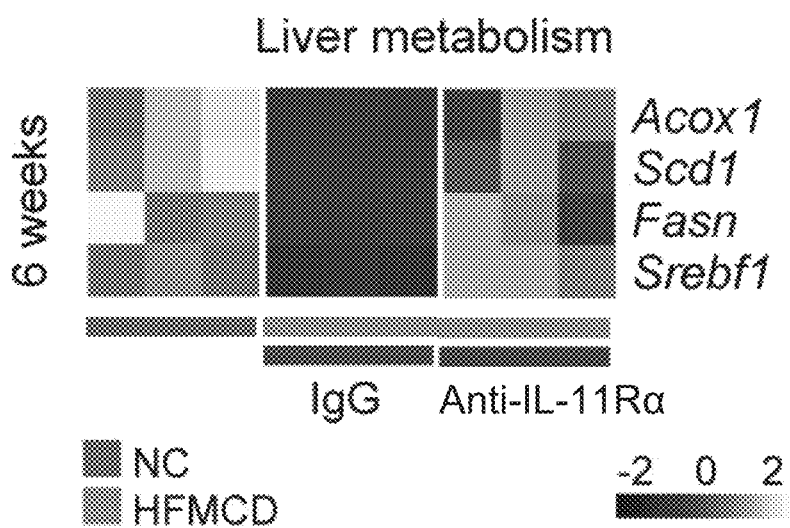

FIG. 16. The reversing effect of anti-IL-11Rα therapy on liver fibrosis. Severe liver fibrosis was established in mice with the HFMCD diet for 10 weeks, then mice were treated with diet+anti-IL-11Rα antibody or IgG (20 mg/kg) twice per week for six weeks whilst still on the HFMCD diet. (16A) Total liver hydroxyproline content.

FIGS. 17A to 17E. The effect of anti-IL-11Rα therapy on transformed HSCs stimulated by TGFβ1 or PDGF for 72 hours then treated with anti-IL-11Rα antibody or IgG control for 24 hours in the presence of ongoing TGFβ1 or PDGF stimulation. (17A) Schedule of treatment and quantification of percentage of ACTA2$^{+ve}$ cells after treatment with TGFβ1 then antibodies. (17B) Quantification of percentage of ACTA2$^{+ve}$ cells after treatment with PDGF then antibodies (schedule of treatment as in 17A). (17C) Amount of secreted collagen after treatment with TGFβ1 then antibodies. (17D) Amount of secreted collagen after treatment with PDGF then antibodies. (17E) ERK activity after treatment with TGFβ1 then antibodies. (A-D) Data are shown as box-and-whisker with median (middle line), 25th-75th percentiles (box) and min-max percentiles (whiskers).

FIGS. 18A to 18K. The effect of anti-IL-11Rα therapy in early stage NASH, established in mice with the HFMCD diet for 1 week, then diet+anti-IL-11Rα antibody or IgG for five weeks. (18A) Representative gross liver images and representative Masson's Trichrome stained images of livers after five weeks of IgG or anti-IL-11Rα treatments. (18B) Hepatic triglyceride levels after five weeks of treatment. (18C) Serum ALT levels. (18D) Dose-dependent effect of 3-week anti-IL-11Rα therapy on reversal of serum ALT levels. (18E) Liver hydroxyproline content. (18F) Dose dependent effects of anti-IL-11Rα therapy on total hydroxyproline content. (18G) Hepatic ERK phosphorylation after five weeks of treatment. (18H) Differential expression heatmap of pro-fibrotic and pro-inflammatory genes Z-scores in mice on normal chow diet and mice on HFMCD diet after treatment with anti-IL-11Rα antibody or IgG control. (18I) RNA expression of pro-inflammatory genes. (18J) RNA expression of pro-fibrotic genes. (18K) Differential expression heatmap of lipogenesis and β-oxidation genes showing that anti-IL-11Rα antibody improved hepatic lipid metabolism as compared to IgG.

Figure 19A:
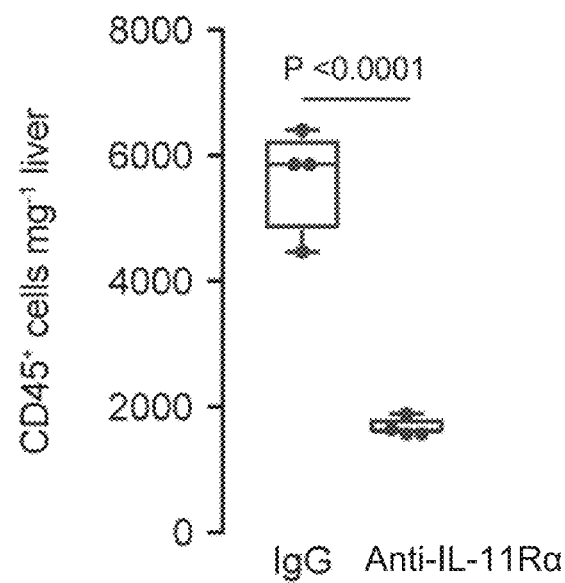
Figure 19B:
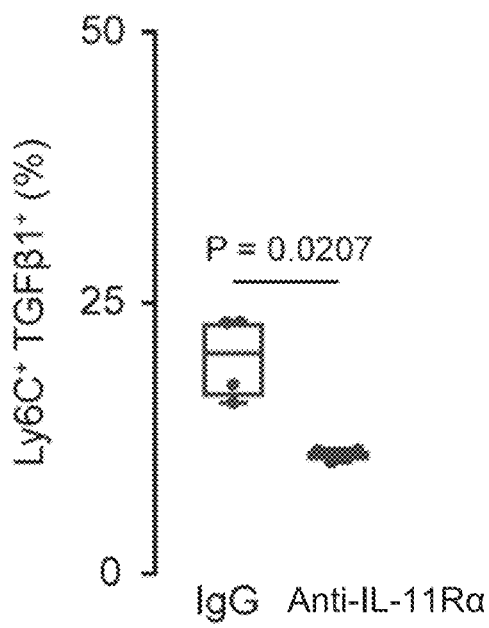
Figure 19C:
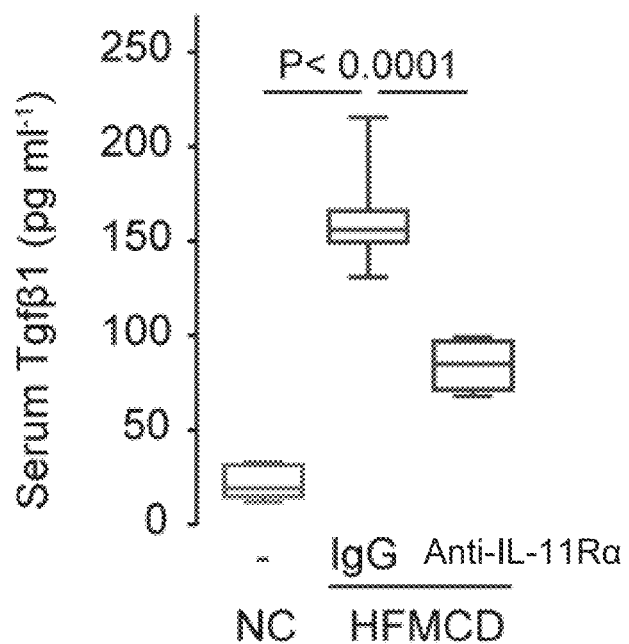

FIGS. 19A to 19C. The effect of anti-IL-11Rα therapy in early stage NASH model on liver inflammatory cell populations. (19A) Liver CD45$^{+ve}$ immune cell numbers. (19B) Ly6C$^{+ve}$ TGFβ1$^{+ve}$ cells in the total CD45$^{+ve}$ populations. (19C) Serum TGFβ levels (n≥5/group). Data are shown as box-and-whisker with median (middle line), 25th-75th percentiles (box) and min-max percentiles (whiskers). (A-B) two-tailed Student's t-test; (C) two-tailed, Tukey-corrected Student's t-test.

Figure 20:
Figure 20:
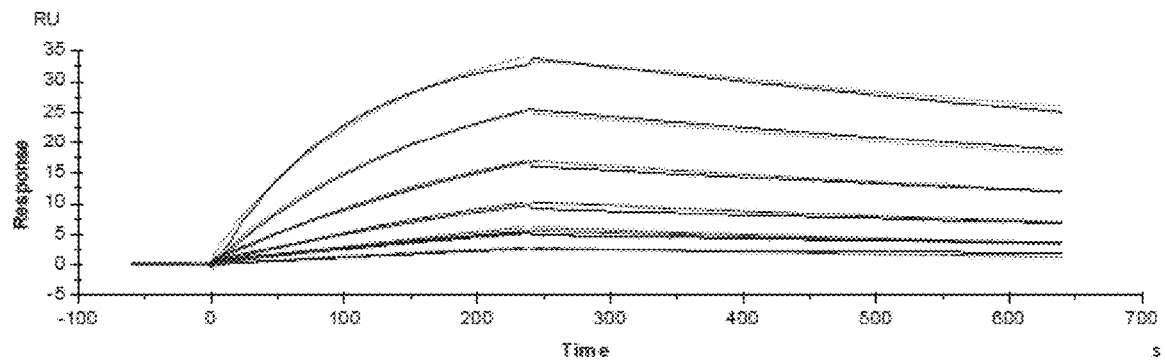
Figure 20:
Figure 20:
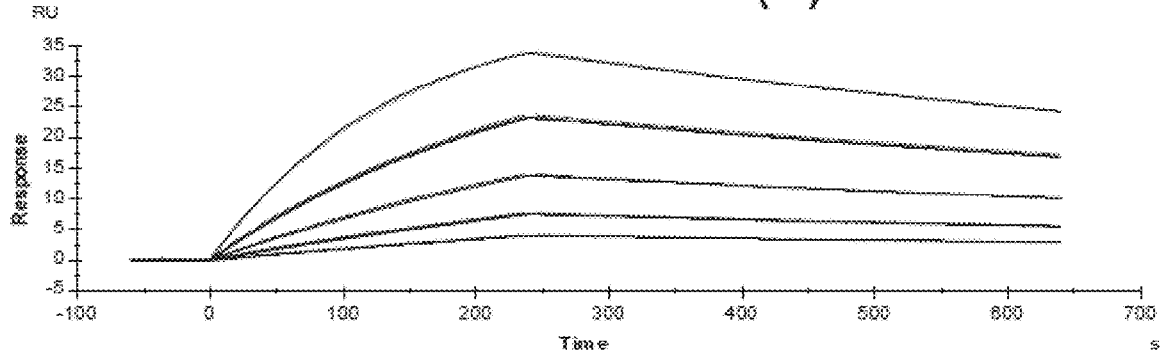

FIG. 20. Sensorgrams and table showing the results of Multi-Cycle Kinetics analysis of affinity of binding of anti-IL-11Rα antibody to human IL-11Rα. The results of two separate analyses are shown.

Figure 21:
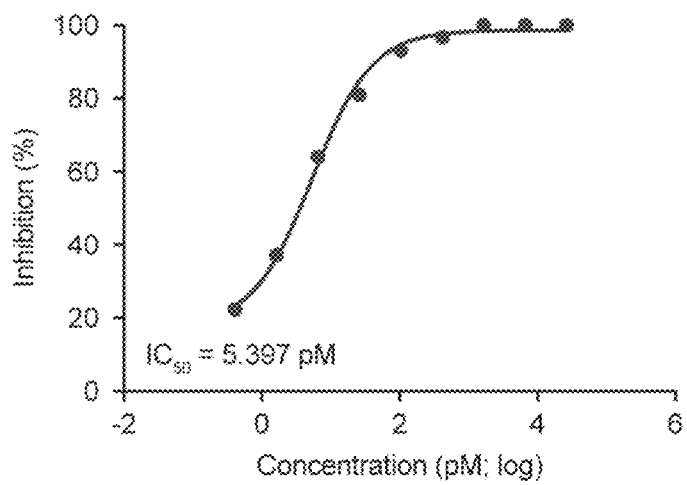

FIG. 21. Dose-response curve and IC50 value of anti-IL-11Rα antibody clone BSO-9A7 In inhibiting MMP2 secretion by HSCs stimulated with 5 ng/ml TGFβ1.

Figure 22A:
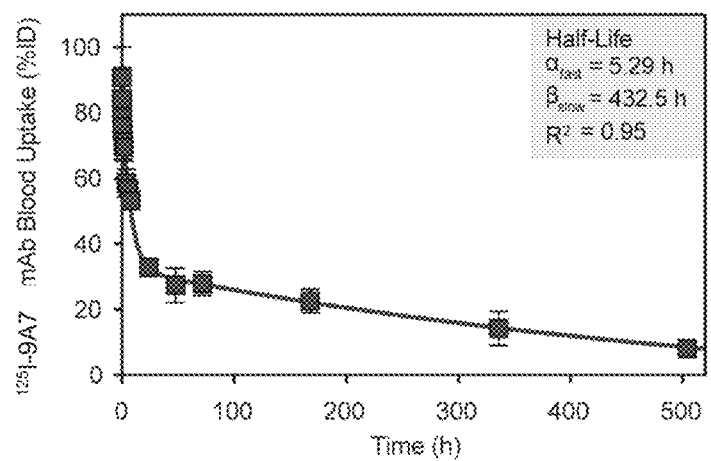
Figure 22B:
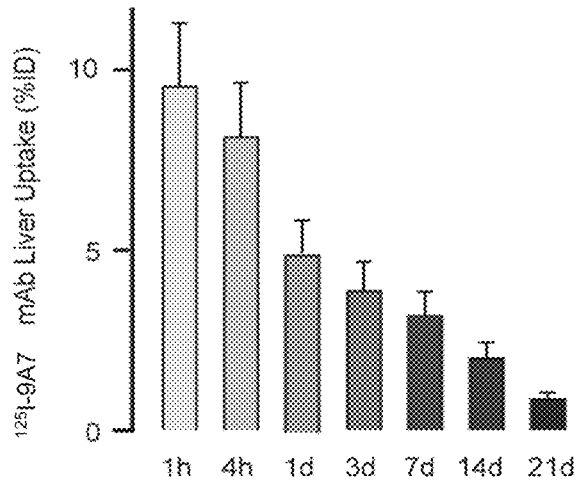

FIGS. 22A and 22B. Graphs showing half-life (22A) and liver uptake (22B) of radiolabelled $^{125}$I-9A7 anti-IL-11Rα antibody clone.

Figure 23A:
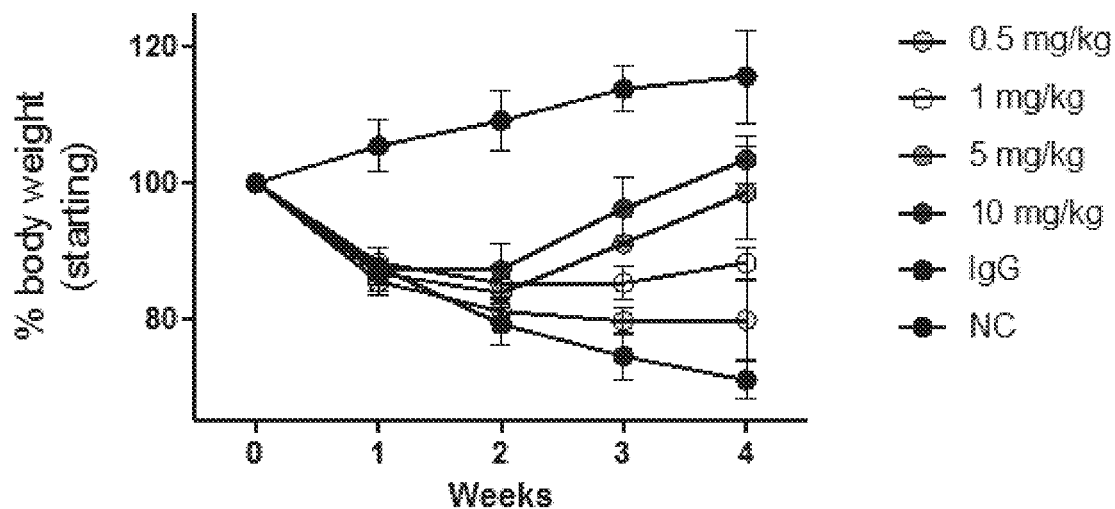
Figure 23B:
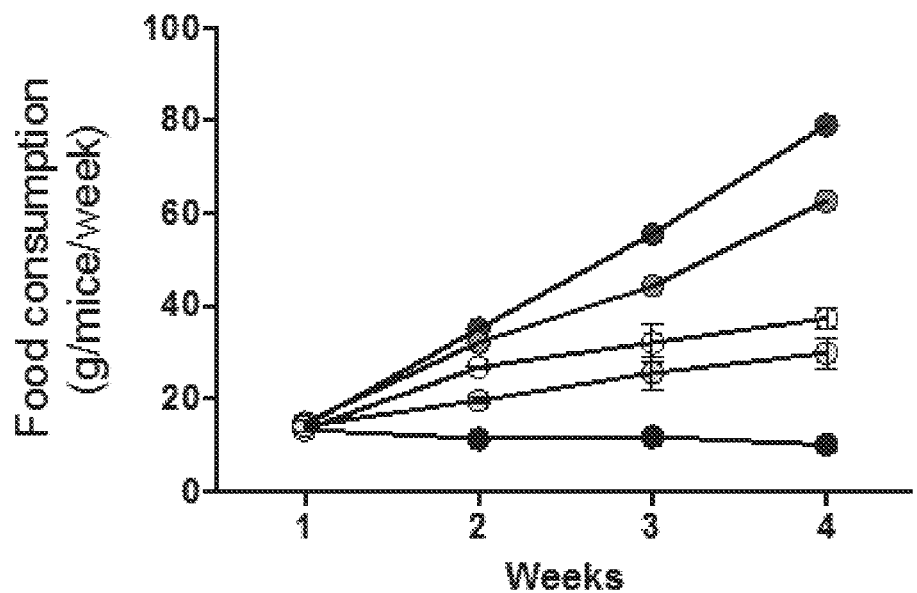

FIGS. 23A and 23B. Graphs showing the effects of anti-IL-11Rα (9A7) antibody treatment on body weight (A) and food consumption (B) in a model of wasting-related weight loss. Mice fed a HFMCD diet were treated 2×/week with 0.5, 1, 5 or 10 mg/kg anti-IL-11Rα antibody. Control mice were either fed with normal chow (NC), or fed on a HFMCD diet and treated with IgG isotype control.

Figure 24:
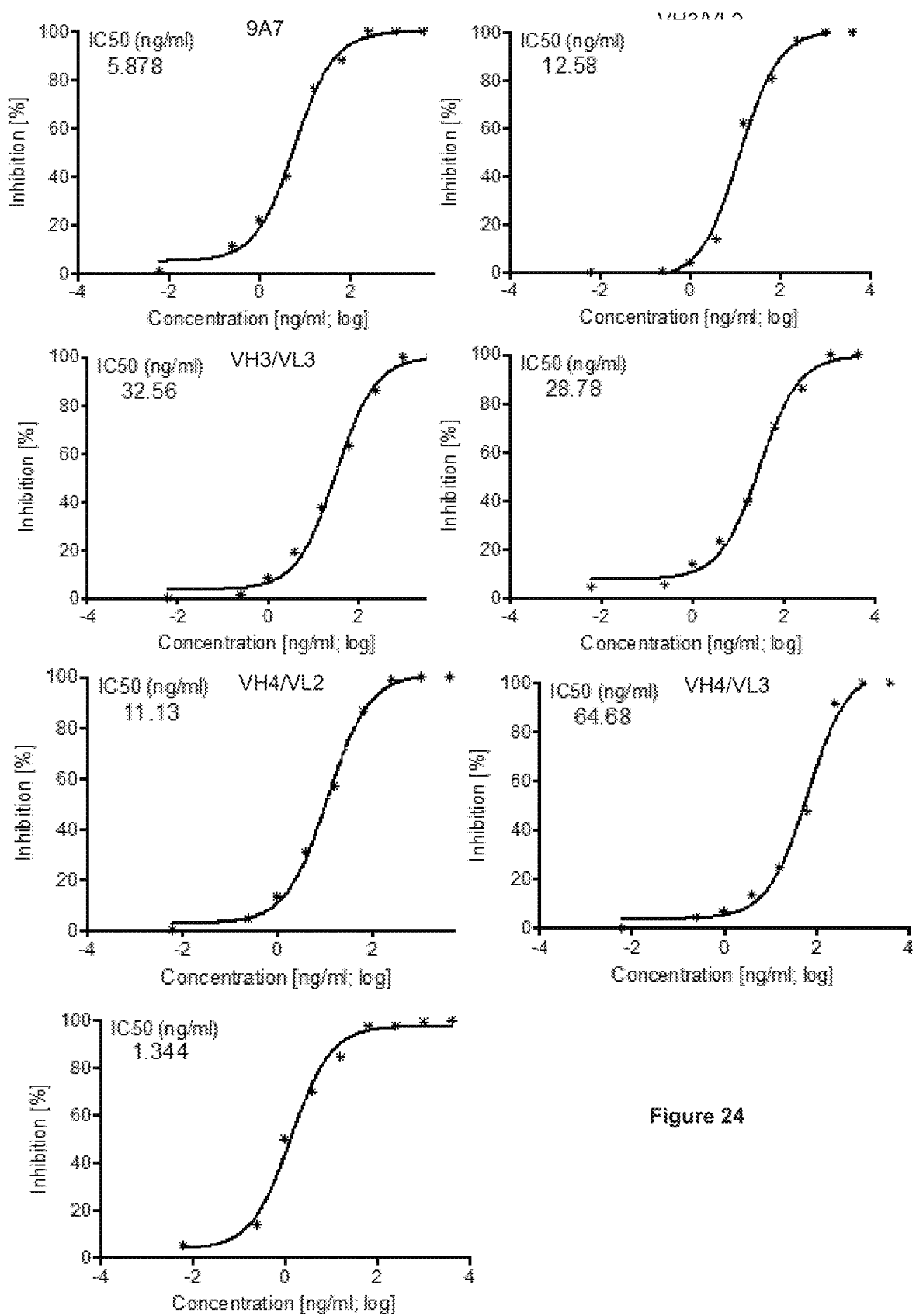

FIG. 24. Graphs showing ability of anti-IL-11Rα antibodies 9A7 and six 9A7 humanised clones to neutralise IL-11 signalling. Primary human atrial fibroblasts were stimulated with TGFβ1 and fibrogenic protein MMP2 production measured at varying concentrations of antibodies. IC50 values are indicated.

Figure 25:
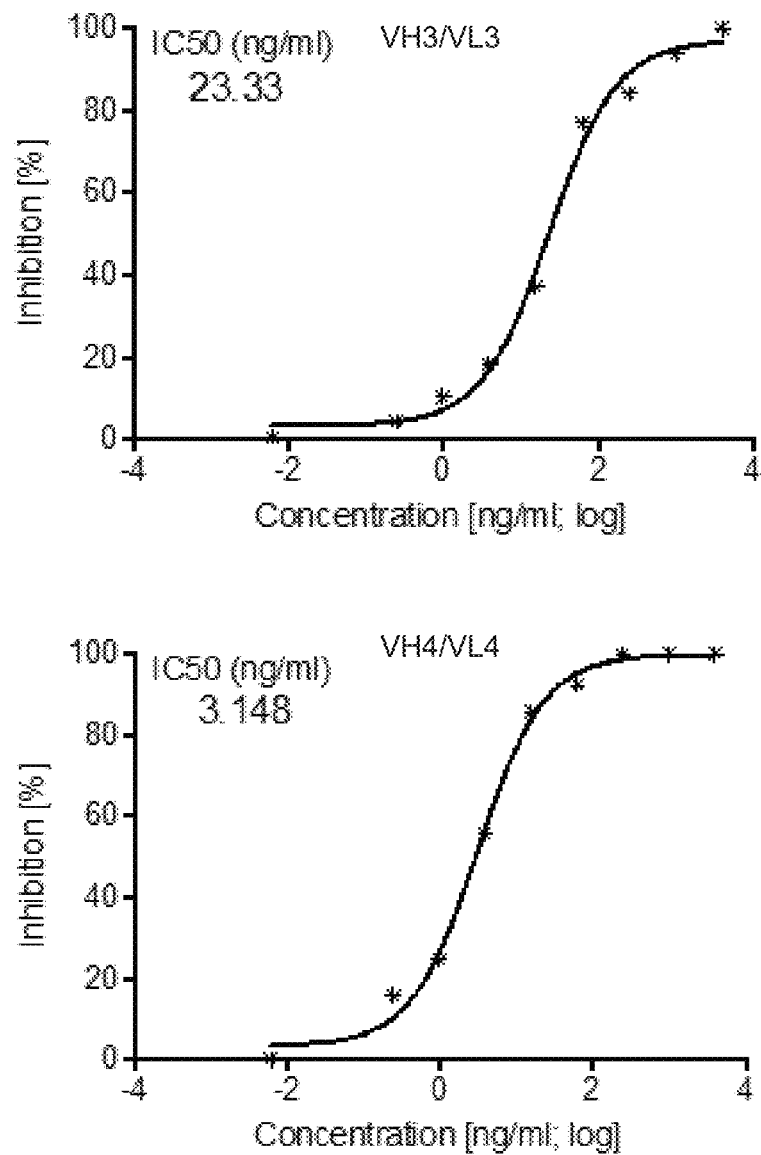

FIG. 25. Graphs showing ability of humanised anti-IL-11Rα antibodies VH3/VL3 and VH4/VL4 to neutralise IL-11 signalling. Human hepatic stellate cells were stimulated with TGFβ1 and fibrogenic protein MMP2 production measured at varying concentrations of antibodies. IC50 values are indicated.

Figure 26:
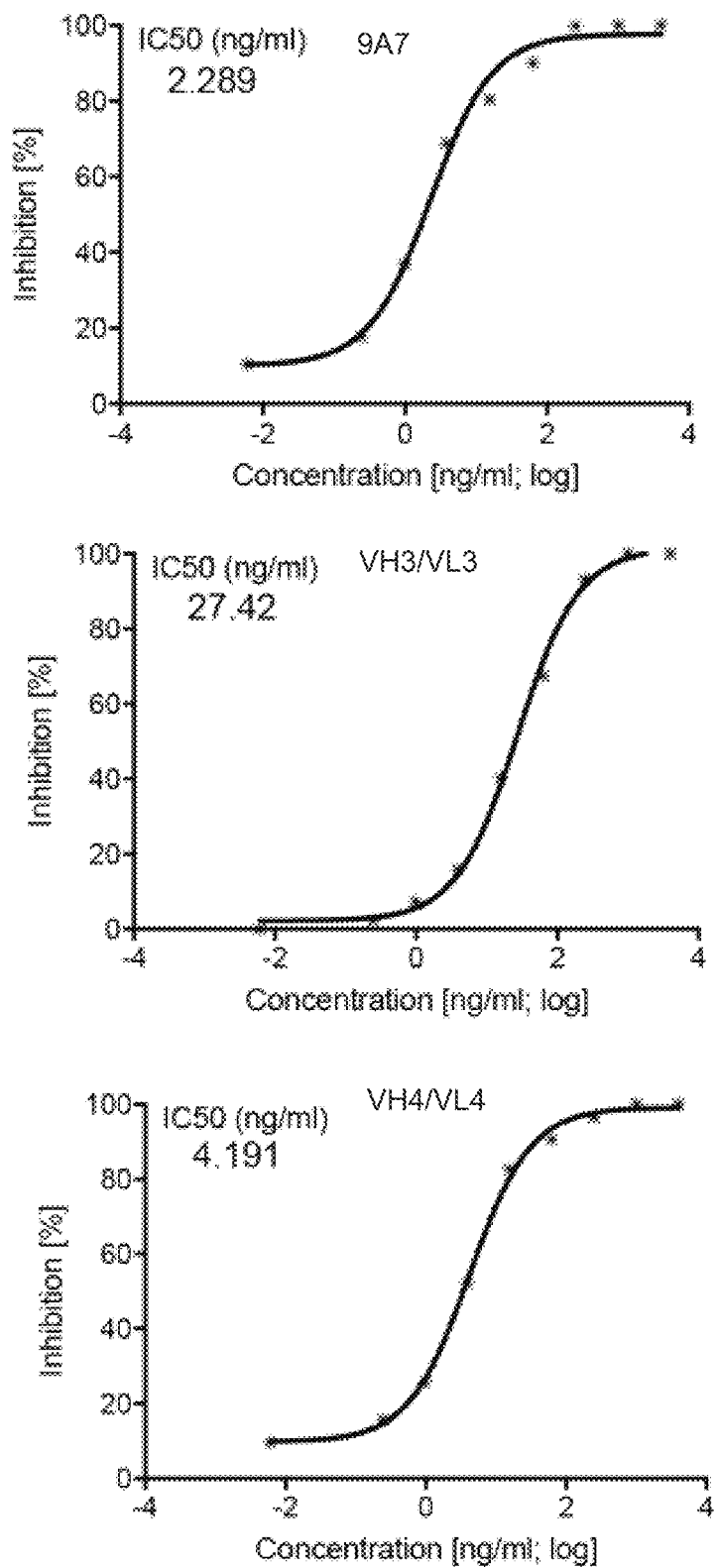

FIG. 26. Graphs showing ability of 9A7 and humanised anti-IL-11Rα antibodies VH3/VL3 and VH4/VL4 to neutralise IL-11 signalling. Human lung fibroblasts were stimulated with TGFβ1 and fibrogenic protein TIMP1 production measured at varying concentrations of antibodies. IC50 values are indicated.

FIGS. 27A to 27J. Results of studies into the effects of anti-IL-11Rα antibody in mice with metabolic diseases. (27A and 27B) Graph and box plot showing change in body weight for mice fed normal chow (NC) or a Western diet with fructose (WDF), and treated with anti-IL-11RA antibody or IgG control. (27A) shows percentage change in body weight over time (weeks). (27B) shows percentage difference between total body fat mass and lean mass. *P<0.05. (27C and 27D). Graph, schematic and bar chart showing glucose tolerance for mice fed a Western diet with fructose (WDF), and treated with anti-IL-11RA antibody or IgG control, as determined by intra-peritoneal glucose tolerance test (ipGTT). (27C) shows changes in the level glucose (mM) from 1 min timepoint. (27D) shows the area under the curve. *P<0.05,  P<0.01. (27E) Box plot showing pancreas weight for mice fed normal chow (NCD) or a Western diet with fructose (WDF), and treated from different time points with anti-IL-11RA antibody or IgG control. **P<0.0001. (27F to 27H) Box plots showing (27F) serum cholesterol levels (mg/dl), (27G) serum triglyceride levels (mg/g) and (27H) fasting blood glucose levels (mM) for mice fed normal chow (NCD) or a Western diet with fructose (WDF), and treated anti-IL-11RA antibody or IgG control, at the indicated time points. (27I and 27J) Images showing the results of immunohistochemical analysis of (27I) glucagon content and (27J) insulin content of sections of pancreatic tissue obtained at week 24 from mice fed normal chow (NCD), or mice fed a Western diet with fructose (WDF) and treated with anti-IL-11RA antibody or IgG control from 16 weeks.

FIGS. 28A to 28G. Neutralizing anti-IL11Rα antibodies inhibit HFMCD- and WDF-induced NASH pathologies. Mice were fed with WDF for 16 weeks to induce NASH and then treated with (10 mg/kg) anti-IL11Rα antibody or IgG for 8 weeks while they were on continuous WDF feeding. (A) Western blots of p-Erk and Erk in the livers from mice on NC or WDF for 24 weeks. (B) Total liver hydroxyproline content, the levels of (C) liver triglycerides, (D) serum ALT, (E), fasting blood glucose, (F) serum triglycerides, and (G) serum cholesterol in mice on NC and IgG- and anti-IL11Rα-treated WDF (n≥5/group). (B-G) Data are shown as box-and-whisker with median (middle line). 25th-75th percentiles (box) and min-max percentiles (whiskers); (B) Two-tailed Student's t-test (C-G) two-tailed, Tukey-corrected Student's t-test. FC: fold change; NC: normal chow; WDF: Western diet+15% (w/v) fructose.

Figure 29A:
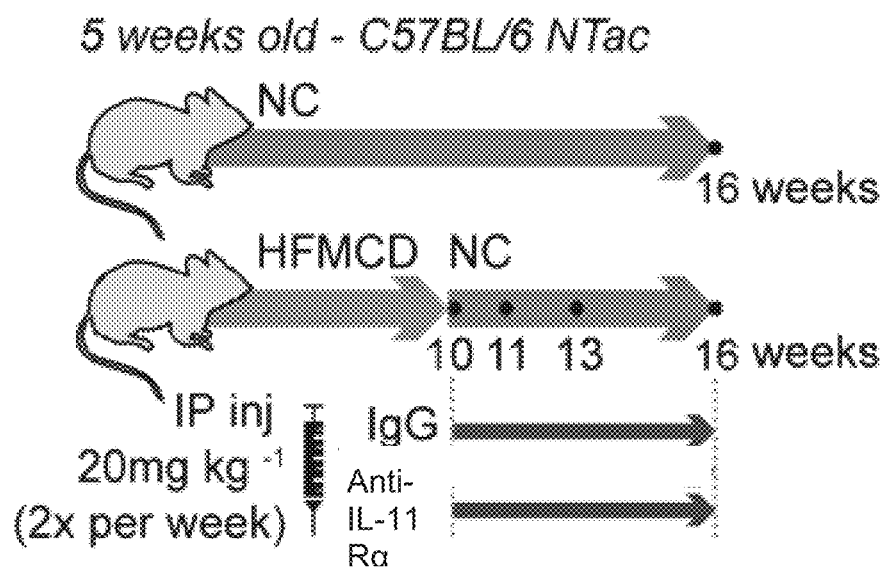
Figure 29B:
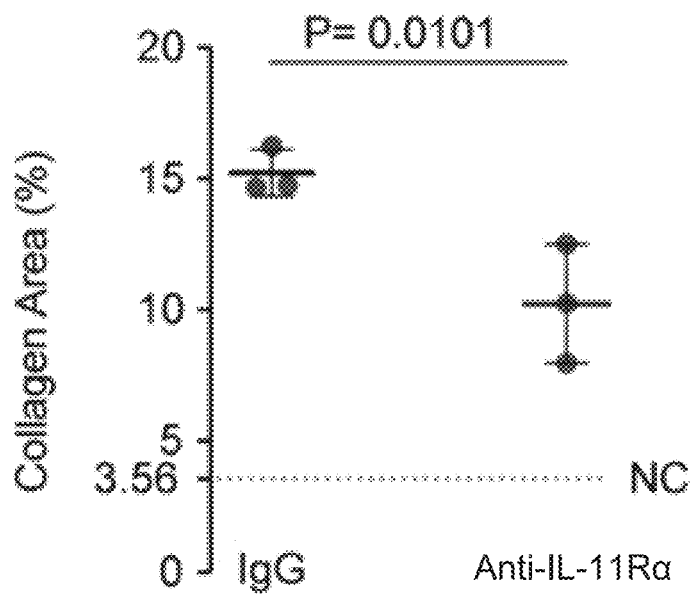

FIGS. 29A and 29B. Reversal of severe liver fibrosis by anti-IL-11Rα antibody at 1, 3, or 6 weeks after establishing fibrosis by 10 weeks on HFMCD. (A) Schematic showing reversal experiment in which fibrosis was established by feeding mice HFMCD for 10 weeks and then replacing this with NC and initiating antibody therapy. Mice were euthanized at the indicated time points. (B) Quantified Masson's Trichrome staining of liver collagen content from mice treated with IgG or anti-IL-11Rα antibody for 6 weeks.

FIGS. 30A to 30F. (A-C) The effect of IL-11 on hepatocytes. (30A) Primary human hepatocytes express the IL-11Rα receptor. (30B) Dose-dependent increase in ALT levels in the supernatant following IL-11 treatment (0.019-10 ng/ml). (30C) $H_2O_2$-induced IL-11 expression. (D-F) The effect of anti-IL-11Rα antibody therapy on hepatotoxicity in a mouse model of APAP-induced liver injury. IgG antibody was used as a control. (30D) ALT levels showing extent of liver damage. (30E) Extent of APAP-induced loss of liver mass. (30F) Hematoxylin&Eosin (H&E) staining showing the extent of centrilobular necrosis in liver tissue from mice treated with anti-IL11Rα antibody or IgG control.

Figure 31A:
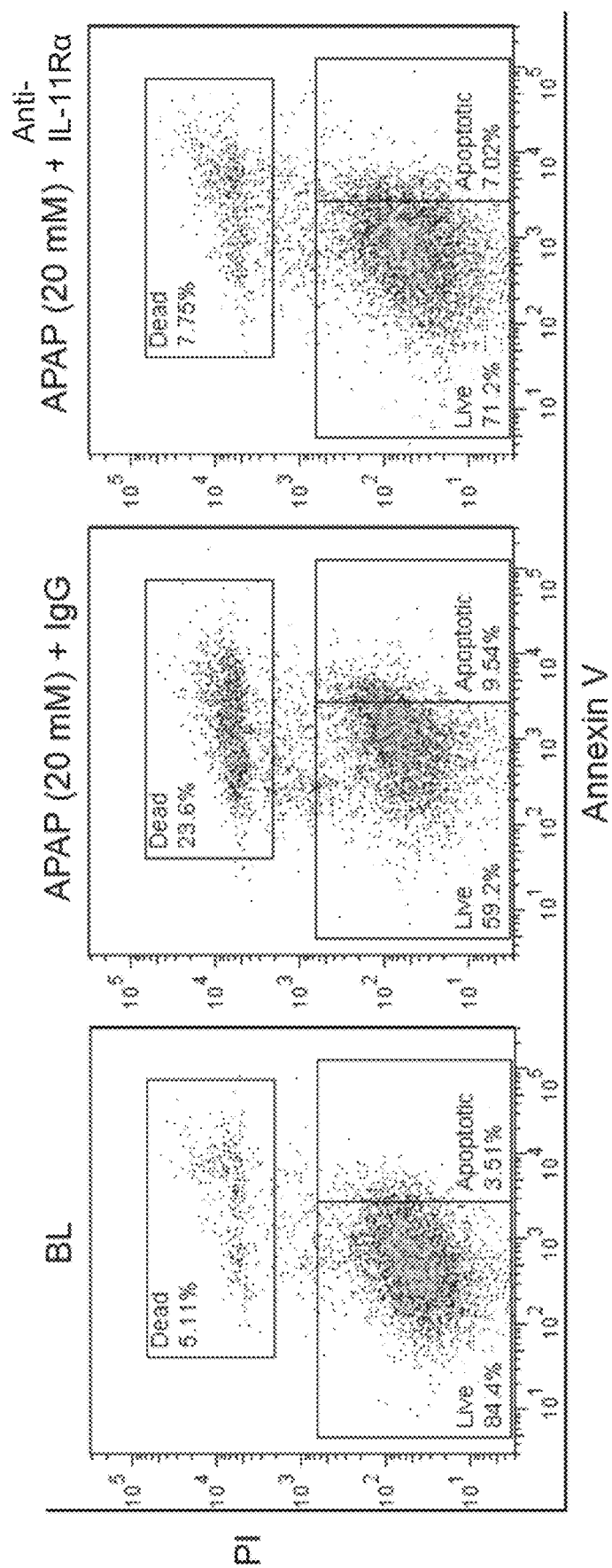
Figure 31B:
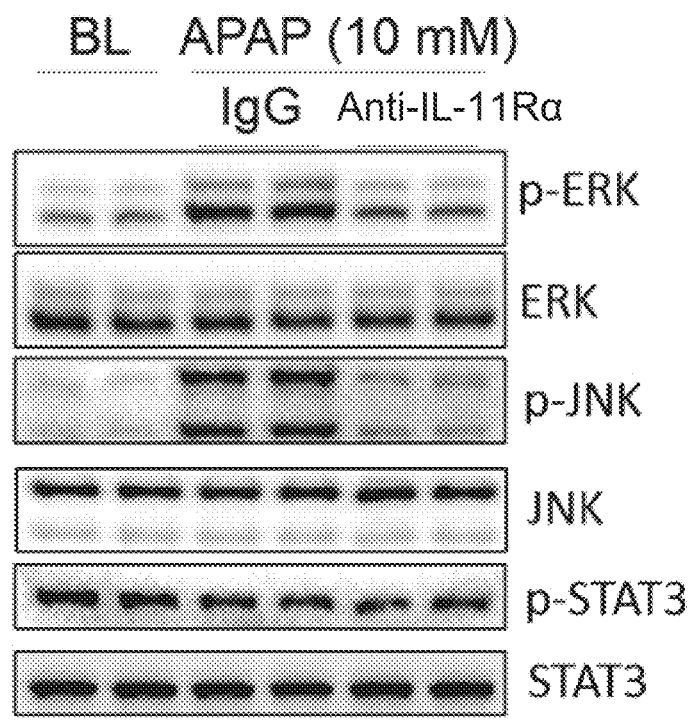

FIGS. 31A and 31B. (31A) Scatterplot showing that anti-IL11Rα antibody prevents APAP-mediated hepatocyte death. Human hepatocytes were treated with APAP (20 mM) in the presence or absence (BL) of anti-IL11Rα (2 μg/ml) or IgG control antibody. Cells were subsequently stained with Annexin V and PI, and cell death was analysed by flow cytometry. BL=baseline. (31B) Image of a western blot showing that anti-IL11Rα antibody prevents APAP-mediated activation of Erk and Jnk. Human hepatocytes were treated with APAP (10 mM) in the presence or absence (BL) of anti-IL11Rα (2 μg/ml) or IgG control antibody. Cell extracts were prepared and western blots were performed to assess the activation (phosphorylation) status of the Erk and Jnk kinases. BL=baseline.

Figure 32A:
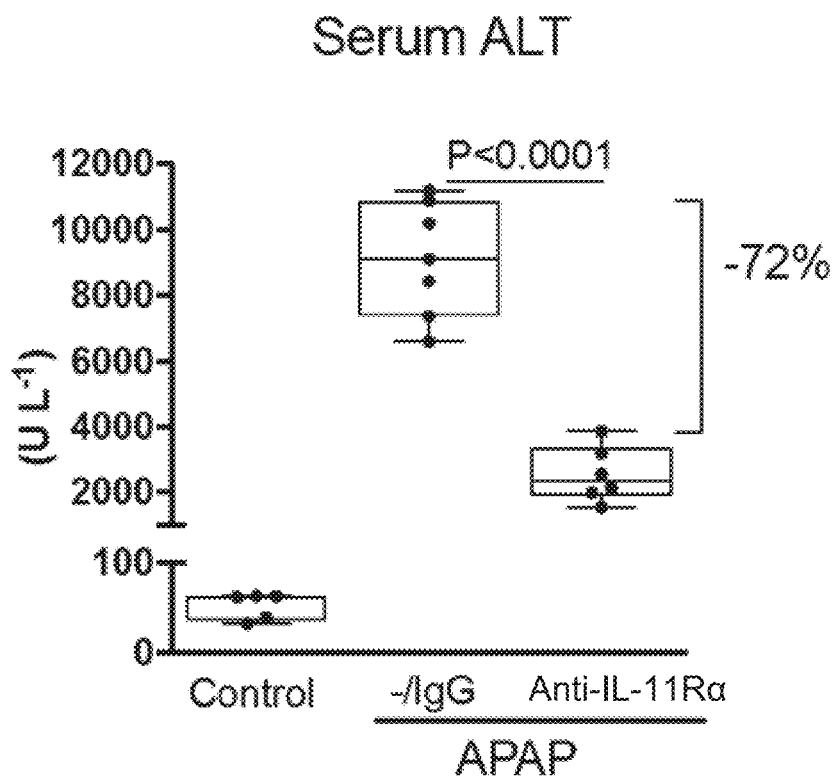
Figure 32B:
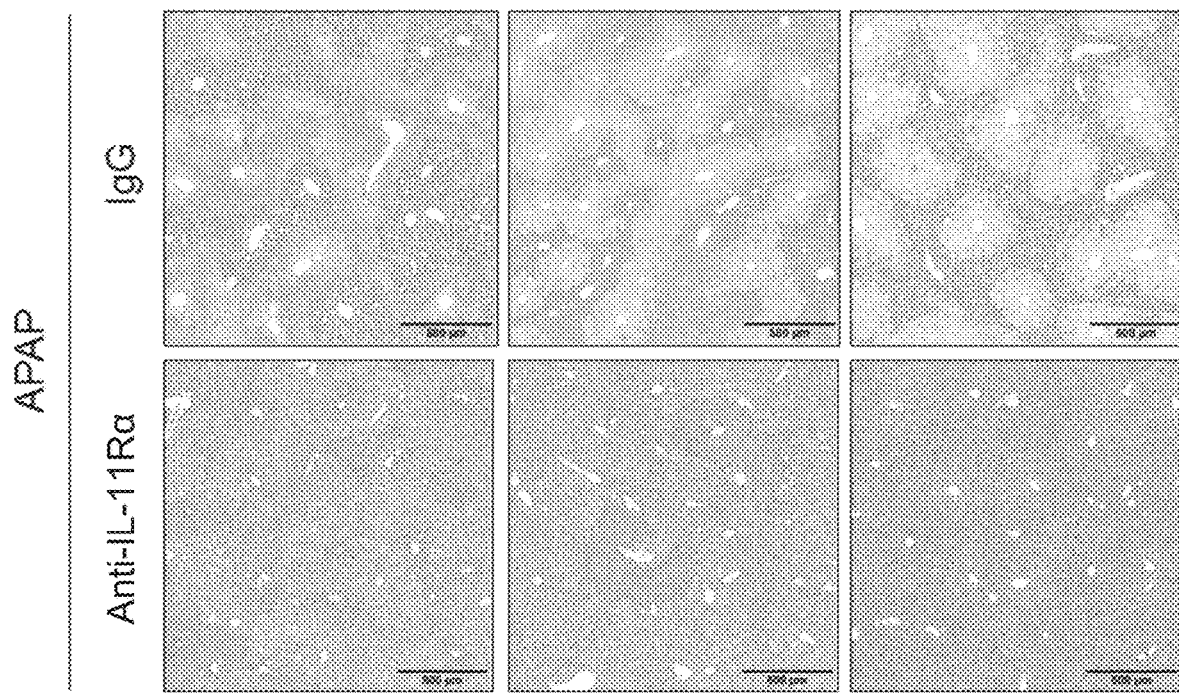

FIGS. 32A and 32B. Box plot and images showing that anti-IL11Rα therapy given 16 hours before APAP overdose prevents acute liver injury. A severe APAP overdose (400 mg/kg) was administered to mice 16 hours after IP administration of 20 mg/kg anti-IL11Rα antibody or IgG control antibody. After 24 hours mice were euthanized. (32A) Serum alanine aminotransferase (ALT) was measured as a marker of acute liver damage and hepatocyte cell death. (32B) Livers were harvested, fixed in 10% neutral-buffered formalin, dehydrated, embedded in paraffin blocks, sectioned and then stained with hematoxylin and eosin to visualize the characteristic centrilobular hepatocyte necrosis seen in APAP overdose.

Figure 33A:
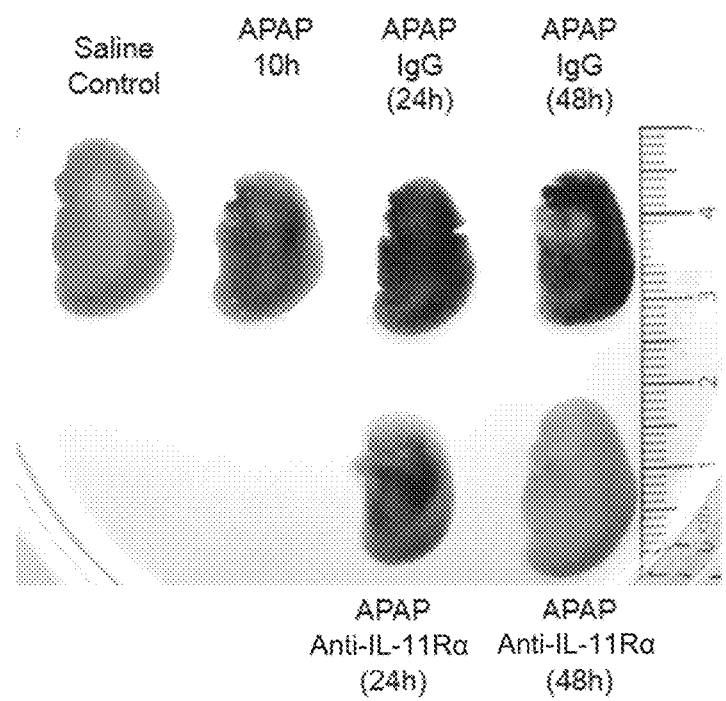
Figure 33B:
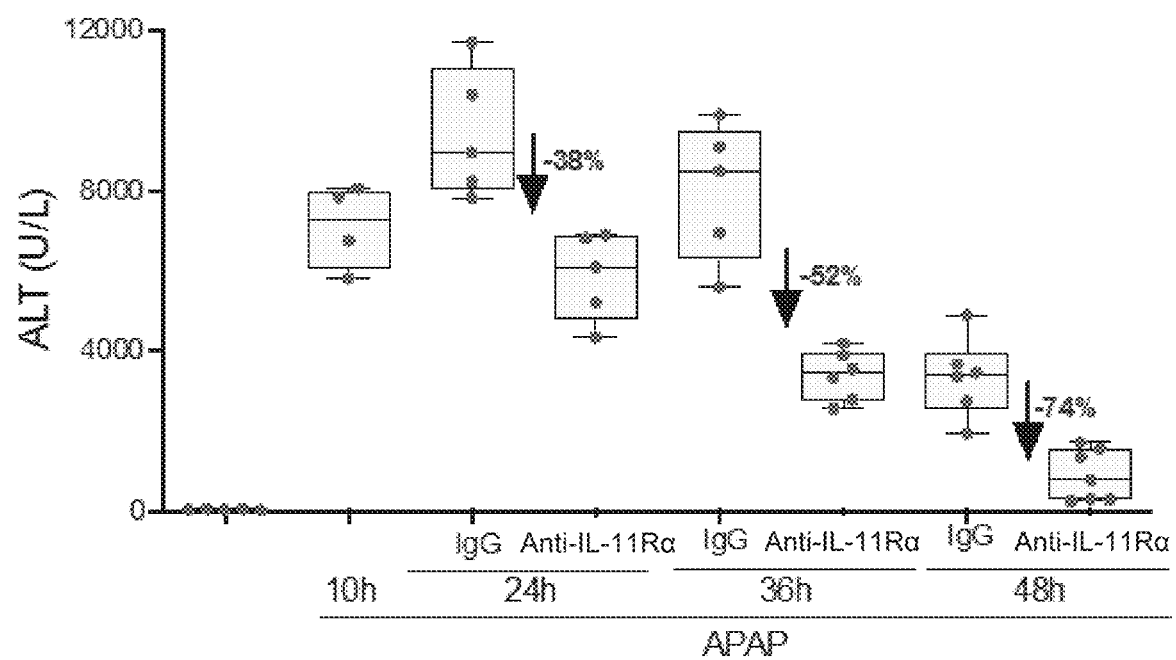
Figure 33C:
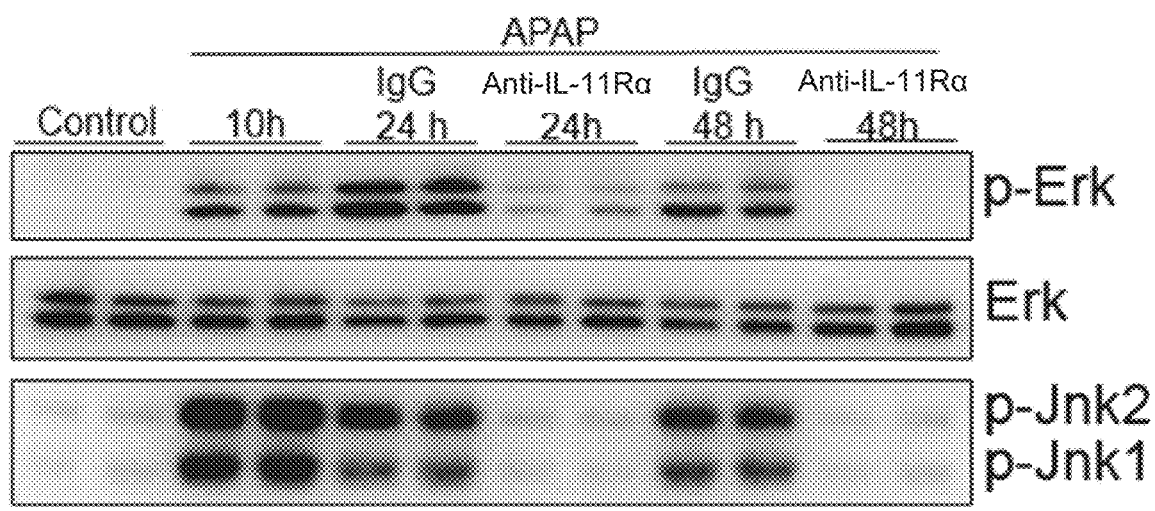

FIGS. 33A to 33C. (A-B) Image and box plot showing that anti-IL11RA therapy given 10 hours after APAP overdose treats acute liver injury. A severe APAP overdose (400 mg/kg) was administered to mice, and 10 hours later mice were administered IP with 20 mg/kg anti-IL11Rα antibody or IgG control antibody. (33A) Livers were harvested at the indicated time points fixed in 10% neutral-buffered formalin and gross morphology and appearance was documented. (33B) serum alanine aminotransferase (ALT) was measured as a marker of acute liver damage and hepatocyte cell death at the indicated time points. (33C) Image of a western blot showing that anti-IL11RA therapy given 10 hours after APAP overdose inhibits activation of Jnk and ERK. A severe APAP overdose (400 mg/kg) was administered to mice, and 10 hours later mice were administered IP with 20 mg/kg anti-IL11Rα antibody or IgG control antibody. Livers were harvested at the indicated time points and western blots were performed to assess the activation (phosphorylation) status of the Erk and Jnk kinases.

Figure 34A:
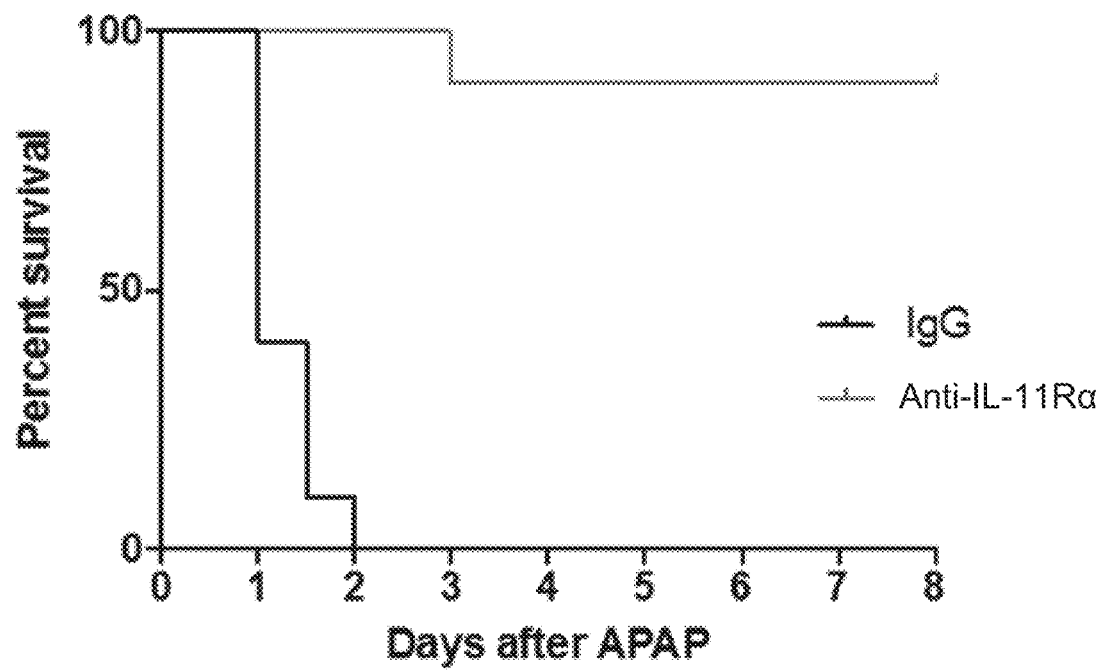
Figure 34B:
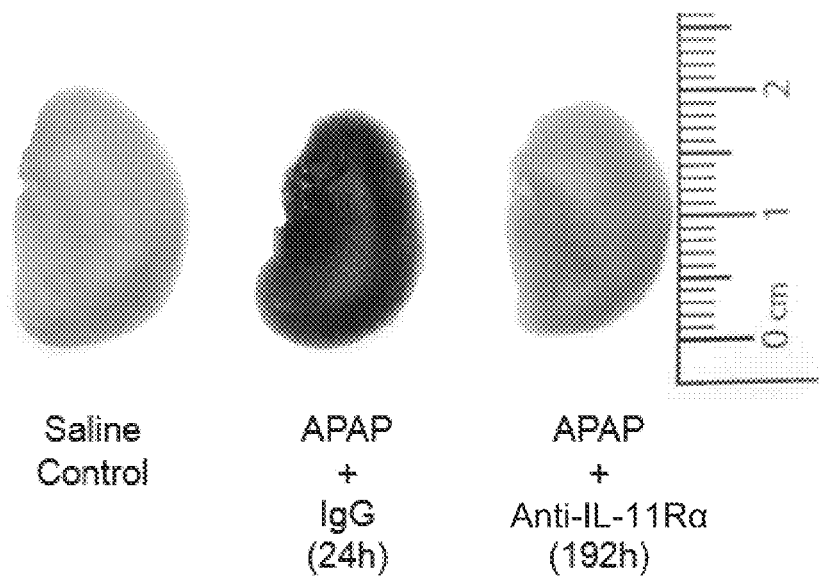
Figure 34C:
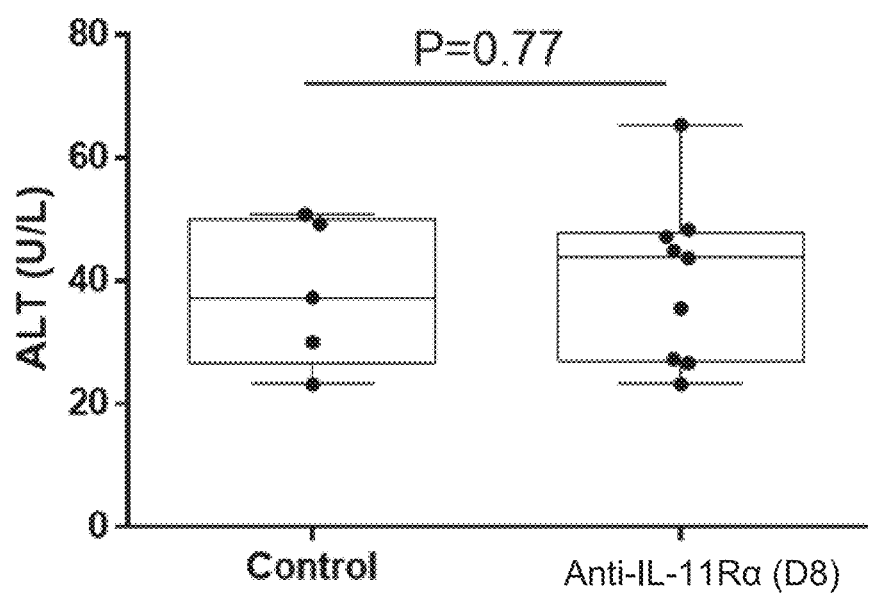

FIGS. 34A to 34C. Graph, Images and box plot showing that anti-IL11Rα therapy given 10 hours after APAP overdose prevents death due to acute liver injury, and restores liver function. A lethal APAP overdose (550 mg/kg) was administered to mice, and 10 hours later mice were administered IP with 20 mg/kg anti-IL11Rα antibody or IgG control antibody. (34A) Graph showing mortality over the 8 days post-overdose in the two treatment groups. (34B) Livers were harvested at the indicated time points fixed in 10% neutral-buffered formalin and gross morphology and appearance was documented. (34C) Serum alanine aminotransferase (ALT) was measured as a marker of liver damage and hepatocyte cell death at 8 days post overdose in anti-IL11Rα antibody treated mice and compared with levels in normal control mice.

EXAMPLES

In the following Examples, the inventors describe the generation of anti-IL-11Rα antibodies, and functional characterisation of the antibodies.

Example 1: Anti-Human IL-11Rα Antibodies

Mouse monoclonal antibodies directed against human IL-11Rα protein were generated as follows. cDNA encoding the amino acid for human IL-11Rα was cloned into expression plasmids (Aldevron GmbH, Freiburg, Germany).

Mice were immunised by intradermal application of DNA-coated gold-particles using a hand-held device for particle-bombardment ("gene gun"). Serum samples were collected from mice after a series of immunisations, and tested In flow cytometry on HEK cells which had been transiently transfected with human IL-11Rα expression plasmids (cell surface expression of human IL-11Rα by transiently transfected HEK cells was confirmed with anti-tag antibodies recognising a tag added to the N-terminus of the IL-11Rα protein).

Antibody-producing cells were isolated from the mice and fused with mouse myeloma cells (Ag8) according to standard procedures.

Hybridomas producing antibodies specific for IL-11Rα were identified by screening for ability to bind to IL-11Rα expressing HEK cells by flow cytometry.

Cell pellets of positive hybridomas cells were prepared using an RNA protection agent (RNAlater, cat. #AM7020 by ThermoFisher Scientific) and further processed for sequencing of the variable domains of the antibodies.

Sequencing was performed using BigDye® Terminator v3.1 Cycle Sequencing kit (Life Technologies®) according to the manufacturers instructions. All data was collected using a 3730xl DNA Analyzer system and Unified Data Collection software (Life Technologies®). Sequence assembly was performed using CodonCode Aligner (CodonCode Corporation). Mixed base calls were resolved by automatically assigning the most prevalent base call to the mixed base calls. Prevalence was determined by both frequency of a base call and the individual quality of the base calls.

In total, 17 mouse monoclonal anti-human IL-11Rα antibody clones were generated (FIG. 1); clones BSO-1E3, BSO-2C1, BSO-2E5, BSO-4G3, BSO-5E5, BSO-7G9, BSO-9A7, BSO-10D11, BSO-13B10, BSW-1D3, BSW-1F6, BSW-4G5, BSW-6H3, BSW-7E9, BSW-7G8, BSW-7H8, and BSW-8B7.

The VL and VH domain sequences were determined for antibody clones BSO-1E3, BSO-2E5, BSO-4G3, BSO-5E5, BSO-7G9, BSO-9A7, BSO-10D11, and BSO-13B10. The VH and VL sequences determined for clone BSO-9A7 are shown in SEQ ID NOs:7 and 13.

Example 2: Functional Characterisation of Anti-Human IL-11Rα Antibodies 2.1 Ability to Inhibit Human IL-11/IL-11R Mediated Signalling To investigate the ability of the anti-IL-11Rα antibodies to neutralise human IL-11/IL-11R mediated signalling, cardiac atrial human fibroblasts were cultured in wells of 96-well plates in the presence of TGFβ1 (5 ng/ml) for 24 hours, in the presence or absence of the anti-IL-11Rα antibodies. This profibrotic stimulus promotes the expression of IL-11, which in turn drives the transistion of quiescent fibroblasts to activated, αSMA-positive fibroblasts. It has previously been shown that neutralising IL-11 prevents TGFβ1-induced transition to activated, αSMA-positive fibroblasts.

Anti-IL-11Rα antibodies (2 μg/ml) were added to fibroblast cultures that were stimulated with TGFβ1, and at the end of the 24 hour culture period, the percentage of αSMA-positive fibroblasts was determined. The percentages were normalised based on the percentage of αSMA-positive fibroblasts observed In cultures of fibroblasts which had not been stimulated with TGFβ1.

Expression of αSMA was analysed with the Operetta High-Content Imaging System in an automated high-throughput fashion.

Figures 1, 2:
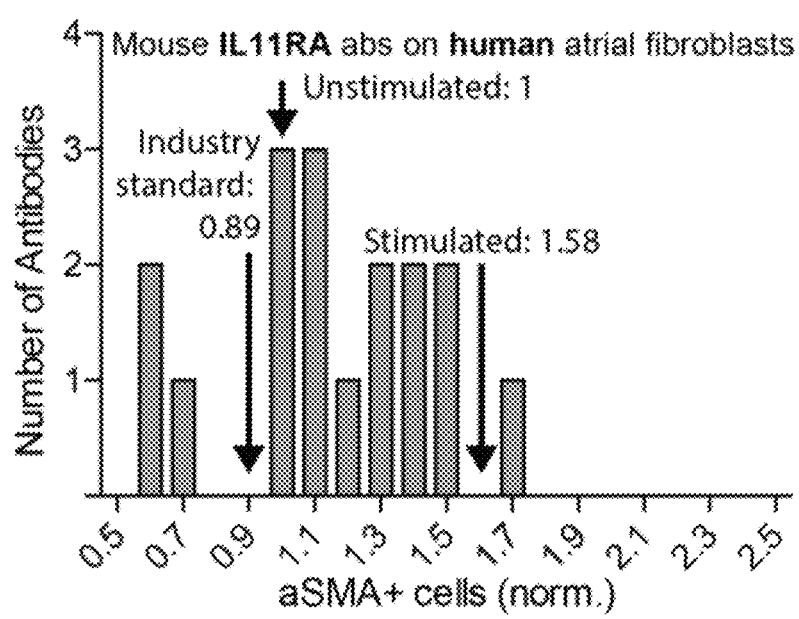
FIG. 1. Table summarising the 17 anti-human IL-11Rα antibody clones.
FIG. 2. Bar chart showing inhibition by the anti-IL-11Rα antibodies of signalling mediated by IL-11 in vitro in human atrial fibroblasts, as determined by fold change in the percentage of αSMA positive cells as compared to control (unstimulated) fibroblasts, following stimulation with TGFβ1, in the presence of the anti-IL-11Rα antibodies.
Figures 5, 6A:
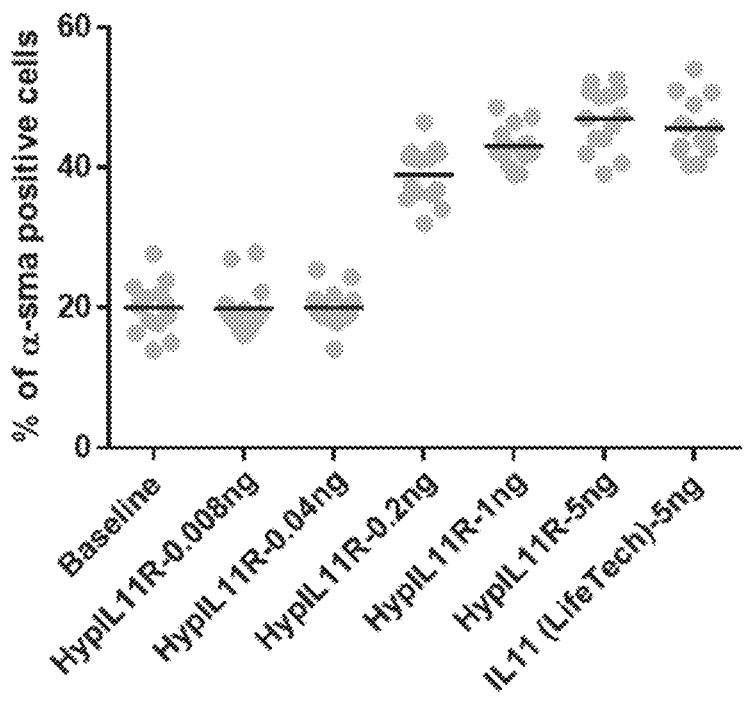
FIG. 5. Table summarising the fold-change data of FIGS. 2 to 4 for the anti-IL-11Rα antibodies. Antibody candidates numbered 1 to 17 correspond to clone designations as indicated in FIG. 1. "Industry Standard" is monoclonal mouse anti-IL-11 IgG2A; Clone #22626; Catalog No. MAB218; R&D Systems, MN, USA.
FIGS. 6A and 6B. Graphs showing fibroblast activation in response to hyper IL-11. Cells were stimulated with the indicated amount (in ng/ml) of hyper IL-11 or recombinant IL-11, and fibroblast activation was measured by analysis of the percentage of α-SMA positive cells. (6A) and (6B) present the results of two different experiments.

The results are shown in FIGS. 2 and 5. Stimulation with TGFβ1 resulted in a 1.58 fold increase in the number of αSMA-positive, activated fibroblasts at the end of the 24 hour culture period in the absence of anti-IL-11Rα antibodies.

A commercial monoclonal mouse anti-IL-11 antibody (Monoclonal Mouse IgG2A; Clone #22626; Catalog No. MAB218; R&D Systems, MN, USA) was included as a control. This antibody was found to be able to reduce the percentage of activated fibroblasts to 0.89 fold of the percentage of activated fibroblasts In unstimulated cultures (i.e. in the absence of stimulation with TGFβ1).

The anti-IL-11Rα antibodies were found to be able to inhibit IL-11/IL-11R signalling in human fibroblasts, and several were able to inhibit IL-11/IL-11R signalling to a greater extent than the monoclonal mouse anti-IL-11 antibody: BSO-1E3, BSO-5E5 and BSO-13B10.

2.2 Ability to Inhibit Mouse IL-11 Mediated Signalling

The ability of the anti-IL-11Rα antibodies to inhibit mouse IL-11-mediated signalling was also investigated, following the same procedure as described in section 2.1 above, but using mouse atrial fibroblasts instead of human atrial fibroblasts.

Figure 3:
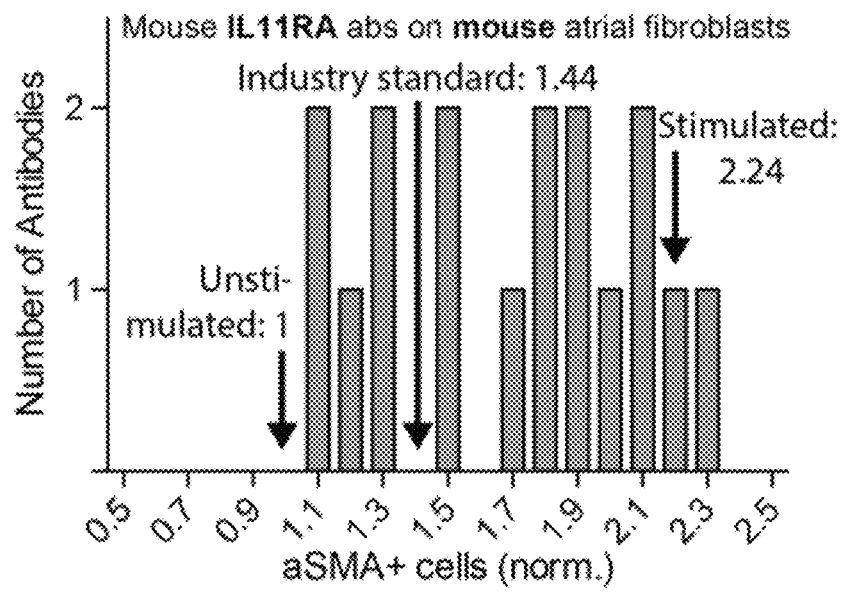
FIG. 3. Bar chart showing inhibition by the anti-IL-11Rα antibodies of signalling mediated by IL-11 In vitro in mouse atrial fibroblasts, as determined by fold change in the percentage of αSMA positive cells as compared to control (unstimulated) fibroblasts, following stimulation with TGFβ1, in the presence of the anti-IL-11Rα antibodies.

The results are shown in FIGS. 3 and 5. Stimulation with TGFβ1 resulted in a 2.24 fold increase In the number of αSMA-positive, activated fibroblasts at the end of the 24 hour culture period in the absence of anti-IL-11Rα antibodies.

The commercial monoclonal mouse anti-IL-11 antibody (Monoclonal Mouse IgG2A; Clone #22626; Catalog No. MAB218; R&D Systems, MN, USA) was included as a control. This antibody was found to be able to reduce the percentage of activated fibroblasts to 1.44 fold of the percentage of activated fibroblasts in unstimulated cultures (i.e. In the absence of stimulation with TGF01).

The anti-IL-11Rα antibodies were found to be able to inhibit IL-11/IL-11R signalling in mouse fibroblasts, and several were able to inhibit IL-11/IL-11R signalling to a greater extent than the monoclonal mouse anti-IL-11 antibody: BSO-1E3, BSO-2C1, BSO-5E5, BSO-9A7 and BSO-13B10.

2.3 Ability to Inhibit IL-11 Trans Signalling, by IL-11 in Complex with IL-11Rα

Trans signalling is recognised as a major aspect of IL-6 signalling, where a complex of IL-6 and soluble IL-6Rα can activate cells that express gp130, but lack the IL-6 receptor (Hunter and Jones, 2015 Nature Immunology 16, 448-457).

It has recently been suggested that trans signalling by a complex of IL-11 and soluble IL-11Rα is also important for IL-11 biology (Lokau et al., Cell Reports (2016) 14, 1761-1773). Using a recombinant fusion protein of IL-11 and IL-11Rα (as described in Pflanz et al., Febs Lett (1999) 450: 117-122), anti-IL-11 antibodies were screened for the ability to inhibit trans signalling mediated by IL-11:IL-11Rα complex.

Importantly, antibodies which are capable of inhibiting both classical IL-11 mediated signalling and IL-11 trans signalling by IL-11:IL-11Rα complex are able to inhibit all known modes of IL-11/IL-11R signalling.

The IL-11:IL-11Rα fusion protein (hereafter referred to as hyper IL-11) consists of the extracellular domain of the IL-11 receptor alpha (IL-11Rα) linked to IL-11. The IL-11:IL-11Rα fusion protein used in the present Example has the amino acid sequence of SEQ ID NO:5.

Figure 6B:
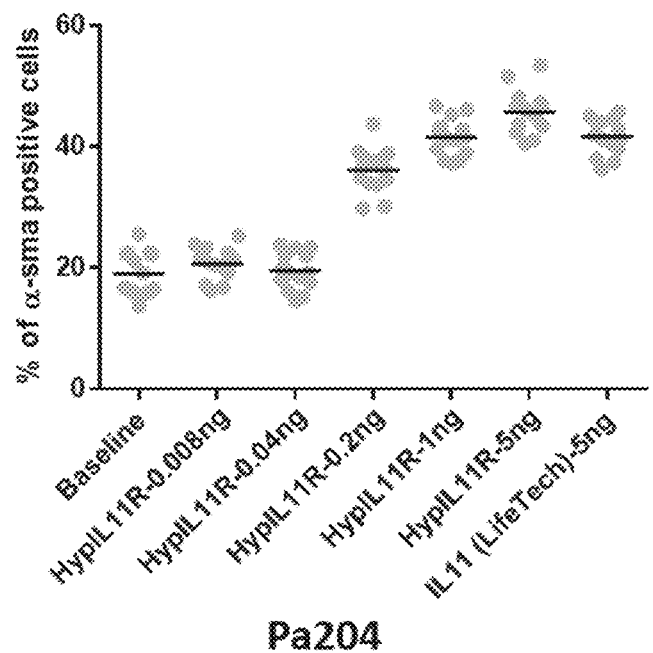

Hyper IL-11 was found to be a more potent activator of human fibroblasts than recombinant IL-11 protein. Briefly, in two separate experiments human fibroblasts were cultured without stimulation (Baseline), in the presence of different amounts of hyper IL-11 (0.008 ng/ml, 0.04 ng/ml, 0.2 ng/ml, 1 ng/ml and 5 ng/ml), or 5 ng/ml recombinant human IL-11 obtained from a commercial source, and fibroblast activation was analysed by determining the percentage of αSMA-positive cells as described herein. The results are shown in (FIGS. 6A and 6B). Hyper-IL-11 activated fibroblasts in a dose-dependent fashion, and was a more potent activator than IL-11.

The IL-11:IL-11Rα fusion protein was prepared as follows:

DNA encoding IL-11:IL-11Rα fusion protein (i.e. SEQ ID NO:98) was cloned into pTT5 vector, and transfected into 293-6E cells in culture in serum-free Free-Style™ 293 Expression Medium (Thermo Fisher Scientific). Cells were maintained in Erlenmeyer Flasks (Corning Inc.) at 37° C. with 5% $CO_2$ on an orbital shaker (VWR Scientific).

Cell culture supernatants were collected on day 6 were used for purification.

Cell culture supernatant was loaded onto an affinity purification column.

After washing and elution with appropriate buffer, the eluted fractions were pooled and buffer exchanged to final formulation buffer.

The purified IL-11:IL-11Rα fusion protein was analyzed by SDS-PAGE, Western blot to confirm molecular weight and purity.

Figure 7:
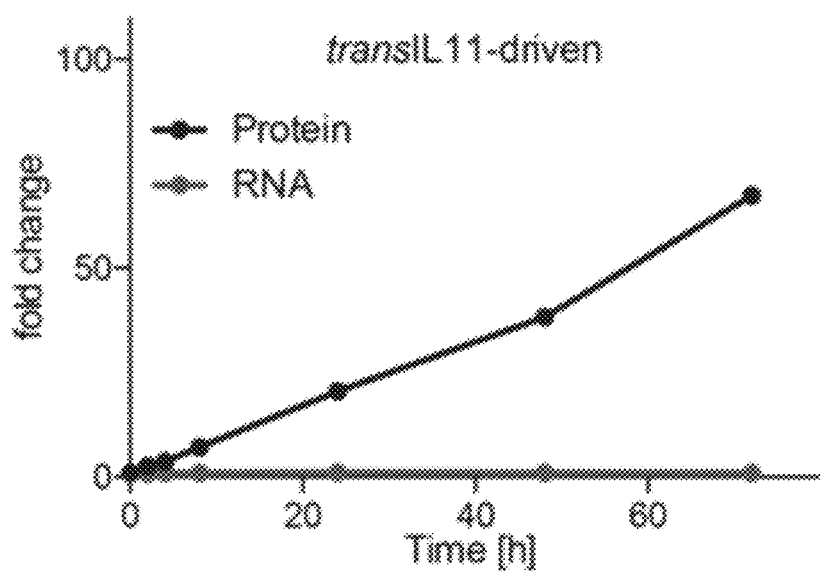
FIG. 7. Graph showing induction of IL-11 secretion in primary fibroblasts by hyper IL-11. Cells were stimulated with hyper IL-11, and IL-11 RNA and native IL-11 protein levels were measured in the cell culture supernatant by ELISA at the indicated time points.

Fibroblasts cultured in vitro and stimulated with hyper IL-11 were shown to upregulate IL-11 protein expression, as determined by ELISA (FIG. 7). Interestingly, an increase in IL-11 RNA level was not detected in response to stimulation with hyper IL-11. Unlike TGFB1, which increases IL-11 expression at both the RNA and the protein level, hyper IL-11 seems to upregulate IL-11 expression only post-transcriptionally, at the protein level.

The ability of the mouse anti-IL-11Rα antibodies to inhibit signalling mediated by hyper IL-11 was investigated.

Human atrial fibroblasts were incubated for 24 h with hyper IL-11 (0.2 ng/ml) in the presence anti-IL-11Rα antibodies (2 µg/ml) or isotype control antibody. Following incubation, cell culture supernatant was analysed for MMP2. Stimulation with hyper IL-11 results in an increase in the secretion of MMP2 as compared to non-stimulated cultures.

Figure 4:
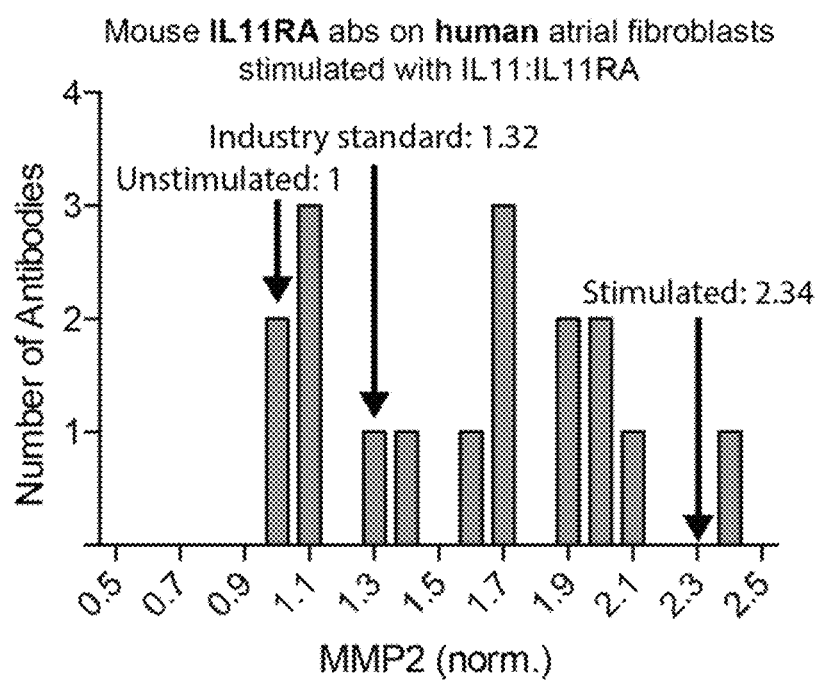
FIG. 4. Bar chart showing inhibition by the anti-IL-11Rα antibodies of IL-11 trans signalling mediated by hyper IL-11 in vitro in human atrial fibroblasts, as determined by fold change in the amount of MMP2 in the cell culture supernatant as compared to control (unstimulated) fibroblasts, following stimulation with hyper IL-11, in the presence of the anti-IL-11Rα antibodies.

The results of the experiments are shown in FIGS. 4 and 5. The anti-IL-11Rα antibodies were found to be capable of neutralising signalling mediated by hyper IL-11 (i.e. IL-11 trans signaling), and several were found to be capable of inhibiting trans signalling to a greater extent than the commercial monoclonal mouse anti-IL-11 antibody (Monoclonal Mouse IgG2A; Clone #22626; Catalog No. MAB218; R&D Systems, MN, USA): BSO-1E3 (RA1), BSO-2E5 (RA3), BSO-5E5 (RA5), BSO-9A7 (RA7), BSO-13B10 (RA9) and BSW-1F6 (RA11).

Clones BSO-1E3 (RA1), BSO-5E5 (RA5). BSO-9A7 (RA7), BSO-13B10 (RA9) were identified as promising candidates for further development (highlighted in FIG. 5), showing good ability to inhibit both human and mouse IL-11/IL-11R signalling, and good inhibition of IL-11 trans signalling.

2.4 Screening for Ability to Bind IL-11Rα

The mouse hybridomas producing anti-human IL-11Rα antibodies were sub-cloned, and cell culture supernatant from the subcloned hybridomas was analysed by "mix-and-measure" iQue assay for (i) ability to bind to human IL-11Rα, and (ii) cross reactivity for antigen other than IL-11Rα.

Briefly, labelled control cells (not expressing IL-11Rα at the cell surface) and unlabelled target cells expressing human IL-11Rα at their surface (following transient transfection with a plasmid encoding a FLAG-tagged human IL-11Rα) were mixed together with the cell culture supernatant (containing mouse-anti-IL-11Rα antibodies) and secondary detection antibodies (fluorescently-labelled anti-mouse IgG antibody).

The cells were then analysed using the HTFC Screening System (iQue) for the two labels (i.e. the cell label and the label on the secondary antibody). Detection of the secondary antibody on the unlabelled, IL-11Rα expressing cells indicated ability of the mouse-anti-IL-11Rα antibodies to bind to IL-11Rα. Detection of the secondary antibody on the labelled, control cells indicated cross-reactivity of the mouse-anti-IL-11Rα antibodies for target other than IL-11Rα.

As a positive control condition, labelled and unlabelled cells were incubated with a mouse anti-FLAG tag antibody as the primary antibody.

Figures 8A, 8B:
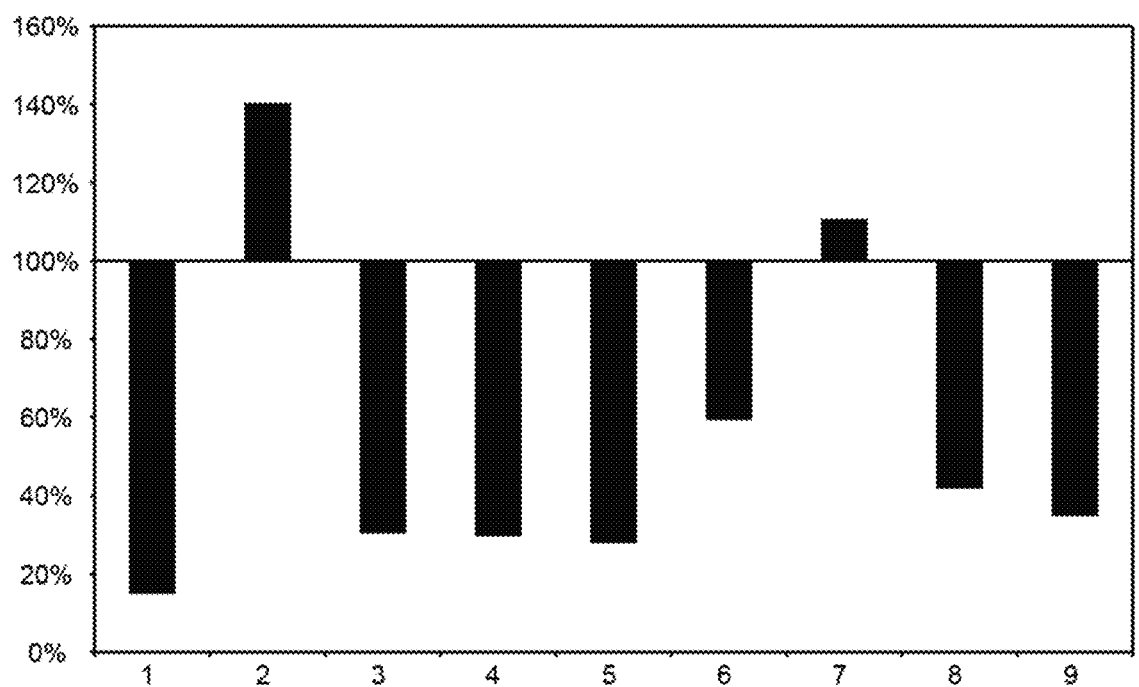
FIGS. 8A to 8H. 8A and 8B: Table and bar chart showing binding of mouse-anti-IL-11Rα antibodies to human IL-11Rα, as determined by iQue analysis (8A) Table summarising the results of the experiments. (8B) Bar chart showing strength of binding relative to the positive control anti-FLAG antibody (100%); numbers correspond to the clones as indicated in FIG. 1. 8C and 8D: Graphs showing the ability of antibodies that specifically bind IL-11Rα to neutraise human (8C) and mouse (8D) fibroblast activation. 100% Inhibition indicates levels of unstimulated fibroblasts and 0% to fully activated fibroblasts. 8E and 8F: Graphs showing ability of anti-IL-11Rα antibodies 5E5, 9A7 and 13B10 to bind to IL-11Rα, block endogenously produced IL-11 from interacting and inhibit production of fibrogenic proteins MMP2 and TIMP1 in human atrial fibroblasts (8E). (8F) confirms that the antibodies neutralise trans IL-11 signalling. (8G) shows that 9A7 blocks exogenous or endogenous IL-11 or hyper IL-11, neutralises cis and trans IL-11 signalling in mouse cardiac fibroblasts and inhibits fibrogenic protein production. (8H) shows the ability of 9A7 to inhibit fibrogenic protein (MMP2) production in human hepatic stellate cells induced by endogenous IL-11 (top) or exogeneous IL-11 (bottom).

The results are shown in FIGS. 8A and 8B. The majority of the subcloned hybridomas expressed antibody which was able to bind to human IL-11Rα, and which recognised this target with high specificity. The antibody produced by subclone BSO-1E3 was found not to bind to human IL-11Rα.

Antibodies BSO-2C1 and BSO-9A7 displayed stronger signal for binding to IL-11Rα than signal for the positive control anti-tag antibody for the tag, indicating that these antibodies bind to IL-11Rα with very high affinity.

2.5 Analysis of Antibody Affinity for Human IL-11Rα

The anti-human IL-11Rα antibodies are analysed for their affinity of binding to human IL-11Rα by ELISA assay.

Recombinant human IL-11Rα is obtained from Genscript and Horseradish peroxidase (HRP)-conjugated anti-human IgG (Fc-specific) antibody is obtained from Sigma. Corning 96-well ELISA plates are obtained from Sigma. Pierce 3,3',5,5'-tetramethylbenzidine (TMB) ELISA substrate kit is obtained from Life Technologies (0.4 g/mL TMB solution, 0.02% hydrogen peroxide in citric acid buffer). Bovine serum albumin and sulphuric acid is obtained from Sigma. Wash buffer comprises 0.05% Tween-20 in phosphate buffered saline (PBS-T). Purified IgG controls are purchased from Life Technologies. Tecan Infinite 200 PRO NanoQuant is used to measure absorbance.

Criss-cross serial dilution analysis was performed as described by Hornbeck et al., (2015) Curr Protoc Immunol 110, 2.1.1-23) to determine the optimal concentration of coating antigen, primary and secondary antibodies.

An indirect ELISA is performed to assess the binding affinity of the mouse anti-IL-11Rα antibodies at 50% of effective concentration ($EC_{50}$) as previously described (Unverdorben et al., (2016) MAbs 8, 120-128). ELISA plates are coated with 1 µg/mL of recombinant human IL-11Rα overnight at 4° C., and remaining binding sites are blocked with 2% BSA in PBS. The antibodies are diluted in 1% BSA in PBS, titrated to obtain working concentrations of 800, 200, 50, 12.5, 3.125, 0.78, 0.195, and 0.049 ng/mL, and incubated in duplicates for 2 hours at room temperature. Detection of antigen-antibody binding is performed with 15.625 ng/mL of HRP-conjugated anti-mouse IgG antibody. Following 2 hours of incubation with the detection antibody, 100 µl of TMB substrate is added for 15 mins and chromogenic reaction stopped with 100 µl of 2 M $H_2SO_4$. Absorbance reading is measured at 450 nm with reference wavelength correction at 570 nm. Data are fitted with GraphPad Prism software with log transformation of antibody concentrations followed by non-linear regression analysis with the asymmetrical (five-parameter) logistic dose-response curve to determine individual EC50 values.

2.5.1 Fibrosis Screening Blocking Endogenous IL-11 Production in Human and Mouse Fibroblasts Fibroblasts were stimulated with a maximum dose of TGFB1, the strongest stimulator of IL-11 expression in atrial fibroblasts, which usually results in an IL-11 concentration between 500 µg ml-1 to 1 ng ml-1 in the supernatant after 24 h. This approach ensures the inhibition of correctly folded, endogenously produced IL-11 at physiologically relevant maximum levels of production. The fibrosis-relevant autocrine activity of IL-11 directly on fibroblasts is neutralised in this assay.

TGFB1 stimulates the expression of IL-11, which subsequently drives the transition from quiescent fibroblasts to activated (ACTA2-positive) myofibroblasts. Neutralising IL11RA antibodies should inhibit this transition. Thus, antibodies lowering the percentage of activated fibroblasts after TGFB1 stimulation can be considered neutralisers and anti-fibrotic agents.

Fibroblasts were seeded in 96-well CellCarrier plates at a density of $1 \times 10^4$/cm and stimulated with pro-fibrotic cytokine TGFB1 (5 ng/ml) and mouse monoclonal anti-IL11RA antibodies (6 µg/ml) for 24 h. Following experimental conditions, cells were rinsed in phosphate-buffered saline (PBS), fixed in 4% paraformaldehyde, and permeabilised with 0.1% Triton X-100 in PBS. Non-specific sites were blocked using blocking solution (0.5% BSA and 0.1% Tween-20 in PBS). Cells were incubated overnight at 4° C. with mouse monoclonal anti-smooth muscle actin was diluted 1:500 in blocking solution, then washed (0.25% BSA and 0.1% Tween-20 in PBS) and incubated with Alexa Fluor 488 goat anti-mouse gG (1:1000) for 1 h at room temperature in the dark. Cells were counter-stained with rhodamine-phalloidin (1:1000) and DAPI (1 µg/ml) in blocking solution. Plates were scanned and images were collected with an Operetta high-content imaging system. The fraction of ACTA2+ve cells was estimated using Harmony software version 4.1 (PerkinElmer).

Figure 8C:
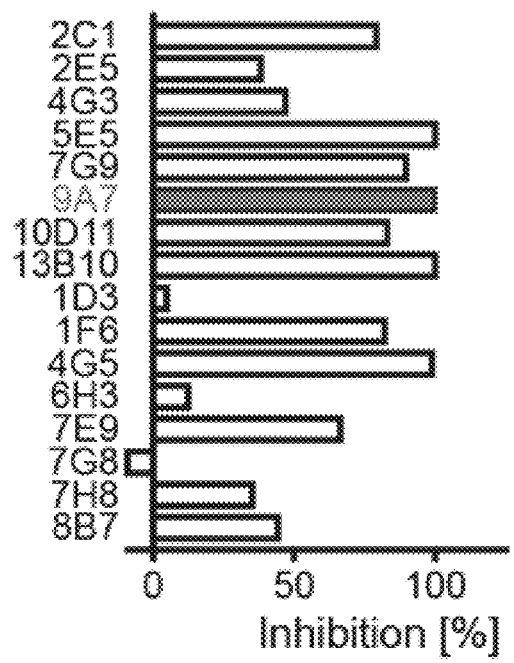

FIG. 8C shows that several antibodies that specifically bind IL11RA were able to neutralise human fibroblast activation. 100% inhibition indicates levels of unstimulated fibroblasts and 0% to fully activated fibroblasts.

Figure 8D:
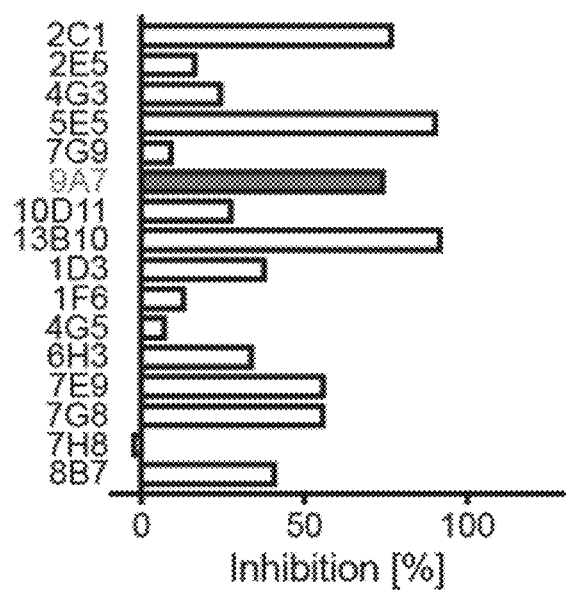

The above experiment was repeated with primary mouse dermal fibroblasts to investigate cross-species neutralisation capabilities. FIG. 8D shows that several antibodies that specifically bind IL11RA were able to neutralise mouse fibroblast activation. 100% inhibition indicates levels of unstimulated fibroblasts and 0% to fully activated fibroblasts.

2.5.2 In Vitro Performance of Anti-IL-11R Antibodies

Neutralisation assays were performed using serial dilutions of the 5E5, 9A7 and 13B10 clones. Human atrial fibroblasts isolated from right atrial appendage biopsies were seeded in 96-well CellCarrier plates at a density of $1 \times 10^4$/cm. Cells were stimulated with pro-fibrotic cytokine TGFB1 (5 ng/ml) and incubated with 5E5, 9A7 or 13B10 at varying concentrations for 24 h. The medium was collected and a MMP2 and TIMP1 ELISA was performed according to the protocol. MMP2 and TIMP1 secretion into the supernatant by fibroblasts was assessed to estimate the % of inhibition. A commercially available anti-IL-11 antibody at a high concentration (2 µg/ml) was used as a positive control and considered to be 100% neutralising. Protein levels of stimulated cells incubated with an IgG control indicate 0% neutralisation.

Figure 8E:
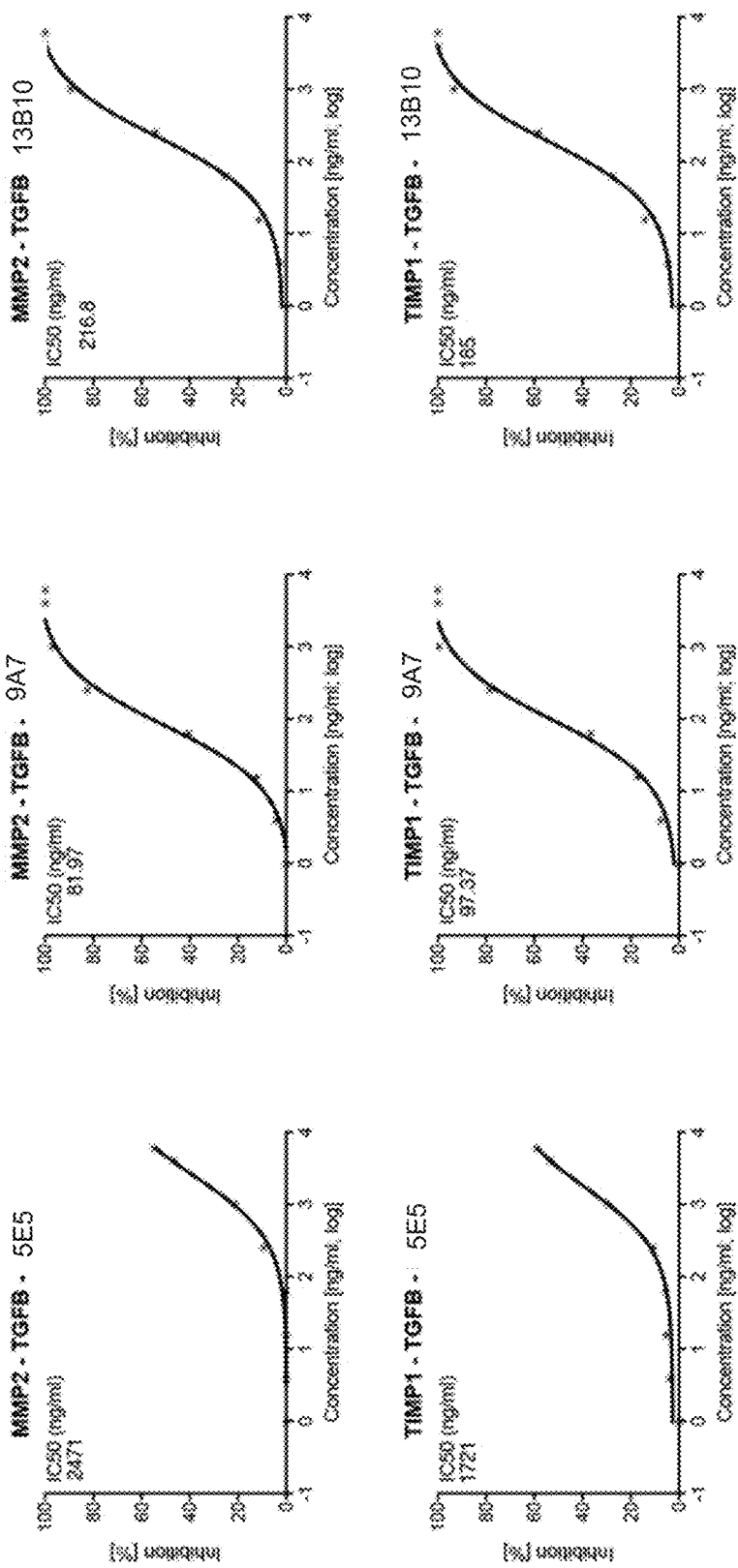

FIG. 8E shows that the antibodies bind to IL-11Rα and block endogenously produced IL-11 from interacting. IL-11 signalling is neutralised, inhibiting production of fibrogenic proteins MMP2 and TIMP1.

The experiment was repeated using IL-11:IL11RA (0.2 ng/ml) and varying concentrations of 5E5, 9A7 and 13B10 to confirm blockage of trans-signalling events.

Figure 8F:
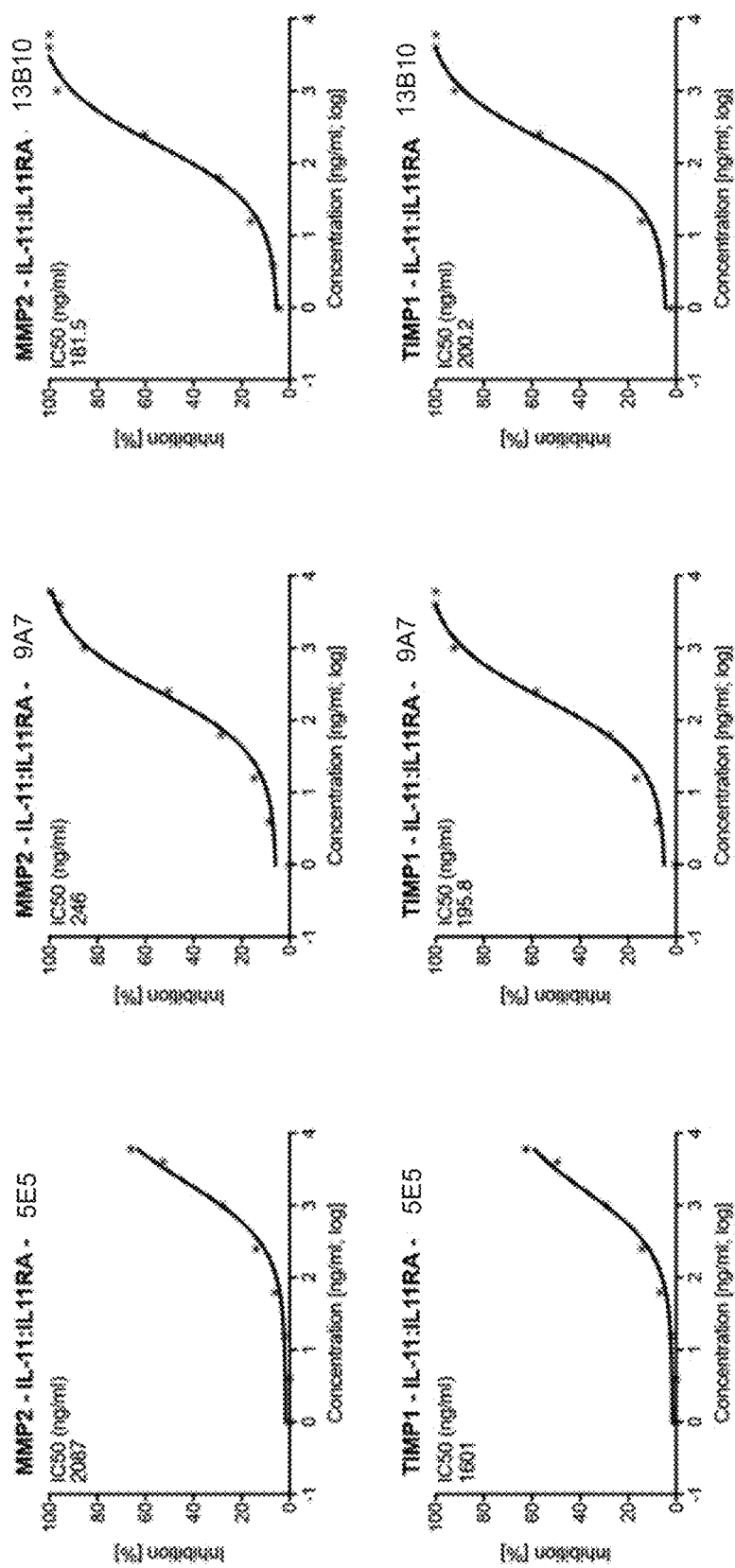

FIG. 8F shows that the antibodies neutralise trans IL-11 signalling in the fibroblasts and inhibit fibrogenic protein production. MMP2 and TIMP1 protein secretion into the supernatant by fibroblasts was assessed to estimate the % of inhibition.

The experiments above were repeated using primary mouse cardiac fibroblasts. Neutralisation of the fibrotic response in vitro assessed by monitoring MMP2 levels. Primary mouse cardiac fibroblasts were incubated with TGFB1 (5 ng/ml), IL-11 (2 ng/ml) or IL-11:IL11RA (0.2 ng/ml) and varying concentrations of 9A7. MMP2 secretion into the supernatant by fibroblasts was assessed to estimate the % of inhibition.

Figure 8G:
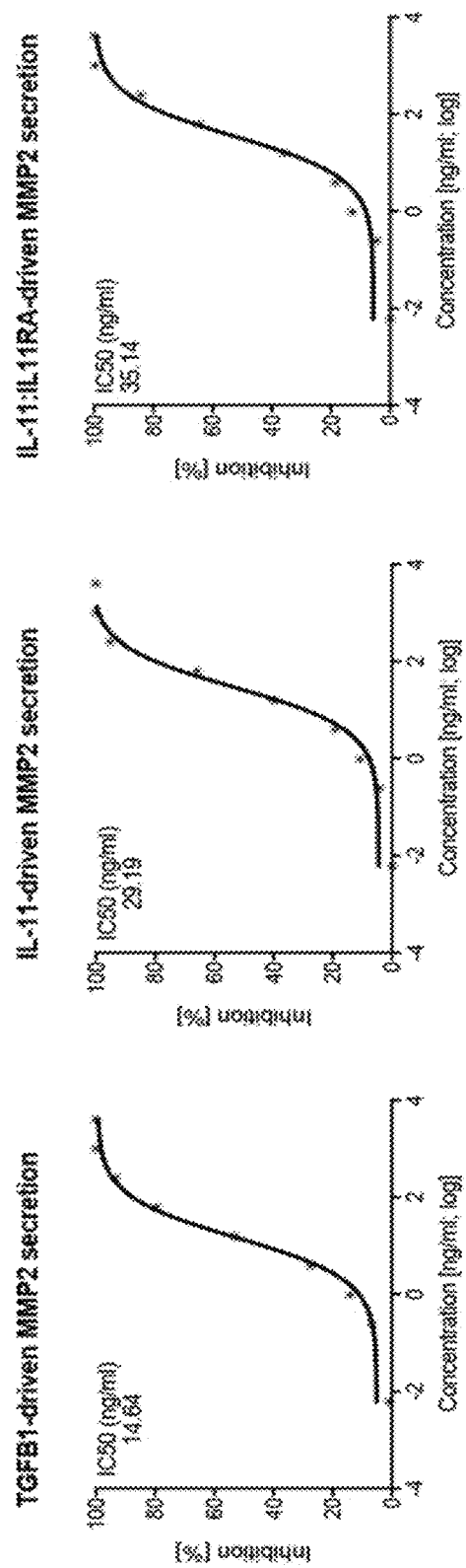

FIG. 8G shows that anti-IL-11Rα antibody 9A7 blocks exogenous or endogenous IL-11 or hyper IL-11, neutralises IL-11 signalling in the fibroblasts and inhibits fibrogenic protein production.

Cross species reactivity was confirmed for 9A7 in macaque skin fibroblasts stimulated with recombinant macaque IL-11 (5 ng/ml) for 24 h in the presence of IgG control or 9A7 antibody at 2 µg/ml. Collagen, ACTA2+ve and EdU+ve cells were quantified using the Operetta High content imaging platform. Secreted collagen was quantified using the calorimetric Sirius Red collagen assay. 9A7 was found to reduce the levels of each fibrotic marker comparable with a non-IL-11 treated control.

2.6 Ability to Inhibit Human IL-11/IL-11R Signalling in a Variety of Tissues

Ability of the antibodies to neutralise IL-11/IL-11R signalling and trans signalling in fibroblasts obtained from a variety of different tissues is investigated, essentially as described in sections 2.1 and 2.3 except that instead of cardiac atrial human fibroblasts, human fibroblasts derived from liver, lung, kidney, eye, skin, pancreas, spleen, bowel, brain, and bone marrow are used for the experiments.

Anti-IL-11Rα antibodies are demonstrated to be capable of neutralising IL-11/IL-11R signaling in fibroblasts derived from the various different tissues, as determined by observation of a relative decrease in the proportion of αSMA-positive fibroblasts at the end of the 24 h culture period in the presence of the anti-IL-11Rα antibodies as compared to culture in the absence of the antibodies.

Example 3: Chimeric and Humanised Versions of the Mouse Anti-Human IL-11 Antibodies Mouse/human chimeric and humanised versions of the mouse monoclonal anti-human IL-11Rα antibodies of Example 1 are prepared according to standard methods.

3.1 Mouse/Human Chimeric Antibodies

Mouse/human chimeric antibodies are prepared from the mouse monoclonal anti-human IL-11Rα antibodies as described in Human Monoclonal Antibodies: Methods and Protocols, Michael Steinitz (Editor). Methods in Molecular Biology 1060, Springer Protocols, Humana Press (2014), in Chapter 8 thereof.

Briefly, the DNA sequences encoding the VH and VL of hybridomas producing the mouse anti-human IL-11Rα antibodies are determined, and combined with DNA sequence encoding human immunoglobulin constant regions to produce a mouse/human chimeric antibody sequence, from which a chimeric mouse/human antibody is expressed in mammalian cells.

3.2 Humanised Antibodies

Humanised versions of BSO-9A7 VH and VL sequences were also designed, and these are shown in SEQ ID NOs:8 to 12 and 14 to 17.

Humanised antibodies are prepared from the mouse monoclonal anti-human IL-11Rα antibodies as described in Human Monocional Antibodies: Methods and Protocols, Michael Steinitz (Editor), Methods in Molecular Biology 1060, Springer Protocols, Humana Press (2014), in Chapter 7 thereof, in particular at section 3.1 of Chapter 7 entitled 'Antibody Humanization'.

Briefly, the DNA sequences encoding the VH and VL of hybridomas producing the mouse anti-human IL-11Rα antibodies are determined, and inserted into DNA sequence encoding human antibody variable region framework regions and immunoglobulin constant regions, to produce a humanised antibody sequence, from which a humanised antibody is expressed in mammalian cells.

Characterisation of humanised antibodies is described in Example 14.

Example 4: Further Biochemical Analysis of Anti-IL-11Rα Antibodies

The antibodies described above are subjected to further biochemical analysis.

The antibodies are analysed by BIAcore, Biolayer interferometry (BLI) and MicroScale Thermophoresis (MST) analysis to determine the affinity of binding to human IL-11Rα.

BIAcore determination of antibody affinity by surface plasmon resonance (SPR) analysis is performed as described in Rich et al., Anal Biochem. 2008 Feb. 1; 373(1):112-20.

Biolayer interferometry analysis of antibody affinity is performed as described in Concepcion et al., Comb Chem High Throughput Screen. 2009 September; 12(8):791-800.

MicroScale Thermophoresis analysis of antibody affinity is performed as described in Jerabek-Willemsen et al., Assay Drug Dev Technol. 2011 August; 9(4): 342-353.

Aggregation of the antibodies is analysed by size exclusion chromatography (SEC), as described in Iacob et al., J Pharm Sci. 2013 December; 102(12): 4315-4329.

Hydophobicity of the antibodies is analysed by Hydrophobic interaction chromatography (HIC) as described in Haverick at al., MAbs. 2014 July-August; 6(4):852-8.

The melting temperature of the antibodies is analysed by Differential scanning fluorimetry (DSF) as described in Menzen and Friess, J Pharm Sci. 2013 February; 102(2): 415-28.

Example 5: Inhibition of Fibrosis In Vivo Using Anti-IL-11Rα Antibodies

The therapeutic utility of the anti-human IL-11Rα antibodies is demonstrated in vive in mouse models of fibrosis for various different tissues. The mice used in the experiments are wikitype (i.e. IL-11RA+/+) mice.

5.1 Heart Fibrosis

A pump is implanted, and mice are treated with AngII (2 mg/kg/day) for 28 days.

Neutralising anti-IL-11Rα antibodies, or control antibodies, are administered to different groups of mice by intravenous injection. At the end of the experiment, collagen content is assessed in the atria of the mice using a calorimetric hydroxyproline-based assay kit, and the level of RNA expression of the markers or fibrosis ColA2, αSMA (ACTA2) and fibronectin (Fn1) were analysed by qPCR.

Mice treated with neutralising anti-IL-11Rα antibodies have a reduced fibrotic response in heart tissue as compared to mice treated with control antibodies, as evidenced by reduced expression of markers of fibrosis.

5.2 Kidney Fibrosis

A mouse model for kidney fibrosis is established, in which fibrosis is induced by intraperitoneal injection of folic acid (180 mg/kg) in vehicle (0.3M NaHCO$_3$); control mice were administered vehicle alone.

Neutralising anti-IL-11Rα antibodies, or control antibodies, are administered to different groups of mice by intravenous injection. Kidneys are removed at day 28, weighed and either fixed in 10% neutral-buffered formalin for Masson's trichrome and Sirius staining or snap-frozen for collagen assay, RNA, and protein studies.

Total RNA is extracted from the snap-frozen kidney using Trizol reagent (Invitrogen) and Qiagen TissueLyzer method followed by RNeasy column (Qiagen) purification. The cDNA is prepared using iScript™ cDNA synthesis kit, in which each reaction contained 1 μg of total RNA, as per the manufacturer's instructions. Quantitative RT-PCR gene expression analysis is performed on triplicate samples with either TaqMan (Applied Biosystems) or fast SYBR green (Qiagen) technology using StepOnePlus™ (Applied Biosystem) over 40 cycles. Expression data are normalized to GAPDH mRNA expression level and the 2-ΔΔCt method is used to calculate the fold-change. The snap-frozen kidneys are subjected to acid hydrolysis by heating in 6M HCl at a concentration of 50 mg/ml (95° C., 20 hours). The amount of total collagen in the hydrolysate is quantified based on the colorimetric detection of hydroxyproline using Quickzyme Total Collagen assay kit (Quickzyme Biosciences) as per the manufacturer's instructions.

Mice treated with neutralising anti-IL-11Rα antibodies have a reduced fibrotic response in kidney tissue as compared to mice treated with control antibodies, as evidenced by reduced expression of markers of fibrosis.

5.3 Lung Fibrosis

Mice are treated by intratracheal administration of bleomycin on day 0 to establish a fibrotic response in the lung (pulmonary fibrosis).

Neutralising anti-IL-11Rα antibodies, or control antibodies, are administered to different groups of mice by intravenous injection. Mice are sacrificed at day 21, and analysed for differences in fibrosis markers.

Mice treated with neutralising anti-IL-11Rα antibodies have a reduced fibrotic response in lung tissue as compared to mice treated with control antibodies, as evidenced by reduced expression of markers of fibrosis.

5.4 Skin Fibrosis

Mice are treated by subcutaneous administration of bleomycin on day 0 to establish a fibrotic response in the skin.

Neutralising anti-IL-11Rα antibodies, or control antibodies, are administered to different groups of mice by intravenous injection. Mice are sacrificed at day 21, and analysed for differences in fibrosis markers.

Mice treated with neutralising anti-IL-11Rα antibodies have a reduced fibrotic response in skin tissue as compared to mice treated with control antibodies, as evidenced by reduced expression of markers of fibrosis.

5.5 Eye Fibrosis

To analyse fibrosis in the eye, IL-11RA −/− mice and IL-11RA +/+ mice undergo trabeculectomy (filtration surgery) on day 0 to initiate a wound healing response in the eye. This mouse model of glaucoma filtration surgery has been shown to be an efficient model to evaluate the wound healing response in the eye (Khaw et al. 2001, Curr Opin Ophthalmol 12, 143-148; Seet et al. 2011, Mol. Med. 17, 557-567) and has successfully shown the beneficial effect of fibrotic modulators in vivo (Mead et al. 2003, Invest. Ophthalmol. Vis. Sci. 44, 3394-3401; Wong et al. 2003 Invest. Ophthalmol. Vis. Sci. 44, 1097-1103; Wong et al. 2005, Invest. Ophthalmol. Vis. Sci. 46, 2018-2022).

Briefly, the conjunctiva are dissected to expose the underlying sclera, after which an incision is made through the sclera into the anterior chamber of the eye using a 30-gauge needle. The created fistula allows aqueous humor to exit into and underneath the conjunctiva. The dissected conjunctiva is then secured and dosed at the limbus by a 10-0 (0.2 metric) Ethilon black monofilament nylon scleral suture. Fucithalmic ointment is instilled at the end of the procedure. The surgery is performed under anaesthesia by intraperitoneal injection of a 0.1 ml ketamine/xylazine mixture, as well as topical application of one drop per eye of 1% xylocaine. Fucithalmic ointment is instilled post-surgery to prevent infection. Surgery is performed with 70% propyl alcohol sterilized surgical scissors and forceps and sterile needles.

The accumulated fluid underneath the sutured conjunctiva is observed as a conjunctival bleb. Mice are euthanized on day 7 post-surgery for analyses. For qualitative immune-histological analyses, eyes from mice are harvested by enucleation and then sectioned. Maturation of collagen fibres is evaluated with using the picro-sirius red/polarization light technique (Szendröi et al. 1984, Acta Morphol Hung 32, 47-55); orange-red indicates mature collagen, and yellow/green indicates newly formed immature collagen.

Neutralising anti-IL-11Rα antibodies, or control antibodies, are administered to different groups of mice by intravenous injection, and fibrosis is monitored in the eye tissue.

Mice treated with neutralising anti-IL-11Rα antibodies have a reduced fibrotic response in eye tissue as compared to mice treated with control antibodies, as evidenced by reduced expression of markers of fibrosis.

5.6 Other Tissues

The effect of treatment with neutralising anti-IL-11Rα antibodies on fibrosis is also analysed in mouse models of fibrosis for other tissues, such as the liver, kidney, bowel, and is also analysed in a model relevant to multiorgan (i.e. systemic) fibrosis.

The fibrotic response is measured and compared between mice treated with neutralising anti-IL-11Rα antibodies and mice treated with control antibodies. Mice treated with neutralising anti-IL-11Rα antibodies have a reduced fibrotic response as compared to mice treated with control antibodies, as evidenced by reduced expression of markers of fibrosis.

The neutralisation performance of anti-IL-11Rα antibody 9A7 was determined in primary human hepatic stellate (liver) cells by measuring MMP2 concentration, following the protocol in Example 2.5.2. Primary human HSCs were incubated with TGFB1 (5 ng/ml; endogenous IL-11) or exogenous IL-11 (2 ng/ml) and varying concentrations of 9A7. MMP2 secretion into the supernatant by fibroblasts was assessed to estimate the % of inhibition.

Figure 8H:
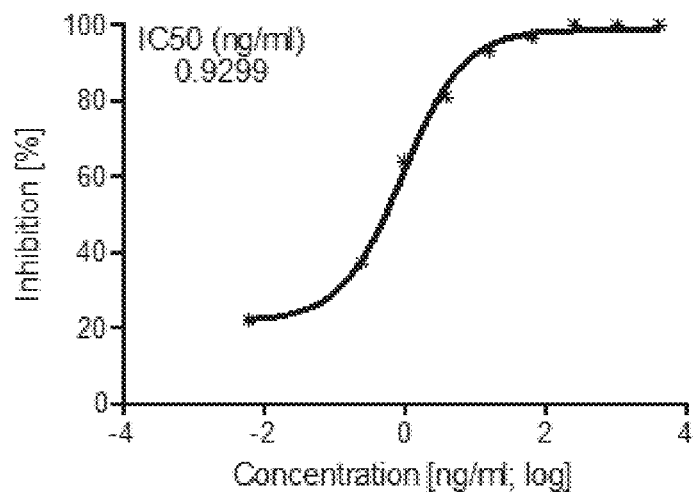
Figure 8H:
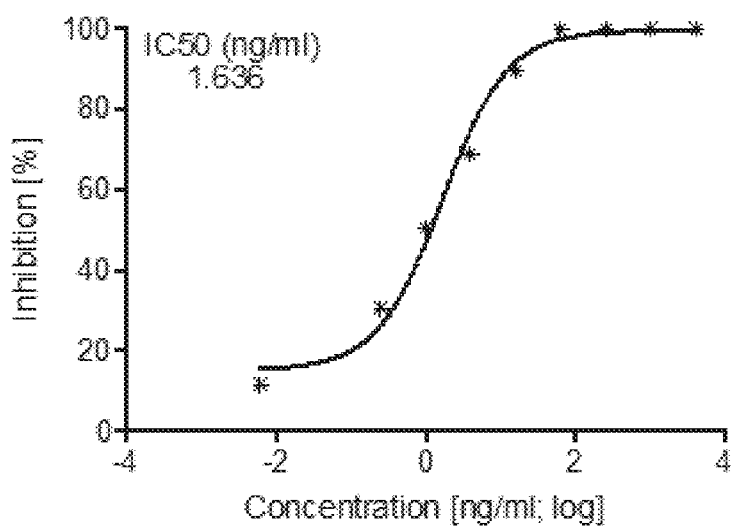

FIG. 8H shows that anti-IL-11Rα antibody 9A7 inhibits fibrogenic protein production induced by endogenous IL-11 (top) or exogenous IL-11 (bottom), thus demonstrating neutralisation of the fibrotic response.

Example 6: Treatment of Cancer In Vivo Using Anti-IL-11Rα Antibodies

The effect of treatment with neutralising anti-IL-11Rα antibodies on cancer is analysed in mouse models of cancer.

Models of breast, lung, and gastrointestinal cancers are established in mice, the mice are treated by administration of neutralising anti-IL-11Rα antibodies, or control antibodies, and the development/progression of cancer is monitored.

An anti-cancer effect is observed for the neutralising anti-IL-11Rα antibodies, as evidenced by reduced symptoms of cancer and/or increased survival as compared to mice treated with control antibodies.

The effect of neutralising anti-IL-11Rα antibodies in combination with chemotherapeutic agents, e.g. cisplatin, is also investigated.

An additive effect is observed on inhibition of tumour growth when using anti-IL-11Rα antibodies in combination with a chemotherapeutic agent.

Example 7: Treatment of AMD Using Anti-IL-11Rα Antibodies

The effect of treatment with neutralising anti-IL-11Rα antibodies is investigated in wet age-related macular degeneration (AMD).

Neutralising anti-IL-11Rα antibody is administered to subjects having wet AMD. In some treatment conditions, subjects are administered with VEGF antagonist therapy (e.g. ranibizumab, bevacizumab, pegaptanib, brolucizumab or aflibercept), PDGF antagonist therapy (e.g. pegpleranib), or are treated by laser coagulation therapy in addition to treatment with anti-IL-11Rα antibody.

A reduction in wet AMD pathology and/or improvement in the symptoms of wet AMD is observed in subjects treated with anti-IL-11Rα antibody as compared to subjects not treated with anti-IL-11Rα antibody.

Example 8: Inhibition of Kidney Fibrosis or Kidney Injury Using Anti-IL-11Rα Antibodies 10-12 week old littermate mice of similar weight had kidney fibrosis induced by intraperitoneal (i.p.) injection of folic acid (180 mg kg$^{-1}$) in vehicle (0.3 M NaHCO$_3$); control mice were administered vehicle alone.

Anti-IL-11Rα antibody clone BSO-9A7 (VH=SEQ ID NO:7, VL=SEQ ID NO:13) was administered one day after folic acid treatment and then 3 times per week at a dose of 20 mg/kg. Mice were euthanized 28 days post-injection.

The mouse plasma levels of urea and creatinine were quantified using urea assay kit (ab83362, Abcam) and creatinine assay kit (ab65340, Abcam), respectively according to the manufacturer's instructions. The amount of total collagen in the kidney was quantified on the basis of colourimetric detection of hydroxyproline using a Quickzyme Total Collagen assay kit (Quickzyme Biosciences). All colourimetric assays were performed according to the manufacturer's instructions.

Tissues were paraffin-embedded, and kidneys were sectioned at 3 µm. For paraffin sections, tissues were fixed for 24 h. at room temperature in 10% neutral-buffered formalin (Sigma-Aldrich), dehydrated and embedded in paraffin. For cryosections, freshly dissected organs were embedded with Tissue-Tek Optimal Cutting Temperature compound (VWR International). Cryomoulds were then frozen in a metal beaker with isopentane cooled in liquid nitrogen and sections were stored in –80° C. Total collagen was stained with Masson's trichrome stain kit (HT15, Sigma-Aldrich) according to the manufacturer's instructions. Images of the sections were captured and blue-stained fibrotic areas were semi-quantitatively determined with ImageJ software (version 1.49). For immunohistochemistry, the tissue sections were incubated with anti-ACTA2 antibody (ab5694, Abcam). Primary antibody staining was visualized using an ImmPRESS HRP Anti-Rabbit IgG Polymer Detection kit (Vector Laboratories) with ImmPACT DAB Peroxidase Substrate (Vector Laboratories) as the chromogen. The sections were then counterstained with Mayer's haematoxylin (Merck).

Figure 9A:
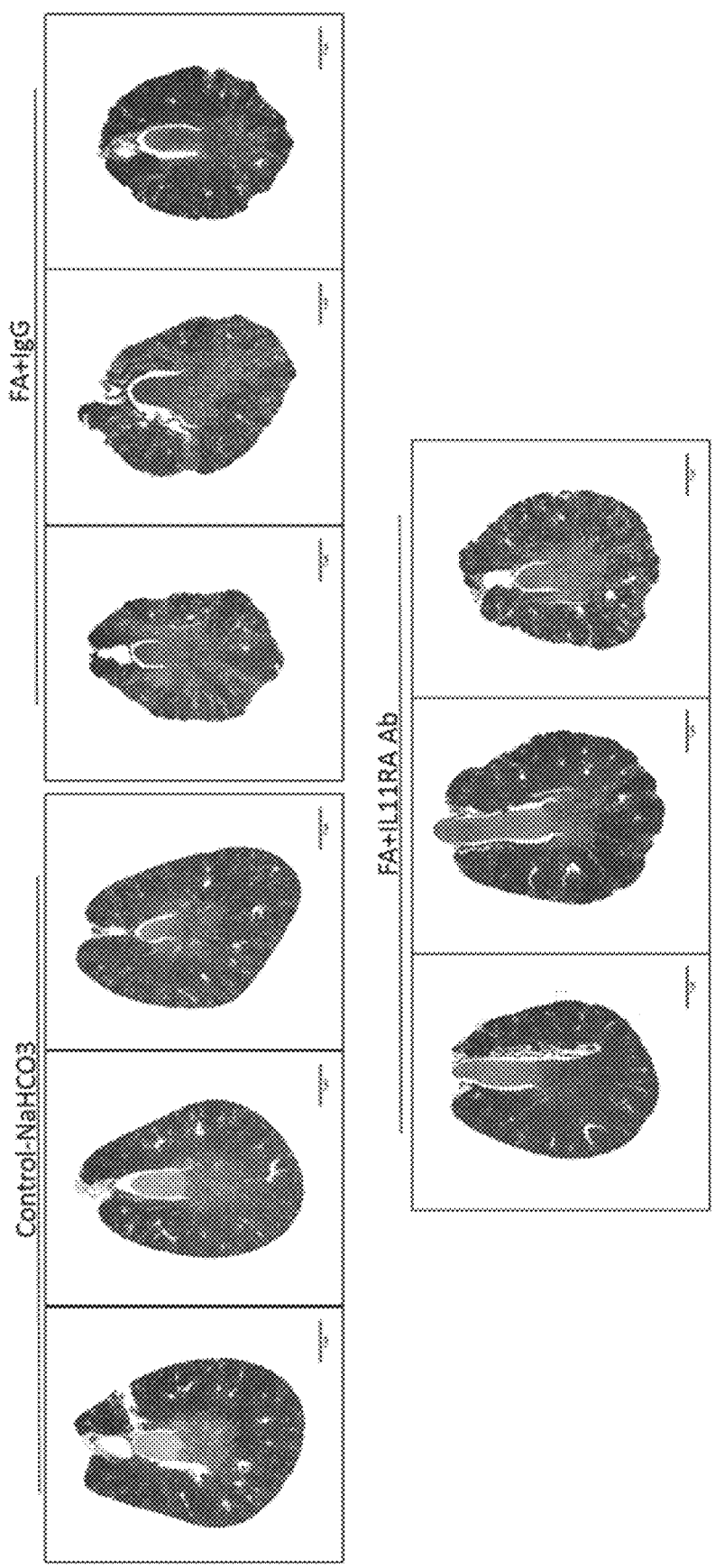
FIGS. 9A and 9B. Images and graph showing the results of histological analysis of kidney sections from mice subjected to different treatments in a mouse model of kidney fibrosis. Kidney fibrosis was induced by intraperitoneal (IP) injection of folic acid (FA, 180 mg/kg) in vehicle (0.3M NaHCO₃) mice; control mice were administered vehicle alone. Mice were administered isotype control IgG2 (20 mg/kg, 3× per week, intraperitoneal), anti-IL-11Rα antibody (20 mg/kg, 3× per week, intraperitoneally) from day 1 post folic acid injury and for the duration of the experiment. Animals were sacrificed 28 days after folic acid-induced kidney damage and analysed for fibrosis histologically using Masson's Trichrome stain. (9A) Images of Masson's Trichrome stained kidney sections. Fibrotic areas containing collagen appear darker as compared to healthy areas that appear lighter. (9B) Graph showing semi-quantitative analysis of collagen area as a percentage (%) of the total kidney area. ***, P<0.001 compared to FA+IgG. ANOVA.
Figure 9B:
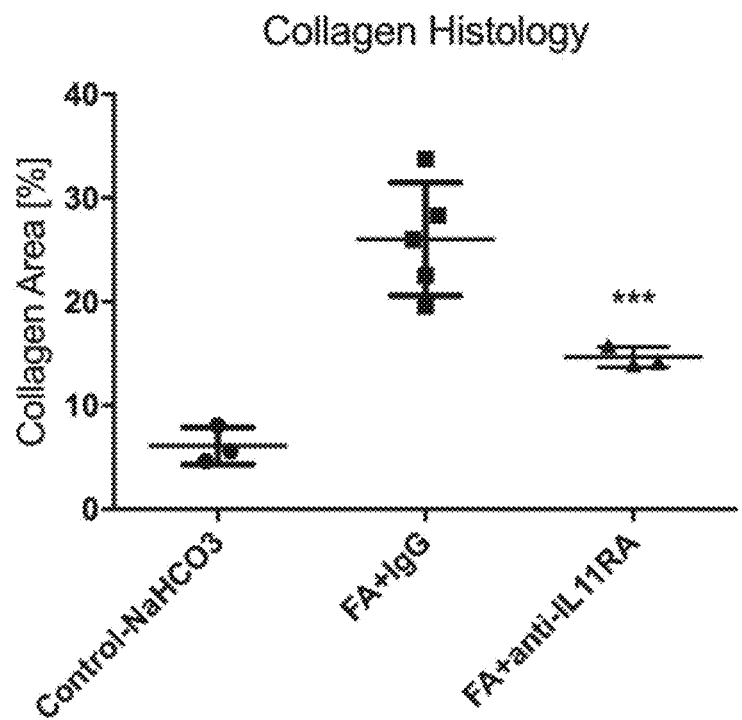

FIGS. 9A and 9B show that mice treated with anti-IL-11Rα antibody were found to have significantly reduced staining for collagen, indicating that anti-IL-11Rα antibody treatment had inhibited kidney fibrosis.

Figure 10A:
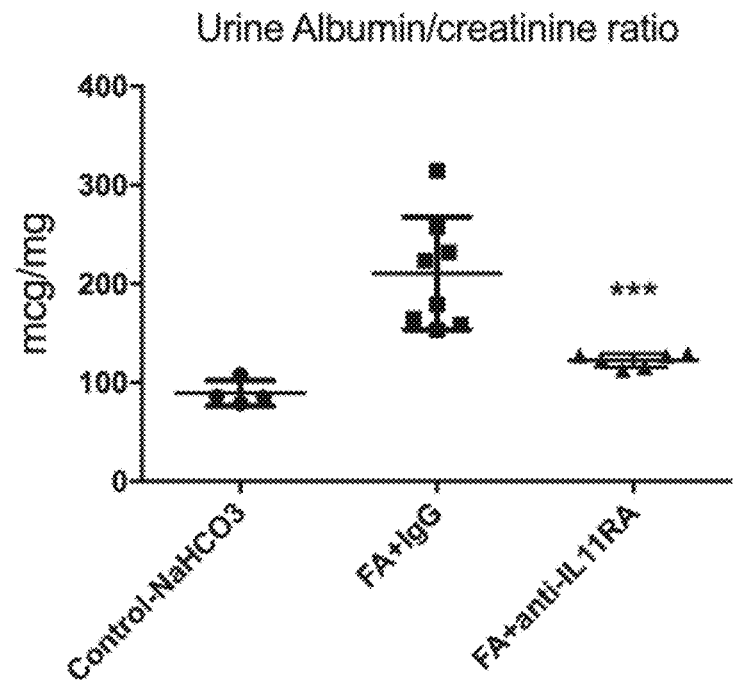
FIGS. 10A and 10B. (10A) Graph showing the urinary albumin/creatine ratio In mice subjected to different treatments in a mouse model of kidney fibrosis. Kidney fibrosis was induced by intraperitoneal (IP) Injection of folic acid (FA, 180 mg/kg) in vehicle (0.3M NaHCO₃) mice; control mice were administered vehicle alone. FA treated mice were administered isotype control IgG2 (20 mg/kg, 3× per week, intraperitoneal) or anti-IL11Rα antibody (20 mg/kg, 3× per week, intraperitoneal) from day 1 post folic acid injury and for the duration of the experiment. Mice were placed in metabolic cages and urinary creatinine and albumin measured using commercial assays (Abcam) according to the manufacturer's instructions. ***, P<0.001 compared to FA+IgG, ANOVA. (10B) Graph showing dose-dependent effects of anti-IL-11Rα antibody on kidney collagen content in folic-acid induced kidney fibrosis in a mouse model.

FIG. 10A shows that the urinary albumin/creatine ratio was significantly reduced by treatment with anti-IL-11Rα antibody, indicating a reduced level of kidney damage in mice treated with anti-IL-11Ra antibody.

Anti-IL-11Rα antibody clone BSO-9A7 was assessed for its ability to reduce folic acid-induced kidney fibrosis at different concentrations (0.5, 1, 5 and 10 mg/kg). IgG (10 mg/kg) was used as a control. Antibody injections were initiated one day before folate treatment and performed biweekly. Animals were sacrificed three weeks after folate induced injury to assess renal collagen content using the HPA assay.

Figure 10B:
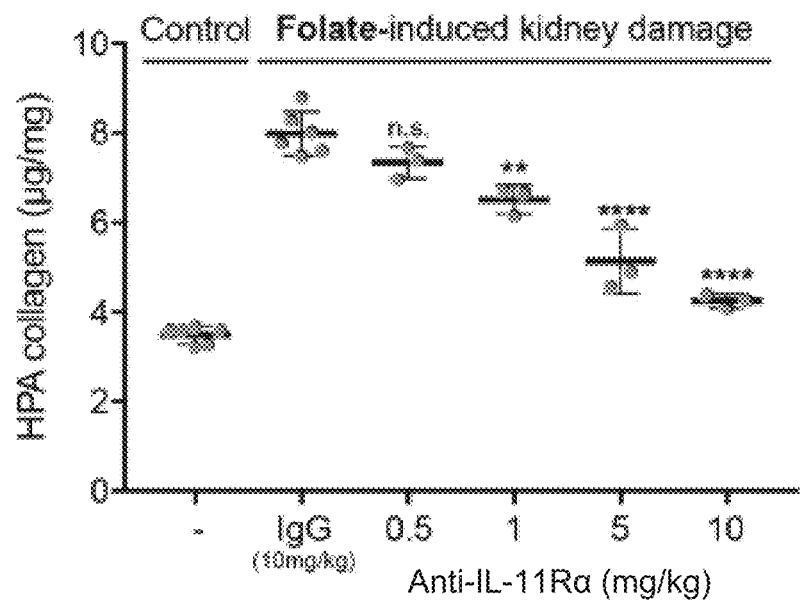

FIG. 10B shows that anti-IL-11Rα therapy was found to reduce kidney collagen content in folic acid-Induced kidney fibrosis In a dose-dependent fashion.

In another experiment a mouse model of acute renal injury was induced by unilateral ureteric obstruction (UUO). Briefly, mice were treated by sham operation or ureteric obstruction of one ureter. Mice received IgG, anti-IL-11Rα antibody clone BSO-9A7 (20 mg/kg; on surgical days −1, 1, 3, 5) and injured kidneys ('UUO') or contralateral uninjured kidneys (Con) were harvested on day 7 post surgery.

Semi-quantitative assessment of tubular injury was performed by histological analysis of casts, tubular atrophy or tubular expansion blinded to experimental conditions (Tubular injury score: 0, none; 1, minimal; 2, mild; 3, moderate; 4, severe).

Figure 11A:
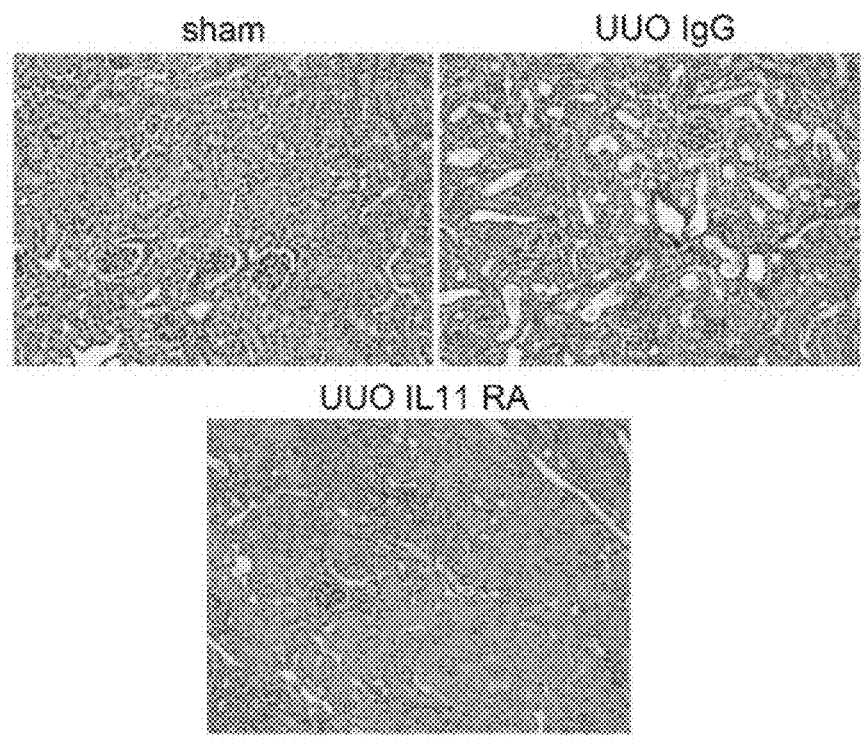
FIGS. 11A and 11B. Images and graph showing the results of histological analysis of kidney sections from mice subjected to different treatments in a mouse model of acute renal injury. (11A) Mice were treated by sham operation or ureteric obstruction of one ureter. Mice received IgG, anti-IL-11Rα antibody (20 mg/kg on surgical days −1, 1, 3, 5) and injured kidneys (UUO IgG, IL-11Rα) or contralateral (Con) uninjured kidneys (Con IgG, IL-11) were harvested on day 7 post surgery. (11B) Semi-quantitative assessment of tubular injury was determined by histological analysis of casts, tubular atrophy or tubular expansion blinded to experimental conditions (Tubular injury score: 0, none; 1, minimal; 2, mild; 3, moderate; 4, severe). *, P<0.05 compared to UUO IgG, ANOVA.
Figure 11B:
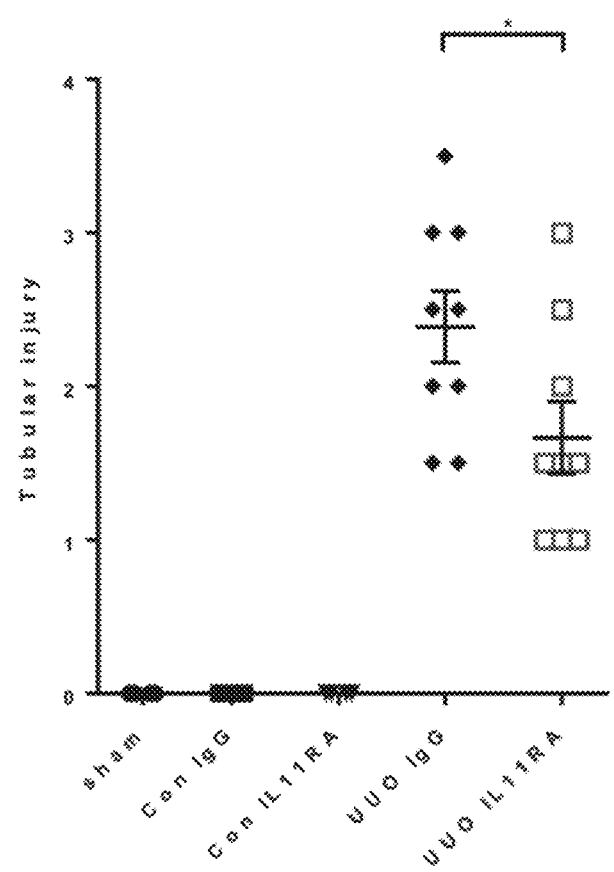

FIGS. 11A and 11B show that treatment with anti-IL-11Rα antibody reduced tubular damage in a mouse model of acute renal injury.

Example 9: Inhibition of Heart Fibrosis Using Anti-IL-11Rα Antibodies

The anti-fibrotic effect of anti-IL-11Rα antibody treatment was analysed in a mouse model of cardiac fibrosis. Briefly, transverse aortic constriction (TAC) was performed in male mice as described previously (Tarnavski, O. et al. Mouse cardiac surgery: comprehensive techniques for the generation of mouse models of human diseases and their application for genomic studies. Physiol. Genomics 16, 349-360 (2004)). Age-matched mice underwent a sham operative procedure without TAC. Trans-thoracic two-dimensional Doppler echocardiography was used to confirm increased pressure gradients (>40 mm Hg), indicative of successful TAC.

Mice were euthanized at 2 weeks post-TAC for histological and molecular assessment. Anti-IL-11Rα antibody clone BSO-9A7 (VH=SEQ ID NO:7, VL=SEQ ID NO:13) or control IgG antibody were administered intraperitoneally 3 times per week at a dose of 20 mg/kg. After two weeks hearts were harvested and assessed for fibrosis extent using Masson's Trichrome stain kit (HT15, Sigma-Aldrich), in accordance with the manufacturer's instructions. The amount of total collagen in the heart was quantified on the basis of colourimetric detection of hydroxyproline using a Quickzyme Total Collagen assay kit (Quickzyme Biosciences).

Figure 12A:
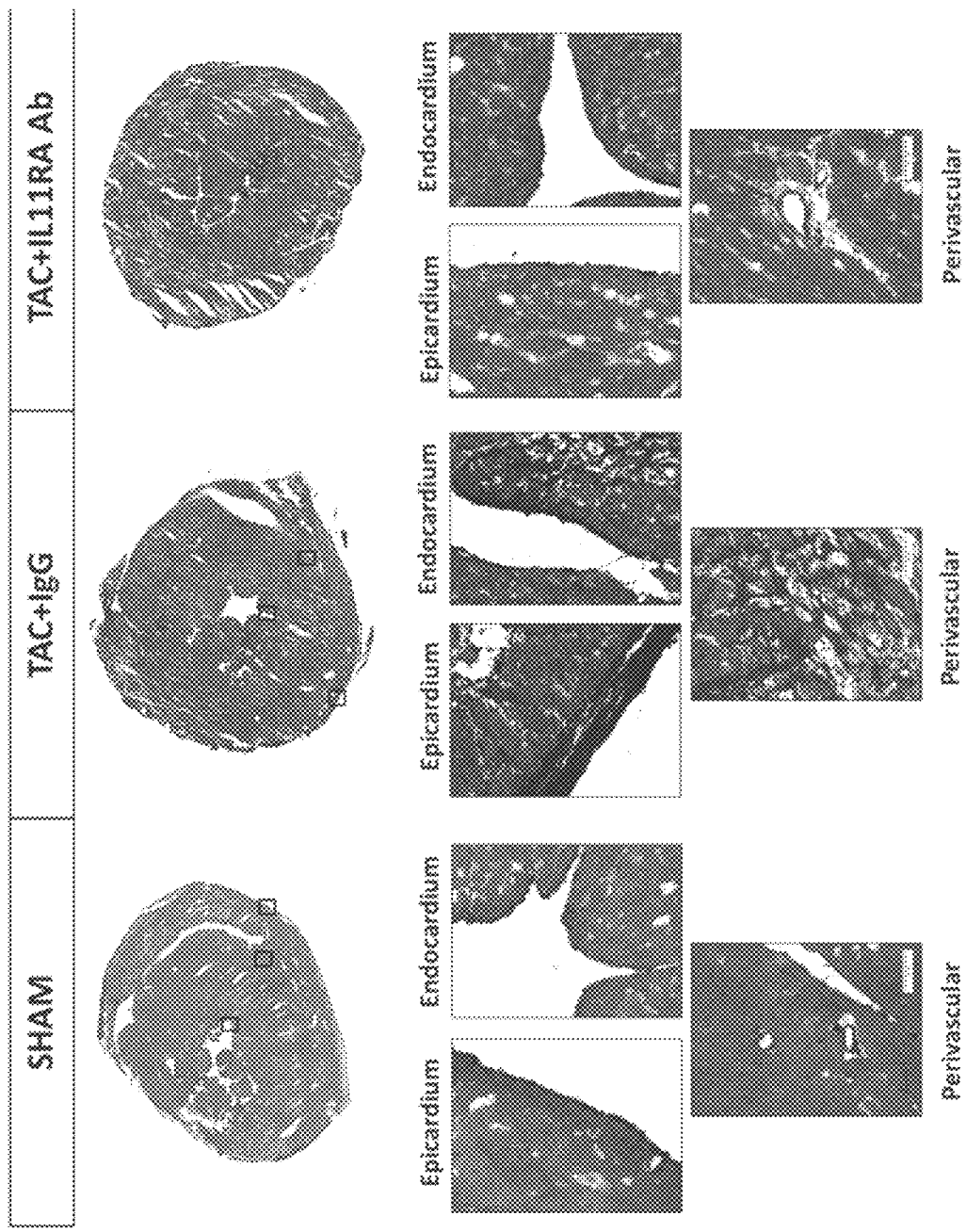
FIGS. 12A and 12B. Images and bar chart showing the results of histological analysis of heart fibrosis in mice subjected to different treatments in a mouse model of cardiac fibrosis. Mice (C57Bl6, male, 8-12 weeks old) were subjected to fibrosis-inducing transverse aortic constriction (TAC) or sham operations. TAC-treated animals received either control antibody (20 mg/kg, 3×/week, intraperitoneal) or neutralizing anti-IL-11Rα antibody (20 mg/kg, 3×/week, intraperitoneal). After two weeks hearts were harvested and assessed for fibrosis extent using Masson's Trichrome stain (12A). (12B) shows the amount of total collagen in the heart as determined by colourimetric detection of hydroxyproline using a Quickzyme Total Collagen assay kit (Quickzyme Biosciences). **, P<0.01; ns, not significant vs SHAM. #, P<0.05, TAC+IgG control vs TAC+anti-IL11RA. Ab, antibody.
Figure 12B:
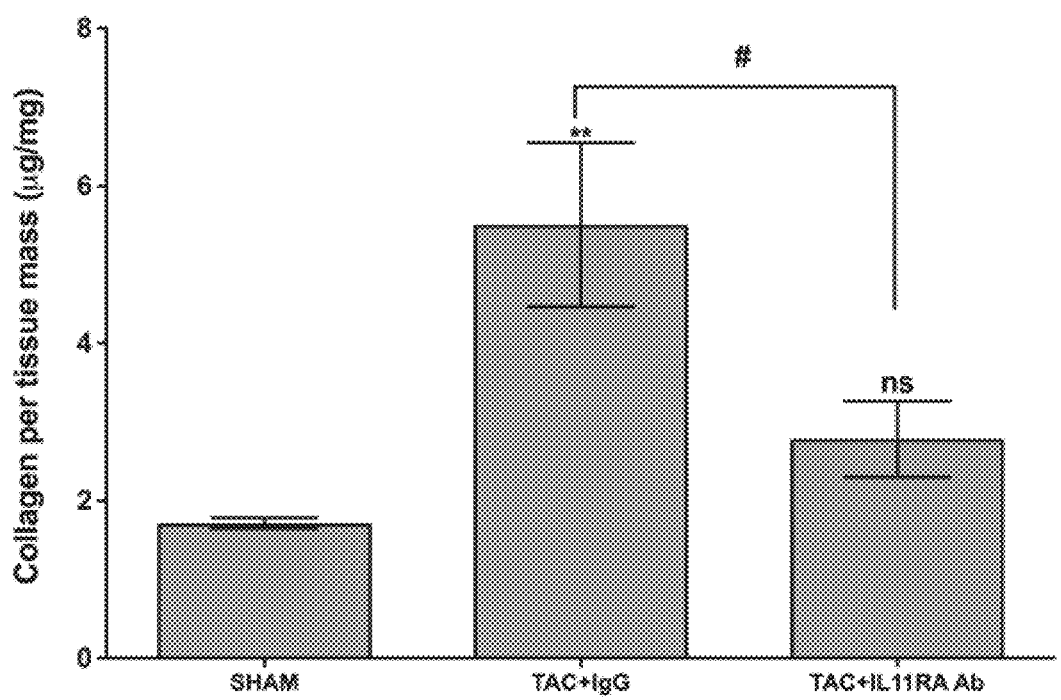

The results of the analysis is shown In FIGS. 12A and 12B. Mice treated with neutralising anti-IL-11Rα antibody were found to have reduced levels of collagen In the heart as compared to mice treated with IgG control antibody (FIG. 12A), and reduced level of fibrosis in the epicardium, endocardium and in perivascular regions as compared to mice treated with IgG control antibody (FIG. 12B).

Example 10: Inhibition and Reversal of Liver Fibrosis Using Anti-IL-11Rα Antibodies Non-alcoholic steatohepatitis (NASH) is a common liver disease characterised by progression from inflammation to fibrosis and eventually liver failure. Hepatic stellate cells (HSCs) play an important role in the pathogenesis of NASH. Pro-fibrotic stimuli e.g. TGFβ1, PDGF and pro-inflammatory factors can activate and transform HSCs into liver myofibroblasts which share features with fibroblast-derived myofibroblasts. NASH was used as an example of liver fibrosis.

10.1 IL-11 and Liver Fibrosis

The expression of IL-11 in HSCs stimulated with TGFβ1 was detected by qPCR. Total RNA was extracted from HSCs lysate using trizol (Invitrogen) followed by RNeasy column (Qiagen) purification. The cDNAs were synthesized with iScript™ cDNA synthesis kit (Bio-Rad) according to manufacturer's instructions. Gene expression analysis was performed on duplicate samples with either TaqMan (Applied Biosystems) or fast SYBR green (Qiagen) technology using StepOnePlus™ (Applied Biosystem) over 40 cycles. Expression data were normalized to GAPDH mRNA expression and fold change (FC) was calculated using 2-ΔΔCt method. The expression levels In HSCs of IL6R, gp130 and IL-11Rα were also detected by qPCR.

IL-11 levels in patient liver samples were detected from human precision cut liver slices that were cut and incubated with TGFβ1 for 24 h. Western blots were performed and densitometry of the blots plotted compared to reference levels of GAPDH.

Figure 13A:
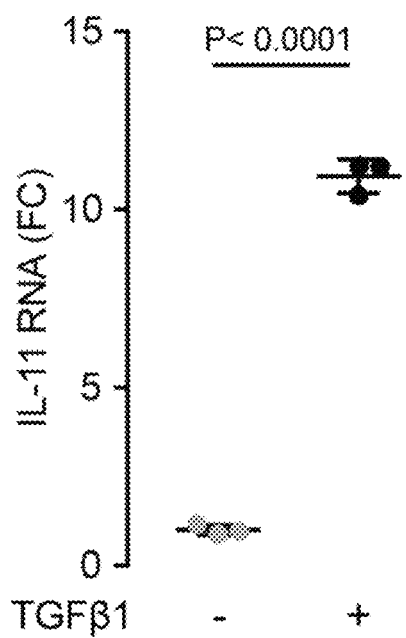
FIGS. 13A to 13H. Graphs showing the relationship between HSCs and IL-11. (13A) IL-11 expression in hepatic stellate cells (HSCs) stimulated with TGFβ1; FC: fold change. (13B) IL6R, gp130, and IL11RA expression in HSCs; TPM: transcripts per million. (13C) Graph showing densitometry of IL-11 expression detected by Western blotting from human liver samples of healthy individuals and patients suffering from NASH. (13D, E) Graphs showing automated fluorescence quantification for (13D) ACTA2 cells and (13E) Collagen I immunostaining following incubation of HSCs without stimulus (−), or with TGFβ1, PDGF, or IL-11. (13F) Graph showing collagen secretion supernatants of HSCs stimulated with TGFβ1, PDGF, or IL-11 (Sirius red assay). (13G) Dose-dependent matrigel invasion of HSCs induced by IL-11. (13H) Graphs showing relative liver hydroxyproline content, mRNA expression of pro-fibrotic markers, and serum ALT levels from mice administered daily with IL-11 for 21 days. FC: fold change.
Figure 13B:
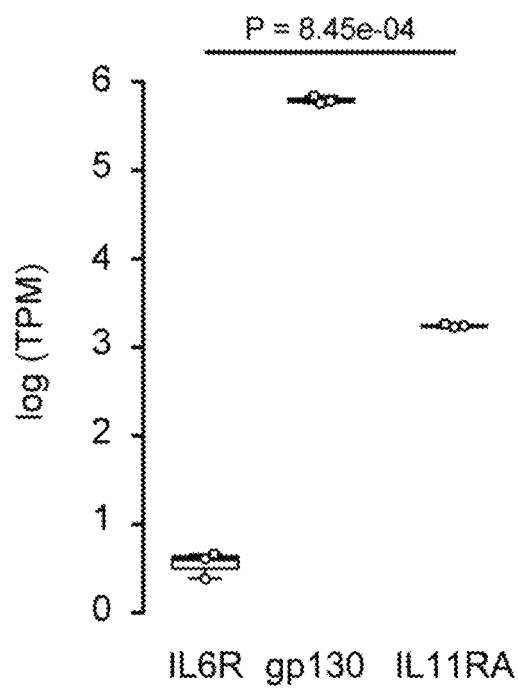
Figure 13C:
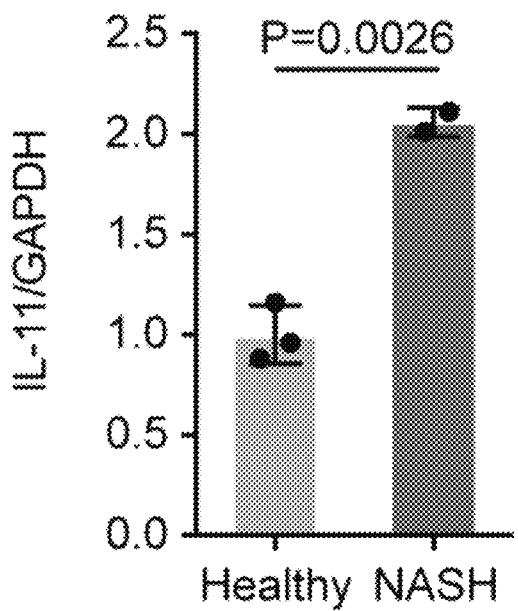
Figure 13D:
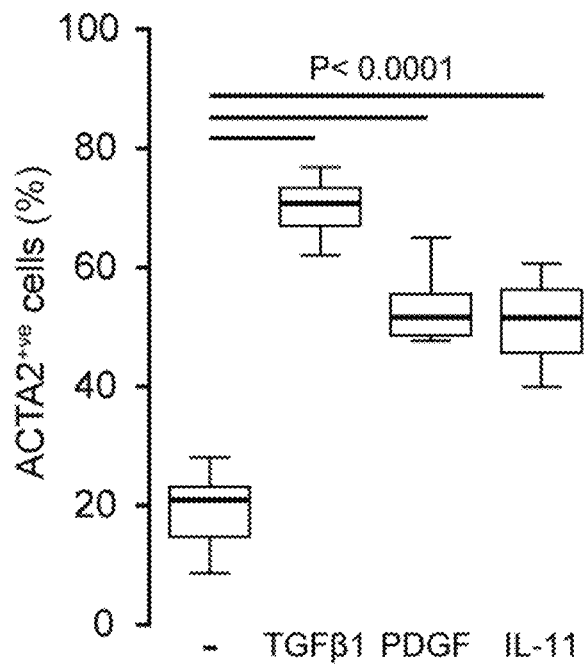
Figure 13E:
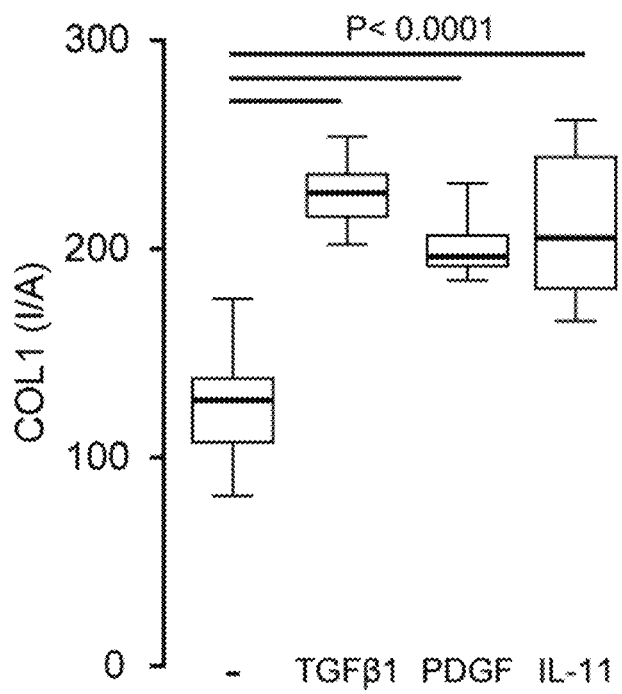
Figure 13F:
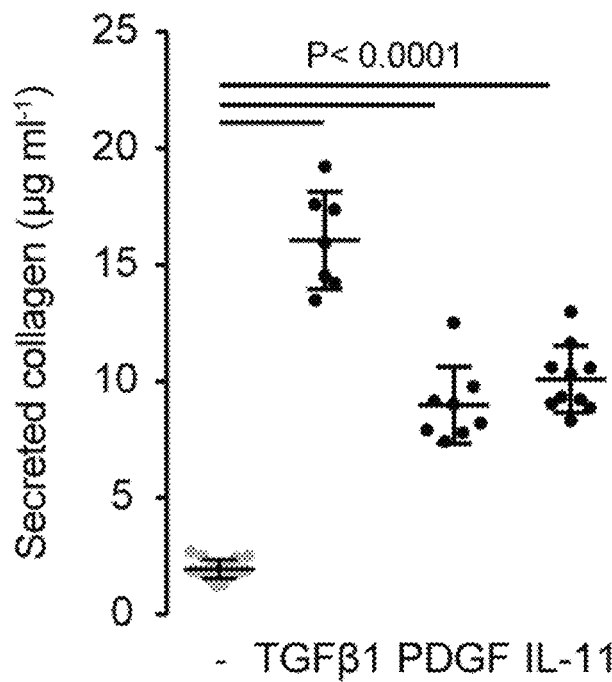
Figure 13G:
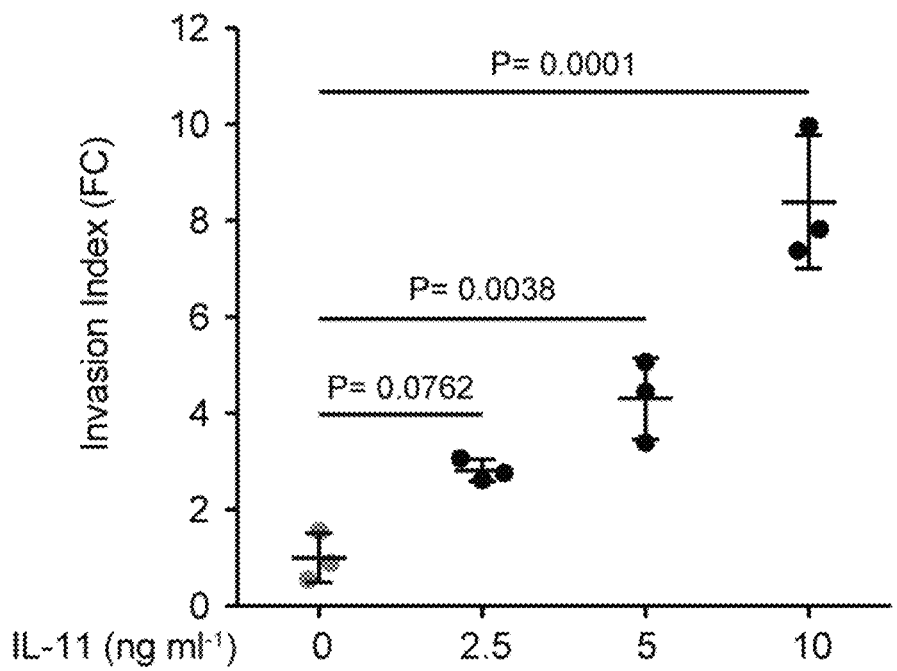

The results are shown in FIGS. 13A to 13C. IL-11 was found to be upregulated in HSCs stimulated with TGFβ1 (13A). HSCs express high levels of the IL-11 receptor subunit alpha (IL-11Rα) (13B). IL-11 levels in NASH patient liver samples were found to be increased compared to healthy individuals (13C).

Cells were stimulated with either IL-11, TGFβ1 or PDGF to investigate the effect of IL-11 on HSCs activation and invasion.

HSCs were seeded in 96-well black CellCarrler plates (PerkinElmer) at a density of $5 \times 10^3$ cells per well.

Following experimental conditions, cells were fixed in 4% paraformaldehyde (PFA, 28908, Thermo Fisher Scientific), permeabilized with 0.1% Triton X-100 (Sigma) and non-specific sites were blocked with 0.5% BSA and 0.1% Tween-20 in PBS. Cells were incubated overnight (4'C) with primary antibodies (1:500), followed by incubation with the appropriate AlexaFluor 488 secondary antibodies (1:1000). EdU-Alexa Fluor 488 was incorporated using a Click-iT EdU Labelling kit (C10350, Thermo Fisher Scientific) according to manufacturer's protocol. Cells were counterstained with 1 μg ml$^{-1}$ DAPI (D1306. Thermo Fisher Scientific) in blocking solution. Each condition was imaged from duplicated wells and a minimum of 7 fields per well using Operetta high-content imaging system 1483 (PerkinElmer). The quantification of ACTA2+ve cells, Indicating number of myofibroblasts, was measured using Harmony v3.5.2 (PerkinElmer). The measurement of fluorescence intensity per area of Collagen I (normalized to the number of cells) was performed with Columbus 2.7.1 (PerkinElmer). Total secreted collagen in the cell culture supernatant was quantified using Sirius red collagen detection kit (9062, Chondrex).

The invasive behaviour of human HSCs was assayed using 24-well Boyden chamber invasion assays (Cell Biolabs Inc.). Equal numbers of HSCs in serum-free HSC media were seeded in triplicates onto the ECM-coated matrigel and were allowed to invade towards HSC media containing 0.2% FBS. After 48 h of incubation with stimuli, media was aspirated and non-invasive cells were removed using cotton swabs. The cells that invaded towards the bottom chamber were stained with cell staining solution (Cell Biolabs Inc.) and invasive cells from 5 non-overlapping fields of each membrane were imaged and counted under 40× magnification.

The results are shown in FIGS. 13D to 13G. IL-11 was found to activate HSCs to a similar extent as TGFβ1 or PDGF, transforming quiescent HSCs into ACTA2$^{+ve}$ myofibroblasts (13D) that produce (13E) and secrete collagen (13F). IL-11 was also found to promote dose-dependent HSC matrix invasion (13G; invasion is an important aspect of HSC pathobiology in NASH).

In vivo, recombinant mouse Il-11 (rmIl-11; 100 μg/kg) was administered subcutaneously to mice daily for 21 days. Total hydroxyproline content in the livers was measured using Quickzyme Total Collagen assay kit (Quickzyme Biosciences). Mouse serum levels of alanine aminotransferase (ALT) was measured using Alanine Transaminase Activity Assay Kit (ab105134, abcam). RNA expression of pro-fibrotic markers Acta2, Col1a1, Col1a2 and Col1a3 was measured by qPCR, as before.

Figure 13H:
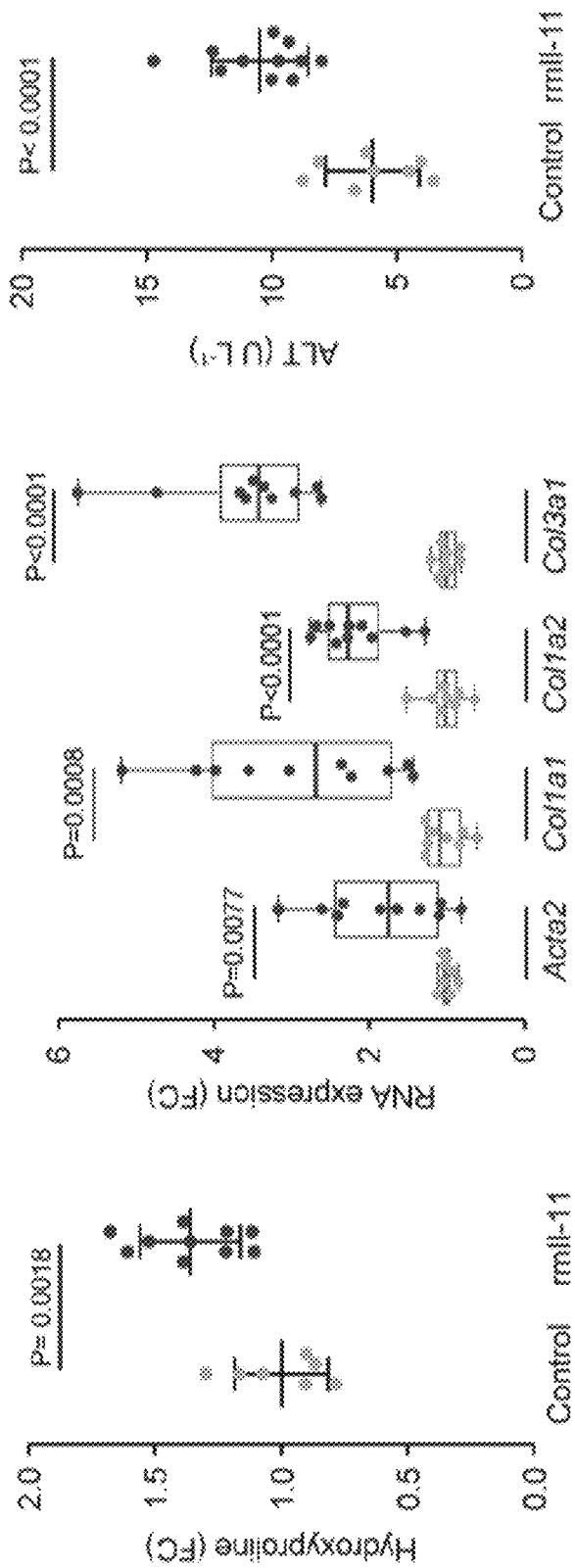

The results are shown in FIG. 13H. IL-11 administration increased hepatic collagen content, fibrosis marker mRNA and serum alanine aminotransferase (ALT) levels.

These data show that HSCs are both a source and prominent target of IL-11 in the human liver and that IL-11 is elevated in NASH. IL-11 induces hepatic stellate cell activation and hepatic fibrosis.

10.2 Treatment of NASH Using Anti-IL-11Rα Therapies

Anti-IL-11Rα antibody clone BSO-9A7 was assessed for its ability to treat fibrosis in NASH.

HSCs were treated with NASH-promoting factors in the presence or absence of anti-IL-11Rα antibody to investigate the transformation of HSCs to myofibroblasts. HSC cultures were stimulated with 5 ng/ml TGFβ1 for 24 hours in the presence of either IgG or anti-IL-11Rα antibody (6 μg/ml). ACTA2$^{+ve}$ cell numbers (activated myofibroblasts) were measured on the Operetta platform as described above. HSC cultures were separately stimulated for 24 hours with NASH stimuli PDGF (20 ng/ml), CCL2 (5 ng/ml), angiotensin II (100 nM), bFGF (10 ng/ml) or oxidative stress ($H_2O_2$; 0.2 mM) in the presence of either IgG or anti-IL-11Rα antibody (2 μg/ml). ACTA2$^{+ve}$ cell proportions and invasion of HSCs were measured as before. Collagen 1 produced by each HSC culture was immunostained and the fluorescence quantified. IgG antibody was used as a control.

The results are shown in FIGS. 14A to 14D. Anti-IL-11Rα antibody was found to reduce ACTA2$^{+ve}$ cell numbers in HSC cultures stimulated with TGFβ1 (14A) as well as HSCs stimulated with PDGF, CCL2, angiotensin II, bFGF or oxidative stress (14B), i.e. antibody treatment blocked the stimuli-driven transition of HSCs into myofibroblasts. Anti-IL-11Rα antibody was also found to reduce HSC invasion induced by PDGF or CCL2 (14C). Collagen 1 production was found to be reduced after treatment with anti-IL-11Rα antibody (14D).

Thus, Inhibition of Il-11 signalling by anti-IL-11Rα therapies prevents hepatic stellate cell activation and hepatic fibrosis.

A liver disease prevention study in early NASH was performed to verify the anti-fibrotic and liver protective activity of 9A7 in vivo. C57Bl/6Ntac mice were fed with a NASH-inducing methionine/choline deficient (MCD) diet supplemented with 60 kcal % fat (A06071302, Research Diets) (HFMCD diet) to induce liver damage and fibrosis. After one week of the NASH diet (when ALT levels are ~800 u/L (~40-fold increase compared to normal chow), and at which time there is an established and robust steatohepatitis), animals were started on either IgG control or anti-IL-11Rα antibody twice-weekly for a four-week period. After 4 weeks, animals were euthanised and samples collected for analysis. Data are mean+−SD; each point indicates a biological replicate; Dunnett's test of 9A7 treatment vs IgG control; * P<0.05;  P<0.01; ** P<0.0001.

Figure 14A:
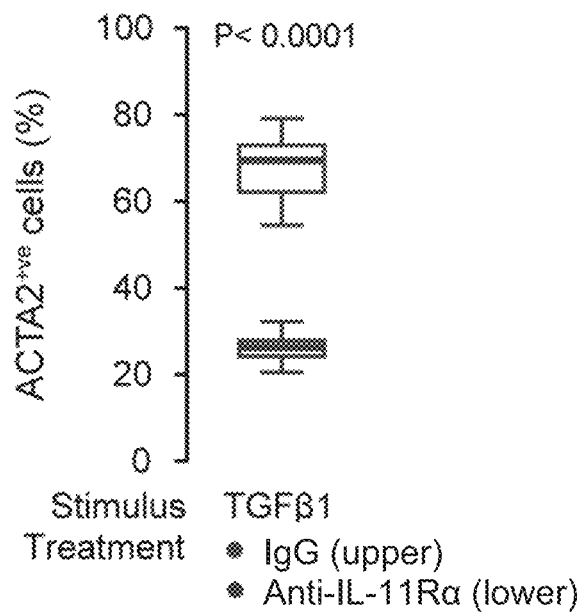
FIGS. 14A to 14D. Charts showing effect of anti-IL-11R antibody on HSC activation to myofibroblasts and HSC invasion ability (A-D) and in mouse models of early stage NASH (E-F). (14A) ACTA2$^{+ve}$ cell numbers in HSC cultures stimulated with TGFβ1 and treated with anti-IL-11Rα antibody or IgG control. (14B) ACTA2$^{+ve}$ cell numbers in HSC cultures stimulated with PDGF (20 ng/ml), CCL2 (5 ng/ml), angiotensin II (100 nM), bFGF (10 ng/ml) or H₂O₂ (0.2 mM) and treated with anti-IL-11Rα antibody or IgG control. (14C) Effect of antibody and IgG control on PDGF- and CCL2-induced HSC invasion. (14D) Effect of anti-IL-11Rα antibody on Collagen I production by stimulated HSC cultures. (14E and 14F) Effect of anti-IL-11Rα antibody on ALT levels and collagen production in early stage NASH induced in mice by HFMCD diet.
Figure 14B:
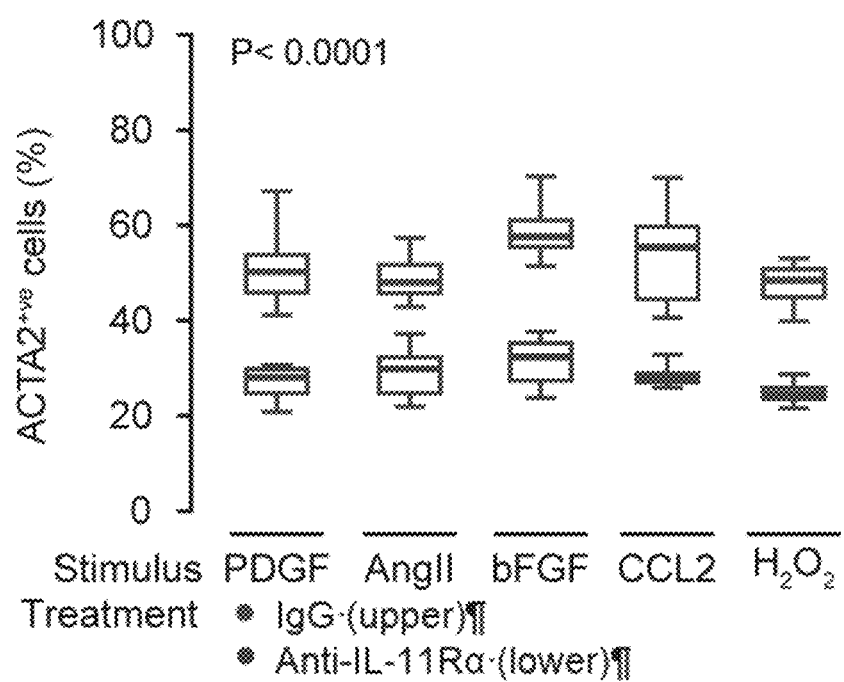
Figure 14C:
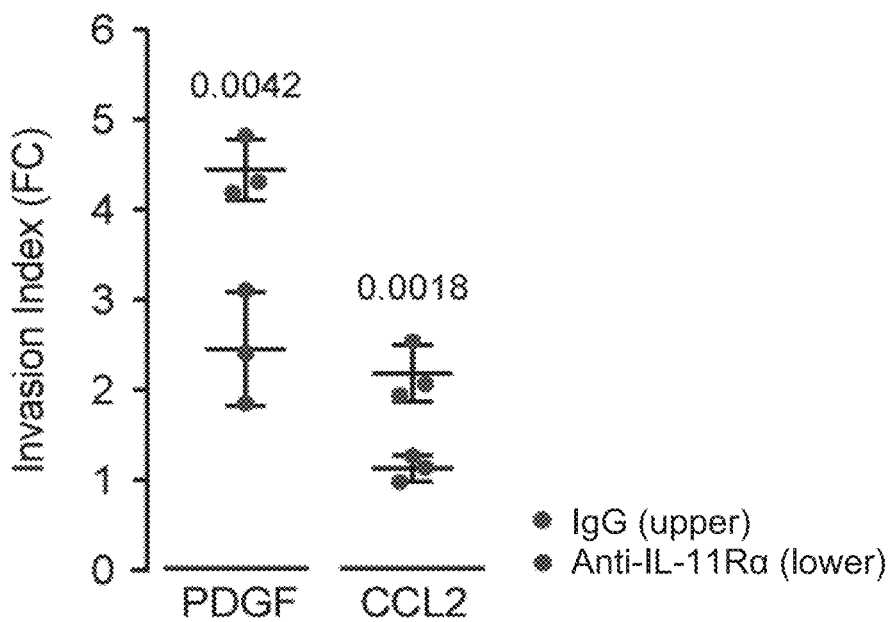
Figure 14D:
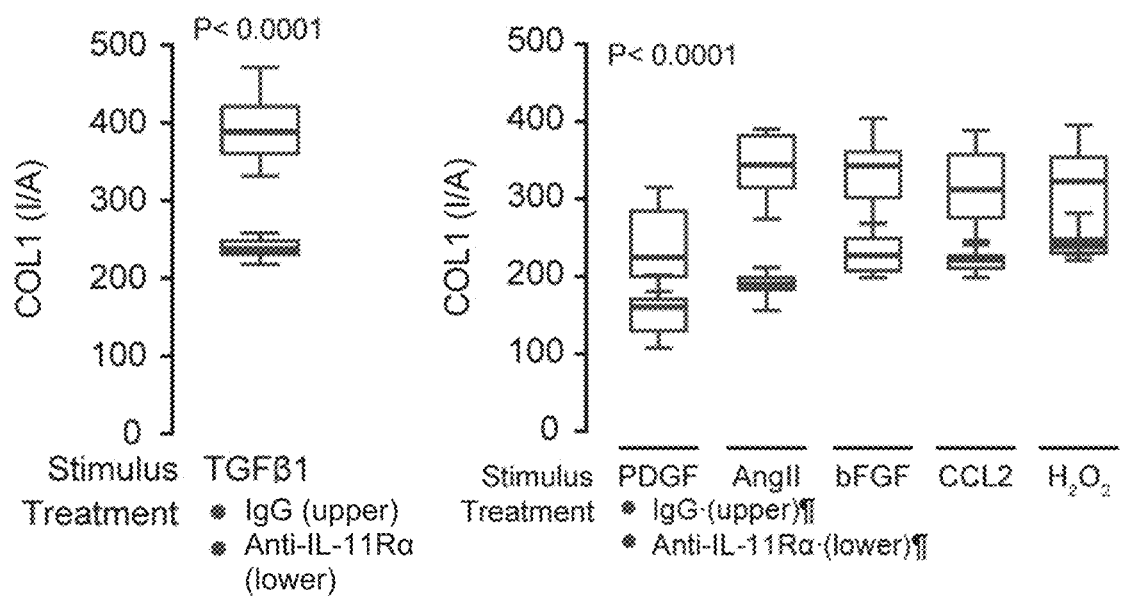
Figure 14E:
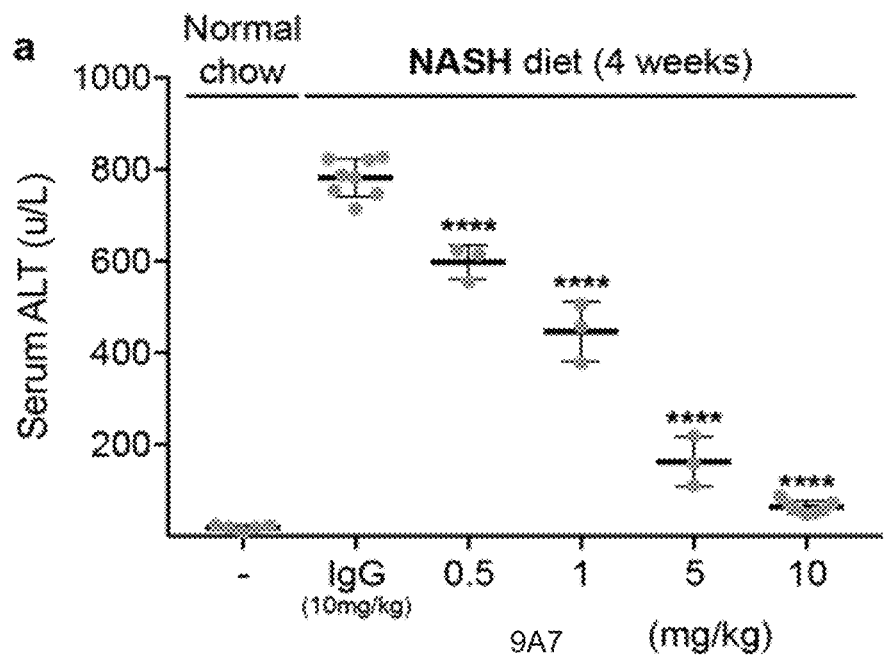
Figure 14F:
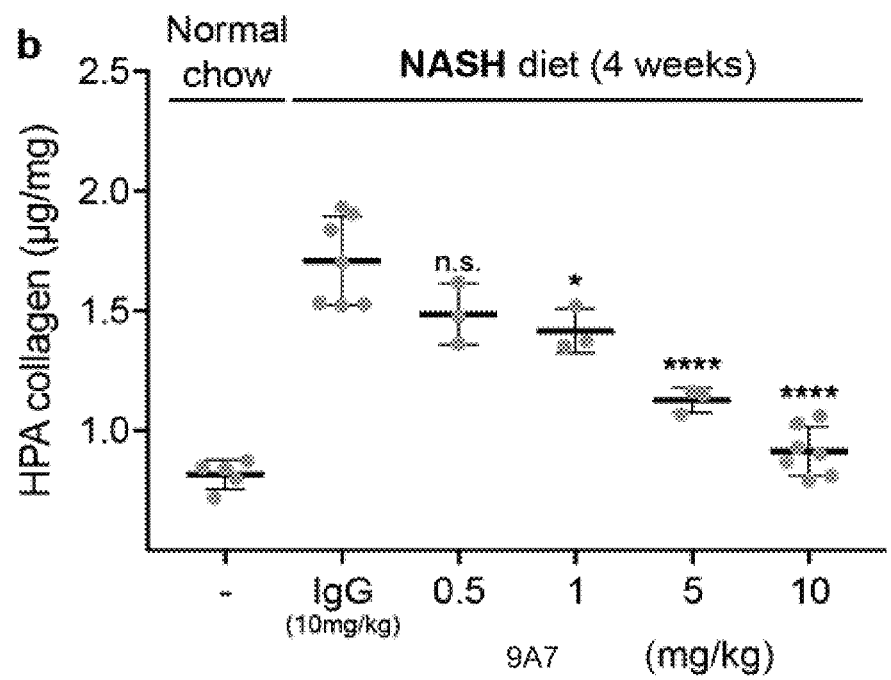

FIGS. 14E and 14F show that even 0.5 mg/kg treatment of anti-IL-11Rα antibody had a significant effect on serum ALT levels in the mouse model. Higher dosing was found to almost completely (>90%) reverse established liver damage and robustly prevents liver fibrosis in this very extreme model.

In vivo experiments were performed to determine the effect of anti-IL-11Rα antibody on late-stage NASH. Five-week old male C57BL/6N mice were fed on the NASH-inducing methionine/choline deficient (MCD) diet supplemented with 60 kcal % fat (A06071302, Research Diets) (HFMCD diet). Control mice were fed with normal chow (NC, Specialty Feeds). After 6 weeks on the HFMCD diet, when IL-11 is strongly upregulated and collagen has accumulated, anti-IL-11Rα antibody BSO-9A7 (10 mg/kg) was administered biweekly for 4 weeks. Livers and serum were collected at week 10 and analysed for ERK activation, liver hydroxyproline content, and serum ALT levels. Total and phosphorylated ERK levels In livers were detected by Western blot, total hydroxyproline content in the livers was measured using Quickzyme Total Collagen assay kit (Quickzyme Biosciences), serum levels of alanine aminotransferase (ALT) were measured using Alanine Transaminase Activity Assay Kit (ab105134, abcam).

Figure 15A:
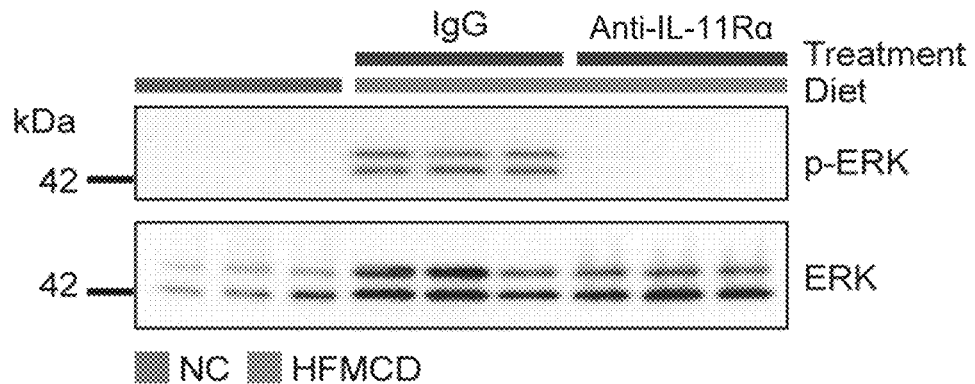
FIGS. 15A to 15D. Therapeutic effect of anti-IL-11Rα antibody in mouse models of advanced NASH. (A-C)
Figure 15B:
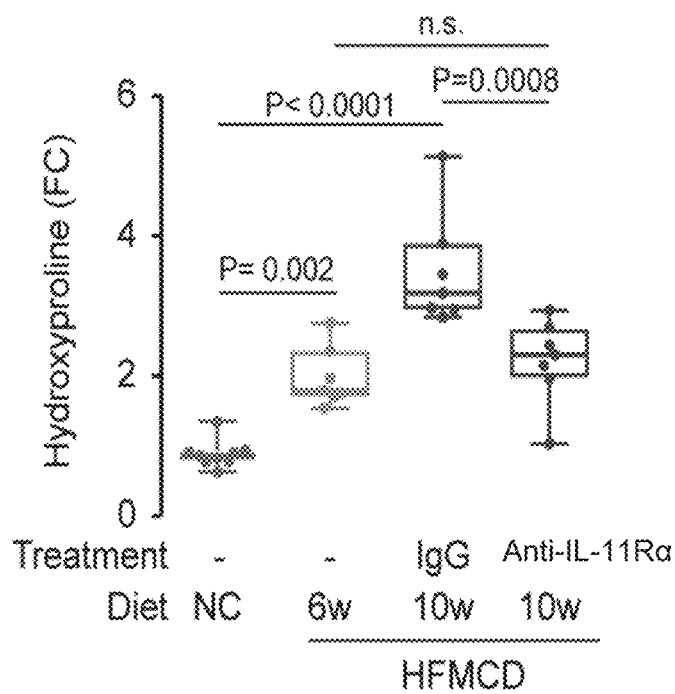
Figure 15C:
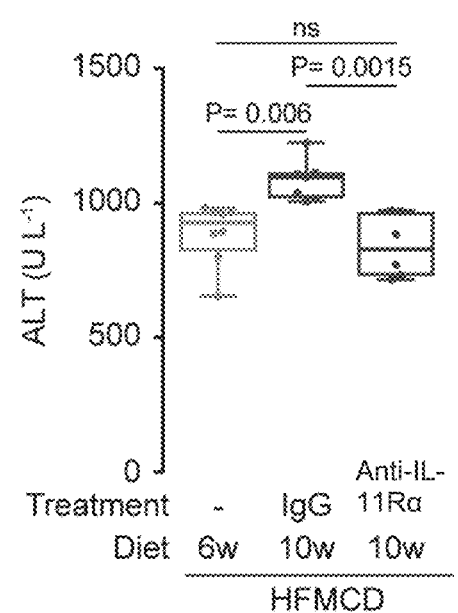

The results are shown in FIGS. 15A to 15C. Anti-IL-11Rα therapy was found to have abolished ERK activation (15A) and inhibited the progression of liver fibrosis (15B) and serum ALT levels (15C), while steatosis was unchanged.

Anti-IL-11Rα therapy was investigated in another model of advanced NASH. 2 day old C57BL/6 mice were administered a single subcutaneous injection of 200 μg streptozotocin and fed on a normal chow diet for 4 weeks. Mice were then switched onto a HFMCD diet for 7 weeks and then treated along with the HFMCD diet with 10 mg/kg anti-IL-11Rα antibody BSO-9A7 or IgG control 3× per week for a subsequent 7 weeks. RNA expression was measured for fibrosis and inflammation genes Col1a1, Col1a2, Col1a3, Timp1, Tgfβ1, Mmp2, Tnfα, Ccl2 and Ccl5.

Figure 15D:
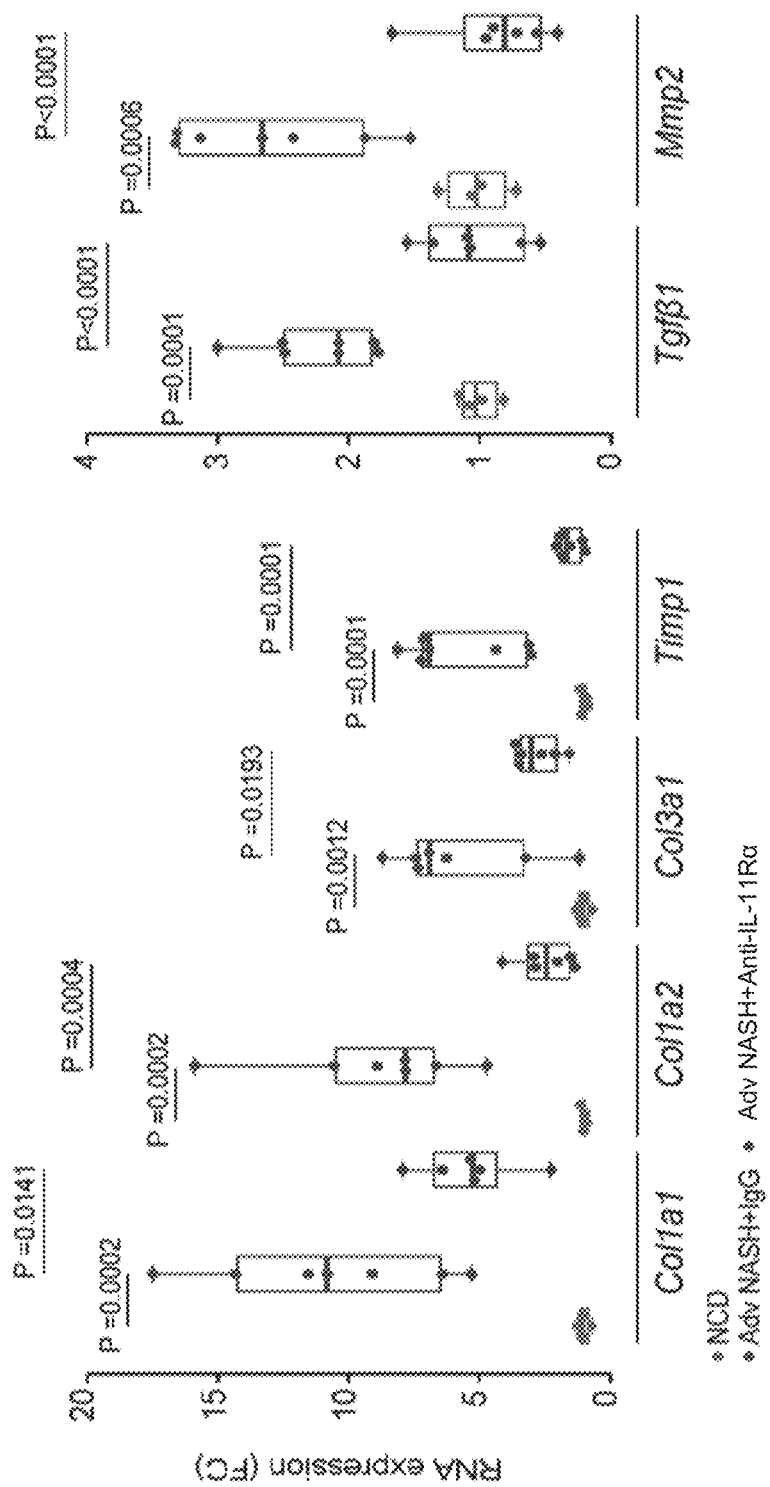
Figure 15D:
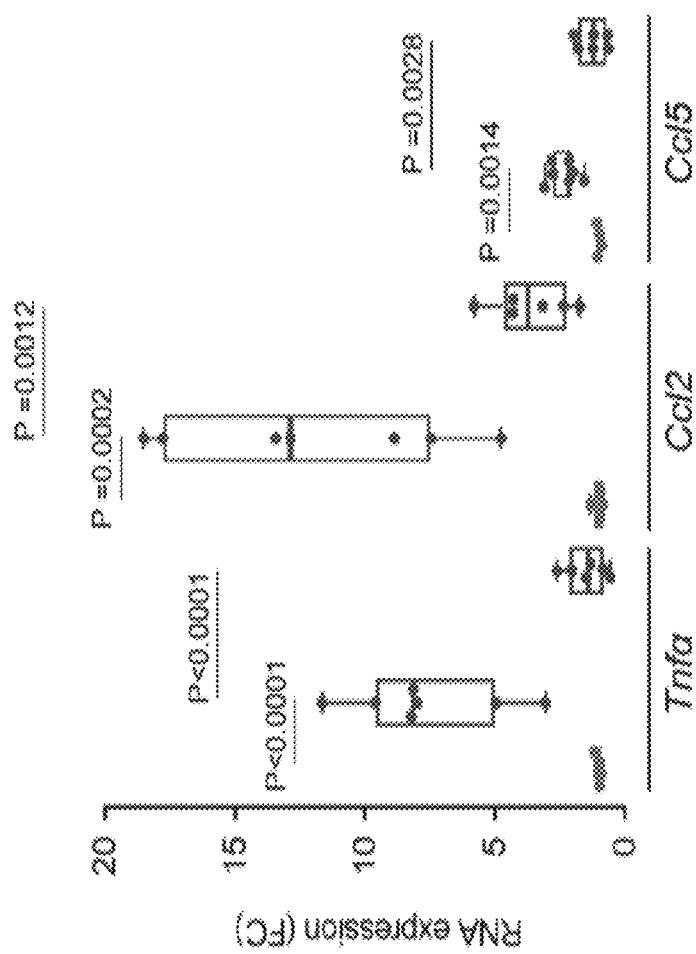

The results are shown in FIG. 15D. Anti-IL-11Rα therapy was found to robustly inhibit expression of genes indicative of fibrosis and inflammation.

10.3 Neutralisation of IL-11 Signalling Reverses Hepatic Fibrosis

Severe liver fibrosis was established by feeding mice the NASH MCD diet for 10 weeks. Feed was then switched to normal chow (NC) and mice were treated with anti-IL-11Rα antibody BSO-9A7 (20 mg/kg) twice per week for six weeks. Mice fed on NC diet for the duration of the experiment and IgG antibody were used as controls. Total collagen was measured by detecting liver hydroxyproline content as described above. mRNA expression was measured by qPCR as described above.

The results are shown in FIG. 16. Hepatic collagen content was significantly reversed after three weeks of anti-IL-11Rα antibody treatment and even greater reversal was seen at six weeks (16A). Notably, hepatic collagen content remained unchanged in IgG control-treated animals for the duration of the experiment. Graphs show total number of weeks after antibody was added at week 10.

Reversal of hepatic fibrosis is favoured when transformed HSCs undergo senescence or reversion to an inactive, ACTA2$^{-ve}$ cellular state. Anti-IL-11Rα antibody therapy was found to decrease Acta2, Mmp2 and Timp1 expression and increase senescence markers p21, p16 and p53.

To check directly if IL-11 signalling is required to maintain HSCs in a transformed state, HSCs were stimulated with TGFβ1 (5 ng/ml) or PDGF (20 ng/ml) for 72 hours and then treated with anti-IL-11Rα antibody BSO-9A7 or IgG control (2 µg/ml) for a further 24 hours in the presence of ongoing TGFβ1 or PDGF stimulation. Unstimulated HSCs were used as a non-fibrotic control. ACTA2$^{+ve}$ cells and secreted collagen were detected by immunostaining and the fluorescence was quantified. ERK activity was detected by Western blotting.

The results are shown in FIGS. 17A to 17E. Anti-IL-11Rα treatment was found to have reversed the percentage of ACTA2$^{+ve}$ cells (17A, B) and the amount of secreted collagen (17C, D) to near baseline levels within 24 hours of IL-11 signalling inhibition. ERK activity was also found to be largely diminished within 24 hours despite ongoing TGFβ1/PDGF stimulation (17E).

Therefore, inhibition of IL-11 dependent HSC transformation by anti-IL-11Rα therapies causes HSC senescence and reversion leading to fibrosis regression.

The effect of anti-IL-11 therapy in early stage NASH was investigated. In the HFMCD diet model of NASH, inflammation peaks at six weeks and is then followed by a phase of severe fibrosis. Mice were fed the HFMCD diet for one week and then treated twice a week for a further five weeks on the diet with 10 mg/kg anti-IL-11Rα antibody BSO-9A7 or IgG control. Normal chow (NC) diet was used as a control. Liver hydroxyproline content and serum ALT levels were also detected using 0.5, 1 and 5 mg/kg anti-IL-11Rα antibody. ERK phosphorylation, liver hydroxyproline content and serum ALT levels were assessed as before. Liver Triglycerides (TG) measurements were performed using triglyceride colorimetric assay kit (Ser. No. 10/010,303, Cayman). Liver tissues were fixed for 48 hours at RT in 10% neutral-buffered formalin (NBF), dehydrated, embedded in paraffin blocks and sectioned at 7 µm. Sections stained with Masson's Trichrome were examined by light microscopy, scale bars 100 µm.

The results are shown in FIGS. 18A to 18G. Inhibition of IL-11 signalling during early steatohepatitis using anti-IL-11Rα therapy was found to result in mice having livers which were strikingly less steatotic and with a significant reduction in both lipid droplets (18A), and in triglyceride content (18B). HFMCD diet induces marked steatohepatitis and liver damage after one week (ALT>700 U L-1), which was reversed in a dose-dependent manner to near normal after three weeks of anti-IL-11Rα therapy (18C, 18D). Liver hydroxyproline (collagen) content (18E) and ERK phosphorylation (18G) did not increase over the six weeks, demonstrating that anti-IL-11Rα treated mice did not develop fibrosis during the experiment and reaffirming the strong anti-fibrotic effects associated with inhibition of IL-11 signalling. Anti-IL-11Rα therapy was found to have a dose-dependent effect on liver hydroxyproline (collagen) content (18F).

The effect of anti-IL-11Rα treatment on the expression of pro-fibrotic and pro-inflammatory genes in the NASH mouse model was assessed using RNA-seq and qPCR, performed as before. The expression of genes involved in lipid metabolism (ACOX1, SCD1, FASN, and SREBF1) was also assessed.

The results are shown in FIGS. 18H to 18K. Upregulation of pro-fibrotic and pro-inflammatory genes was abolished after anti-IL-11Rα therapy. Differential expression heatmap of pro-fibrotic and pro-inflammatory genes Z-scores (Transcripts Per Million mapped reads, TPM) shows that anti-IL-11Rα treatment produced similar expression of pro-fibrotic and pro-inflammatory genes as observed in mice on a NC control diet (non-NASH) (18G). Neither inflammation markers Tnfα and Ccl2 (18I) nor pro-fibrotic markers Tgfβ1, Acta2, Timp1, Col1a1, Col1a2 or Col3a1 (18J) were upregulated in mice treated with anti-IL-11Rα therapy. Lipid metabolism gene expression was also found to be re-established by anti-IL-11Rα therapy (18K).

Thus, neutralisation of IL-11 signalling reverses liver damage in early stage NASH.

Resident macrophages and infiltrating monocytes are important for NASH pathogenesis and a major source of TGFβ1 during disease progression. Liver inflammatory cell populations in the early NASH model were examined for the presence of immune (CD45) cells in general and the presence of Ly6C$^{+ve}$TGFβ1$^{+ve}$ cells in particular.

Immune cells were isolated from liver as described previously (Sheng, J., Ruedl, C. & Karjalainen, K. Most Tissue-Resident Macrophages Except Microglia Are Derived from Fetal Hematopoietic Stem Cells. Immunity 43, 382-393 (2015)). Liver tissues were minced and digested with 100 µg/ml Collagenase IV and 20 U/ml DNase I, at 37° C. for 1 h. Following digestion, cells were passed through strainer to obtain single cell suspension and subjected to percoll gradient centrifugation for isolation of immune cells. CyTOF (Mass cytometry by Time of Flight) staining was performed as previously described (Chew, V. et al. Delineation of an immunosuppressive gradient in hepatocellular carcinoma using high-dimensional proteomic and transcriptomic analyses. Proc. Natl. Acad. Sci. U.S.A. 114, E5900-E5909 (2017)). Cells were thawed and stained with cisplatin (Fluidigm) to identify live cells, followed by staining with metal-conjugated CD45 antibody, for barcoding purpose. After barcoding, cells were stained with metal-conjugated cell surface antibody (Ly6C). Cells were then fixed with 1.6% PFA, permeabilised with 100% methanol, and subjected to intracellular antibody staining (TGFβ1). Cells were finally labelled with DNA intercalator before acquisition on Hellos mass cytometer (Fluidigm). For analysis, first live single cells were identified, followed by debarcoding to identify individual samples. Manual gating was performed using Flowjo software (Flowjo, LLC. USA).

The results are shown in FIGS. 19A to 19C. Anti-IL-11Rα antibody therapy was found to reduce the number of CD45$^+$ cells (19A) in treated livers and caused a specific reduction in Ly6C$^{+ve}$TGFβ1$^{+ve}$ cells (19B). Circulating TGFβ1 levels were elevated by HFMCD diet but reduced by antibody therapy, which shows that anti-IL11Rα therapy is disease-modifying (19C).

In summary, IL-11 is required for HSC activation and transformation and has a central role in HSC pathobiology. IL-11 neutralising antibodies show disease-modifying therapeutic impact beyond anti-fibrotic effects alone. IL-11Rα antibodies can reverse hepatic stellate cell (HSC) activation downstream of TGFβ1 or PDGF. Inhibition of IL-11 signalling prevents inflammation and steatosis and can reverse liver fibrosis and hepatocyte damage during late stages of the disease. When given earlier, during steatohepatitis, anti-IL-11 therapy blocks inflammatory signals from HSCs, prevents hepatocyte damage and improves metabolic function through inhibition of HSCs-macrophages interactions. The inventors have identified an unappreciated and central role for IL-11 in liver pathobiology. Targeting IL-11 signalling with neutralizing antibodies reverses fibrosis, steatosis, hepatocyte death and inflammation across the spectrum of NASH.

Example 11: Analysis of Affinity of Binding of 9A7 to IL-11Rα

Anti-IL-11Ra antibody clone BSO-9A7 (VH=SEQ ID NO:7, VL=SEQ ID NO:13) was analysed for affinity of binding to human IL-11Rα by Multi-Cycle Kinetics analysis using a BIAcore T200.

Briefly, recombinant human IL-11Rα (Sino Biological Cat. No. 10252-H08H) was immobilised on a chip, and associations were performed by flowing different concentrations of antibody in IgG1 format over the chip at a flow rate of 40 µl/min in running buffer (HBS-P+ buffer containing 0.5% BSA and 150 mM NaCl). The association time was 240 seconds, and the dissociation time was 400 seconds. The surface was regenerated using glycine pH 1.7.

Two separate analyses were performed:
A first ((1) in FIG. 20) used following concentrations of BSO-9A7: 100 nM, 50 nM, 25 nM, 12.5 nM, 6.25 nM, 3.125 nM and 1.56 nM.
The second ((2) in FIG. 20) using the following concentrations of BSO-9A7: 50 nM, 25 nM, 12.5 nM. 6.25 nM, 3.125 nM and 1.56 nM.

The analysis of the raw data obtained was performed using BIAcore T200 evaluation software V2.0.1, fitting the background-subtracted data to a 1:1 interaction model.

The results of the two analyses are shown in FIG. 20. BSO-9A7 was found to bind to human IL-11Rα with nanomolar affinity.

Example 12: Biochemical Analysis of 9A7

Anti-IL-11Rα antibody clone BSO-9A7 was analysed for its ability to inhibit IL-11 signalling.

HSCs were stimulated with TGFβ1 (5 ng/ml, 24 h) in the presence of IgG (4 µg/ml) and varying concentrations of 9A7 (4 µg/ml to 61 µg/ml; 4-fold dilutions). Supernatants were collected and assayed for the amount of secreted MMP2. Dose-response curves were generated by plotting the logarithm of 9A7 tested concentration (pM) versus corresponding percent inhibition values using least squares (ordinary) fit. The IC50 value was calculated using log (inhibitor) versus normalized response-variable slope equation.

The results are shown in FIG. 21. BSO-9A7 blocked fibrogenic protein secretion from HSCs with an IC50 of 5.4 pM.

Anti-IL-11Ra antibody clone BSO-9A7 was used in pharmacokinetic studies. C57BL/6J mice (10-12-weeks old) were retro-orbitally injected (nalysed e edth 100 µl of freshly radiolabeled $^{125}$I-9A7 (5 µCi, 2.5 µg) in PBS. Mice were anesthetized with 2% isoflurane and blood were collected at several time points (2, 5, 10, 15, 30 m, 1, 175 2, 4, 6, 8 h, 1, 2, 3, 7, 14 and 21 days) post injection via submandibular bleeding. For biodistribution studies, blood was collected via cardiac puncture and tissues were harvested at the following time points: 1, 4 h, 1, 3, 7, 14, 21 days post injection. The radioactivity contents were measured using a gamma counter (2480 Wizard2, Perkin Elmer) with decay-corrections (100× dilution of 100 µl dose). The measured radioactivity was normalized to % injected dose/g tissue.

The results are shown in FIGS. 22A and 22B. Pharmacokinetic studies using $^{125}$I-9A7 revealed an in vivo half-life of more than 18 days (22A) and strong uptake in the liver (22B).

Example 13: Effect of Anti-IL-11Rα Antibodies on Wasting Disorders

Animals on an HFMCD diet lose weight and become very unwell, see also Example 10.2. Inhibition of IL-11 signalling ameliorates HFMCD-induced loss of weight and 9A7 antibody showed a dose dependent effect on weight gain.

Five-week old male mice were fed on the HFMCD or normal chow (NC) diet as before for one week to induce wasting, resulting in a ~15% loss in body weight in MCD mice. After the initial week, mice were intraperitoneally injected twice per week with 0.5, 1, 5 or 10 mg/kg of anti-L-11 RA antibody 9A7. 10 mg/kg of IgG isotype antibody was used as a control. Body weight and food consumption were measured weekly. For food consumption, average food intake was measured (g/mouse/week) in food hoppers from cages (n=3 mice per cage).

The results are shown in FIGS. 23A and 23B. Anti-IL-11Rα therapy was found to provide a dose-dependent gain in body weight (23A) and food consumption (23B), indicating reversal of wasting. The highest doses showed the greatest wasting-reversing effect. Mice fed with an NC diet steadily gained weight, whilst mice fed on the HFMCD diet and treated with IgG control lost ~30% of body weight over the course of the treatment. The highest doses had the greatest effect on food consumption, whereas mice treated with IgG control showed a slight reduction in food consumption.

Acute disease, e.g. trauma or sepsis, can also be associated with wasting e.g. anorexia and cachexia. The effects of antagonism of IL-11-mediated signaling on anorexia and cachexia in mouse models of acute kidney injury was studied. Kidney injury was induced by IP injection of folic acid (180 mg/kg) in vehicle (0.3M NaHCO$_3$) to 10-week old male mice; control mice were administered vehicle alone. Animals were sacrificed 28 days post-injection. Mice were intraperitoneally injected every 3 days with 20 mg/kg of anti-IL-11RA antibody or identical concentration of IgG isotype control starting from 1 hour before folic acid administration until the mice were sacrificed.

It was found that folate-induced kidney injury resulted in rapid anorexia/cachexia-associated weight loss associated with the acute phase of severe and bilateral kidney injury. Mice (n=7/group) receiving anti-IL-11Rα antibody at the time of injury, and for the duration of the injury, regained weight more quickly compared to the IgG control and returned to normal, or near normal, weight by 3 weeks later.

Separately, kidney injury is induced as before by IP injection of folic acid. Mice are only treated with anti-IL-11Rα antibody or IgG control from 21 days after kidney injury. Animal weight is assessed before and after antibody treatment. Healthy mice that do not receive folic acid were used as a control. Animals treated with anti-IL-11Rα antibody start to regain weight upon initiation of treatment showing that wasting-associated weight loss can be improved in late-stage disease.

Example 14: Characterisation of Humanised Variants of BSO-9A7

Humanised versions of BSO-9A7 VH and VL sequences were designed, as shown in SEQ ID NOs:8 to 12 and 14 to 17.

14.1 Binding Analysis

Combinations of the 5 humanised heavy chains and 4 humanised light chains were generated and tested for binding to IL-11Rα. The binding of 20 humanised variants to IL-11R was tested by single cycle kinetic analysis:

VH1/VL1; VH1/VL2; VH1/VL3; VH1/VL4;
VH2/VL1; VH2/VL2; VH2/VL3; VH2/VL4;
VH3/VL1; VH3/VL2; VH3/VL3; VH3/VL4;
VH4/VL1; VH4/VL2; VH4/VL3; VH4/VL4;
VH5/VL1; VH5/VL2; VH5/VL3; VH5/VL4.

From this analysis, six antibodies were identified for further assessment: VH3/VL2; VH3/VL3; VH3/VL4; VH4/VL2; VH4/VL3 and; VH4/VL4.

| Name | Heavy chain | Light chain |
|---|---|---|
| VH3/VL2 | SEQ ID NO: 10 | SEQ ID NO: 15 |
| VH3/VL3 | SEQ ID NO: 10 | SEQ ID NO: 16 |
| VH3/VL4 | SEQ ID NO: 10 | SEQ ID NO: 17 |
| VH4/VL2 | SEQ ID NO: 11 | SEQ ID NO: 15 |
| VH4/VL3 | SEQ ID NO: 11 | SEQ ID NO: 16 |
| VH4/VL4 | SEQ ID NO: 11 | SEQ ID NO: 17 |

The six antibodies were assessed by multi-cycle kinetics analysis at a final concentration of 1 μg/ml, run at 25° C. with HBS-P+ running buffer (pH 7.4) containing 0.1% BSA using a Biacore T200 instrument.

The kinetic parameters are shown in the table below. The relative $K_D$ was calculated by dividing the $K_D$ of the humanised variant by that of the 9A7 antibody assayed in the same experiment. All six humanised antibodies bound to IL-11R within two-fold of 9A7 (SEQ ID NO:7 and 13).

| Analyte | $k_a$ (1/Ms) | $k_d$ (1/s) | | | |
|---|---|---|---|---|---|
| 9A7 VH/VL | $2.16 \times 10^5$ | $9.26 \times 10^{-4}$ | $4.29 \times 10^{-9}$ | 1.00 | 0.0515 |
| VH3/VL2 | $2.21 \times 10^5$ | $8.01 \times 10^{-4}$ | $3.63 \times 10^{-9}$ | 0.85 | 0.0267 |
| VH3/VL3 | $2.08 \times 10^5$ | $7.51 \times 10^{-4}$ | $3.61 \times 10^{-9}$ | 0.84 | 0.0541 |
| VH3/VL4 | $2.01 \times 10^5$ | $7.47 \times 10^{-4}$ | $3.71 \times 10^{-9}$ | 0.86 | 0.0251 |
| VH4/VL2 | $1.64 \times 10^5$ | $9.32 \times 10^{-4}$ | $5.67 \times 10^{-9}$ | 1.32 | 0.034 |
| VH4/VL3 | $1.78 \times 10^5$ | $9.92 \times 10^{-4}$ | $5.57 \times 10^{-9}$ | 1.30 | 0.0279 |
| VH4/VL4 | $1.41 \times 10^5$ | $7.81 \times 10^{-4}$ | $5.55 \times 10^{-9}$ | 1.29 | 0.0963 |

14.2 In Vitro Performance of Humanised Anti-IL-11Rα Antibodies

The six antibodies were tested for the ability to neutralise endogenous IL-11 secreted from primary human atrial fibroblasts in response to TGFβ1. 9A7 was included as a positive control. The assay was performed as described in Example 2.5.2. MMP2 secretion into the supernatant by human fibroblasts was assessed to estimate the % of inhibition.

The results are shown in FIG. 24. All antibodies bind to IL-11Rα and block endogenously produced IL-11 from interacting with the receptor. IL-11 signalling is neutralised, which inhibits production of fibrogenic protein MMP2.

The performance of select humanised clones was further tested in human hepatic stellate cells. As before, cells were incubated with 5 ng/ml TGFβ1 and varying concentrations of VH3/VL3 or VH4/VH4. Neutralisation of the fibrotic response in vitro was assessed by monitoring MMP2 secretion into the supernatant to estimate the % of inhibition.

FIG. 25 shows that the anti-IL-11Rα antibodies block endogenous IL-11 signalling and inhibit production of fibrogenic protein MMP2.

A similar assay was performed in human lung fibroblasts. Primary human lung fibroblasts were incubated with TGFB1 (5 ng/ml) and varying concentrations of 9A7, VH3/VL3 or VH4/VH4. Neutralisation of the fibrotic response was assessed by monitoring TIMP1 secretion into the supernatant to estimate the % of inhibition.

FIG. 26 shows that the anti-IL-11Rα antibodies block endogenous IL-11 signalling and inhibit production of fibrogenic protein TIMP1.

14.3 In Vivo Performance of Humanised Anti-IL-11Rα Antibodies

The therapeutic utility of the humanised anti-human IL-11Rα antibodies is demonstrated in vivo in mouse models of fibrosis for various different tissues, for example as performed in Examples 5, 6, 10 and 12.

Mice treated with neutralising humanised anti-IL-11Rα antibodies have a reduced fibrotic response.

Example 15: Effect of Anti-IL-11Rα Antibodies on Metabolic Disorders

The effect of humanised anti-IL-11Rα antibody VH4/VL4 was investigated in mice with metabolic diseases such as obesity and type II diabetes. Western diet along with fructose (WDF) was used to establish metabolic disorders that closely resemble those in humans during obesity, type II diabetes and non-alcoholic fatty liver disease (NAFLD) (Baena et al., Sci Rep (2016) 6: 26149, Machado et al., PLoS One (2015) 10:e0127991). Mice were fed Western diet (D12079B, Research Diets), supplemented with 15% weight/volume fructose in drinking water (WDF) for 16 weeks, from 12 weeks of age. Control subjects were fed normal chow (NC, Specialty Feeds) and drinking water. IgG antibody was used as a control.

Figure 27A:
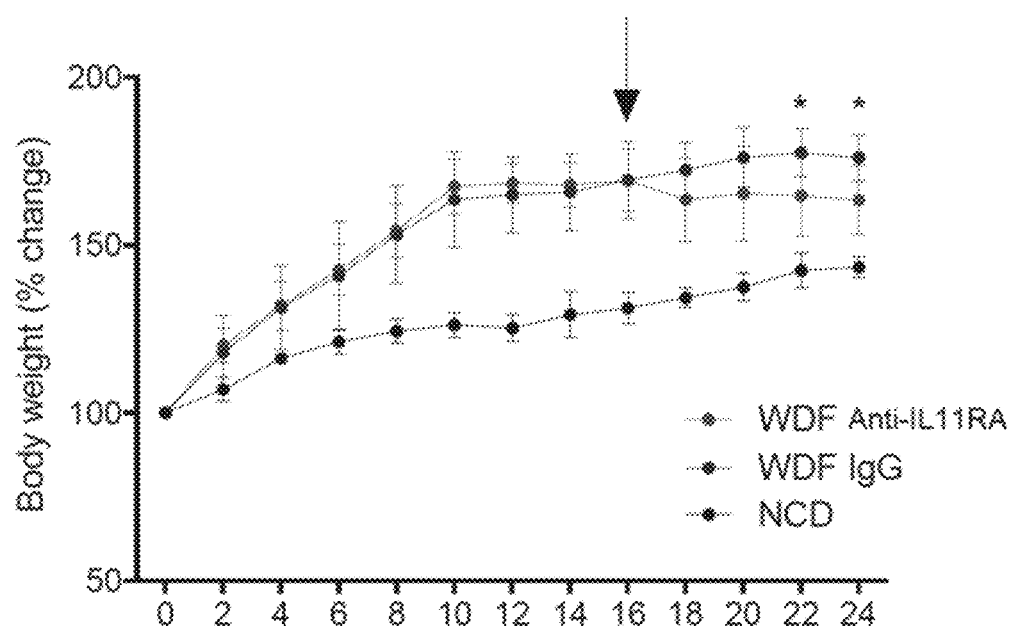
Figure 27B:
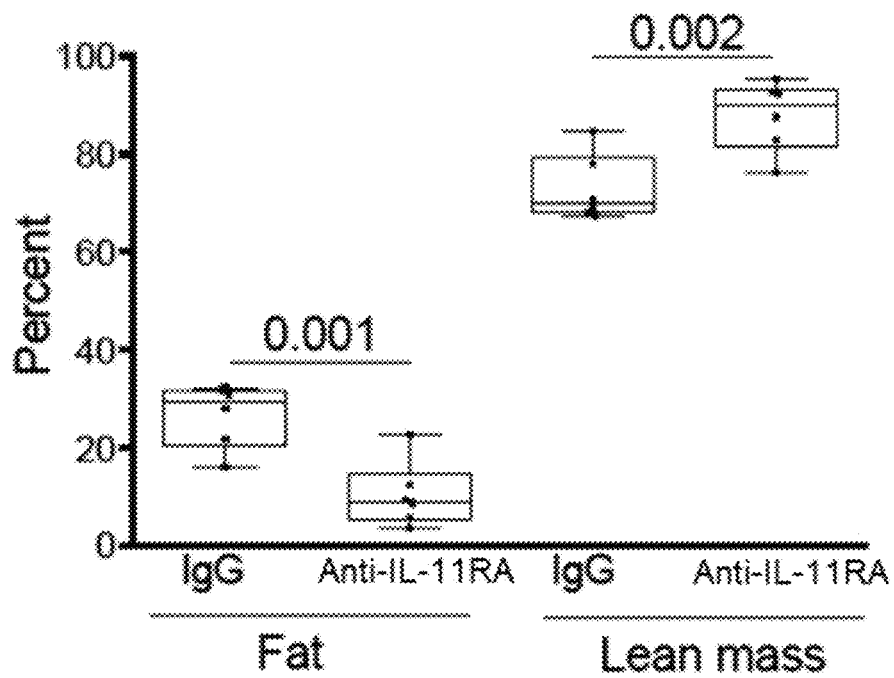
Figure 27C:
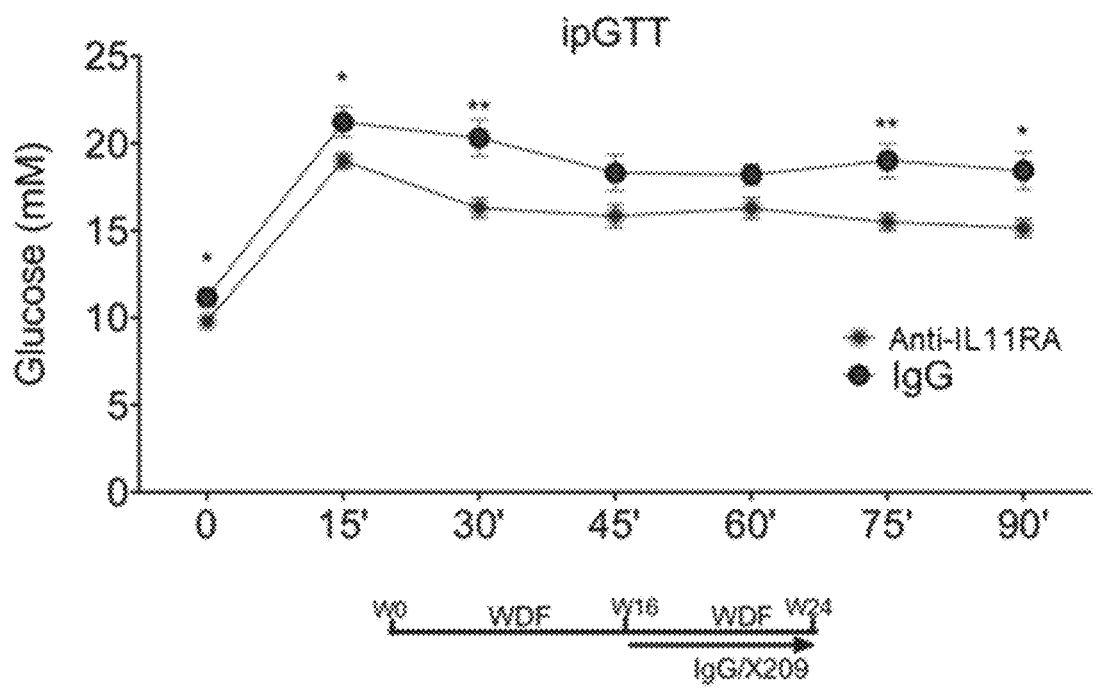
Figure 27D:
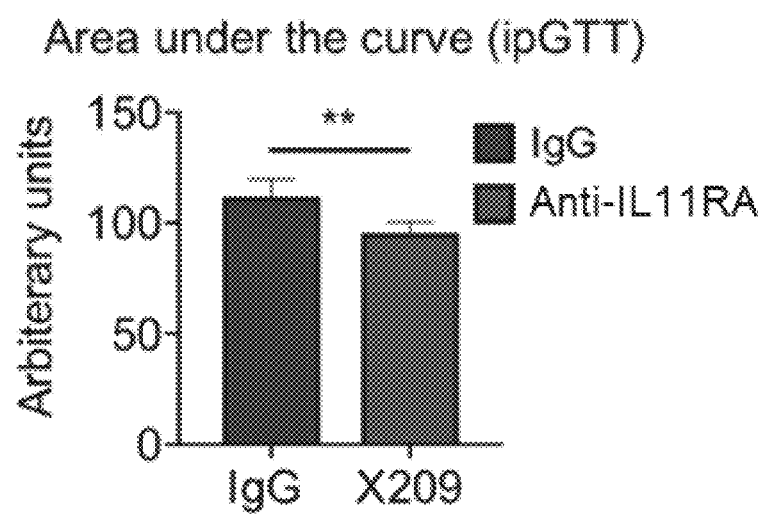
Figure 27E:
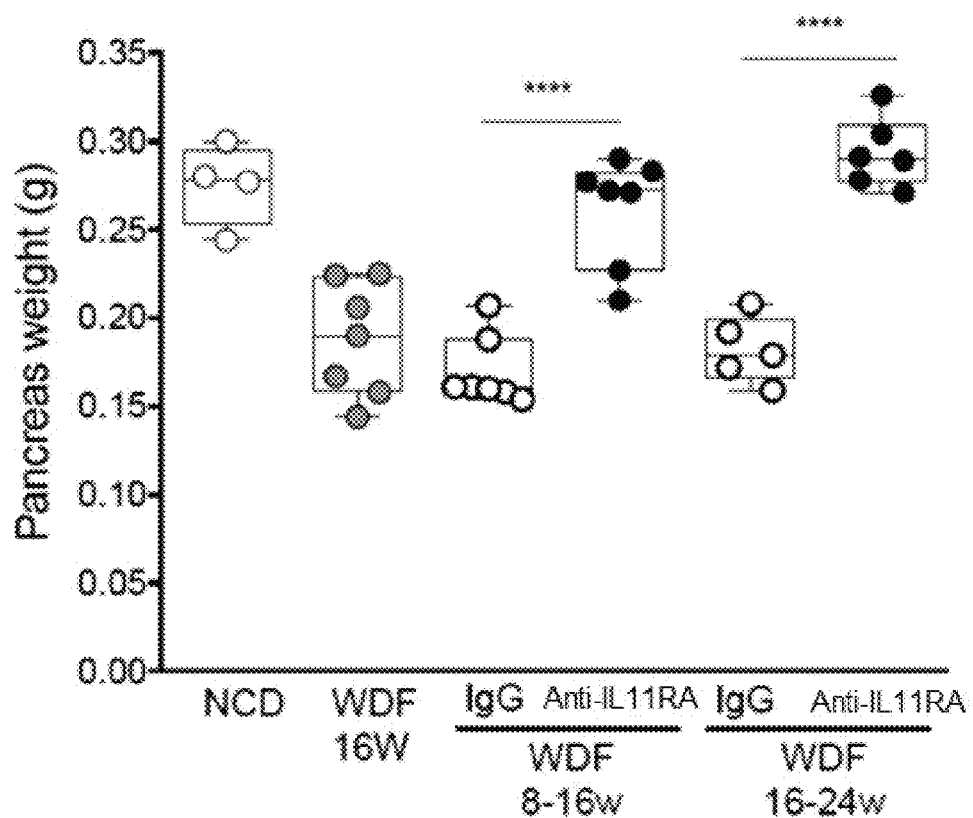

FIGS. 27A and 27B shows that anti-IL-11Rα antibody-treated mice fed on WDF showed significant reduction in body weight (A) and fat mass (B) when compared to control IgG anybody-treated mice fed on WDF. An increase in lean mass was also observed in mice treated with anti-IL-11Rα antibody compared to IgG control-treated mice, suggesting that inhibition of IL-11 signalling during WDF-induced metabolic pathogenesis recovered muscle mass. Furthermore, intraperitoneal glucose tolerance test (ipGTT) results showed, along with fasting glucose, significant improvement in glucose tolerance in mice treated with anti-IL-11Rα antibody (FIGS. 27C and 27D).

The analysis was extended to the effects on the pancreas. Anti-IL-11Rα antibody-treated mice fed on WDF were unexpectedly found to display remarkable protection against WDF-induced loss of pancreas (FIG. 27E) whether treated from 8 to 16 weeks (for protecting against effects associated with metabolic disease) or treated from 16 to 24 week (for reversing effects associated with metabolic disease) when compared to IgG control-treated mice.

Figure 27F:
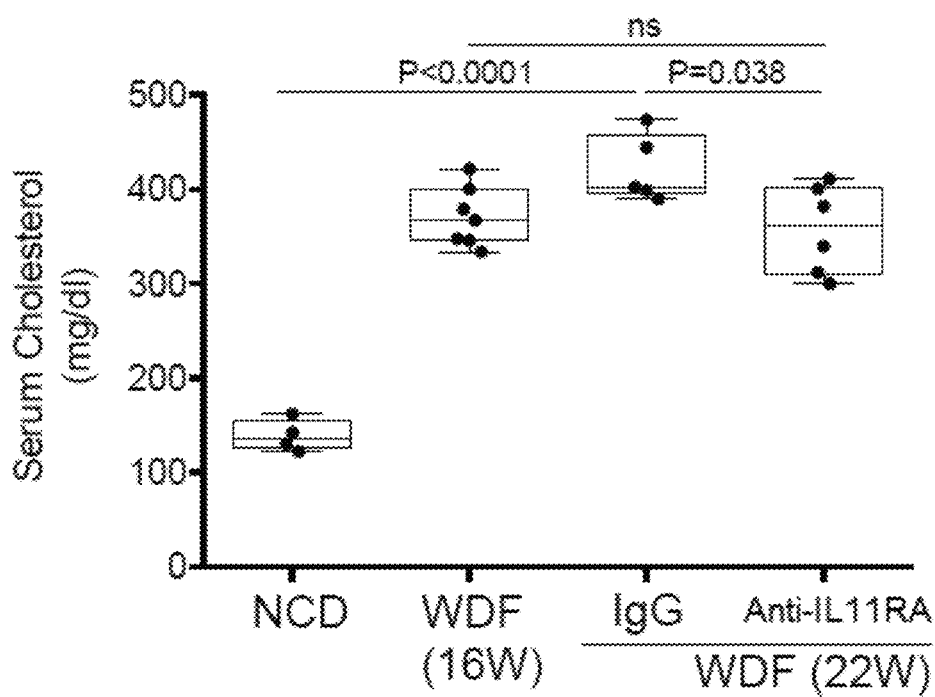
Figure 27G:
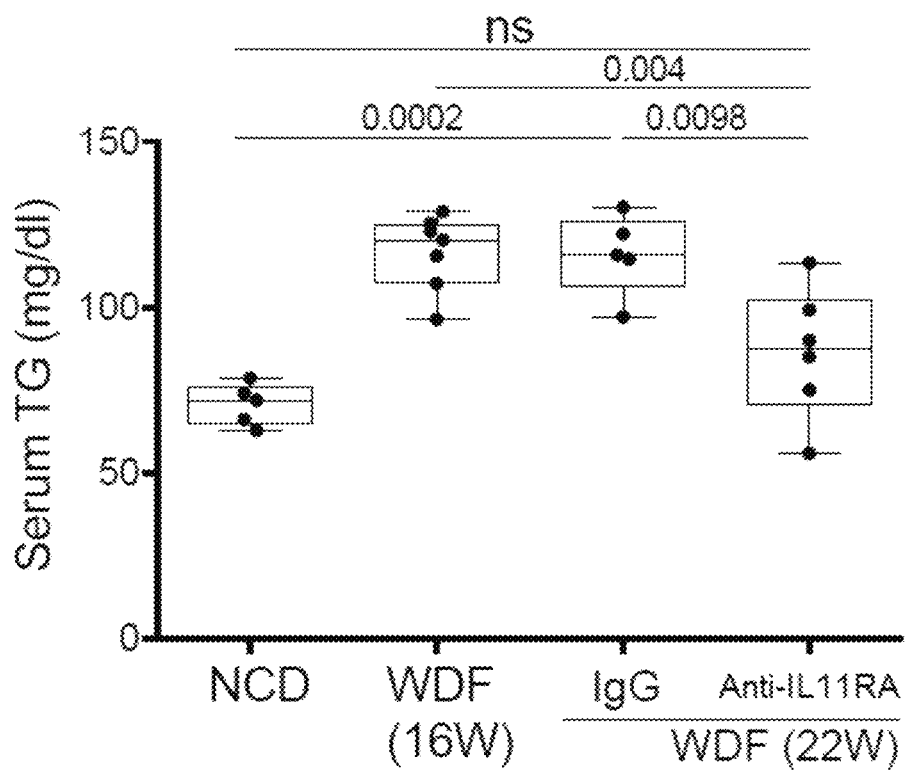
Figure 27H:
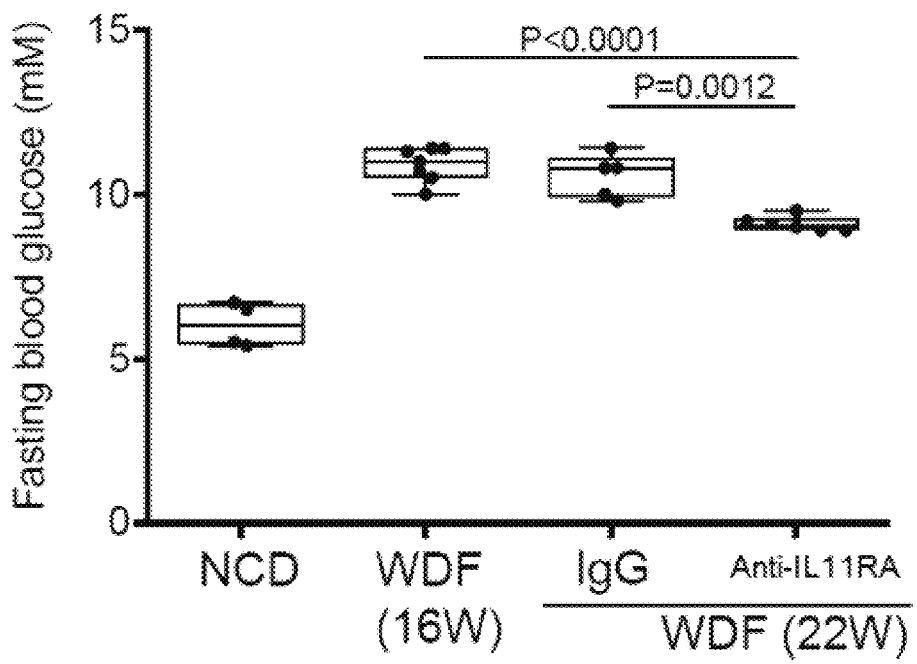
Figure 27I:
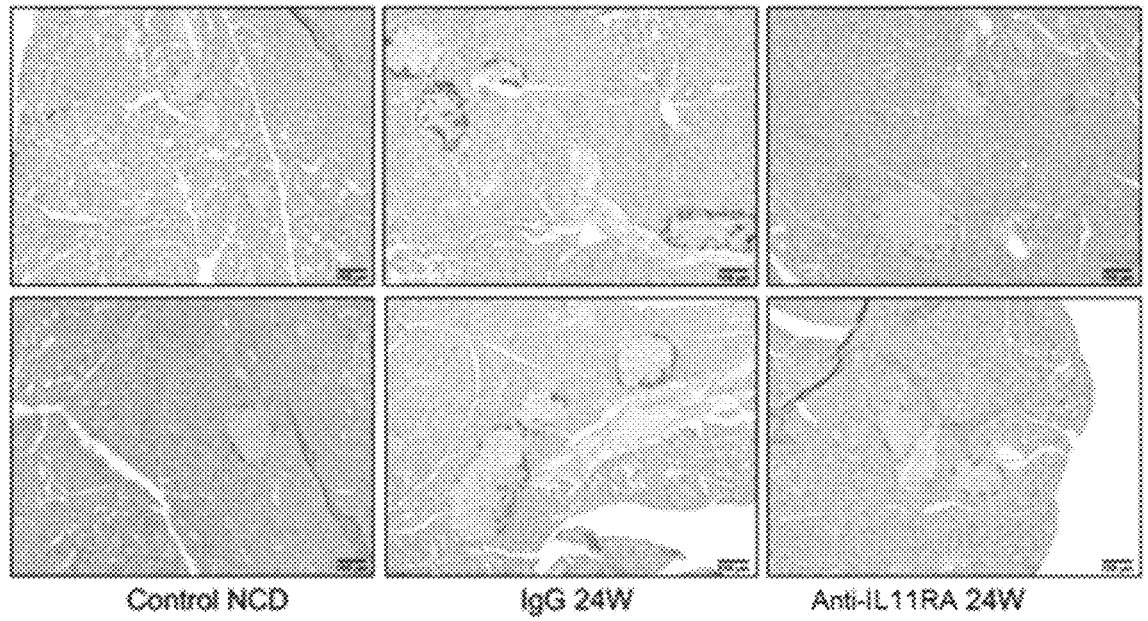
Figure 27J:
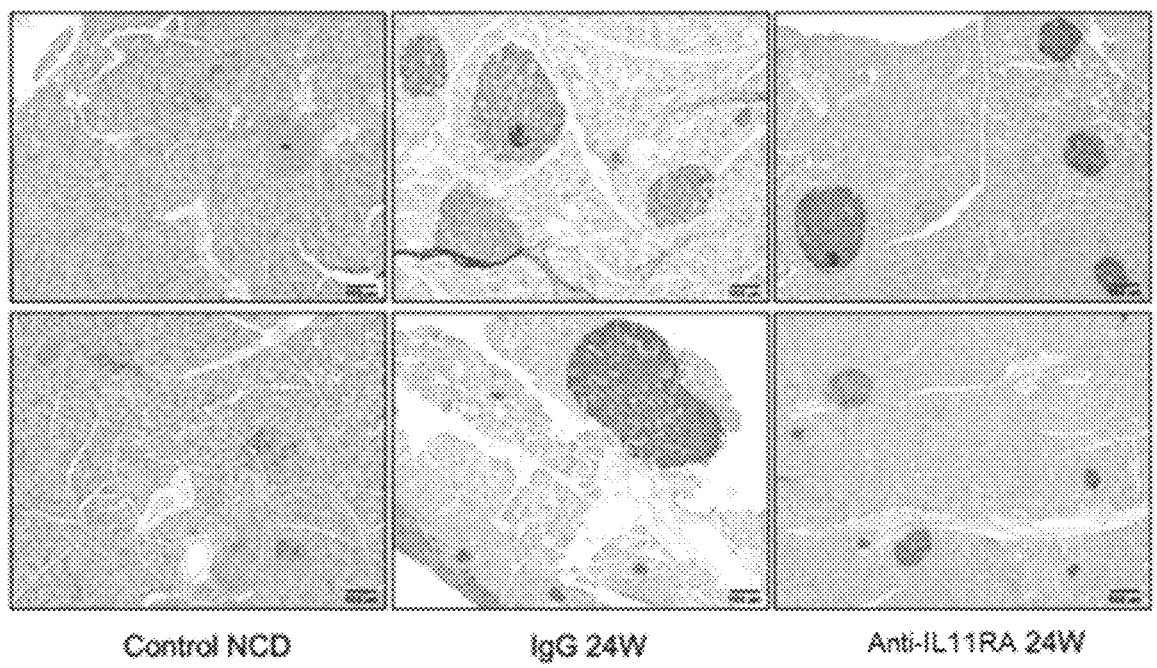

FIG. 27F shows that anti-IL-11Rα antibody-treated mice fed on WDF had significantly lower serum cholesterol levels compared to control IgG anybody-treated mice fed on WDF, and FIG. 27G shows that anti-IL-11Rα antibody-treated mice fed on WDF had significantly lower serum triglyceride levels compared to control IgG anybody-treated mice fed on WDF. FIG. 27H shows that anti-IL-11Rα antibody-treated mice fed on WDF had significantly lower fasting blood glucose levels compared to control IgG anybody-treated mice fed on WDF.

Moreover, immune-histology of pancreas also revealed increase in glucagon and insulin staining in pancreatic islets along with islet hyperplasia in IgG treated WDF fed mice (FIGS. 27I and 27J), which are classical features of type II diabetes (Bonner-Weir and O'Brien Diabetes (2008) 57:2899-2904). Anti-IL-11Rα antibody treatment in WDF fed mice from 16 to 24 weeks remarkably reduced islet hyperplasia and glucagon staining as well as improving insulin expression in the islets of mice fed on WDF, suggesting that antagonism of IL-11 mediated signalling is useful to improve and reverse metabolic diseases caused by a Western-type diet.

Figure 28A:
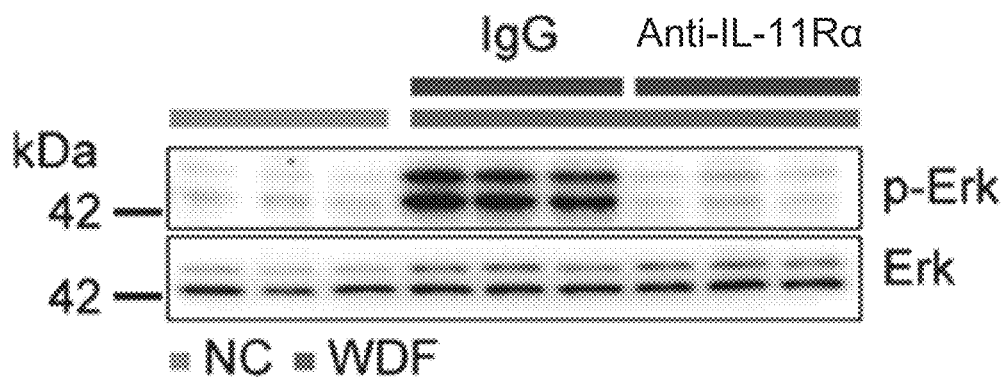
Figure 28B:
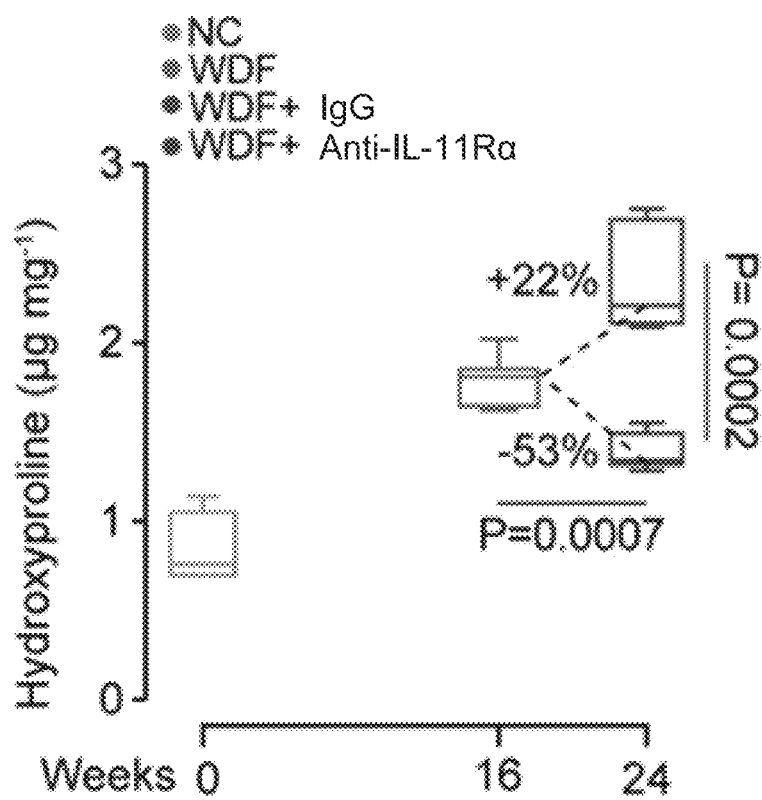
Figure 28C:
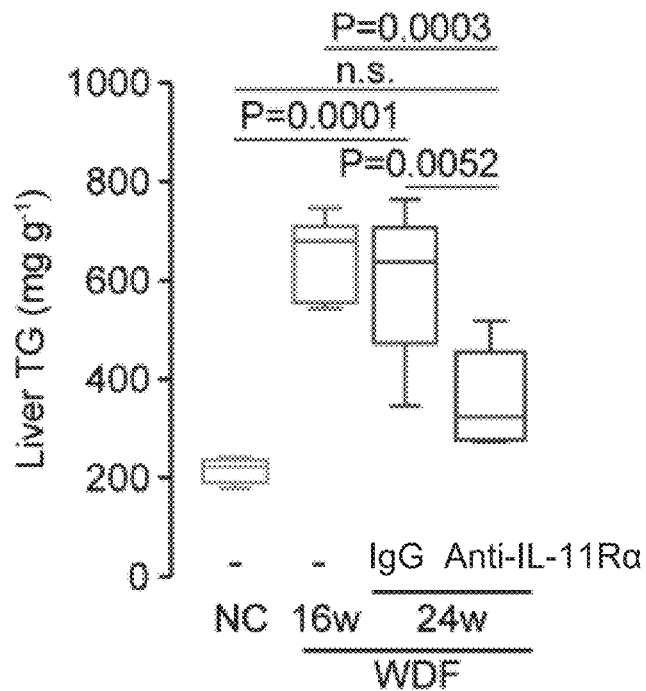
Figure 28D:
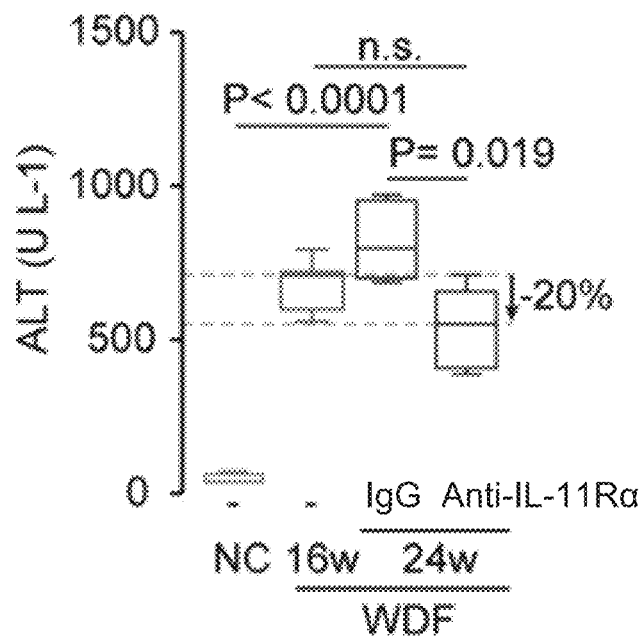
Figure 28E:
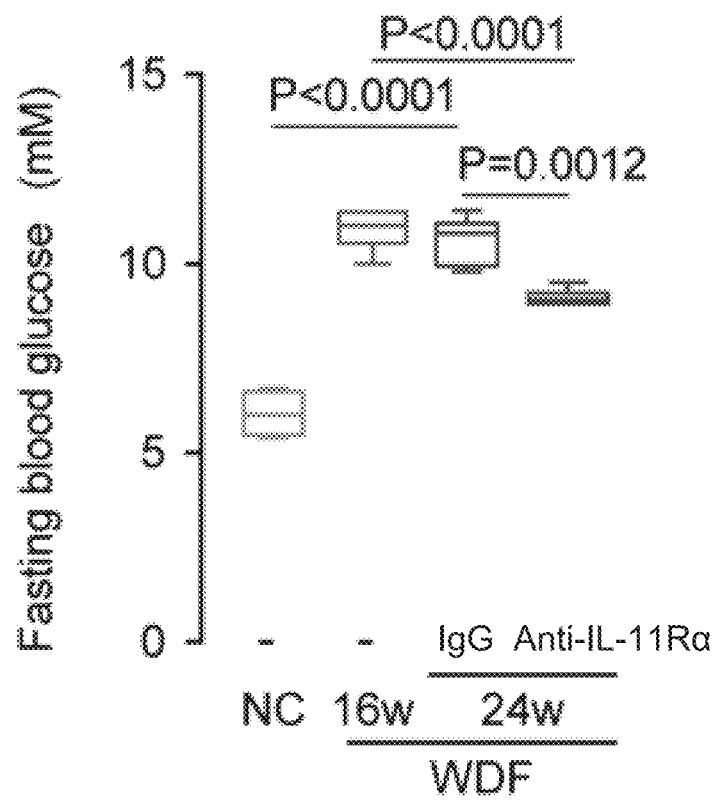
Figure 28F:
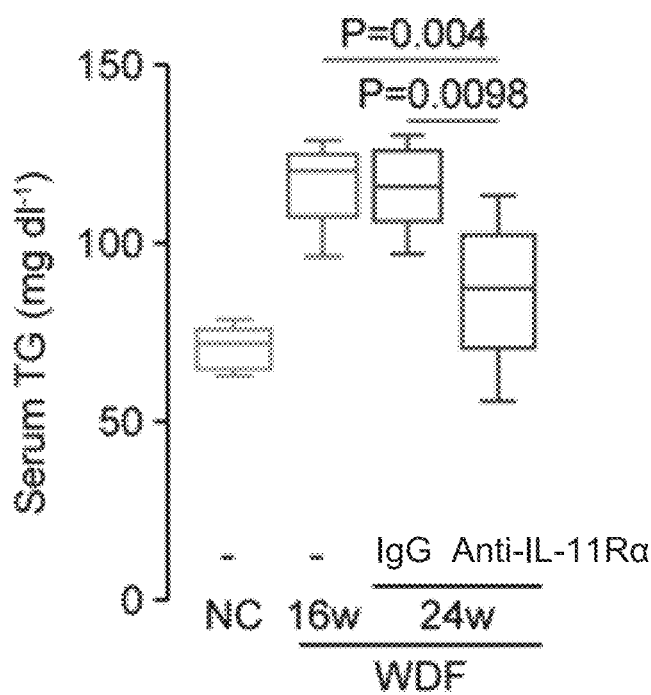
Figure 28G:
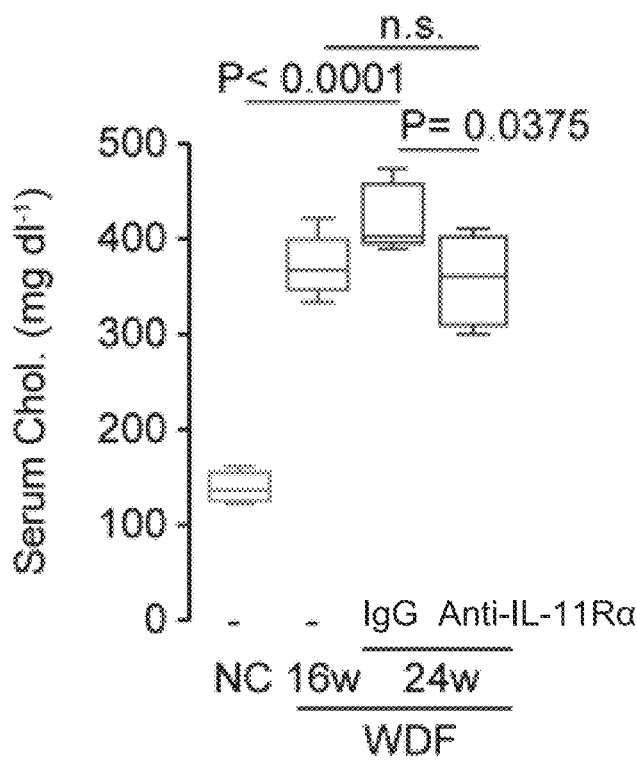

The HFMCD model has early onset steatotic hepatitis followed by fibrosis. However, this model is not obese or insulin resistant. A model of WDF-induced NASH was used to test effects of anti-IL-11R therapy in the context of obesity, insulin resistance and diabetes. Mice were fed WDF for 16 weeks by which time they were obese and insulin resistant with liver steatosis, inflammation and fibrosis. Treatment with anti-IL11Rα antibody was then initiated. Hepatic Erk activation was inhibited in NASH livers when IL-11 signalling was targeted (FIG. 28A). Despite similar weight gain, reversal of liver fibrosis, steatosis, inflammation, and reduction in serum ALT levels in mice on anti-IL11Rα therapy was observed. This was accompanied by a reduction in serum glucose, triglycerides and cholesterol levels (FIG. 28B-28G). Thus, neutralizing anti-IL11Rα therapy reverses WDF-induced NASH pathologies.

Thus, the data show that anti-IL-11 therapy reversed fibrosis but did not assess whether this effect was sustained or progressive. Furthermore, combination therapies may be beneficial for reversing fibrosis in NASH. To address these points, severe liver fibrosis was established using HFMCD for 10 weeks, then mice were converted to normal chow, mimicking a robust metabolic intervention, and initiated anti-IL-11Rα antibody treatment in parallel (FIG. 29A). Upon removal of the metabolic stimulus, Erk activation slowly regressed, which was accelerated by antibody treatment. Fibrosis was unchanged in IgG treated animals for the duration of the experiment, suggesting complete metabolic correction alone does not reverse fibrosis, or very slowly reverses fibrosis. In contrast, hepatic collagen content was significantly reversed (24%) after three weeks of antibody treatment with further reversal (46%) at six weeks, showing a progressive and sustained effect (FIG. 29B).

Regression of fibrosis is associated with lower TIMP and higher MMP levels, which promotes favorable matrix remodelling. Consistent with this, anti-IL11Rα antibody treated mice with severe fibrosis were found to rapidly upregulate Mmp2 and downregulate Timp1. Reversal of hepatic fibrosis is favoured when transformed HSCs undergo apoptosis, senescence and/or revert to an inactive ACTA2-ve state. To check if IL-11 is required to maintain HSCs in a transformed state, HSCs were stimulated with TGFβ1 or PDGF followed by inhibition of IL-11 signalling. Within 24 h of IL-11 inhibition, the percentage of ACTA2+ ve cells and the amount of secreted collagen were reversed to near baseline levels, and ERK activity was largely diminished despite ongoing TGFβ1/PDGF stimulation.

Figure 30A:
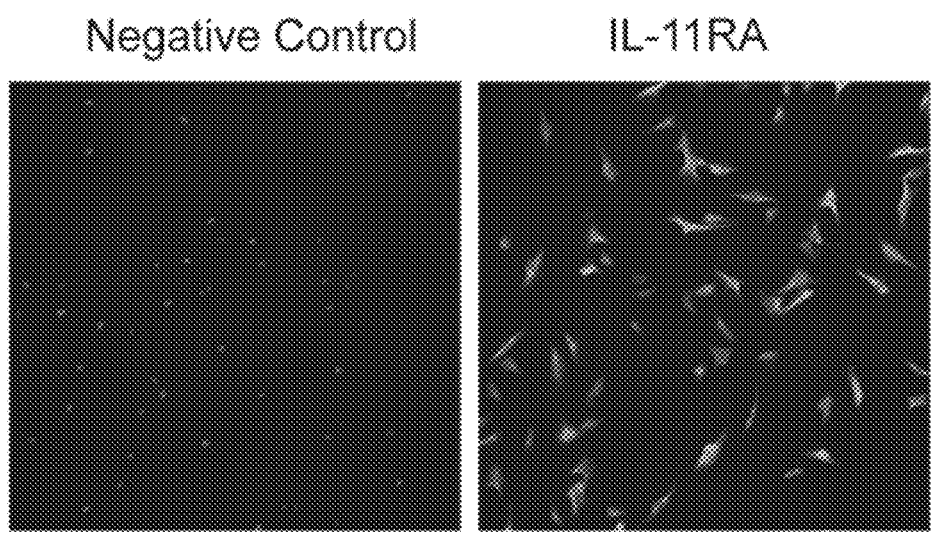
Figure 30B:
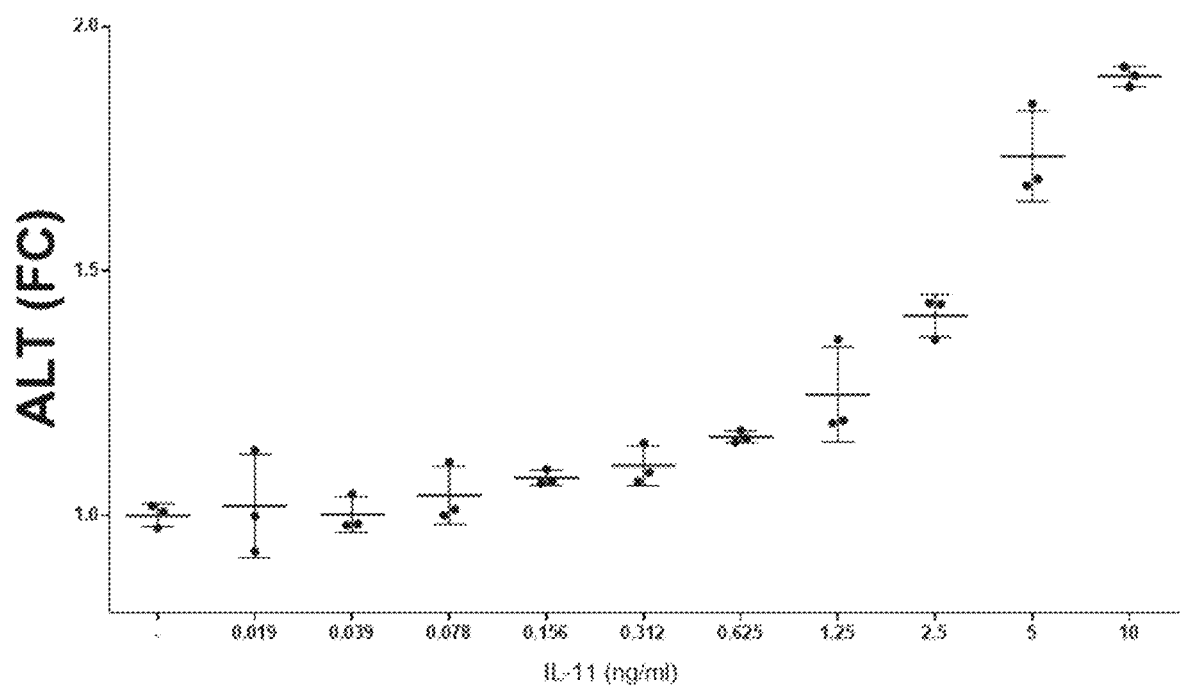
Figure 30C:
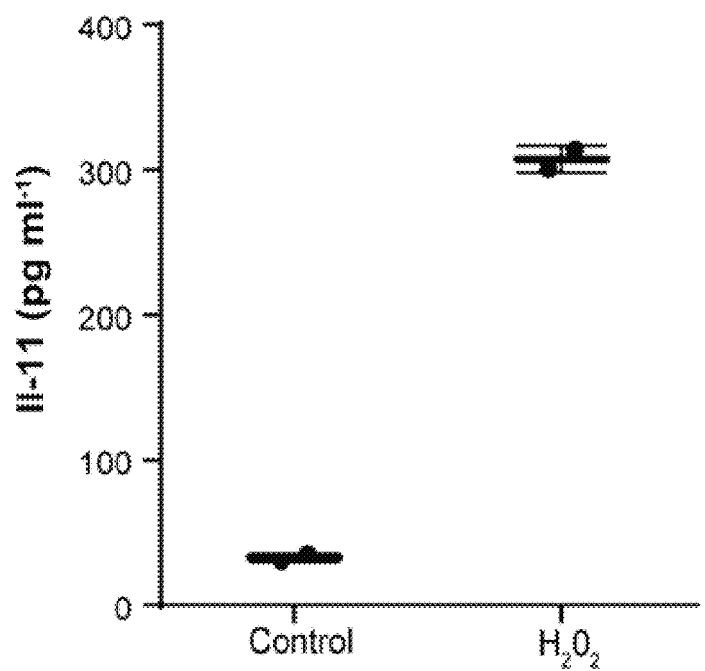

Example 16: Effect of Inhibiting IL-11 Signalling in Hepatotoxicity 16.1 Effect of Anti-IL-11 Therapy on Hepatotoxicity IL-11 directly causes hepatocyte cell death and drives hepatocyte to dysfunctional partial epithelial-mesenchymal cell transition (EMT) state that is known to limit the regenerative capacity of the liver (Grant Rowe et al. Molecular and Cellular Biology 2011; 31 (12): 2392-2403). Primary human hepatocytes were found to highly express the IL-11Rα receptor, IL-11 stimulation was found to induce dose-dependent hepatocyte cell death as evidenced by a progressive increase in alanine aminotransferase (ALT) over the physiologically relevant dose range, and stimulation of human hepatocytes with $H_2O_2$ results in IL-11 upregulation by 10-fold in the supernatant (FIGS. 30A to 30C).

A mouse model of acetaminophen (APAP)-induced liver injury was employed to investigate the effect of anti-IL-11 therapy on hepatotoxicity. 12-14 weeks old male mice were starved and intraperitoneally (IP) injected with 10 mg/kg of anti-IL-11Rα antibody or IgG isotype control 16 hours prior to APAP (A3035, Sigma) injection (IP, 400 mg/kg). Mice were sacrificed 24 hours post-APAP administration. The levels of IL-11 in mouse serum and hepatocyte supernatant were quantified using Mouse IL-11 DuoSet (DY418 and DY008, R&D Systems) and Human IL-11 Quantikine ELISA kit D1100, R&D Systems), respectively, according to the manufacturer's protocol. Liver samples were excised and fixed for 48 hours at room temperature in 10% neutral-buffered formalin (NBF), dehydrated, embedded in paraffin blocks and sectioned at 7 μm. Sections were stained with Hematoxylin&Eosin (H&E) according to standard protocol and examined by light microscopy.

Figure 30D:
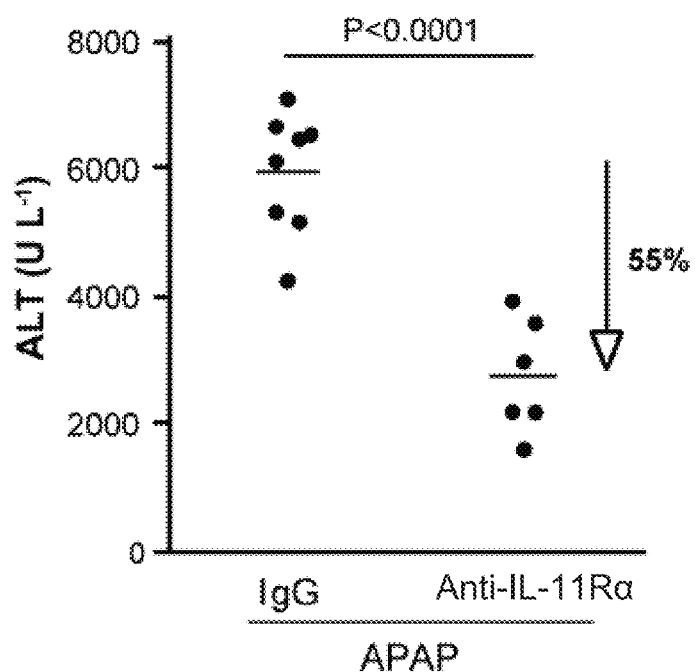
Figure 30E:
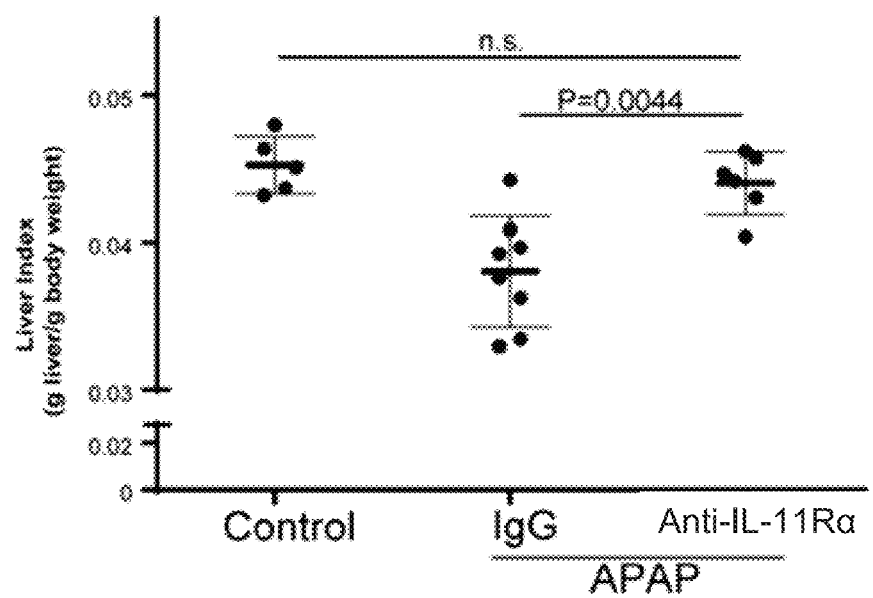
Figure 30F:
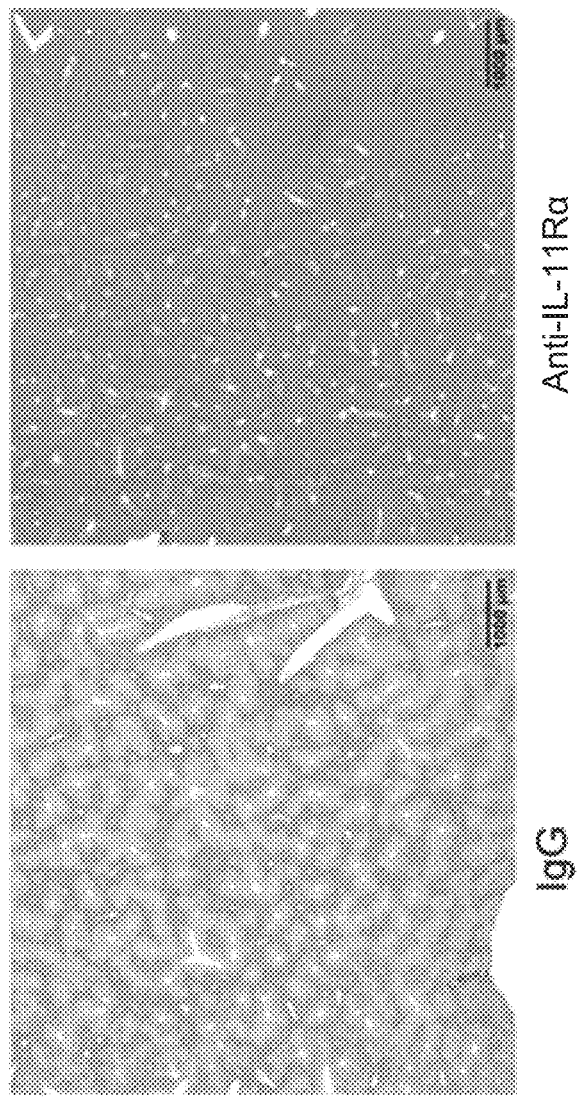

FIGS. 30D to 30F show that mice receiving a single dose of anti-IL11Rα antibody therapy were found to have significantly lower ALT levels (55% lower compared to IgG control; 30D), i.e. markedly reduced the extent of liver damage. Anti-IL-11 therapy was also found to prevent APAP-induced loss in liver mass, which reflects destruction of liver cells, as compared to 24% loss of liver mass with IgG control antibody (liver index; 30E). Liver histology by Hematoxylin&Eosin (H&E) staining showed severe centrilobular necrosis in IgG-treated mice, a typical histological feature of APAP toxicity, which was found to be reduced with anti-IL11Rα therapy (30F).

The mobility and activity of the mice treated with IgG control or anti-IL-11Rα antibody was observed at 24 hours post-APAP treatment. Control IgG-treated mice were found to be static/moribund with visible features of ill health (e.g. piloerection, hunched posture), whereas mice treated with anti-IL11Rα antibody had normal mobility and activity.

Hence Inhibiting IL-11 signalling by blocking IL-11Rα prevents hepatotoxicity in the accepted, translational model of APAP-induced liver injury (drug induced liver injury; DILI).

16.2 Antagonism of IL-11 Mediated Signalling Protects Hepatocytes Against Drug-Induced Cell Death The effects of antagonism of IL-11 mediated signalling on hepatocyte viability was analysed in vitro.

Human hepatocytes were treated with APAP (A3035, Sigma) at a final concentration of 20 mM for 24 hours, in the absence (baseline, BL) or presence of antagonist anti-IL11Rα antibody (2 μg/ml) or isotype-matched IgG control antibody (IgG, 2 μg/ml).

Hepatocytes were then stained using the FITC Annexin V/Dead Cell Apoptosis Kit (V13242, Thermo Fisher) according to the manufacturer's instructions, and Annexin V-FITC/PI-stained cells were analysed by flow cytometry using a BD LSRFortessa flow cytometer (BD Bioscience). 10,000 cells were analysed per sample. Data was analysed using FlowJo version 7 software.

FIG. 31A shows that treatment of the hepatocytes with antagonist antibody inhibitor of IL-11 mediated signalling was found to substantially reduce the proportion of dead hepatocytes.

In a separate experiment, hepatocytes were treated with APAP (A3035, Sigma) at a final concentration of 10 mM for 24 hours, in the absence (baseline, BL) or presence of antagonist anti-IL11Rα antibody (2 μg/m) or isotype-matched IgG control antibody (IgG, 2 μg/ml). Protein extracts were prepared from the hepatocytes using radioimmunoprecipitation assay (RIPA) buffer containing protease and phosphatase inhibitors (Thermo Scientifics), followed by centrifugation to clear the lysate. Protein concentrations were determined by Bradford assay (Bio-Rad). Equal amounts of protein lysates were separated by SDS-PAGE, transferred to PVDF membrane, and subjected to immunoblot analysis for the indicated primary antibodies (ERK, pERK, pJNK). Proteins were visualized using the ECL detection system (Pierce) with the appropriate secondary antibodies.

FIG. 31B shows that treatment of hepatocytes with APAP was found to significantly upregulate levels of p-ERK and pJNK (cf. BL vs. IgG). Treatment of hepatocytes with antagonist antibody inhibitor of IL-11 mediated signalling was found to substantially reduce the levels of p-ERK and pJNK (cf. IgG vs. anti-IL-11Rα antibody).

16.3 Antagonism of IL-11 Mediated Signalling Protects Against Drug-Induced Liver Injury A severe APAP overdose (400 mg/kg) or an equivalent volume of saline was administered to 12-14 weeks old male mice by IP injection, 16 hours after IP administration of 20 mg/kg of antagonist anti-IL11RA antibody or isotype-matched IgG control antibody.

24 hours after APAP administration, mice were euthanized. Serum alanine aminotransferase (ALT) levels were measured using ALT Activity Assay Kit (ab105134, Abcam) according to the manufacturer's instructions, and livers were harvested, fixed for 48 h at room temperature in 10% neutral-buffered formalin (NBF), dehydrated, embedded in paraffin blocks and sectioned at 7 μm. Sections were stained with Hematoxylin&Eosin (H&E) according to standard protocol and examined by light microscopy.

The results are shown in FIGS. 32A and 32B. Pre-treatment with antagonist antibody inhibitor of IL-11 mediated signalling was shown to significantly protect mice from DILI-associated inhibition of liver function, as determined by a substantial reduction in serum ALT levels (FIG. 32A). The livers of mice pre-treated with antagonist antibody inhibitor of IL-11 mediated signalling also displayed substantially less hepatocyte necrosis as compared to livers from IgG-treated controls (FIG. 32B).

16.4 Antagonism of IL-11 Mediated Signalling after Drug-Induced Liver Injury Reverse Symptoms of Liver Damage and Restores Liver Function A severe APAP overdose (400 mg/kg) or an equivalent volume of saline was administered to 12-14 weeks old male mice by IP injection, and 10 hours later mice were administered IP with 20 mg/kg of antagonist anti-IL11Rα antibody, isotype-matched IgG control antibody, or untreated. Mice were euthanized at 24, 36 and 48 hours. Serum ALT levels were analysed as described in Example 16.3. Livers were harvested, and fixed as described in Example 16.3, and digital photographs were taken.

The results are shown in FIGS. 33A and 33B. Antagonist antibody inhibitor of IL-11 mediated signalling administered 10 hours after severe APAP overdose was shown to restore gross liver morphology to that mice which had not been treated with APAP (FIG. 33A). Antagonist antibody inhibitor of IL-11 mediated signalling administered 10 hours after severe APAP overdose was furthermore demonstrated to rescue mice from DILI-associated inhibition of liver function, as determined by substantial reduction in serum ALT levels (FIG. 33B).

Western blots were also performed on protein extracts prepared from the livers of the mice. Liver tissue was homogenized in radioimmunoprecipitation assay (RIPA) buffer containing protease and phosphatase inhibitors (Thermo Scientifics), and lysates were subsequently separated by SDS-PAGE and analysed by western blot. FIG. 33C shows that APAP overdose significantly upregulated levels of p-ERK, pJNK1 and pJNK2 (cf. Control vs. 10 h), whilst subsequent treatment with antagonist antibody inhibitor of IL-11 mediated signalling substantially reduced the levels of p-ERK, pJNK1 and pJNK2 (cf. IgG vs. anti-IL-11Rα).

In further experiments, a lethal APAP overdose (550 mg/kg) or an equivalent volume of saline was administered to 12-14 weeks old male mice by IP injection, and 10 hours later mice were administered IP with 20 mg/kg of antagonist anti-IL11Rα antibody, isotype-matched IgG control antibody, or untreated.

Survival of mice was monitored for 8 days after APAP/saline administration, and the results are shown in FIG. 34A. Treatment with antagonist antibody inhibitor of IL-11 mediated signalling significantly improved survival of mouse administered with a lethal dose of APAP relative to IgG-treated controls.

Mice were euthanized at 24 hours and 192 hours (8 days). Serum ALT levels were analysed as described in Example 16.3. Livers were harvested, and fixed as described in Example 16.3, and digital photographs were taken.

The results are shown in FIGS. 34B and 34C. Antagonist antibody inhibitor of IL-11 mediated signaling administered 10 hours after lethal APAP overdose was shown to restore gross liver morphology to that mice which had not been treated with APAP after 8 days (FIG. 34B). Antagonist antibody inhibitor of IL-11 mediated signalling administered 10 hours after lethal APAP overdose was furthermore demonstrated to rescue mice from DILI-associated inhibition of liver function; serum ALT levels were not significantly different to the levels of normal (saline administered) control mice after 8 days (FIG. 34C).

The ability of treatment with antagonist of IL-11 mediated signaling administered 10 hours after hepatotoxic insult to reverse DILI-associated hepatotoxicity and prevent death of subjects administered a severe/lethal APAP overdose was a truly remarkable result. 10 hours after overdose in mice is thought to be equivalent to about 24 hours after overdose in humans.

The invention claimed is:

1. An antigen-binding molecule that specifically binds to IL-11Rα, comprising:
   (i) a heavy chain variable (VH) region incorporating the following CDRs:
      HC-CDR1 having the amino acid sequence of SEQ ID NO: 18;
      HC-CDR2 having the amino acid sequence of SEQ ID NO: 52; and
      HC-CDR3 having the amino acid sequence of SEQ ID NO: 21; and
   (ii) a light chain variable (VL) region incorporating the following CDRs:
      LC-CDR1 having the amino acid sequence of SEQ ID NO: 22;
      LC-CDR2 having the amino acid sequence of SEQ ID NO: 23; and
      LC-CDR3 having the amino acid sequence of SEQ ID NO: 24.

2. The antigen-binding molecule according to claim 1, wherein the antigen-binding molecule comprises:
   (i) a VH region incorporating the following CDRs:
      HC-CDR1 having the amino acid sequence of SEQ ID NO: 18;
      HC-CDR2 having the amino acid sequence of SEQ ID NO: 19; and
      HC-CDR3 having the amino acid sequence of SEQ ID NO: 21; and
   (ii) a VL region incorporating the following CDRs:
      LC-CDR1 having the amino acid sequence of SEQ ID NO: 22;
      LC-CDR2 having the amino acid sequence of SEQ ID NO: 23; and
      LC-CDR3 having the amino acid sequence of SEQ ID NO: 24.

3. The antigen-binding molecule according to claim 1, wherein the antigen-binding molecule comprises:
   (i) a VH region comprising an amino acid sequence having at least 70% sequence identity to the amino acid sequence of SEQ ID NO: 7, 8, 9, 10, 11, or 12; and
   (ii) a VL region comprising an amino acid sequence having at least 70% sequence identity to the amino acid sequence of SEQ ID NO: 13, 14, 15, 16, or 17.

4. The antigen-binding molecule according to claim 1, wherein the antigen-binding molecule comprises:
   (i) a VH region comprising an amino acid sequence having at least 70% sequence identity to the amino acid sequence of SEQ ID NO: 11; and
   (ii) a VL region comprising an amino acid sequence having at least 70% sequence identity to the amino acid sequence of SEQ ID NO: 17.

5. The antigen-binding molecule according to claim 1, wherein the antigen-binding molecule comprises a heavy chain comprising the amino acid sequence of SEQ ID NO: 68.

6. The antigen-binding molecule according to claim 1, wherein the antigen-binding molecule comprises:
   (i) a heavy chain comprising the amino acid sequence of SEQ ID NO: 73; and
   (ii) a light chain comprising the amino acid sequence of SEQ ID NO: 74.

* * * * *

SEQUENCE LISTING

<160> NUMBER OF SEQ ID NOS: 79

<210> SEQ ID NO 1
<211> LENGTH: 199
<212> TYPE: PRT
<213> ORGANISM: Homo sapiens

<400> SEQUENCE: 1

```
Met Asn Cys Val Cys Arg Leu Val Leu Val Leu Ser Leu Trp Pro
1               5                   10                  15

Asp Thr Ala Val Ala Pro Gly Pro Pro Gly Pro Pro Arg Val Ser
            20                  25                  30

Pro Asp Pro Arg Ala Glu Leu Asp Ser Thr Val Leu Leu Thr Arg Ser
        35                  40                  45

Leu Leu Ala Asp Thr Arg Gln Leu Ala Ala Gln Leu Arg Asp Lys Phe
    50                  55                  60

Pro Ala Asp Gly Asp His Asn Leu Asp Ser Leu Pro Thr Leu Ala Met
65                  70                  75                  80

Ser Ala Gly Ala Leu Gly Ala Leu Gln Leu Pro Gly Val Leu Thr Arg
                85                  90                  95

Leu Arg Ala Asp Leu Leu Ser Tyr Leu Arg His Val Gln Trp Leu Arg
                100                 105                 110

Arg Ala Gly Gly Ser Ser Leu Lys Thr Leu Glu Pro Glu Leu Gly Thr
            115                 120                 125

Leu Gln Ala Arg Leu Asp Arg Leu Leu Arg Arg Leu Gln Leu Leu Met
    130                 135                 140

Ser Arg Leu Ala Leu Pro Gln Pro Pro Asp Pro Pro Ala Pro Pro
145                 150                 155                 160

Leu Ala Pro Pro Ser Ser Ala Trp Gly Gly Ile Arg Ala Ala His Ala
                165                 170                 175

Ile Leu Gly Gly Leu His Leu Thr Leu Asp Trp Ala Val Arg Gly Leu
                180                 185                 190

Leu Leu Leu Lys Thr Arg Leu
            195

<210> SEQ ID NO 2
<211> LENGTH: 918
<212> TYPE: PRT
<213> ORGANISM: Homo sapiens

<400> SEQUENCE: 2

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
                100                 105                 110

Gln Asn Val Tyr Gly Ile Thr Ile Ile Ser Gly Leu Pro Pro Glu Lys
            115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175
```

-continued

```
Asp Thr Pro Thr Ser Cys Thr Val Asp Tyr Ser Thr Val Tyr Phe Val
                180                 185                 190

Asn Ile Glu Val Trp Val Glu Ala Glu Asn Ala Leu Gly Lys Val Thr
            195                 200                 205

Ser Asp His Ile Asn Phe Asp Pro Val Tyr Lys Val Lys Pro Asn Pro
        210                 215                 220

Pro His Asn Leu Ser Val Ile Asn Ser Glu Leu Ser Ser Ile Leu
225                 230                 235                 240

Lys Leu Thr Trp Thr Asn Pro Ser Ile Lys Ser Val Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590
```

```
Ala Ala Tyr Thr Asp Glu Gly Gly Lys Asp Gly Pro Glu Phe Thr Phe
            595                 600                 605

Thr Thr Pro Lys Phe Ala Gln Gly Glu Ile Glu Ala Ile Val Val Pro
    610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
        675                 680                 685

Thr Asp Val Ser Val Val Glu Ile Glu Ala Asn Asp Lys Lys Pro Phe
    690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Asp Glu Asn Glu Ser Ser Gln Asn
            740                 745                 750

Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
    770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Gln
    850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
            900                 905                 910

Gly Gly Tyr Met Pro Gln
        915

<210> SEQ ID NO 3
<211> LENGTH: 422
<212> TYPE: PRT
<213> ORGANISM: Homo sapiens

<400> SEQUENCE: 3

Met Ser Ser Ser Cys Ser Gly Leu Ser Arg Val Leu Val Ala Val Ala
1               5                   10                  15

Thr Ala Leu Val Ser Ala Ser Ser Pro Cys Pro Gln Ala Trp Gly Pro
            20                  25                  30

Pro Gly Val Gln Tyr Gly Gln Pro Gly Arg Ser Val Lys Leu Cys Cys
        35                  40                  45
```

Pro Gly Val Thr Ala Gly Asp Pro Val Ser Trp Phe Arg Asp Gly Glu
            50                  55                  60

Pro Lys Leu Leu Gln Gly Pro Asp Ser Gly Leu Gly His Glu Leu Val
 65                  70                  75                  80

Leu Ala Gln Ala Asp Ser Thr Asp Glu Gly Thr Tyr Ile Cys Gln Thr
                        85                  90                  95

Leu Asp Gly Ala Leu Gly Gly Thr Val Thr Leu Gln Leu Gly Tyr Pro
                100                 105                 110

Pro Ala Arg Pro Val Val Ser Cys Gln Ala Ala Asp Tyr Glu Asn Phe
                115                 120                 125

Ser Cys Thr Trp Ser Pro Ser Gln Ile Ser Gly Leu Pro Thr Arg Tyr
            130                 135                 140

Leu Thr Ser Tyr Arg Lys Lys Thr Val Leu Gly Ala Asp Ser Gln Arg
145                 150                 155                 160

Arg Ser Pro Ser Thr Gly Pro Trp Pro Cys Pro Gln Asp Pro Leu Gly
                    165                 170                 175

Ala Ala Arg Cys Val Val His Gly Ala Glu Phe Trp Ser Gln Tyr Arg
                180                 185                 190

Ile Asn Val Thr Glu Val Asn Pro Leu Gly Ala Ser Thr Arg Leu Leu
            195                 200                 205

Asp Val Ser Leu Gln Ser Ile Leu Arg Pro Asp Pro Pro Gln Gly Leu
210                 215                 220

Arg Val Glu Ser Val Pro Gly Tyr Pro Arg Arg Leu Arg Ala Ser Trp
225                 230                 235                 240

Thr Tyr Pro Ala Ser Trp Pro Cys Gln Pro His Phe Leu Leu Lys Phe
                    245                 250                 255

Arg Leu Gln Tyr Arg Pro Ala Gln His Pro Ala Trp Ser Thr Val Glu
                260                 265                 270

Pro Ala Gly Leu Glu Glu Val Ile Thr Asp Ala Val Ala Gly Leu Pro
            275                 280                 285

His Ala Val Arg Val Ser Ala Arg Asp Phe Leu Asp Ala Gly Thr Trp
290                 295                 300

Ser Thr Trp Ser Pro Glu Ala Trp Gly Thr Pro Ser Thr Gly Thr Ile
305                 310                 315                 320

Pro Lys Glu Ile Pro Ala Trp Gly Gln Leu His Thr Gln Pro Glu Val
                    325                 330                 335

Glu Pro Gln Val Asp Ser Pro Ala Pro Pro Arg Pro Ser Leu Gln Pro
                340                 345                 350

His Pro Arg Leu Leu Asp His Arg Asp Ser Val Glu Gln Val Ala Val
            355                 360                 365

Leu Ala Ser Leu Gly Ile Leu Ser Phe Leu Gly Leu Val Ala Gly Ala
370                 375                 380

Leu Ala Leu Gly Leu Trp Leu Arg Leu Arg Arg Gly Gly Lys Asp Gly
385                 390                 395                 400

Ser Pro Lys Pro Gly Phe Leu Ala Ser Val Ile Pro Val Asp Arg Arg
                405                 410                 415

Pro Gly Ala Pro Asn Leu
            420

<210> SEQ ID NO 4
<211> LENGTH: 390
<212> TYPE: PRT
<213> ORGANISM: Homo sapiens -continued

```
<400> SEQUENCE: 4

Met Ser Ser Ser Cys Ser Gly Leu Ser Arg Val Leu Ala Val Ala
1               5                   10                  15

Thr Ala Leu Val Ser Ala Ser Ser Pro Cys Pro Gln Ala Trp Gly Pro
            20                  25                  30

Pro Gly Val Gln Tyr Gly Gln Pro Gly Arg Ser Val Lys Leu Cys Cys
        35                  40                  45

Pro Gly Val Thr Ala Gly Asp Pro Val Ser Trp Phe Arg Asp Gly Glu
    50                  55                  60

Pro Lys Leu Leu Gln Gly Pro Asp Ser Gly Leu Gly His Glu Leu Val
65                  70                  75                  80

Leu Ala Gln Ala Asp Ser Thr Asp Glu Gly Thr Tyr Ile Cys Gln Thr
                85                  90                  95

Leu Asp Gly Ala Leu Gly Gly Thr Val Thr Leu Gln Leu Gly Tyr Pro
            100                 105                 110

Pro Ala Arg Pro Val Val Ser Cys Gln Ala Ala Asp Tyr Glu Asn Phe
        115                 120                 125

Ser Cys Thr Trp Ser Pro Ser Gln Ile Ser Gly Leu Pro Thr Arg Tyr
    130                 135                 140

Leu Thr Ser Tyr Arg Lys Lys Thr Val Leu Gly Ala Asp Ser Gln Arg
145                 150                 155                 160

Arg Ser Pro Ser Thr Gly Pro Trp Pro Cys Pro Gln Asp Pro Leu Gly
                165                 170                 175

Ala Ala Arg Cys Val Val His Gly Ala Glu Phe Trp Ser Gln Tyr Arg
            180                 185                 190

Ile Asn Val Thr Glu Val Asn Pro Leu Gly Ala Ser Thr Arg Leu Leu
        195                 200                 205

Asp Val Ser Leu Gln Ser Ile Leu Arg Pro Asp Pro Gln Gly Leu
    210                 215                 220

Arg Val Glu Ser Val Pro Gly Tyr Pro Arg Arg Leu Arg Ala Ser Trp
225                 230                 235                 240

Thr Tyr Pro Ala Ser Trp Pro Cys Gln Pro His Phe Leu Leu Lys Phe
                245                 250                 255

Arg Leu Gln Tyr Arg Pro Ala Gln His Pro Ala Trp Ser Thr Val Glu
            260                 265                 270

Pro Ala Gly Leu Glu Glu Val Ile Thr Asp Ala Val Ala Gly Leu Pro
        275                 280                 285

His Ala Val Arg Val Ser Ala Arg Asp Phe Leu Asp Ala Gly Thr Trp
    290                 295                 300

Ser Thr Trp Ser Pro Glu Ala Trp Gly Thr Pro Ser Thr Gly Thr Ile
305                 310                 315                 320

Pro Lys Glu Ile Pro Ala Trp Gly Gln Leu His Thr Gln Pro Glu Val
                325                 330                 335

Glu Pro Gln Val Asp Ser Pro Ala Pro Pro Arg Pro Ser Leu Gln Pro
            340                 345                 350

His Pro Arg Leu Leu Asp His Arg Asp Ser Val Glu Gln Val Ala Val
        355                 360                 365

Leu Ala Ser Leu Gly Ile Leu Ser Phe Leu Gly Leu Val Ala Gly Ala
    370                 375                 380

Leu Ala Leu Gly Leu Trp
385                 390

<210> SEQ ID NO 5
```

```
<211> LENGTH: 516
<212> TYPE: PRT
<213> ORGANISM: Artificial Sequence
<220> FEATURE:
<223> OTHER INFORMATION: IL-11:IL-11Ralpha fusion protein

<400> SEQUENCE: 5
```

Met Gly Trp Ser Cys Ile Ile Leu Phe Leu Val Ala Thr Ala Thr Gly
1               5                   10                  15

Val His Ser Pro Gln Ala Trp Gly Pro Pro Gly Val Gln Tyr Gly Gln
            20                  25                  30

Pro Gly Arg Ser Val Lys Leu Cys Cys Pro Gly Val Thr Ala Gly Asp
        35                  40                  45

Pro Val Ser Trp Phe Arg Asp Gly Glu Pro Lys Leu Leu Gln Gly Pro
50                  55                  60

Asp Ser Gly Leu Gly His Glu Leu Val Leu Ala Gln Ala Asp Ser Thr
65                  70                  75                  80

Asp Glu Gly Thr Tyr Ile Cys Gln Thr Leu Asp Gly Ala Leu Gly Gly
                85                  90                  95

Thr Val Thr Leu Gln Leu Gly Tyr Pro Pro Ala Arg Pro Val Val Ser
            100                 105                 110

Cys Gln Ala Ala Asp Tyr Glu Asn Phe Ser Cys Thr Trp Ser Pro Ser
        115                 120                 125

Gln Ile Ser Gly Leu Pro Thr Arg Tyr Leu Thr Ser Tyr Arg Lys Lys
130                 135                 140

Thr Val Leu Gly Ala Asp Ser Gln Arg Arg Ser Pro Ser Thr Gly Pro
145                 150                 155                 160

Trp Pro Cys Pro Gln Asp Pro Leu Gly Ala Ala Arg Cys Val Val His
                165                 170                 175

Gly Ala Glu Phe Trp Ser Gln Tyr Arg Ile Asn Val Thr Glu Val Asn
            180                 185                 190

Pro Leu Gly Ala Ser Thr Arg Leu Leu Asp Val Ser Leu Gln Ser Ile
        195                 200                 205

Leu Arg Pro Asp Pro Pro Gln Gly Leu Arg Val Glu Ser Val Pro Gly
210                 215                 220

Tyr Pro Arg Arg Leu Arg Ala Ser Trp Thr Tyr Pro Ala Ser Trp Pro
225                 230                 235                 240

Cys Gln Pro His Phe Leu Leu Lys Phe Arg Leu Gln Tyr Arg Pro Ala
                245                 250                 255

Gln His Pro Ala Trp Ser Thr Val Glu Pro Ala Gly Leu Glu Glu Val
            260                 265                 270

Ile Thr Asp Ala Val Ala Gly Leu Pro His Ala Val Arg Val Ser Ala
        275                 280                 285

Arg Asp Phe Leu Asp Ala Gly Thr Trp Ser Thr Trp Ser Pro Glu Ala
290                 295                 300

Trp Gly Thr Pro Ser Thr Gly Pro Ala Gly Gln Ser Gly Gly Gly Gly
305                 310                 315                 320

Gly Gly Ser Gly Gly Gly Ser Gly Gly Gly Ser Val Pro Gly Pro Pro
                325                 330                 335

Pro Gly Pro Pro Arg Val Ser Pro Asp Pro Arg Ala Glu Leu Asp Ser
            340                 345                 350

Thr Val Leu Leu Thr Arg Ser Leu Leu Ala Asp Thr Arg Gln Leu Ala
        355                 360                 365

Ala Gln Leu Arg Asp Lys Phe Pro Ala Asp Gly Asp His Asn Leu Asp
370                 375                 380

```
Ser Leu Pro Thr Leu Ala Met Ser Ala Gly Ala Gly Ala Leu Gln
385                 390                 395                 400

Leu Pro Gly Val Leu Thr Arg Leu Arg Ala Asp Leu Leu Ser Tyr Leu
            405                 410                 415

Arg His Val Gln Trp Leu Arg Arg Ala Gly Gly Ser Ser Leu Lys Thr
        420                 425                 430

Leu Glu Pro Glu Leu Gly Thr Leu Gln Ala Arg Leu Asp Arg Leu Leu
    435                 440                 445

Arg Arg Leu Gln Leu Leu Met Ser Arg Leu Ala Leu Pro Gln Pro Pro
450                 455                 460

Pro Asp Pro Pro Ala Pro Pro Leu Ala Pro Pro Ser Ser Ala Trp Gly
465                 470                 475                 480

Gly Ile Arg Ala Ala His Ala Ile Leu Gly Gly Leu His Leu Thr Leu
            485                 490                 495

Asp Trp Ala Val Arg Gly Leu Leu Leu Leu Lys Thr Arg Leu His His
            500                 505                 510

His His His His
        515

<210> SEQ ID NO 6
<211> LENGTH: 1575
<212> TYPE: DNA
<213> ORGANISM: Artificial Sequence
<220> FEATURE:
<223> OTHER INFORMATION: Nucleotide sequence encoding IL-11:IL-11Ralpha
      fusion protein

<400> SEQUENCE: 6
gaattcccgc cgccaccatg ggctggtcct gcatcatcct gtttctggtg gccacagcca      60
ccggcgtgca ctctccacag gcttggggac ctccaggcgt gcagtatggc cagcctggca     120
gatccgtgaa gctgtgctgt cctggcgtga cagctggcga ccctgtgtcc tggttcagag     180
atggcgagcc caagctgctg cagggcccag attctggact gggccacgaa ctggtgctgg     240
cccaggccga ttctaccgac gagggcacct acatctgcca gacccctggt ggcgcccctg     300
gcggaacagt gacactgcag ctgggctacc ctcccgccag acctgtggtg tcttgtcagg     360
ccgccgacta cgagaacttc agctgcacat ggtcccccag ccagatcagc ggcctgccca     420
ccagatacct gaccagctac cggaagaaaa ccgtgctggg cgccgacagc cagagaagaa     480
gcccttctac aggcccctgg ccctgccctc aggatcctct gggagctgcc agatgtgtgg     540
tgcacggcgc cgagttctgg tcccagtacc ggatcaacgt gaccgaagtg aaccccctgg     600
gcgcctccac aagactgctg gatgtgtccc tgcagagcat cctgcggccc gatcctccac     660
agggcctgag agtggaaagc gtgcccggct accccgaaag gctgagagcc agctggacat     720
accccgcctc ttggccttgc agccccact tcctgctgaa gtttcggctg cagtaccggc     780
cagcccagca ccctgcttgg agcacagtgg aacctgccgg cctggaagaa gtgatcacag     840
acgccgtggc cggactgcct catgctgtgc gggtgtccgc cagagacttt ctggatgccg     900
gcacctggtc tacctggtcc ccagaagcct ggggcacacc ttctactggc ggacctgctg     960
gacagtctgg cggaggcgga ggaagtggcg gaggatcagg ggaggatct gtgcctggac    1020 ctcctccagg accccctaga gtgtccccag atcctagggc cgagctggac tctaccgtgc    1080
tgctgaccag atcctgctg gccgacacaa ggcagctggc tgcccagctg agagacaagt    1140
tccccgccga cggcgaccac aacctggata gcctgctac cctggccatg tctgctggcg    1200
```

-continued

```
cactgggggc tctgcagctg cctggggtgc tgactagact gagagccgac ctgctgagct    1260
acctgcggca tgtgcagtgg ctgagaaggg ctggcggcag cagccctgaaa accctggaac    1320 ctgagctggg cacactgcag gccagactgg acagactgct gcgcagactg cagctgctga    1380
tgagcagact ggctctgccc cagcctcctc ctgaccctcc tgctcctcca ctggctcctc    1440
caagctctgc ttggggcgga attagagccg cccacgccat tctgggaggc ctgcacctga    1500
cactggattg ggcagtgcgg ggcctgctgc tgctgaaaac cagactgcac caccaccatc    1560
accactgata agctt                                                    1575
```

<210> SEQ ID NO 7
<211> LENGTH: 117
<212> TYPE: PRT
<213> ORGANISM: Artificial Sequence
<220> FEATURE:
<223> OTHER INFORMATION: 9A7 VH

<400> SEQUENCE: 7

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Asn Tyr
            20                  25                  30

Trp Met His Trp Leu Lys Gln Arg Pro Val Gln Gly Leu Glu Trp Ile
        35                  40                  45

Gly Asn Ile Gly Pro Ser Asp Ser Lys Thr His Tyr Asn Gln Lys Phe
    50                  55                  60

Lys Asp Lys Ala Thr Leu Thr Val Asp Lys Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Asp Tyr Val Leu Phe Thr Tyr Trp Gly Gln Gly Thr Leu
            100                 105                 110

Val Thr Val Ser Ala
        115

<210> SEQ ID NO 8
<211> LENGTH: 117
<212> TYPE: PRT
<213> ORGANISM: Artificial Sequence
<220> FEATURE:
<223> OTHER INFORMATION: 9A7 VH 1

<400> SEQUENCE: 8

Gln Val Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr Asn Tyr
            20                  25                  30

Trp Met His Trp Leu Lys Gln Arg Pro Gly Gln Gly Leu Glu Trp Ile
        35                  40                  45

Gly Asn Ile Gly Pro Ser Asp Ser Lys Thr His Tyr Asn Gln Lys Phe
    50                  55                  60

Lys Asp Arg Ala Thr Leu Thr Val Asp Lys Ser Thr Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Asp Tyr Val Leu Phe Thr Tyr Trp Gly Gln Gly Thr Leu
            100                 105                 110

<210> SEQ ID NO 9
<211> LENGTH: 117
<212> TYPE: PRT
<213> ORGANISM: Artificial Sequence
<220> FEATURE:
<223> OTHER INFORMATION: 9A7 VH 2

<400> SEQUENCE: 9

```
Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Asn Tyr
            20                  25                  30

Trp Met His Trp Leu Lys Gln Arg Pro Gly Gln Gly Leu Glu Trp Ile
        35                  40                  45

Gly Asn Ile Gly Pro Ser Asp Ser Lys Thr His Tyr Asn Gln Lys Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Val Leu Phe Thr Tyr Trp Gly Gln Gly Thr Leu
            100                 105                 110

Val Thr Val Ser Ser
        115
```

<210> SEQ ID NO 10
<211> LENGTH: 117
<212> TYPE: PRT
<213> ORGANISM: Artificial Sequence
<220> FEATURE:
<223> OTHER INFORMATION: 9A7 VH 3

<400> SEQUENCE: 10

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Leu Arg Gln Arg Pro Gly Gln Gly Leu Glu Trp Ile
        35                  40                  45

Gly Asn Ile Gly Pro Ser Asp Ser Lys Thr His Tyr Asn Gln Lys Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Val Leu Phe Thr Tyr Trp Gly Gln Gly Thr Leu
            100                 105                 110

Val Thr Val Ser Ser
        115
```

<210> SEQ ID NO 11
<211> LENGTH: 117
<212> TYPE: PRT
<213> ORGANISM: Artificial Sequence
<220> FEATURE:
<223> OTHER INFORMATION: 9A7 VH 4

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Leu Arg Gln Arg Pro Gly Gln Gly Leu Glu Trp Ile
        35                  40                  45

Gly Asn Ile Gly Pro Ser Asp Ser Lys Thr His Tyr Asn Gln Lys Phe
    50                  55                  60

Lys Asp Arg Val Thr Met Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Val Leu Phe Thr Tyr Trp Gly Gln Gly Thr Leu
            100                 105                 110

Val Thr Val Ser Ser
            115

<210> SEQ ID NO 12
<211> LENGTH: 117
<212> TYPE: PRT
<213> ORGANISM: Artificial Sequence
<220> FEATURE:
<223> OTHER INFORMATION: 9A7 VH 5

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Ile
        35                  40                  45

Gly Asn Ile Gly Pro Ser Asp Ser Lys Thr His Tyr Asn Gln Lys Phe
    50                  55                  60

Gln Asp Arg Val Thr Met Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Val Leu Phe Thr Tyr Trp Gly Gln Gly Thr Leu
            100                 105                 110

Val Thr Val Ser Ser
            115

<210> SEQ ID NO 13
<211> LENGTH: 107
<212> TYPE: PRT
<213> ORGANISM: Artificial Sequence
<220> FEATURE:
<223> OTHER INFORMATION: 9A7 VL

<400> SEQUENCE: 13

Asp Ile Val Leu Thr Gln Ser Pro Ala Thr Leu Ser Met Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

```
Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Phe Asn Ser Val Glu Thr
 65                 70                  75                  80

Glu Asp Phe Gly Val Tyr Phe Cys Gln Gln Ser Tyr Ser Trp Pro Leu
                85                  90                  95

Thr Phe Gly Ala Gly Thr Lys Leu Glu Leu Lys
            100                 105
```

<210> SEQ ID NO 14
<211> LENGTH: 107
<212> TYPE: PRT
<213> ORGANISM: Artificial Sequence
<220> FEATURE:
<223> OTHER INFORMATION: 9A7 VL 1

<400> SEQUENCE: 14

```
Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Ile Ser Asn Asn
                20                  25                  30

Leu His Trp Tyr Gln Gln Lys Ser His Glu Ala Pro Arg Leu Leu Ile
            35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Ser Phe Ser Ser Leu Glu Thr
 65                 70                  75                  80

Glu Asp Phe Ala Val Tyr Phe Cys Gln Gln Ser Tyr Ser Trp Pro Leu
                85                  90                  95

Thr Phe Gly Gln Gly Thr Lys Leu Glu Ile Lys
            100                 105
```

<210> SEQ ID NO 15
<211> LENGTH: 107
<212> TYPE: PRT
<213> ORGANISM: Artificial Sequence
<220> FEATURE:
<223> OTHER INFORMATION: 9A7 VL 2

<400> SEQUENCE: 15

```
Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Ile Ser Asn Asn
                20                  25                  30

Leu His Trp Tyr Gln Gln Lys Ser Gly Gln Ala Pro Arg Leu Leu Ile
            35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Thr
 65                 70                  75                  80

Glu Asp Phe Ala Val Tyr Phe Cys Gln Gln Ser Tyr Ser Trp Pro Leu
                85                  90                  95

Thr Phe Gly Gln Gly Thr Lys Leu Glu Ile Lys
            100                 105
```

<210> SEQ ID NO 16
<211> LENGTH: 107
<212> TYPE: PRT
<213> ORGANISM: Artificial Sequence

```
<220> FEATURE:
<223> OTHER INFORMATION: 9A7 VL 3

<400> SEQUENCE: 16

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Ser Tyr Ser Trp Pro Leu
                85                  90                  95

Thr Phe Gly Gln Gly Thr Lys Leu Glu Ile Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: 9A7 VL 4

<400> SEQUENCE: 17

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Tyr Ser Trp Pro Leu
                85                  90                  95

Thr Phe Gly Gln Gly Thr Lys Leu Glu Ile Lys
            100                 105

<210> SEQ ID NO 18
<211> LENGTH: 5
<212> TYPE: PRT
<213> ORGANISM: Artificial Sequence
<220> FEATURE:
<223> OTHER INFORMATION: 9A7 VH, 9A7 VH 1, 9A7 VH 2, 9A7 VH 3, 9A7 VH 4,
    9A7 VH 5 HC-CDR1

<400> SEQUENCE: 18

Asn Tyr Trp Met His
1               5

<210> SEQ ID NO 19
<211> LENGTH: 17
<212> TYPE: PRT
<213> ORGANISM: Artificial Sequence
<220> FEATURE:
<223> OTHER INFORMATION: 9A7 VH, 9A7 VH 1, 9A7 VH 2, 9A7 VH 3, 9A7 VH 4
    HC-CDR2
```

<400> SEQUENCE: 19

Asn Ile Gly Pro Ser Asp Ser Lys Thr His Tyr Asn Gln Lys Phe Lys
1               5                   10                  15

Asp

<210> SEQ ID NO 20
<211> LENGTH: 17
<212> TYPE: PRT
<213> ORGANISM: Artificial Sequence
<220> FEATURE:
<223> OTHER INFORMATION: 9A7 VH 5 HC-CDR2

<400> SEQUENCE: 20

Asn Ile Gly Pro Ser Asp Ser Lys Thr His Tyr Asn Gln Lys Phe Gln
1               5                   10                  15

Asp

<210> SEQ ID NO 21
<211> LENGTH: 8
<212> TYPE: PRT
<213> ORGANISM: Artificial Sequence
<220> FEATURE:
<223> OTHER INFORMATION: 9A7 VH, 9A7 VH 1, 9A7 VH 2, 9A7 VH 3, 9A7 VH 4,
      9A7 VH 5 HC-CDR3

<400> SEQUENCE: 21

Gly Asp Tyr Val Leu Phe Thr Tyr
1               5

<210> SEQ ID NO 22
<211> LENGTH: 11
<212> TYPE: PRT
<213> ORGANISM: Artificial Sequence
<220> FEATURE:
<223> OTHER INFORMATION: 9A7 VL, 9A7 VL 1, 9A7 VL 2, 9A7 VL 3, 9A7 VL 4
      LC-CDR1

<400> SEQUENCE: 22

Arg Ala Ser Gln Ser Ile Ser Asn Asn Leu His
1               5                   10

<210> SEQ ID NO 23
<211> LENGTH: 7
<212> TYPE: PRT
<213> ORGANISM: Artificial Sequence
<220> FEATURE:
<223> OTHER INFORMATION: 9A7 VL, 9A7 VL 1, 9A7 VL 2, 9A7 VL 3, 9A7 VL 4
      LC-CDR2

<400> SEQUENCE: 23

Tyr Ala Ser Gln Ser Ile Ser
1               5

<210> SEQ ID NO 24
<211> LENGTH: 9
<212> TYPE: PRT
<213> ORGANISM: Artificial Sequence
<220> FEATURE:
<223> OTHER INFORMATION: 9A7 VL, 9A7 VL 1, 9A7 VL 2, 9A7 VL 3, 9A7 VL 4
      LC-CDR3

<400> SEQUENCE: 24

Gln Gln Ser Tyr Ser Trp Pro Leu Thr
1               5

<210> SEQ ID NO 25
<211> LENGTH: 30
<212> TYPE: PRT
<213> ORGANISM: Artificial Sequence
<220> FEATURE:
<223> OTHER INFORMATION: 9A7 VH HC-FR1

<400> SEQUENCE: 25

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: 9A7 VH 1 HC-FR1

<400> SEQUENCE: 26

Gln Val Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: 9A7 VH 2 HC-FR1

<400> SEQUENCE: 27

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: 9A7 VH 3, 9A7 VH 4, 9A7 VH 5 HC-FR1

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 29
<211> LENGTH: 14
<212> TYPE: PRT
<213> ORGANISM: Artificial Sequence
<220> FEATURE:
<223> OTHER INFORMATION: 9A7 VH HC-FR2

<400> SEQUENCE: 29

Trp Leu Lys Gln Arg Pro Val Gln Gly Leu Glu Trp Ile Gly
1               5                   10

<210> SEQ ID NO 30

```
<211> LENGTH: 14
<212> TYPE: PRT
<213> ORGANISM: Artificial Sequence
<220> FEATURE:
<223> OTHER INFORMATION: 9A7 VH 1, 9A7 VH 2 HC-FR2

<400> SEQUENCE: 30

Trp Leu Lys Gln Arg Pro Gly Gln Gly Leu Glu Trp Ile Gly
1               5                   10

<210> SEQ ID NO 31
<211> LENGTH: 14
<212> TYPE: PRT
<213> ORGANISM: Artificial Sequence
<220> FEATURE:
<223> OTHER INFORMATION: 9A7 VH 3, 9A7 VH 4 HC-FR2

<400> SEQUENCE: 31

Trp Leu Arg Gln Arg Pro Gly Gln Gly Leu Glu Trp Ile Gly
1               5                   10

<210> SEQ ID NO 32
<211> LENGTH: 14
<212> TYPE: PRT
<213> ORGANISM: Artificial Sequence
<220> FEATURE:
<223> OTHER INFORMATION: 9A7 VH 5 HC-FR2

<400> SEQUENCE: 32

Trp Val Arg Gln Ala Pro Gly Gln Gly Leu Glu Trp Ile Gly
1               5                   10

<210> SEQ ID NO 33
<211> LENGTH: 32
<212> TYPE: PRT
<213> ORGANISM: Artificial Sequence
<220> FEATURE:
<223> OTHER INFORMATION: 9A7 VH HC-FR3

<400> SEQUENCE: 33

Lys Ala Thr Leu Thr Val Asp Lys Ser Ser Ser Thr Ala Tyr Met Gln
1               5                   10                  15

Leu Asn Ser Leu Thr Ser Glu Asp Ser Ala Val Tyr Tyr Cys Ala Arg
                20                  25                  30

<210> SEQ ID NO 34
<211> LENGTH: 32
<212> TYPE: PRT
<213> ORGANISM: Artificial Sequence
<220> FEATURE:
<223> OTHER INFORMATION: 9A7 VH 1 HC-FR3

<400> SEQUENCE: 34

Arg Ala Thr Leu Thr Val Asp Lys Ser Thr Ser Thr Ala Tyr Met Gln
1               5                   10                  15

Leu Asn Ser Leu Thr Ser Glu Asp Ser Ala Val Tyr Tyr Cys Ala Arg
                20                  25                  30

<210> SEQ ID NO 35
<211> LENGTH: 32
<212> TYPE: PRT
<213> ORGANISM: Artificial Sequence
<220> FEATURE:
<223> OTHER INFORMATION: 9A7 VH 2, 9A7 VH 3 HC-FR3

<400> SEQUENCE: 35
```

```
Arg Ala Thr Leu Thr Val Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 36
<211> LENGTH: 32
<212> TYPE: PRT
<213> ORGANISM: Artificial Sequence
<220> FEATURE:
<223> OTHER INFORMATION: 9A7 VH 4, 9A7 VH 5 HC-FR3

<400> SEQUENCE: 36

Arg Val Thr Met Thr Val Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 37
<211> LENGTH: 11
<212> TYPE: PRT
<213> ORGANISM: Artificial Sequence
<220> FEATURE:
<223> OTHER INFORMATION: 9A7 VH HC-FR4

<400> SEQUENCE: 37

Trp Gly Gln Gly Thr Leu Val Thr Val Ser Ala
1               5                   10

<210> SEQ ID NO 38
<211> LENGTH: 11
<212> TYPE: PRT
<213> ORGANISM: Artificial Sequence
<220> FEATURE:
<223> OTHER INFORMATION: 9A7 VH 1, 9A7 VH 2, 9A7 VH 3, 9A7 VH 4, 9A7 VH
      5 HC-FR4

<400> SEQUENCE: 38

Trp Gly Gln Gly Thr Leu Val Thr Val Ser Ser
1               5                   10

<210> SEQ ID NO 39
<211> LENGTH: 23
<212> TYPE: PRT
<213> ORGANISM: Artificial Sequence
<220> FEATURE:
<223> OTHER INFORMATION: 9A7 VL LC-FR1

<400> SEQUENCE: 39

Asp Ile Val Leu Thr Gln Ser Pro Ala Thr Leu Ser Met Thr Pro Gly
1               5                   10                  15

Asp Ser Val Ser Leu Ser Cys
            20

<210> SEQ ID NO 40
<211> LENGTH: 23
<212> TYPE: PRT
<213> ORGANISM: Artificial Sequence
<220> FEATURE:
<223> OTHER INFORMATION: 9A7 VL 1, 9A7 VL 2, 9A7 VL 3, 9A7 VL 4 LC-FR1

<400> SEQUENCE: 40

Asp Ile Val Leu Thr Gln Ser Pro Ala Thr Leu Ser Leu Ser Pro Gly
1               5                   10                  15

Glu Arg Ala Thr Leu Ser Cys
```

-continued

```
<210> SEQ ID NO 41
<211> LENGTH: 15
<212> TYPE: PRT
<213> ORGANISM: Artificial Sequence
<220> FEATURE:
<223> OTHER INFORMATION: 9A7 VL LC-FR2

<400> SEQUENCE: 41

Trp Tyr Gln Gln Lys Ser His Glu Ser Pro Arg Leu Leu Ile Lys
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: 9A7 VL 1 LC-FR2

<400> SEQUENCE: 42

Trp Tyr Gln Gln Lys Ser His Glu Ala Pro Arg Leu Leu Ile Lys
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: 9A7 VL 2 LC-FR2

<400> SEQUENCE: 43

Trp Tyr Gln Gln Lys Ser Gly Gln Ala Pro Arg Leu Leu Ile Lys
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: 9A7 VL 3, 9A7 VL 4 LC-FR2

<400> SEQUENCE: 44

Trp Tyr Gln Gln Lys Pro Gly Gln Ala Pro Arg Leu Leu Ile Lys
1               5                   10                  15

<210> SEQ ID NO 45
<211> LENGTH: 32
<212> TYPE: PRT
<213> ORGANISM: Artificial Sequence
<220> FEATURE:
<223> OTHER INFORMATION: 9A7 VL LC-FR3

<400> SEQUENCE: 45

Gly Ile Pro Ser Arg Phe Ser Gly Ser Gly Ser Gly Thr Asp Phe Thr
1               5                   10                  15

Leu Ser Phe Asn Ser Val Glu Thr Glu Asp Phe Gly Val Tyr Phe Cys
                20                  25                  30

<210> SEQ ID NO 46
<211> LENGTH: 32
<212> TYPE: PRT
<213> ORGANISM: Artificial Sequence
<220> FEATURE:
<223> OTHER INFORMATION: 9A7 VL 1 LC-FR3

<400> SEQUENCE: 46
```

```
Gly Ile Pro Ala Arg Phe Ser Gly Ser Gly Ser Gly Thr Asp Phe Thr
1               5                   10                  15

Leu Ser Phe Ser Ser Leu Glu Thr Glu Asp Phe Ala Val Tyr Phe Cys
            20                  25                  30
```

<210> SEQ ID NO 47
<211> LENGTH: 32
<212> TYPE: PRT
<213> ORGANISM: Artificial Sequence
<220> FEATURE:
<223> OTHER INFORMATION: 9A7 VL 2 LC-FR3

<400> SEQUENCE: 47

```
Gly Ile Pro Ala Arg Phe Ser Gly Ser Gly Ser Gly Thr Asp Phe Thr
1               5                   10                  15

Leu Thr Ile Ser Ser Leu Glu Thr Glu Asp Phe Ala Val Tyr Phe Cys
            20                  25                  30
```

<210> SEQ ID NO 48
<211> LENGTH: 32
<212> TYPE: PRT
<213> ORGANISM: Artificial Sequence
<220> FEATURE:
<223> OTHER INFORMATION: 9A7 VL 3 LC-FR3

<400> SEQUENCE: 48

```
Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Phe Cys
            20                  25                  30
```

<210> SEQ ID NO 49
<211> LENGTH: 32
<212> TYPE: PRT
<213> ORGANISM: Artificial Sequence
<220> FEATURE:
<223> OTHER INFORMATION: 9A7 VL 4 LC-FR3

<400> SEQUENCE: 49

```
Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30
```

<210> SEQ ID NO 50
<211> LENGTH: 10
<212> TYPE: PRT
<213> ORGANISM: Artificial Sequence
<220> FEATURE:
<223> OTHER INFORMATION: 9A7 VL LC-FR4

<400> SEQUENCE: 50

```
Phe Gly Ala Gly Thr Lys Leu Glu Leu Lys
1               5                   10
```

<210> SEQ ID NO 51
<211> LENGTH: 10
<212> TYPE: PRT
<213> ORGANISM: Artificial Sequence
<220> FEATURE:
<223> OTHER INFORMATION: 9A7 VL 1, 9A7 VL 2, 9A7 VL 3, 9A7 VL 4 LC-FR4

<400> SEQUENCE: 51

Phe Gly Gln Gly Thr Lys Leu Glu Ile Lys

-continued

<210> SEQ ID NO 52
<211> LENGTH: 17
<212> TYPE: PRT
<213> ORGANISM: Artificial Sequence
<220> FEATURE:
<223> OTHER INFORMATION: 9A7 VH HC-CDR2 consensus
<220> FEATURE:
<221> NAME/KEY: MISC_FEATURE
<222> LOCATION: (16)..(16)
<223> OTHER INFORMATION: Xaa - K or Q

<400> SEQUENCE: 52

Asn Ile Gly Pro Ser Asp Ser Lys Thr His Tyr Asn Gln Lys Phe Xaa
1               5                   10                  15

Asp

<210> SEQ ID NO 53
<211> LENGTH: 330
<212> TYPE: PRT
<213> ORGANISM: Homo sapiens

<400> SEQUENCE: 53

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 54
<211> LENGTH: 98
<212> TYPE: PRT
<213> ORGANISM: Artificial Sequence
<220> FEATURE:
<223> OTHER INFORMATION: CH1 IgG1 (positions 1-98 of P01857-1, v1)

<400> SEQUENCE: 54

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
```

<210> SEQ ID NO 55
<211> LENGTH: 12
<212> TYPE: PRT
<213> ORGANISM: Artificial Sequence
<220> FEATURE:
<223> OTHER INFORMATION: Hinge IgG1 (positions 99-110 of P01857-1, v1)

<400> SEQUENCE: 55

```
Glu Pro Lys Ser Cys Asp Lys Thr His Thr Cys Pro
1               5                   10
```

<210> SEQ ID NO 56
<211> LENGTH: 113
<212> TYPE: PRT
<213> ORGANISM: Artificial Sequence
<220> FEATURE:
<223> OTHER INFORMATION: CH2 IgG1 (positions 111-223 of P01857-1, v1)

<400> SEQUENCE: 56

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
```

65                      70                      75                      80

Val Leu His Gln Asp Trp Leu Asn Gly Lys Glu Tyr Lys Cys Lys Val
                            85                      90                      95

Ser Asn Lys Ala Leu Pro Ala Pro Ile Glu Lys Thr Ile Ser Lys Ala
                100                     105                     110

Lys

<210> SEQ ID NO 57
<211> LENGTH: 107
<212> TYPE: PRT
<213> ORGANISM: Artificial Sequence
<220> FEATURE:
<223> OTHER INFORMATION: CH3 IgG1 (positions 224-330 of P01857-1, v1)

<400> SEQUENCE: 57

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 58
<211> LENGTH: 107
<212> TYPE: PRT
<213> ORGANISM: Artificial Sequence
<220> FEATURE:
<223> OTHER INFORMATION: Ckappa CL (IGCK; UniProt: P01834-1, v2)

<400> SEQUENCE: 58

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 59
<211> LENGTH: 107
<212> TYPE: PRT
<213> ORGANISM: Artificial Sequence
<220> FEATURE:
<223> OTHER INFORMATION: 9A70 VL

<400> SEQUENCE: 59

Asp Ile Val Leu Thr Gln Ser Pro Ala Thr Leu Ser Met Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Phe Asn Ser Val Glu Thr
65                  70                  75                  80

Glu Asp Phe Gly Val Tyr Phe Cys Gln Gln Arg Tyr Ser Trp Pro Leu
                85                  90                  95

Thr Phe Gly Ala Gly Thr Lys Leu Glu Met Lys
            100                 105

<210> SEQ ID NO 60
<211> LENGTH: 9
<212> TYPE: PRT
<213> ORGANISM: Artificial Sequence
<220> FEATURE:
<223> OTHER INFORMATION: 9A70 VL LC-CDR3

<400> SEQUENCE: 60

Gln Gln Arg Tyr Ser Trp Pro Leu Thr
1               5

<210> SEQ ID NO 61
<211> LENGTH: 327
<212> TYPE: PRT
<213> ORGANISM: Homo sapiens

<400> SEQUENCE: 61

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp

```
                  180                 185                 190
Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 62
<211> LENGTH: 98
<212> TYPE: PRT
<213> ORGANISM: Artificial Sequence
<220> FEATURE:
<223> OTHER INFORMATION: CH1 IgG4 (positions 1-98 of P01861, v1)

<400> SEQUENCE: 62

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 63
<211> LENGTH: 12
<212> TYPE: PRT
<213> ORGANISM: Artificial Sequence
<220> FEATURE:
<223> OTHER INFORMATION: Hinge IgG4 (positions 99-110 of P01861, v1)

<400> SEQUENCE: 63

Glu Ser Lys Tyr Gly Pro Pro Cys Pro Ser Cys Pro
1               5                   10

<210> SEQ ID NO 64
<211> LENGTH: 110
<212> TYPE: PRT
<213> ORGANISM: Artificial Sequence
<220> FEATURE:
<223> OTHER INFORMATION: CH2 IgG4 (positions 111-220 of P01861, v1)
```

<400> SEQUENCE: 64

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 65
<211> LENGTH: 107
<212> TYPE: PRT
<213> ORGANISM: Artificial Sequence
<220> FEATURE:
<223> OTHER INFORMATION: CH3 IgG4 (positions 221-327 of P01861, v1)

<400> SEQUENCE: 65

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 66
<211> LENGTH: 327
<212> TYPE: PRT
<213> ORGANISM: Homo sapiens

<400> SEQUENCE: 66

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys

```
                85                  90                  95
Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 67
<211> LENGTH: 12
<212> TYPE: PRT
<213> ORGANISM: Artificial Sequence
<220> FEATURE:
<223> OTHER INFORMATION: Hinge IgG4 (positions 99-110 of P01861, v1;
      S241P)

<400> SEQUENCE: 67

Glu Ser Lys Tyr Gly Pro Pro Cys Pro Pro Cys Pro
1               5                   10

<210> SEQ ID NO 68
<211> LENGTH: 327
<212> TYPE: PRT
<213> ORGANISM: Homo sapiens

<400> SEQUENCE: 68

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
```

```
              50                  55                  60
Leu Ser Ser Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
                100                 105                 110

Glu Phe Glu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 69
<211> LENGTH: 110
<212> TYPE: PRT
<213> ORGANISM: Artificial Sequence
<220> FEATURE:
<223> OTHER INFORMATION: CH2 IgG4 (positions 111-220 of P01861, v1;
      L248E)

<400> SEQUENCE: 69

Ala Pro Glu Phe Glu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
 65                  70                  75                  80
```

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 70
<211> LENGTH: 447
<212> TYPE: PRT
<213> ORGANISM: Artificial Sequence
<220> FEATURE:
<223> OTHER INFORMATION: 9A7 VH4 - Human IgG1 constant region (IGHG1;
      UniProt:P01857-1, v1)

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Leu Arg Gln Arg Pro Gly Gln Gly Leu Glu Trp Ile
        35                  40                  45

Gly Asn Ile Gly Pro Ser Asp Ser Lys Thr His Tyr Asn Gln Lys Phe
    50                  55                  60

Lys Asp Arg Val Thr Met Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Val Leu Phe Thr Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

```
Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 71
<211> LENGTH: 444
<212> TYPE: PRT
<213> ORGANISM: Artificial Sequence
<220> FEATURE:
<223> OTHER INFORMATION: 9A7 VH4 - Human IgG4 constant region (IGHG4;
      UniProt: P01861, v1)

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Leu Arg Gln Arg Pro Gly Gln Gly Leu Glu Trp Ile
            35                  40                  45

Gly Asn Ile Gly Pro Ser Asp Ser Lys Thr His Tyr Asn Gln Lys Phe
    50                  55                  60

Lys Asp Arg Val Thr Met Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Val Leu Phe Thr Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Ser Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
```

-continued

```
                245                 250                 255
Thr Cys Val Val Val Asp Val Ser Gln Glu Asp Pro Glu Val Gln Phe
            260                 265                 270
Asn Trp Tyr Val Asp Gly Val Glu Val His Asn Ala Lys Thr Lys Pro
        275                 280                 285
Arg Glu Glu Gln Phe Asn Ser Thr Tyr Arg Val Val Ser Val Leu Thr
    290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
            325                 330                 335
Lys Gly Gln Pro Arg Glu Pro Gln Val Tyr Thr Leu Pro Pro Ser Gln
        340                 345                 350
Glu Glu Met Thr Lys Asn Gln Val Ser Leu Thr Cys Leu Val Lys Gly
    355                 360                 365
Phe Tyr Pro Ser Asp Ile Ala Val Glu Trp Glu Ser Asn Gly Gln Pro
370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
            405                 410                 415
Gly Asn Val Phe Ser Cys Ser Val Met His Glu Ala Leu His Asn His
        420                 425                 430
Tyr Thr Gln Lys Ser Leu Ser Leu Ser Leu Gly Lys
    435                 440
```

<210> SEQ ID NO 72
<211> LENGTH: 444
<212> TYPE: PRT
<213> ORGANISM: Artificial Sequence
<220> FEATURE:
<223> OTHER INFORMATION: 9A7 VH4 - Human IgG4 constant region (IGHG4; UniProt: P01861, v1; S241P)

<400> SEQUENCE: 72

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
            20                  25                  30
Trp Met His Trp Leu Arg Gln Arg Pro Gly Gln Gly Leu Glu Trp Ile
        35                  40                  45
Gly Asn Ile Gly Pro Ser Asp Ser Lys Thr His Tyr Asn Gln Lys Phe
    50                  55                  60
Lys Asp Arg Val Thr Met Thr Val Asp Lys Ser Thr Ser Thr Ala Tyr
65                  70                  75                  80
Met Glu Leu Ser Ser Leu Arg Ser Glu Asp Thr Ala Val Tyr Tyr Cys
            85                  90                  95
Ala Arg Gly Asp Tyr Val Leu Phe Thr Tyr Trp Gly Gln Gly Thr Leu
        100                 105                 110
Val Thr Val Ser Ser Ala Ser Thr Lys Gly Pro Ser Val Phe Pro Leu
    115                 120                 125
Ala Pro Cys Ser Arg Ser Thr Ser Glu Ser Thr Ala Ala Leu Gly Cys
    130                 135                 140
Leu Val Lys Asp Tyr Phe Pro Glu Pro Val Thr Val Ser Trp Asn Ser
145                 150                 155                 160
```

```
Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 73
<211> LENGTH: 444
<212> TYPE: PRT
<213> ORGANISM: Artificial Sequence
<220> FEATURE:
<223> OTHER INFORMATION: 9A7 VH4 - Human IgG4 constant region (IGHG4;
      UniProt: P01861, v1; S241P and L248E)

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Leu Arg Gln Arg Pro Gly Gln Gly Leu Glu Trp Ile
            35                  40                  45

Gly Asn Ile Gly Pro Ser Asp Ser Lys Thr His Tyr Asn Gln Lys Phe
        50                  55                  60

Lys Asp Arg Val Thr Met Thr Val Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Gly Asp Tyr Val Leu Phe Thr Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 74
<211> LENGTH: 214
<212> TYPE: PRT
<213> ORGANISM: Artificial Sequence
<220> FEATURE:
<223> OTHER INFORMATION: 9A7 VL4 - VL-Ckappa CL (IGCK; UniProt:
      P01834-1, v2)
```

<400> SEQUENCE: 74

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Tyr Ser Trp Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 75
<211> LENGTH: 106
<212> TYPE: PRT
<213> ORGANISM: Artificial Sequence
<220> FEATURE:
<223> OTHER INFORMATION: CL CL (IGLC1; UniProt: P0CG04, v1)

<400> SEQUENCE: 75

```
Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 76
<211> LENGTH: 106
<212> TYPE: PRT

<213> ORGANISM: Artificial Sequence
<220> FEATURE:
<223> OTHER INFORMATION: CL CL (IGLC2; UniProt: P0DOY2, v1)

<400> SEQUENCE: 76

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 77
<211> LENGTH: 106
<212> TYPE: PRT
<213> ORGANISM: Artificial Sequence
<220> FEATURE:
<223> OTHER INFORMATION: CL CL (IGLC3; UniProt: P0DOY3, v1)

<400> SEQUENCE: 77

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 78
<211> LENGTH: 106
<212> TYPE: PRT
<213> ORGANISM: Artificial Sequence
<220> FEATURE:
<223> OTHER INFORMATION: CL CL (IGLC6; UniProt: P0CF74, v1)

<400> SEQUENCE: 78

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Thr Pro Ser Lys Gln Ser Asn Asn
    50                  55                  60

```
Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Ala Glu Cys Ser
            100                 105

<210> SEQ ID NO 79
<211> LENGTH: 106
<212> TYPE: PRT
<213> ORGANISM: Artificial Sequence
<220> FEATURE:
<223> OTHER INFORMATION: CL CL (IGLC7; UniProt: A0M8Q6, v3)

<400> SEQUENCE: 79

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Val Ser Asp
             20                  25                  30

Phe Asn Pro Gly Ala Val Thr Val Ala Trp Lys Ala Asp Gly Ser Pro
             35                  40                  45

Val Lys Val Gly Val Glu Thr Thr Lys Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Arg Val Thr His Glu Gly Ser Thr Val
                 85                  90                  95

Glu Lys Thr Val Ala Pro Ala Glu Cys Ser
            100                 105
```